US011891391B2

(12) United States Patent
Sintim et al.

(10) Patent No.: US 11,891,391 B2
(45) Date of Patent: *Feb. 6, 2024

(54) INHIBITORS OF KINASE NETWORKS AND USES THEREOF

(71) Applicant: PURDUE RESEARCH FOUNDATION, West Lafayette, IN (US)

(72) Inventors: Herman O. Sintim, West Lafayette, IN (US); Neetu Dayal, Uttar Pradesh (IN); Clement Opoku-Temeng, Worcester, MA (US)

(73) Assignee: Purdue Research Foundation, West Lafayette, IN (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/243,629

(22) Filed: Apr. 29, 2021

(65) Prior Publication Data

US 2021/0371420 A1    Dec. 2, 2021

Related U.S. Application Data

(62) Division of application No. 16/499,133, filed as application No. PCT/US2018/024991 on Mar. 29, 2018, now Pat. No. 11,040,973.

(60) Provisional application No. 62/478,069, filed on Mar. 29, 2017, provisional application No. 62/616,643, filed on Jan. 12, 2018.

(51) Int. Cl.
| C07D 471/06 | (2006.01) |
| A61K 31/437 | (2006.01) |
| C07D 471/14 | (2006.01) |
| C07D 209/08 | (2006.01) |
| C07D 231/56 | (2006.01) |
| C07D 401/14 | (2006.01) |
| C07D 413/14 | (2006.01) |
| C07D 417/12 | (2006.01) |
| C07D 471/04 | (2006.01) |
| C07D 491/147 | (2006.01) |
| C07D 495/14 | (2006.01) |
| C07D 498/04 | (2006.01) |
| C07D 513/04 | (2006.01) |
| C07D 519/00 | (2006.01) |

(52) U.S. Cl.
CPC ......... *C07D 471/14* (2013.01); *C07D 209/08* (2013.01); *C07D 231/56* (2013.01); *C07D 401/14* (2013.01); *C07D 413/14* (2013.01); *C07D 417/12* (2013.01); *C07D 471/04* (2013.01); *C07D 491/147* (2013.01); *C07D 495/14* (2013.01); *C07D 498/04* (2013.01); *C07D 513/04* (2013.01); *C07D 519/00* (2013.01); *C07B 2200/05* (2013.01)

(58) Field of Classification Search
CPC .......................... C07D 471/06; A61K 31/437; A61K 31/4738; A61P 35/00; A61P 29/00
USPC ............................................ 546/64; 514/287
See application file for complete search history.

(56) References Cited

U.S. PATENT DOCUMENTS

| 3,947,434 | A | 3/1976 | Spencer et al. |
| 11,040,973 | B2 * | 6/2021 | Sintim ................. C07D 413/14 |
| 2004/0024208 | A1 | 2/2004 | Das et al. |
| 2005/0002945 | A1 | 1/2005 | McBride et al. |
| 2005/0043233 | A1 | 2/2005 | Stefanic et al. |
| 2005/0080260 | A1 | 4/2005 | Mills et al. |
| 2006/0281771 | A1 | 12/2006 | Baumann et al. |
| 2016/0083379 | A1 | 3/2016 | Boloor et al. |

FOREIGN PATENT DOCUMENTS

| EP | 0187705 A2 | 7/1986 |
| EP | 0638571 A1 | 2/1995 |
| JP | 61210085 A | 9/1986 |
| JP | 2002531523 A | 9/2002 |
| JP | 2002542193 A | 12/2002 |
| JP | 2006524634 A | 11/2006 |
| JP | 2008545785 A | 12/2008 |
| JP | 2013542243 A | 11/2013 |
| WO | 2006138347 A2 | 12/2006 |
| WO | 2007005887 A2 | 1/2007 |
| WO | 2011043359 A1 | 4/2011 |
| WO | 2012065963 A2 | 5/2012 |
| WO | 2016112284 A1 | 7/2016 |

OTHER PUBLICATIONS

Notification of Reasons of Rejection dated Nov. 30, 2021 in related Japanese Patent Application No. 2019-552978 (English translation).
Aly, et al., "Quinoline-based small molecules as effective protein kinases inhibitors (Review)," Journal of American Science, 2016, vol. 12(5), pp. 10-32.
Carta, et al., "Novel 3-Substituted 7-Phenylpyrrolo[3,2-f]quinolin-9(6H)-ones as Single Entities with Multitarget Antiproliferative Activity", Journal of Medicinal Chemistry, 2015, vol. 58, pp. 7991-8010.
Chou, et al., "Design, Synthesis, and Preclinical Evaluation of New 5,6- (or 6,7-) Disubstituted-2-(fluorophenyl) quinolin-4-one Derivates as Potent Antitumor Agents", J. Med. Chem., 2010, vol. 53, pp. 8047-8058.
Ferlin, et al., "New water soluble pyrroloquinoline derivatives as new potential anticancer agents," Bioorganic & Medicinal Chemistry, vol. 13, (2005), pp. 4733-4739.

(Continued)

Primary Examiner — Charanjit Aulakh
(74) Attorney, Agent, or Firm — Purdue Research Foundation

(57) ABSTRACT

The present invention generally relates to compounds as a dual kinase-demethylase inhibitor useful for the treatment of diseases mediated by a kinase and/or a histone demethylase, such as inflammation, cancer, viral and bacterial infections, neurological and immunological disorders. Pharmaceutical compositions and methods for treating those diseases are within the scope of this invention.

10 Claims, No Drawings

(56) References Cited

OTHER PUBLICATIONS

Ferlin, et al., "DNA Bidning Ellipticine Analogues: Synthesis, Biological Evaluation, and Structure-Activity Relationships," ChemMedChem, 2009, vol. 4, pp. 363-377.
Frey, et al., "Synthesis of a Bis-macrocycle Containing Two Back-to-Back Rigidly Connected 1, 10-Phenanthroline Units as a Central Core and its Incorporation in a Handcuff-Like Catenane," Chem., Eur., 2007, vol. 13, pp. 7584-7594.
Wang, et al., "Iodine-Catalyzed Synthesis of Cyclopenta[c]quinoline Derivatives via Imino Diels-Alder Reaction," Journal of Heterocyclic Chemistry, 2014, vol. 51, pp. 830-834.
Zhang, et al., "Iodine-Catalyzed Synthesis of Fused Polycyclic Heterocycles Containing Pyrazoloquinoline via Povarov Reaction," Polycyclic Aromatic Compounds, 2016, vol. 36, pp. 275-283.
Ferlin, et al., "Design, Synthesis, and Structure—Activity Relationships of Azolylmethylpyrroloquinolines as Nonsteroidal Aromatase Inhibitors," Journal of Medicinal Chemistry, 2013, vol. 56, pp. 7536-7551.
European Examination Report dated Oct. 12, 2021 in EP Application No. 18 776 719.9.
Partial Supplementary European Search Report issued in corresponding EP 18776719.9 dated Nov. 11, 2020.
Rabah Serya et al; "Quinoline-based small molecules as effective protein kinases inhibitors (Review)", Journal of American Science, Jan. 1, 2016; 12(5), pp. 10-32.
Ferlin, M.G., et al., "New water soluble pyrroloquinoline derivatives as new potential anticancer agents", Bioorganic & Medicinal Chemistry, Elsevier, NL, vol. 13, No. 15, Aug. 1, 2005, pp. 4733-4739.
Samoilova, M.E., et al. "Pyrrolophenanthridines" Chemical Abstracts Service 1993 (abstract).
Huang, Jin et al., "An approach to the synthesis of 1-propenylnaphthols and 3-arylnaphtho[2,1-b] furans", Journal of Organic Chemistry, vol. 82, No. 5, pp. 2523-2534, 2017, (abstract).
El Kihel, A., et al., "Condensation of 5-(amino)benzimidazole derivatives with.beta.-keto ester", Arabian Journal of Chemistry, vol. 3, No. 1, pp. 9-12, 2011 (abstract).
Ferlin, Maria Grazia et al., "DNA binding ellipticine analogues: synthesis, biological evaluation, and structure-activity relationships", vol. 4, No. 3, 2009, pp. 363-377, Chemical Abstracts Service, (abstract).
El Kihel, A., et al., "Synthesis of new imidazo-[4,5-f]-quinoline derivatives", Physical & Chemical News, vol. 2005, No. 24, pp. 112-115, 2006, Chemical Abstracts Service (abstract).
Sanna, Paolo et al., "Triazolo[4,5-f]quinolines derived from 5-amino-1H-bezotriazole with.beta.-diketones and 3-buten-2-one", Heterocycles, Chemical Abstracts Service, vol. 51, No. 9, pp. 2171-2181, 1999, (abstract).
Beviere, Corinne et al., "A case of competitive demethylation by boron tribromide-methyl sulfide complex. A new route to oxazoloquinolines", Synthetic Communications, vol. 26(6), p. 945, 1998, Chemical Abstracts Service (abstract).
Yamashkin, S.A., et al., "Synthesis of pyrroloquinolines from 2,3-dimethyl-5-methoxy-6-aminoindole", Chemistry of Heterocyclic compounds, vol. 33, No. 7, 1997, Chemical Abstracts Service (abstract).

Nebois, Pascal et al., "2-Ethoxy-2-butenal N,N-dimethylhydrazone: a useful reagent for the synthesis of furo[2,3-f] quinoline-4-5-diones", pp. 8457-8464, 1994, Chemical Abstracts Service (abstract).
Szczepankiewicz, Bruce G., et al., "Total Synthesis of Diplamine, a Cytotoxic Pyridocridine Alkaloid from aPacific Tunicate", Journal of Organic Chemistry, vol. 59, No. 13, pp. 3512-3513, 1994, Chemical Abstracts Service (abstract).
Nebois, Pascal et al., "Synthesis and NMR Structural Study of Furoquinolines and Naphthofuransfrom Quinones and a 1-azadiene", vol. 49, No. 43, pp. 9767-9774, 1993, Chemical Abstracts Service (abstract).
Fukatsu, Hiroshi et al., Synthesis and Cardiotonic Activity of 5-(2-substitutedthiazol-4-yl)-2-pyridones and thiazolo[4,5-f] quinolinones, Heterocycles, vol. 29, No. 8, pp. 1517-1518, 1989, Chemical Abstracts Service (abstract).
Akhylediani, R., "Chichibabin reaction in a series of angular pyrroloquinolines", vol. 17, No. 7, pp. 1542-1546, 1981, Chemical Abstracts Service (Abstract).
Sharma, K.S. et al., "Oxidation of thieno]3,2-f]quinoline and its 2-carbethoxy analog andeletrophilic and nucleophic substitution reactions of the resulting oxides", Indian Journal of Chemistry, Section B,. vol. 17B, No. 4, pp. 342-3451979, Chemical Abstracts Service (abstract).
Ishiwata, Saburo et al., "Synthesis of Benzimidazoles and related compounds. 11. Synthesis of 3H-imidazo[4,5-f]- and 1H-imidazo[5,4-g]quinolines," vol. 17, No. 12, Chemical & Pharmaceutical Bulletin, pp. 2455-2460, 1969, Chemical Abstracts Service (abstract).
Royer, Rene et al., "Benzofurans. XXXIII, Preparation of hydroxylated derivatives of furo[f]-, -[g]-, or -[h]quinolines from 4(5, 6, or 7)-amino- and 4(5, 6, or 7)-methoxy-2,3-dimethylbenzfurans", Bulletin De La Societe Chimique De France, vol. 1967, No. 3, pp. 915-922, Chemical Abstracts Service.
Nath Bhargara, et al., "Synthesis of Some Antituberculars:N-aryl-N'-[2-(4-arylthiazolyl)]thioureas", Bulletin of the Chemical Society of Japan, vol. 38, No. 6, 1965, pp. 905-909, Chemical Abstracts Service.
Huisgen, Rolf "Strychnos alkaloids. XXXI, Further Syntheses in the 5, 6(N)-pyrroquinolineseries", Justus Liebigs Annalen Der Chemie, vol. 1948, No. 559, pp. 174-190, 1948, Chemical Abstracts Service.
Notification of Reasons of Rejection (Final) dated Jun. 21, 2022 in corresponding Japanese Patent Application No. 2019-552978. (English translation).
First Office Action dated Jul. 18, 2022 in corresponding Chinese Patent Application No. 2018800347865. (English translation).
Maria Grazia Ferlin et. al., "New water soluble pyrroloquinoline derivatives as new potential anticancer agents," Bioorganic & Medicinal Chemistry, vol. 13, No. 15, pp. 4733-4739, Aug. 1, 2005.
Rabah Serya, "Quinoline-based small molecules as effective protein kinases inhibitors (review)," Journal of American Science, vol. 12, No. 5, pp. 10-32, 2016.
International Searching Authority, International Search Report, PCT Application Serial No. PCT/US2018/024991, dated Sep. 6, 2018.
International Searching Authority, Written Opinion of the International Searching Authority, PCT Application Serial No. PCT/US2018/024991, dated Sep. 6, 2018.

* cited by examiner

INHIBITORS OF KINASE NETWORKS AND USES THEREOF

CROSS REFERENCE TO RELATED APPLICATIONS

The present U.S. patent application is a divisional application of U.S. patent application Ser. No. 16/499,133, filed Sep. 27, 2019, which relates to, claims the priority benefit of, and is a 35 U.S.C. 371 national stage application of International Patent Application Serial No. PCT/US2018/024991 to Sintim et al., filed Mar. 29, 2018, which relates to and claims the priority benefit of U.S. Provisional Application Ser. No. 62/478,069, filed Mar. 29, 2017, and U.S. Provisional Application Ser. No. 62/616,643, filed Jan. 12, 2018. The entire contents of each of the aforementioned priority applications are hereby expressly incorporated herein by reference in their entireties.

TECHNICAL FIELD

The present invention generally relates to compounds as a kinase inhibitor and methods for the treatment of diseases mediated by a kinase, such as inflammation, cancer, viral and bacterial infections, neurological and immunological disorders.

BACKGROUND

This section introduces aspects that may help facilitate a better understanding of the disclosure. Accordingly, these statements are to be read in this light and are not to be understood as admissions about what is or is not prior art.

The cell contains over 500 kinases, which regulate diverse processes such as cell cycle, growth, migration, immune response.[1] Several deregulated kinases, i.e. kinases that have attained a gain-of-function mutation or are over-expressed, drive cancer proliferation.[1] Small molecule inhibitors of cancer-driver kinases (for example BCR-ABL1 fusion protein, FLT3-ITD, mutated or over-expressed ALK, EGFR, PDGFR, Kit, VEGFR, B-Raf, BTK, PI3Kδ, ErbB2) have seen clinical successes.[2] Recently efforts have been made to target other kinases, such as cell cycle kinases (CDKs), or kinases that target histones, cytoskeleton or other processes that are important for the cell, to arrest cancer growth. Most of the kinase inhibitors that proceed to the clinic work initially hut over time resistant clones emerge that render the drugs ineffective.[3] Various mechanisms account for cancer cell resistance to kinase inhibitors. For example copy number multiplication, additional kinase mutations (such as secondary mutations that arise in in the tyrosine kinase domain of FLT3-ITD kinase) or the activation of alternative kinase pathways and/or downstream targets can bypass the inhibition of a particular kinase target.[4] Kinase inhibitors that inhibit a cancer-driver kinase and also downstream targets (both kinase and non-kinase targets, such as histone demethylase) and/or kinases that collaborate with the driver kinase could have enhanced potency and reduced probability of resistance being generated against that kinase inhibitor.[5] A challenge however with such a polypharmacophore is to avoid promiscuous binding, which can lead to toxicity.

Kinase inhibitors have also been shown to be effective for the treatment of immune disorders (such as JAK kinases[6]), hypertension and erectile dysfunction (ROCK1/2 kinases[7]) and glaucoma (ROCK and LIMK kinases[8]). Other kinase targets, such as LRRK2, have also been shown to be important for CNS-related diseases, such as Alzheimer's or Parkinsons.[9] A privileged chemical scaffold, which can be tuned to selectively inhibit a disease-related kinase or inhibit a group of kinases that lie in a particular pathway or network could facilitate the treatment of diverse disease states.

SUMMARY OF THE INVENTION

The present invention generally relates to compounds that inhibit kinase and/or histone demethylase networks as useful compounds for the treatment of diseases mediated by a kinase, such as inflammation, cancer, viral and bacterial infections, neurological and immunological disorders. Pharmaceutical compositions and methods for treating those diseases are within the scope of this invention.

In some illustrative embodiments, the present invention relates to a compound having a formula

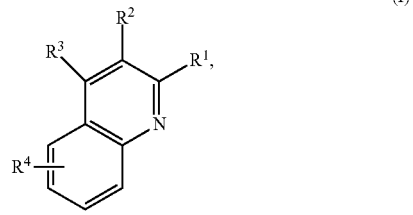

(I)

or a pharmaceutically acceptable salt thereof, wherein $R^1$ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^2$ and $R^3$ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or $R^2$ and $R^3$ are taken together with the attached carbons to form an optionally substituted cyclic or heterocyclic moiety; and $R^4$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or any two adjacent substituents of the four substituents are taken together with the attached carbons form an optionally substituted cyclic or heterocyclic moiety.

In some illustrative embodiments, the present invention relates to a compound having a formula:

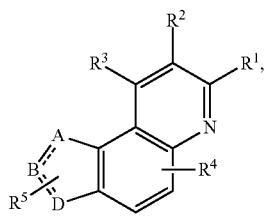

(II)

or a pharmaceutically acceptable salt thereof, wherein n=1~5; the bonding between A and B, between B and D may be a double bond or a single bond, but cannot be double bond at the same time; A, B, and D represents, independently, C, O, N, and S wherein at least one of A, B, and D is a heteroatom;

$R^1$ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^2$ and $R^3$ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or $R^2$ and $R^3$ are taken together with the attached carbons to form an optionally substituted cyclic or heterocyclic moiety;

$R^4$ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or the two substituents are taken together with the attached carbons form an optionally substituted cyclic or heterocyclic moiety; and depending on the element of A, B and D, $R^5$ represents two or three substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some illustrative embodiments, the present invention relates to a compound having a formula (II), wherein $R^1$ is:

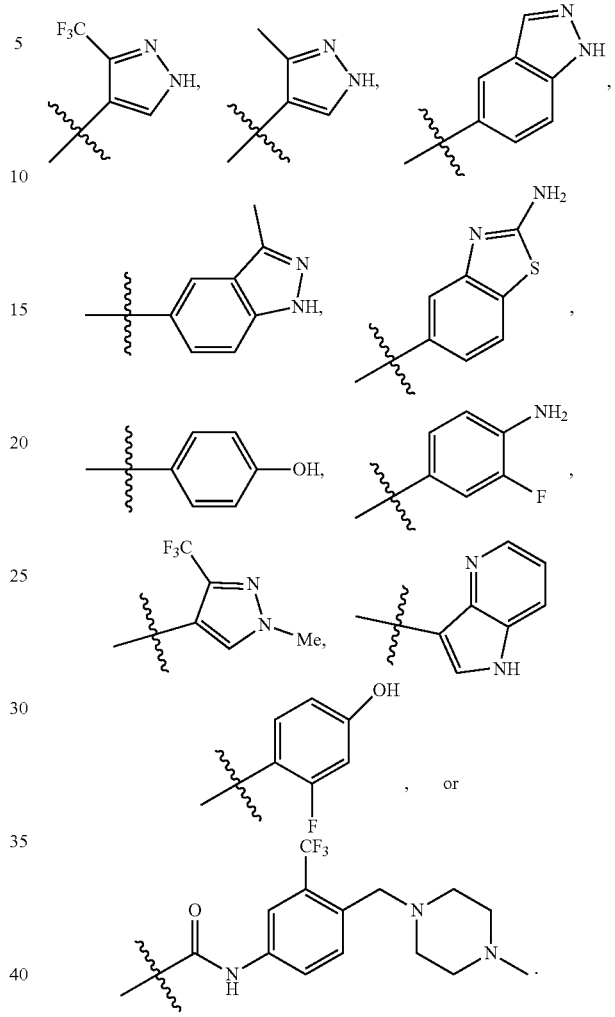

In some illustrative embodiments, the present invention relates to a compound having a formula (III),

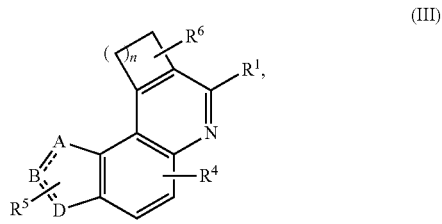

(III)

or a pharmaceutically acceptable salt thereof, wherein n=1~5; the bonding between A and B, between B and D may be a double bond or a single bond, but cannot be double bond at the same time; A, B, and D represents, independently, C, O, N, and S wherein at least one of A, B, and D is a heteroatom;

$R^1$ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

R⁴ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or the two substituents are taken together with the attached carbons form an optionally substituted cyclic or heterocyclic moiety.

depending on the element of A, B and D, R⁵ represents two or three substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and depending on the value of n, R⁶ represents two to six substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some illustrative embodiments, the present invention relates to a compound having a formula (III), wherein R¹ is

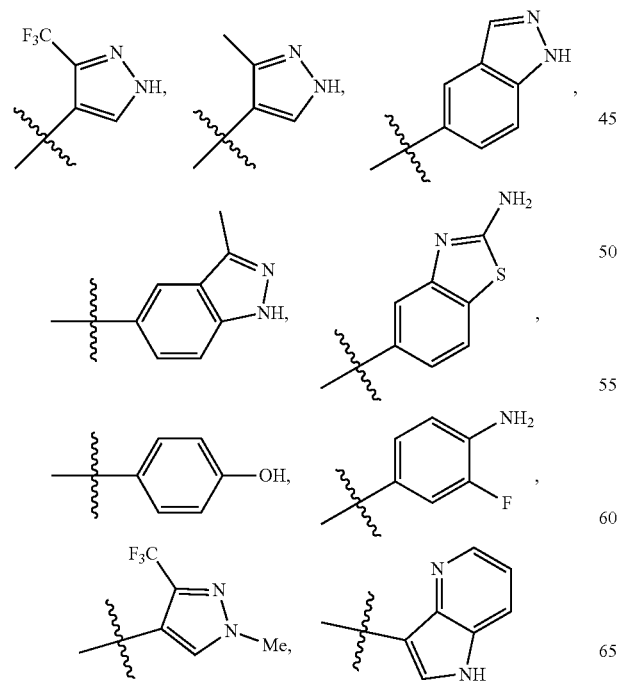

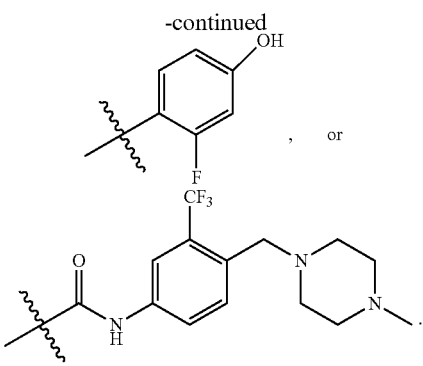

In some illustrative embodiments, the present invention relates to a compound having a formula (IV),

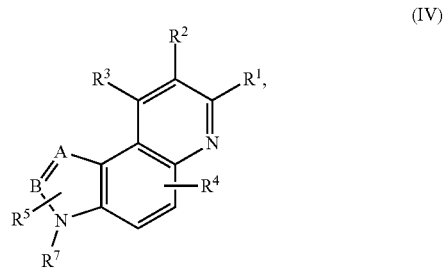

(IV)

or a pharmaceutically acceptable salt thereof, wherein n=1~5;

R¹ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

R² and R³ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or R² and R³ are taken together with the attached carbons to form an optionally substituted cyclic or heterocyclic moiety;

R⁴ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or the two substituents are taken together with the attached carbons form an optionally substituted cyclic or heterocyclic moiety;

depending on the element of A and B specified below, R⁵ represents one or two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

A and B represents, independently, $CR^8$, N, or $NR^9$, wherein $R^8$ and $R^9$ represent independently hydrogen, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

depending on the value of n, $R^6$ represents two to six substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and $R^7$ is an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted.

In some illustrative embodiments, the present invention relates to a compound having a formula (IV), wherein $R^1$ is

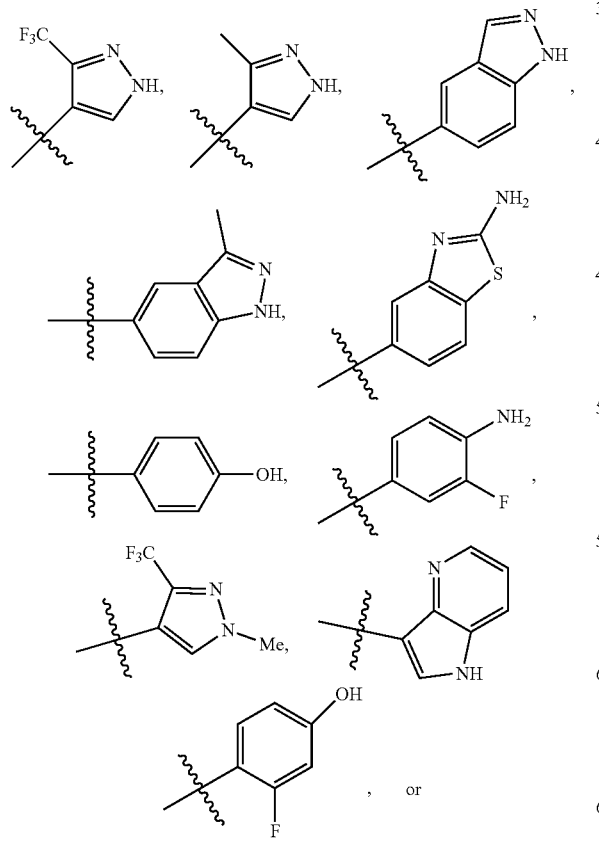

-continued

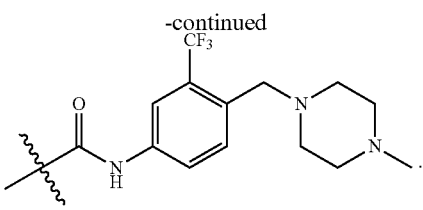

In some illustrative embodiments, the present invention relates to a compound having a formula (IV), wherein $R^1$ is

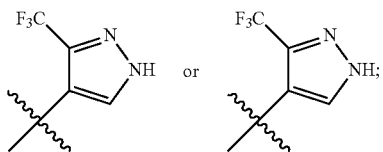 [SMILES: *c1c[nH]nc1C(F)(F)F ; *c1c[nH]nc1C(F)(F)F]

A is carbon (C); B is nitrogen (N); $R^5$, $R^6$, and $R^7$ all represent hydrogen, and $R^4$ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkynyl, and arylalkynyl, each of which is optionally substituted;

or the two substituents are taken together with the attached carbons form an optionally substituted cyclic or heterocyclic moiety.

In some illustrative embodiments, the present invention relates to a compound having a formula (IV), wherein $R^3$ is

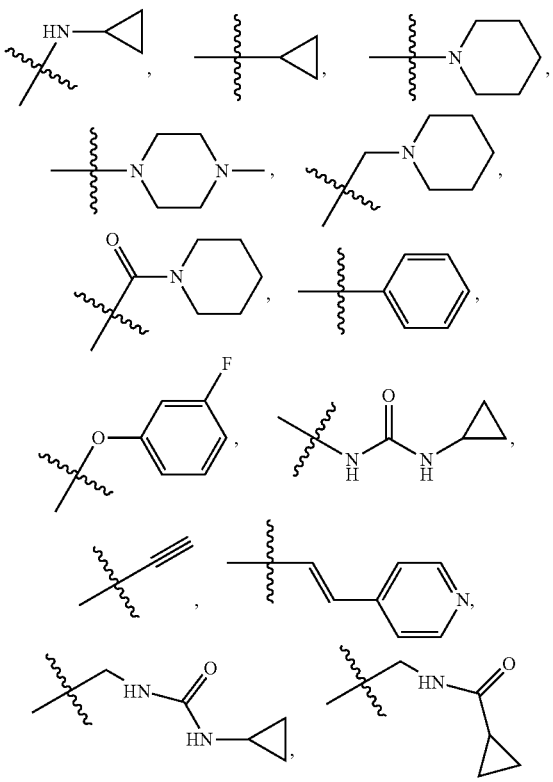

-continued
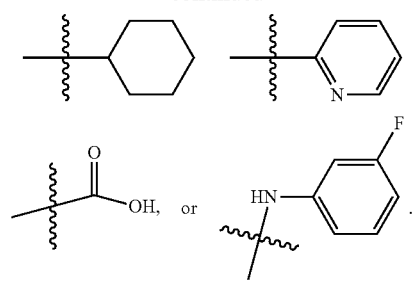
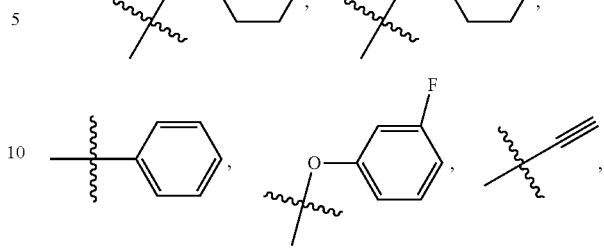
In some illustrative embodiments, the present invention relates to a compound having a formula (IV), wherein R¹ is
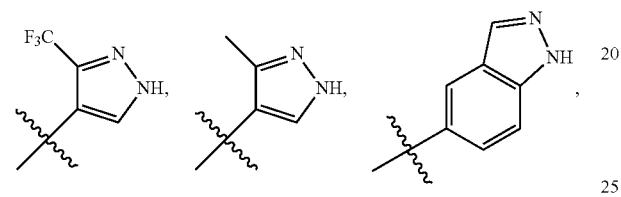
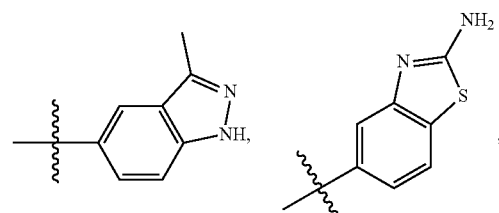
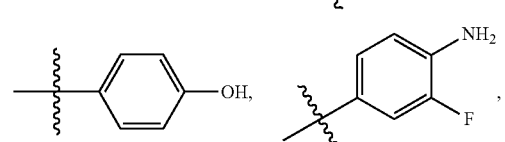
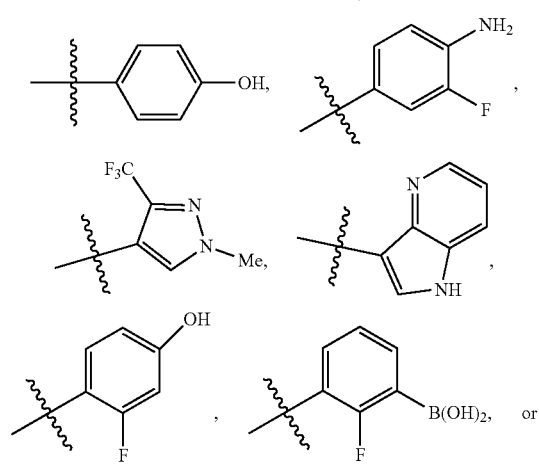
; and R³ is
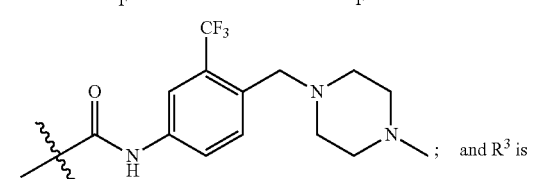
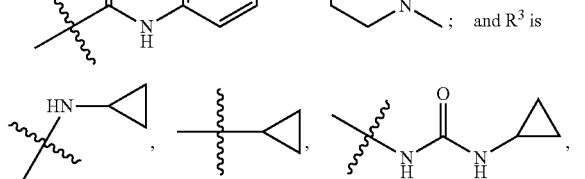
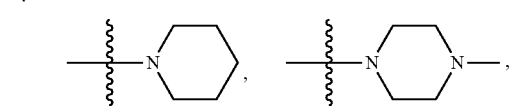
In some illustrative embodiments, the present invention relates to a compound having a formula (I), wherein the compound is
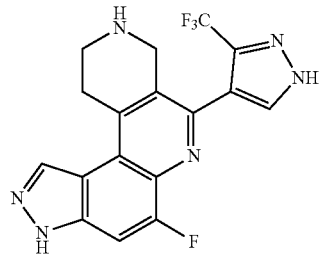
HSD1342
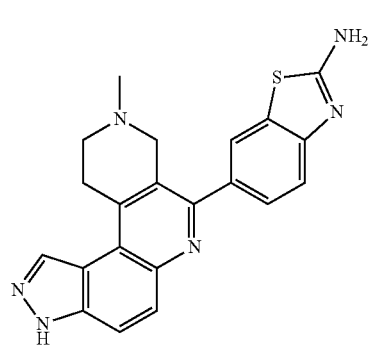
HSD1335

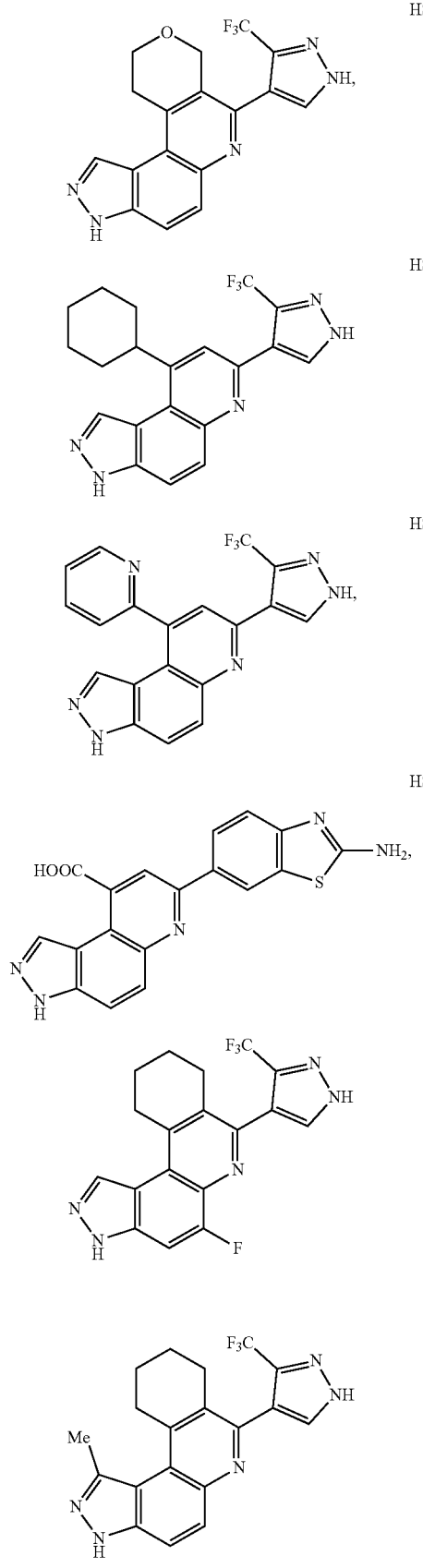
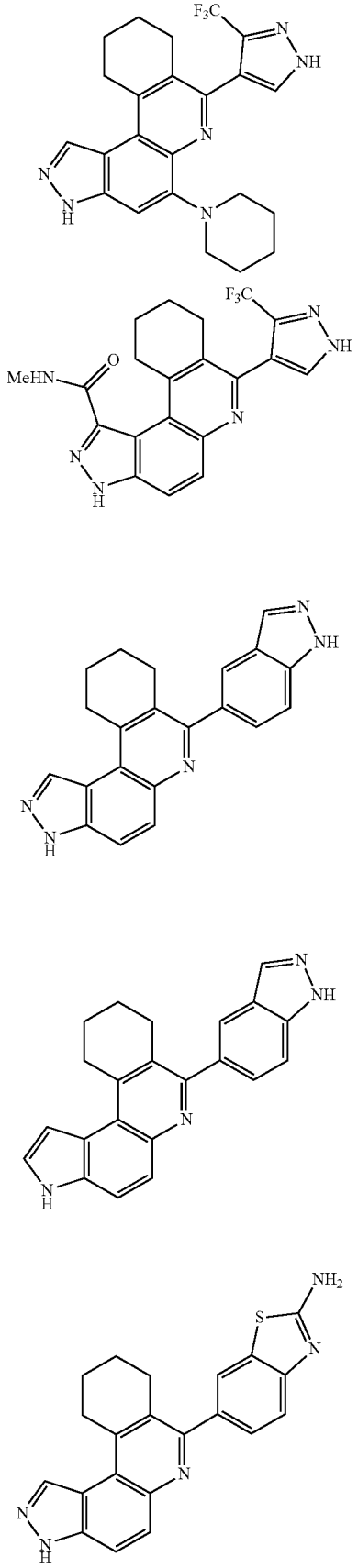

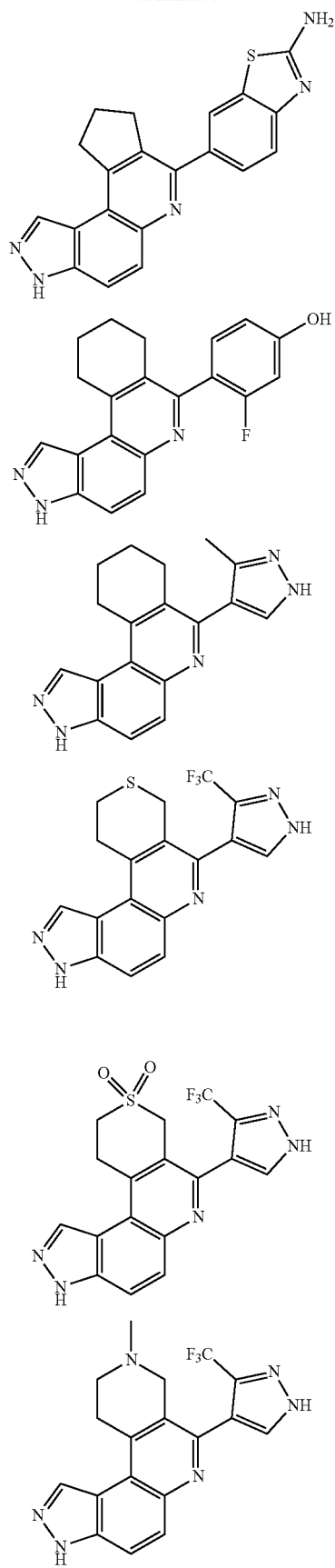
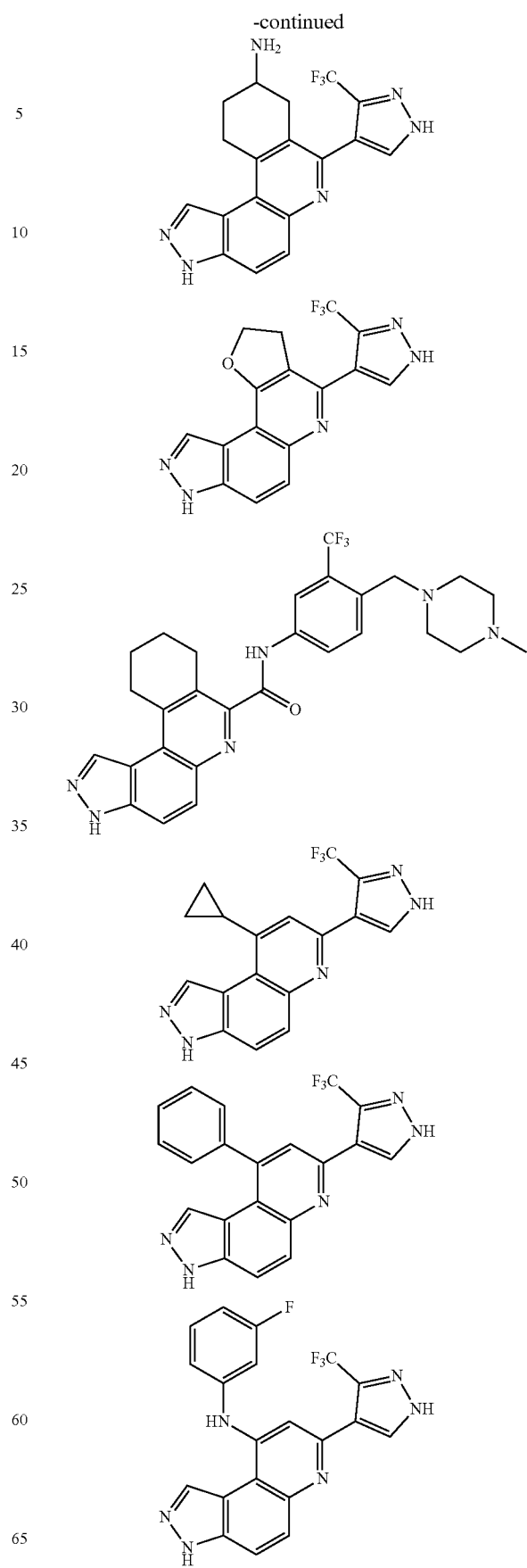

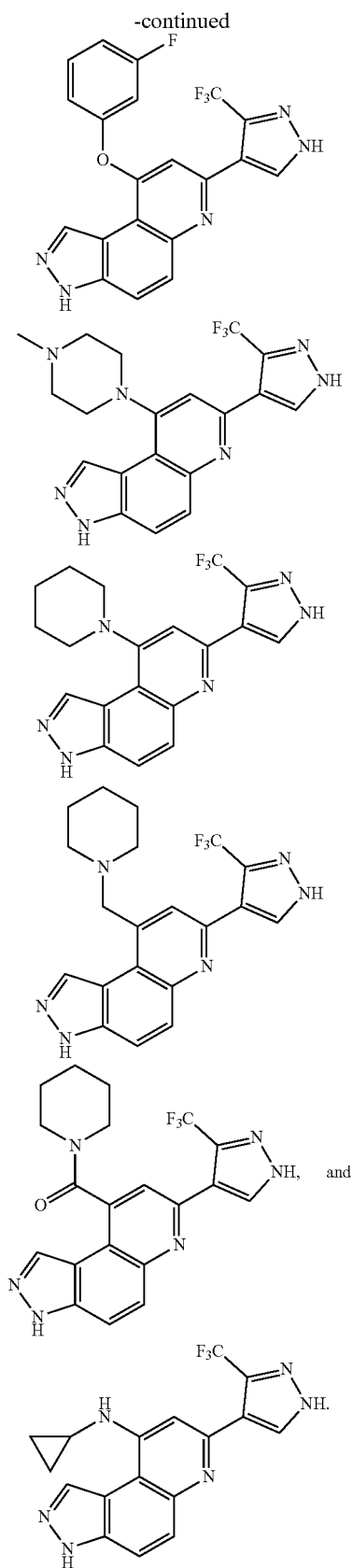

In some illustrative embodiments, the present invention relates to a pharmaceutical composition comprising one or more compounds disclosed herein, or a pharmaceutically acceptable salt thereof, together with one or more diluents, excipients or carriers.

In some illustrative embodiments, the present invention relates to a kinase inhibitor, wherein the kinase is selected from the group consisting of FLT3, MNK1/2, JAK1/2/3, Limk1/2, various CDKs, Haspin, ROCK1/2, TOPK, LRRK2, GSK3a/3b, RSK1-4, ERK, P70S6K, AKT, PI3K, p38, PKC, PKA, FGFR1-4, VEGFR1-3, ALK, AXL, LIMK1/2, Aurora A/B, ABL1, AKT, CSF1R, CSNK1D, DCAMKL1, CSNK1G2, EPHA2, ERBB2, IKK-alpha, IKK-beta, JNK1/2/3, MARK3, MEK1/2, MET, MLK1, PAK1/2/4, PDGFRa/b, PIM1/2/3, PLK1/2/3/4, PRKCE, PRKX, RET, TAOK2, TRKA/B/C, ULK2, and receptor-interacting protein kinase 4 (RIPK4).

In some illustrative embodiments, the present invention relates to a method for treating diseases mediated by a kinase and/or histone demethylases, including inflammation, cancer, viral and bacterial infections, gastrointestinal disorders, eye diseases, neurological, cardiovascular and immunological disorders, comprising the step of administering a therapeutically effective amount of one or more compounds disclosed herein, and one or more carriers, diluents, or excipients, to a patient in need of relief from said cancer.

In some illustrative embodiments, the present invention relates to a method for treating diseases mediated by a kinase and histone demethylases, including inflammation, cancer, viral and bacterial infections, gastrointestinal disorders, eye diseases, neurological, cardiovascular and immunological disorders, comprising the step of administering a therapeutically effective amount of a compound disclosed herein in combination with one or more other compounds of the same or different mode of action, and one or more carriers, diluents, or excipients, to a patient in need of relief from said cancer.

These and other features, aspects and advantages of the present invention will become better understood with reference to the following detailed description and claims.

DETAILED DESCRIPTION

While the concepts of the present disclosure are illustrated and described in detail in the description herein, results in the their description are to be considered as exemplary and not restrictive in character; it being understood that only the illustrative embodiments are shown and described and that all changes and modifications that come within the spirit of the disclosure are desired to be protected.

The present invention generally relates to compounds as kinase inhibitor useful for the treatment of diseases mediated by a kinase, such as inflammation, cancer, viral and bacterial infections, neurological and immunological disorders. Pharmaceutical compositions and methods for treating those diseases are within the scope of this invention.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure the term "substantially" can allow for a degree of variability in a value or range, for example, within 90%, within 95%, 99%, 99.5%, 99.9%, 99.99%, or at least about 99.999% or more of a stated value or of a stated limit of a range.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting. Further, information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

The term "alkyl" as used herein refers to substituted or unsubstituted straight chain and branched alkyl groups and cycloalkyl groups having from 1 to about 20 carbon atoms ($C_1$-$C_{20}$), 1 to 12 carbons ($C_1$-$C_{12}$), 1 to 8 carbon atoms ($C_1$-$C_8$), or, in some embodiments, from 1 to 6 carbon atoms ($C_1$-$C_6$). Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to substituted or unsubstituted straight chain and branched divalent alkenyl and cycloalkenyl groups having from 2 to 20 carbon atoms ($C_2$-$C_{20}$), 2 to 12 carbons ($C_2$-$C_{12}$), 2 to 8 carbon atoms ($C_2$-$C_8$) or, in some embodiments, from 2 to 4 carbon atoms ($C_2$-$C_4$) and at least one carbon-carbon double bond. Examples of straight chain alkenyl groups include those with from 2 to 8 carbon atoms such as —CH=CH—, —CH=CHCH$_2$—, and the like. Examples of branched alkenyl groups include, but are not limited to, —CH=C(CH$_3$)— and the like.

An alkynyl group is the fragment, containing an open point of attachment on a carbon atom that would form if a hydrogen atom bonded to a triply bonded carbon is removed from the molecule of an alkyne. The term "hydroxyalkyl" as used herein refers to alkyl groups as defined herein substituted with at least one hydroxyl (—OH) group.

The term "cycloalkyl" as used herein refers to substituted or unsubstituted cyclic alkyl groups such as, but not limited to, cyclopropyl, cyclobutyl, cyclopentyl, cyclohexyl, cycloheptyl, and cyclooctyl groups. In some embodiments, the cycloalkyl group can have 3 to about 8-12 ring members, whereas in other embodiments the number of ring carbon atoms range from 3 to 4, 5, 6, or 7. In some embodiments, cycloalkyl groups can have 3 to 6 carbon atoms ($C_3$-$C_6$). Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

The term "acyl" as used herein refers to a group containing a carbonyl moiety wherein the group is bonded via the carbonyl carbon atom. The carbonyl carbon atom is also bonded to another carbon atom, which can be part of a substituted or unsubstituted alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-40, 6-10, 1-5 or 2-5 additional carbon atoms bonded to the carbonyl group. An acryloyl group is an example of an acyl group. An acyl group can also include heteroatoms within the meaning here. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to substituted or unsubstituted cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons ($C_6$-$C_{14}$) or from 6 to 10 carbon atoms ($C_6$-$C_{10}$) in the ring portions of the groups. Aryl groups can be unsubstituted or substituted, as defined herein. Representative substituted aryl groups can be mono-substituted or substituted more than once, such as, but not limited to, 2-, 3-, 4-, 5-, or 6-substituted phenyl or 2-8 substituted naphthyl groups, which can be substituted with carbon or non-carbon groups such as those listed herein.

The term "aralkyl" and "arylalkyl" as used herein refers to alkyl groups as defined herein in which a hydrogen or carbon bond of an alkyl group is replaced with a bond to an aryl group as defined herein. Representative aralkyl groups include benzyl and phenylethyl groups and fused (cycloalkylaryl)alkyl groups such as 4-ethyl-indanyl. Aralkenyl groups are alkenyl groups as defined herein in which a hydrogen or carbon bond of an alkyl group is replaced with a bond to an aryl group as defined herein.

The term "heterocyclyl" as used herein refers to substituted or unsubstituted aromatic and non-aromatic ring compounds containing 3 or more ring members, of which, one or more is a heteroatom such as, but not limited to, B, N, O, and S. Thus, a heterocyclyl can be a cycloheteroalkyl, or a heteroaryl, or if polycyclic, any combination thereof. In some embodiments, heterocyclyl groups include 3 to about 20 ring members, whereas other such groups have 3 to about 15 ring members. In some embodiments, heterocyclyl groups include heterocyclyl groups that include 3 to 8 carbon atoms ($C_3$-$C_8$), 3 to 6 carbon atoms ($C_3$-$C_6$) or 6 to 8 carbon atoms ($C_6$-$C_8$).

A heteroaryl ring is an embodiment of a heterocyclyl group. The phrase "heterocyclyl group" includes fused ring species including those that include fused aromatic and non-aromatic groups. Representative heterocyclyl groups include, but are not limited to pyrrolidinyl, azetidinyl, piperidynyl, piperazinyl, morpholinyl, chromanyl, indolinonyl, isoindolinonyl, furanyl, pyrrolidinyl, pyridinyl, pyrazinyl, pyrimidinyl, triazinyl, thiophenyl, tetrahydrofuranyl, pyrrolyl, oxazolyl, oxadiazolyl, imidazolyl, triazyolyl, tetrazolyl, benzoxazolinyl, benzthiazolinyl, and benzimidazolinyl groups.

The term "heterocyclylalkyl" as used herein refers to alkyl groups as defined herein in which a hydrogen or carbon bond of an alkyl group as defined herein is replaced with a bond to a heterocyclyl group as defined herein. Representative heterocyclylalkyl groups include, but are not limited to, furan-2-yl methyl, furan-3-yl methyl, pyridine-3-yl methyl, tetrahydrofuran-2-yl methyl, and indol-2-yl propyl.

The term "heteroarylalkyl" as used herein refers to alkyl groups as defined herein in which a hydrogen or carbon bond of an alkyl group is replaced with a bond to a heteroaryl group as defined herein.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula N(group)$_3$ wherein each group can independently be H or non-H, such as alkyl, aryl, and the like. Amines include but are not limited to R—$NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form —$NH_2$, —NHR, —$NR_2$, —$NR_3^+$, wherein each R is independently selected, and protonated forms of each, except for —$NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "haloalkyl" group, as used herein, includes mono-halo alkyl groups, poly-halo alkyl groups wherein all halo atoms can be the same or different, and per-halo alkyl groups, wherein all hydrogen atoms are replaced by halogen atoms, such as fluoro. Examples of haloalkyl include trifluoromethyl, 1,1-dichloroethyl, 1,2-dichloroethyl, 1,3-dibromo-3,3-difluoropropyl, perfluorobutyl, —$CF(CH_3)_2$ and the like.

The term "optionally substituted," or "optional substituents," as used herein, means that the groups in question are either unsubstituted or substituted with one or more of the substituents specified. When the groups in question are substituted with more than one substituent, the substituents may be the same or different. When using the terms "independently," "independently are," and "independently selected from" mean that the groups in question may be the same or different. Certain of the herein defined terms may occur more than once in the structure, and upon such occurrence each term shall be defined independently of the other.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, E, and Z double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term "salts" and "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. Pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

Pharmaceutically acceptable salts can be synthesized from the parent compound which contains a basic or acidic moiety by conventional chemical methods. In some instances, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, the disclosure of which is hereby incorporated by reference.

The term "solvate" means a compound, or a salt thereof, that further includes a stoichiometric or non-stoichiometric amount of solvent bound by non-covalent intermolecular forces. Where the solvent is water, the solvate is a hydrate.

The term "prodrug" means a derivative of a compound that can hydrolyze, oxidize, or otherwise react under biological conditions (in vitro or in vivo) to provide an active compound, particularly a compound of the invention. Examples of prodrugs include, but are not limited to, derivatives and metabolites of a compound of the invention that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Specific prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers GmbH).

Further, in each of the foregoing and following embodiments, it is to be understood that the formulae include and represent not only all pharmaceutically acceptable salts of the compounds, but also include any and all hydrates and/or solvates of the compound formulae or salts thereof. It is to be appreciated that certain functional groups, such as the hydroxy, amino, and like groups form complexes and/or coordination compounds with water and/or various solvents, in the various physical forms of the compounds. Accordingly, the above formulae are to be understood to include and represent those various hydrates and/or solvates. In each of the foregoing and following embodiments, it is also to be understood that the formulae include and represent each possible isomer, such as stereoisomers and geometric isomers, both individually and in any and all possible mixtures. In each of the foregoing and following embodiments, it is also to be understood that the formulae include and represent any and all crystalline forms, partially crystalline forms, and non-crystalline and/or amorphous forms of the compounds.

The term "pharmaceutically acceptable carrier" is art-recognized and refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, the term "administering" includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically acceptable carriers, adjuvants, and vehicles.

Illustrative formats for oral administration include tablets, capsules, elixirs, syrups, and the like. Illustrative routes for parenteral administration include intravenous, intraarterial, intraperitoneal, epidural, intraurethral, infrasternal, intramuscular and subcutaneous, as well as any other art recognized route of parenteral administration.

Illustrative means of parenteral administration include needle (including microneedle) injectors, needle-free injectors and infusion techniques, as well as any other means of parenteral administration recognized in the art. Parenteral formulations are typically aqueous solutions which may contain excipients such as salts, carbohydrates and buffering agents (preferably at a pH in the range from about 3 to about 9), but, for some applications, they may be more suitably formulated as a sterile non-aqueous solution or as a dried form to be used in conjunction with a suitable vehicle such as sterile, pyrogen-free water. The preparation of parenteral formulations under sterile conditions, for example, by lyophilization, may readily be accomplished using standard pharmaceutical techniques well known to those skilled in the art. Parenteral administration of a compound is illustratively performed in the form of saline solutions or with the compound incorporated into liposomes. In cases where the compound in itself is not sufficiently soluble to be dissolved, a solubilizer such as ethanol can be applied.

The dosage of each compound of the claimed combinations depends on several factors, including: the administration method, the condition to be treated, the severity of the condition, whether the condition is to be treated or prevented, and the age, weight, and health of the person to be treated. Additionally, pharmacogenomic (the effect of genotype on the pharmacokinetic, pharmacodynamic or efficacy profile of a therapeutic) information about a particular patient may affect the dosage used.

It is to be understood that in the methods described herein, the individual components of a co-administration, or combination can be administered by any suitable means, contemporaneously, simultaneously, sequentially, separately or in a single pharmaceutical formulation. Where the co-administered compounds or compositions are administered in separate dosage forms, the number of dosages administered per day for each compound may be the same or different. The compounds or compositions may be administered via the same or different routes of administration. The compounds or compositions may be administered according to simultaneous or alternating regimens, at the same or different times during the course of the therapy, concurrently in divided or single forms.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

Depending upon the route of administration, a wide range of permissible dosages are contemplated herein, including doses falling in the range from about 1 µg/kg to about 1 g/kg. The dosages may be single or divided, and may administered according to a wide variety of protocols, including q.d. (once a day), b.i.d. (twice a day), t.i.d. (three times a day), or even every other day, once a week, once a month, once a quarter, and the like. In each of these cases it is understood that the therapeutically effective amounts described herein correspond to the instance of administration, or alternatively to the total daily, weekly, month, or quarterly dose, as determined by the closing protocol.

In addition to the illustrative dosages and dosing protocols described herein, it is to be understood that an effective amount of any one or a mixture of the compounds described herein can be determined by the attending diagnostician or physician by the use of known techniques and/or by observing results obtained under analogous circumstances. In determining the effective amount or dose, a number of factors are considered by the attending diagnostician or physician, including, but not limited to the species of mammal, including human, its size, age, and general health, the specific disease or disorder involved, the degree of or involvement or the severity of the disease or disorder, the response of the individual patient, the particular compound administered, the mode of administration, the bioavailability characteristics of the preparation administered, the dose regimen selected, the use of concomitant medication, and other relevant circumstances.

The term "patient" includes human and non-human animals such as companion animals (dogs and cats and the like) and livestock animals. Livestock animals are animals raised for food production. The patient to be treated is preferably a mammal, in particular a human being.

In some illustrative embodiments, the present invention relates to a compound having a formula

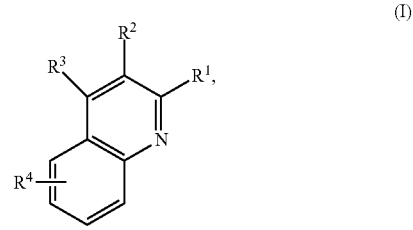

(I)

or a pharmaceutically acceptable salt thereof, wherein
$R^1$ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;
$R^2$ and $R^3$ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;
or $R^2$ and $R^3$ are taken together with the attached carbons to form an optionally substituted cyclic or heterocyclic moiety; and
$R^4$ represents four substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;
or any two adjacent substituents of the four substituents are taken together with the attached carbons form an optionally substituted cyclic or heterocyclic moiety.

In some illustrative embodiments, the present invention relates to a compound having a formula:

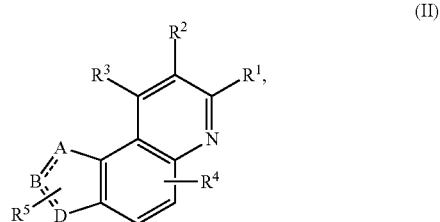

(II)

or a pharmaceutically acceptable salt thereof, wherein n=1~5; the bonding between A and B, between B and D may be a double bond or a single bond, but cannot be double bond at the same time; A, B, and D represents, independently, C, O, N, and S wherein at least one of A, B, and D is a heteroatom;

R¹ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

R² and R³ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or R² and R³ are taken together with the attached carbons to form an optionally substituted cyclic or heterocyclic moiety;

R⁴ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or the two substituents are taken together with the attached carbons form an optionally substituted cyclic or heterocyclic moiety; and depending on the element of A, B and D, R⁵ represents two or three substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some illustrative embodiments, the present invention relates to a compound having a formula (II), wherein R¹ is:

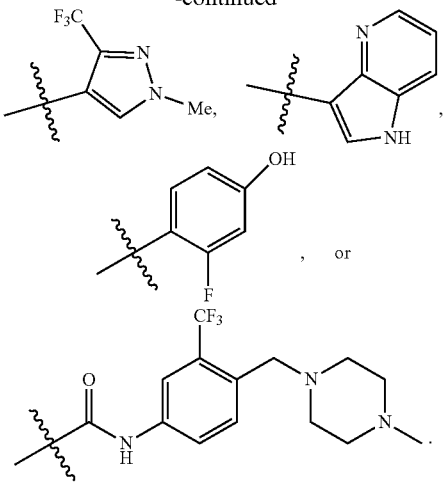
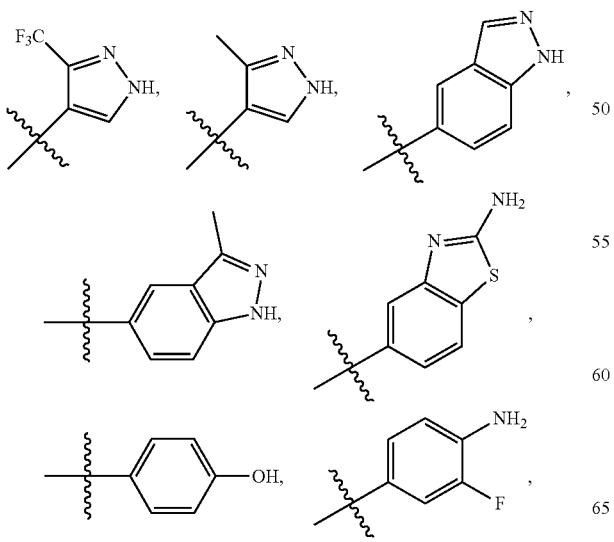
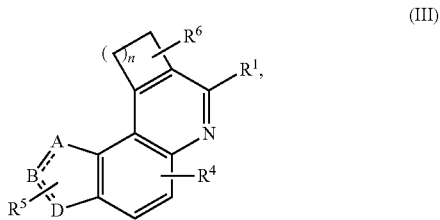

In some illustrative embodiments, the present invention relates to a compound having a formula (III), (III)

or a pharmaceutically acceptable salt thereof, wherein n=1~5; the bonding between A and B, between B and D may be a double bond or a single bond, but cannot be double bond at the same time; A, B, and D represents, independently, C, O, N, and S wherein at least one of A, B, and D is a heteroatom;

R¹ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

R⁴ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; or the two substituents are taken together with the attached carbons form an optionally substituted cyclic or heterocyclic moiety.

depending on the element of A, B and D, R⁵ represents two or three substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and depending on the value of n, $R^6$ represents two to six substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

In some illustrative embodiments, the present invention relates to a compound having a formula (III), wherein $R^1$ is

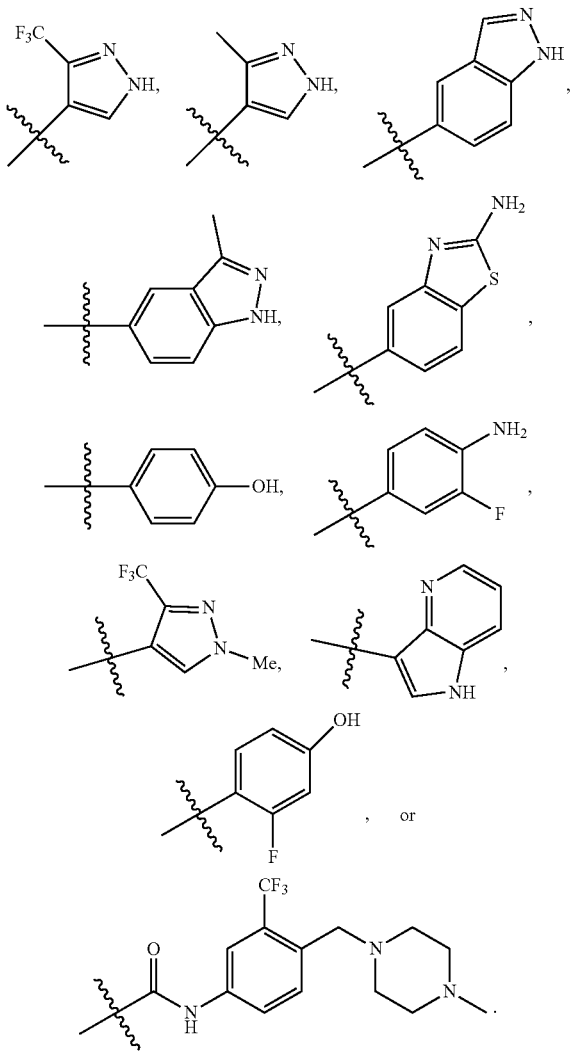

In some illustrative embodiments, the present invention relates to a compound having a formula (IV),

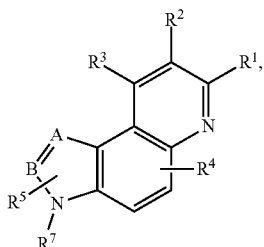

(IV)

or a pharmaceutically acceptable salt thereof, wherein n=1~5;

$R^1$ is amino, hydroxyl, and derivatives thereof, an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

$R^2$ and $R^3$ are each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or $R^2$ and $R^3$ are taken together with the attached carbons to form an optionally substituted cyclic or heterocyclic moiety;

$R^4$ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or the two substituents are taken together with the attached carbons form an optionally substituted cyclic or heterocyclic moiety;

depending on the element of A and B specified below, $R^5$ represents one or two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

A and B represents, independently, $CR^8$, N, or $NR^9$, wherein $R^8$ and $R^9$ represent independently hydrogen, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

depending on the value of n, $R^6$ represents two to six substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and $R^7$ is an alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted.

In some illustrative embodiments, the present invention relates to a compound having a formula (IV), wherein $R^1$ is

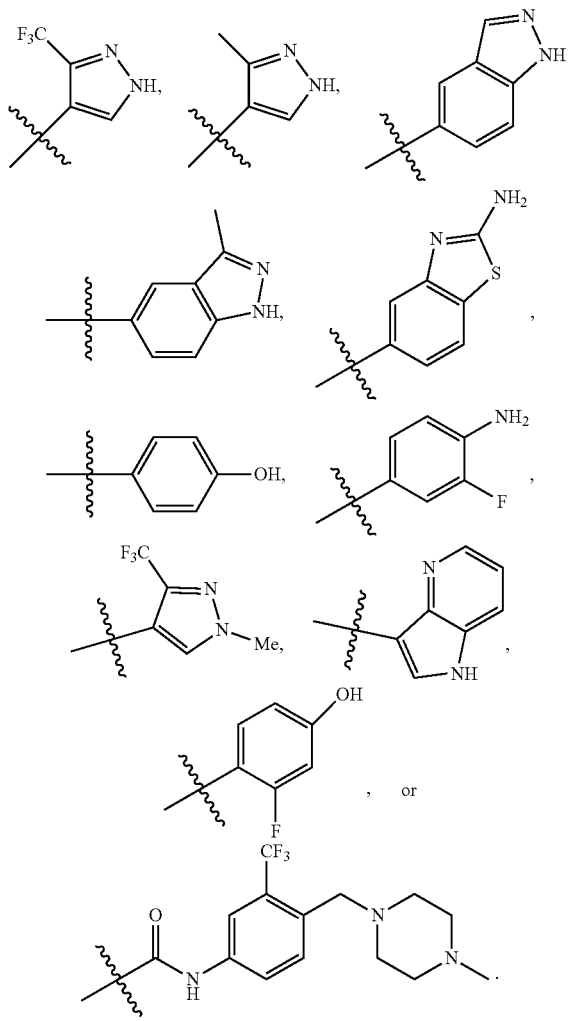

A is carbon (C); B is nitrogen (N); $R^5$, $R^6$, and $R^7$ all represent hydrogen, and $R^4$ represents two substituents, each independently selected from the group consisting of hydrogen, deuterium, halo, azido, cyano, nitro, hydroxy, amino, thio, carboxy, ester, amide, and derivatives thereof, and acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or the two substituents are taken together with the attached carbons form an optionally substituted cyclic or heterocyclic moiety.

In some illustrative embodiments, the present invention relates to a compound having a formula (IV), wherein $R^3$ is

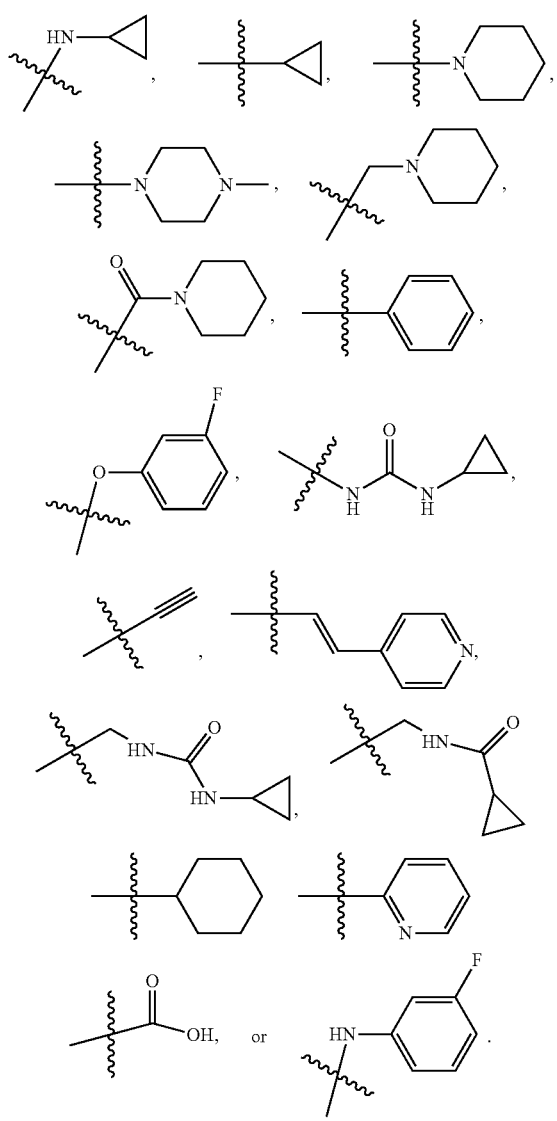

In some illustrative embodiments, the present invention relates to a compound having a formula (IV), wherein $R^1$ is

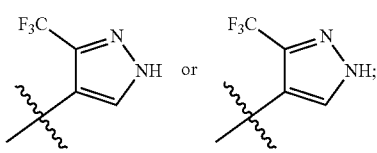 [SMILES: *c1c[nH]nc1C(F)(F)F ; "or" ; *c1c[nH]nc1C(F)(F)F]

In some illustrative embodiments, the present invention relates to a compound having a formula (IV), wherein $R^1$ is

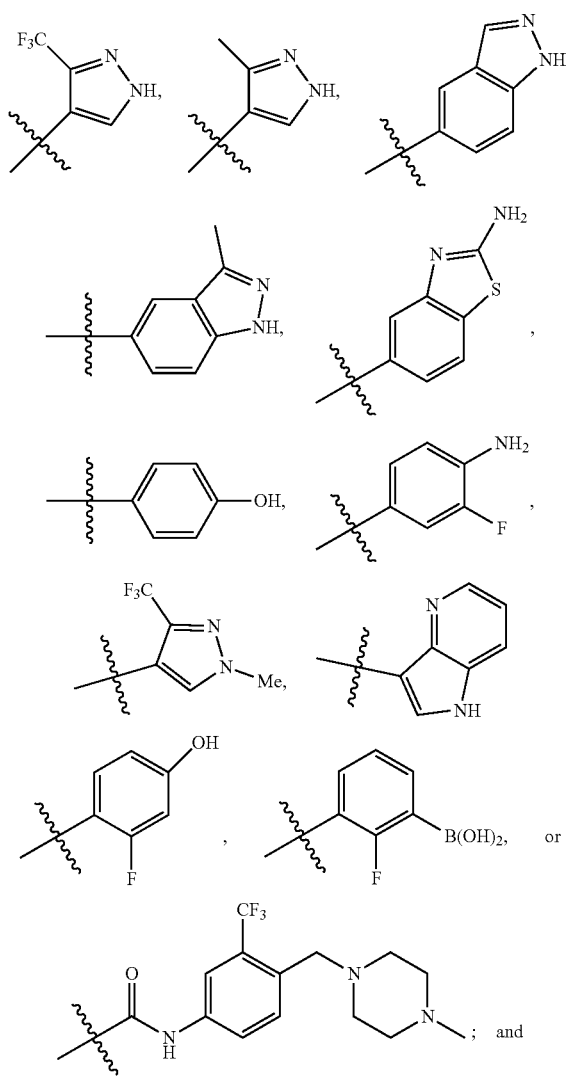
$R^3$ is
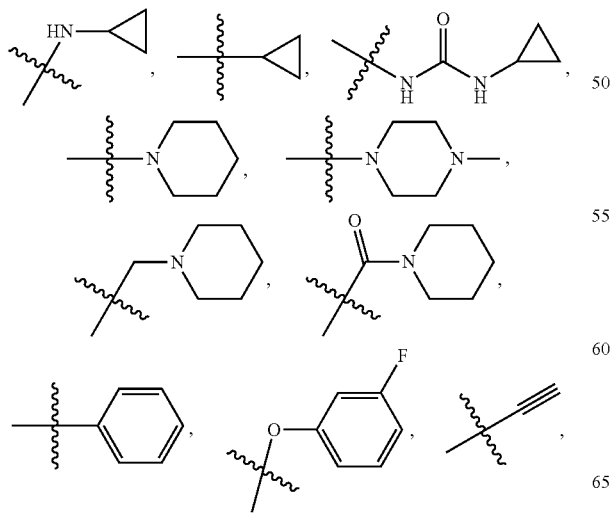
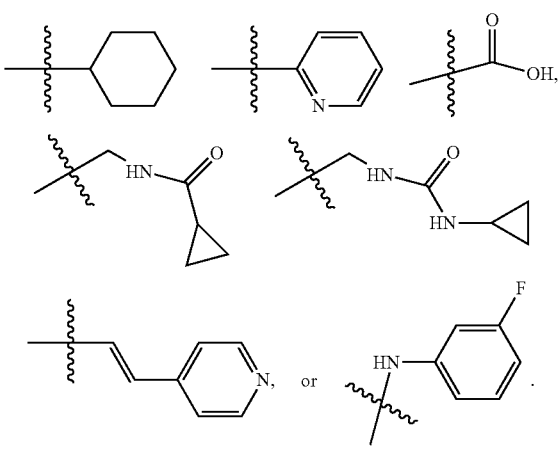
In some illustrative embodiments, the present invention relates to a compound having a formula (I), wherein the compound is
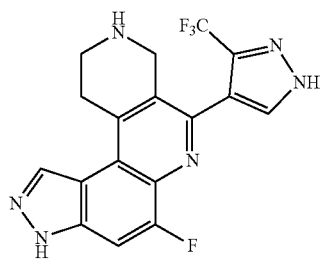
HSD1342
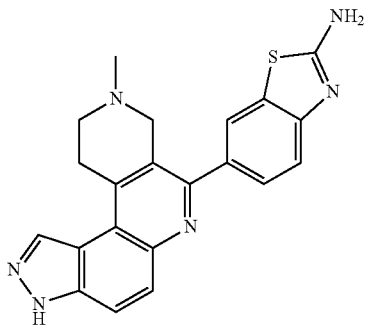
HSD1335
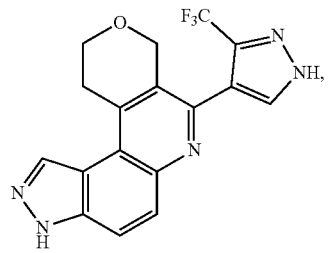
HSD1336

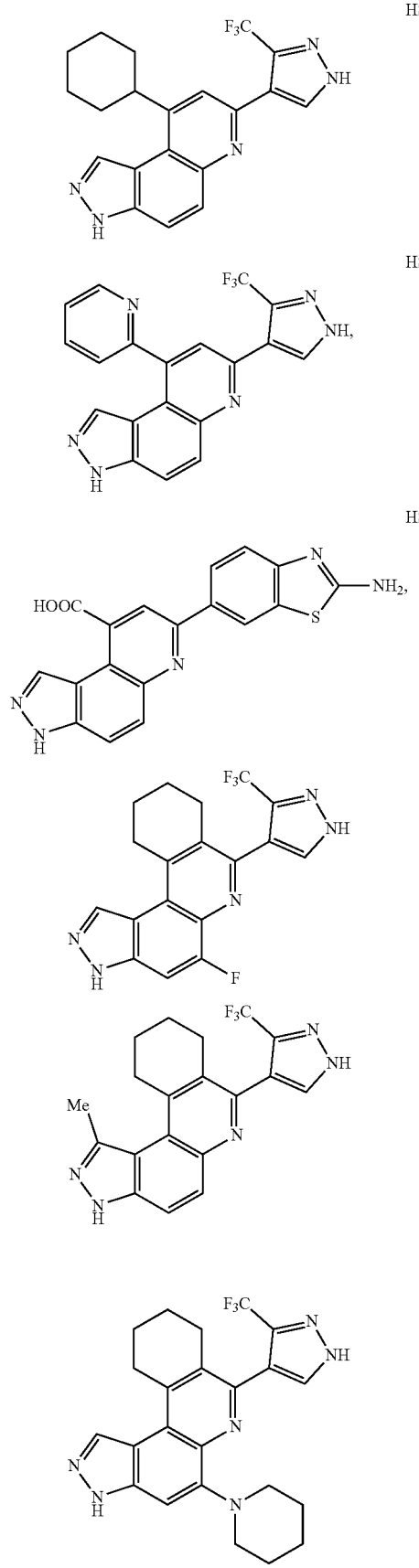
HSD1355
HSD1356
HSD1345
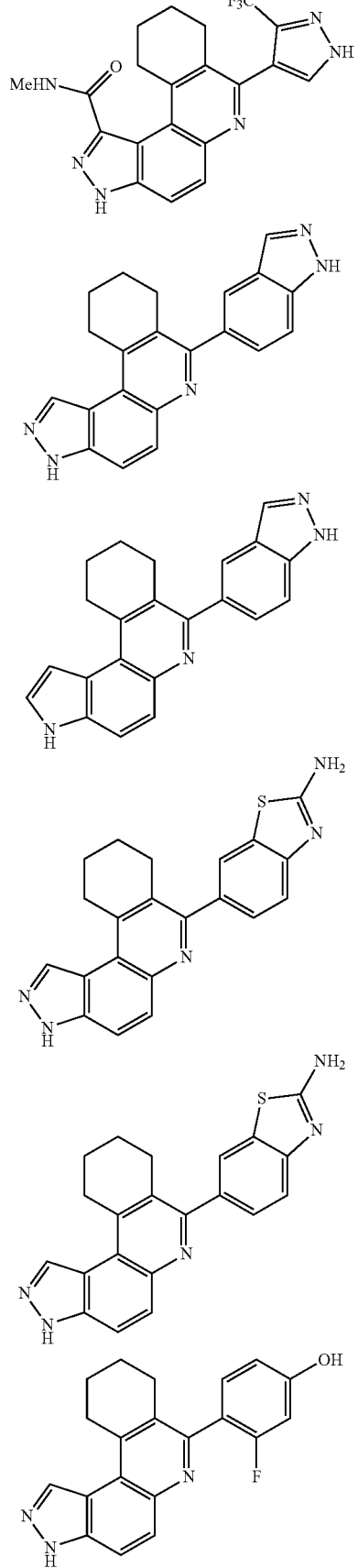

35
-continued
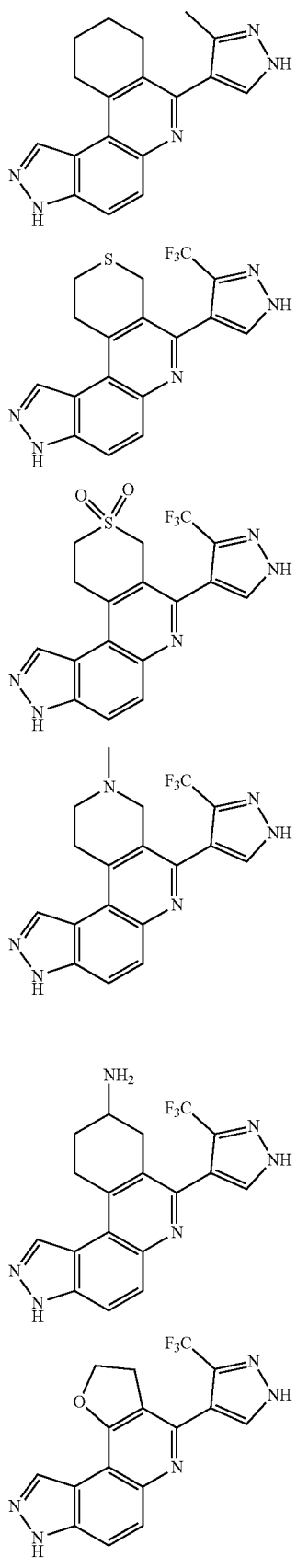
36
-continued
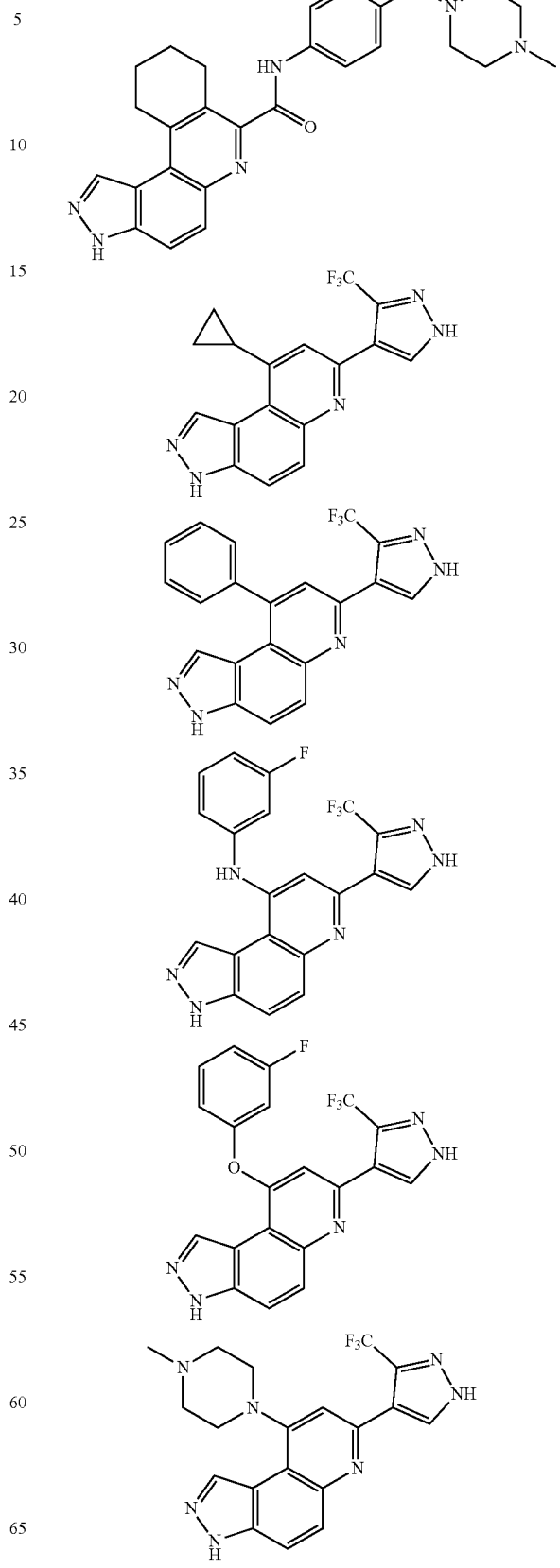

-continued
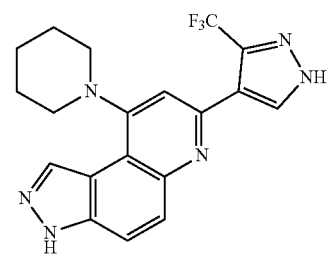
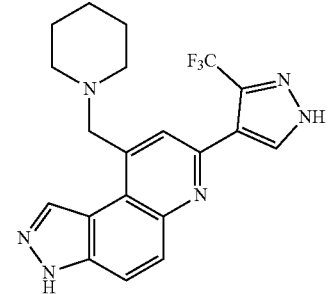
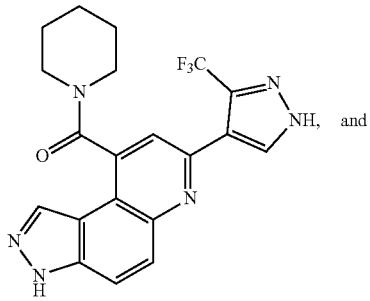 and
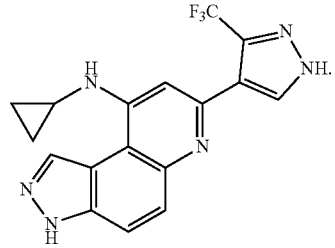
In some illustrative embodiments, the present invention relates to a compound having a formula (I), wherein the compound is
HSD-02-935
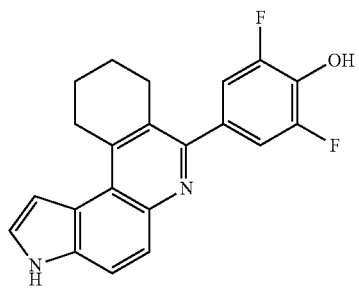
-continued
HSD-02-936
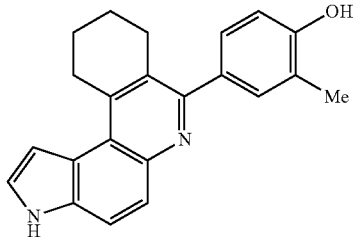
HSD-02-937
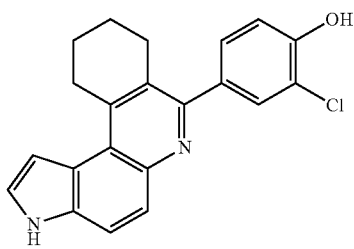
HSD-02-938
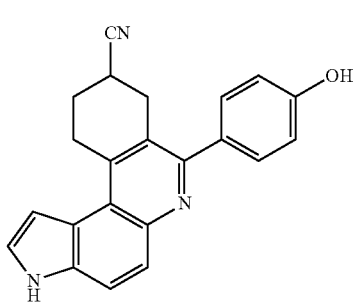
HSD-02-939
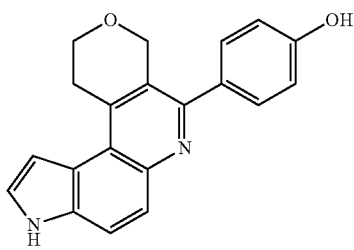
HSD-02-940
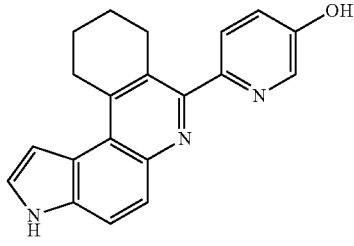
HSD-02-941
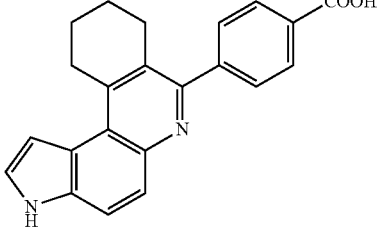

HSD-02-942 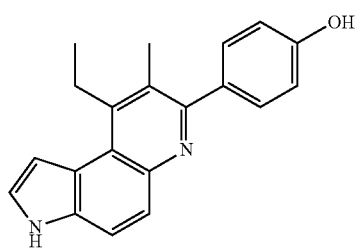
HSD-02-943 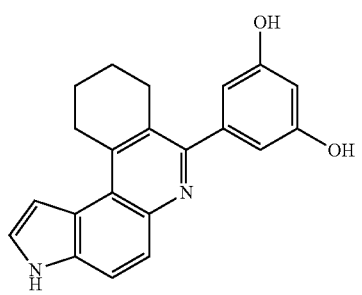
HSD-02-944 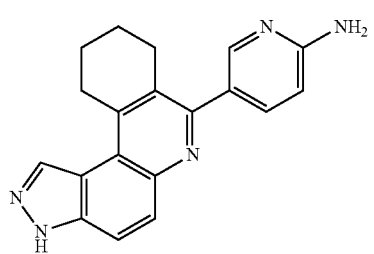
HSD-02-98 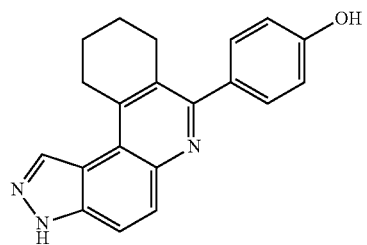
HSD-02-09 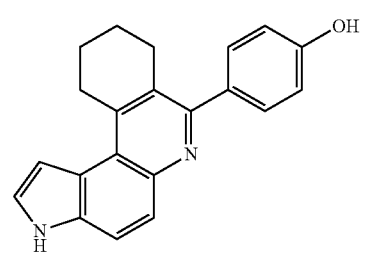
HSD-02-91 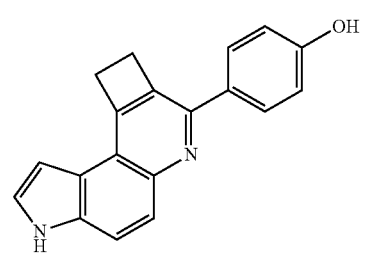
HSD-02-92 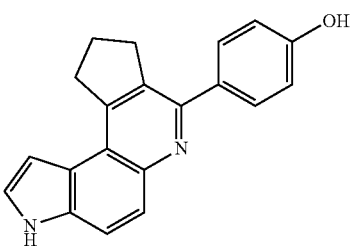
HSD-02-93 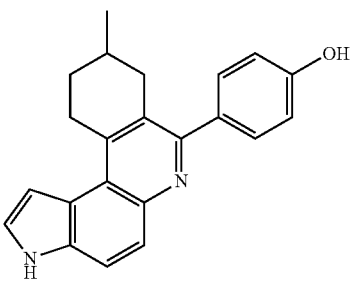
HSD-02-94 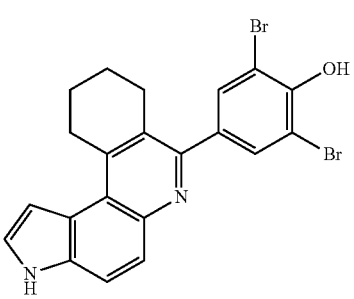
HSD-02-95 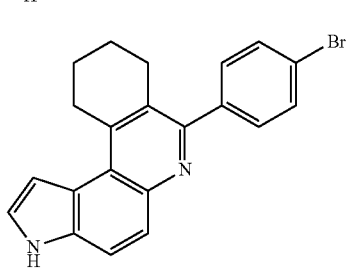
HSD-02-96 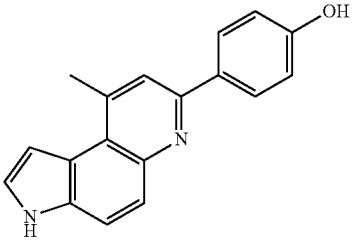
HSD-02-97 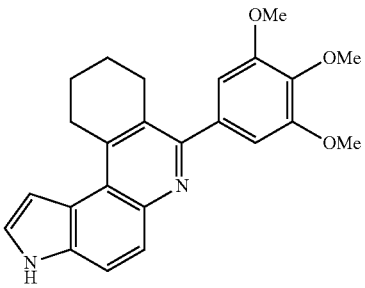

HSD-02-99
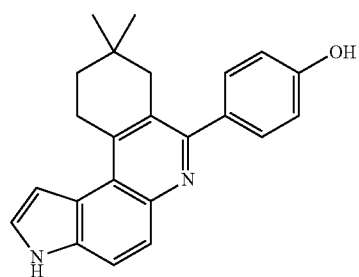
HSD-02-910
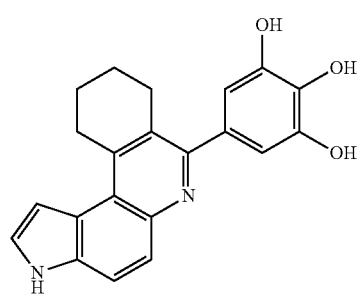
HSD-02-911
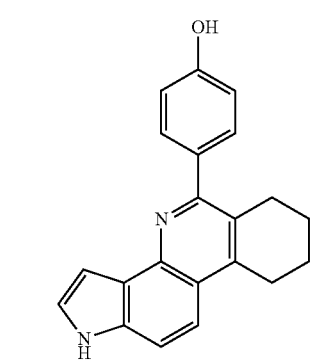
HSD-02-912
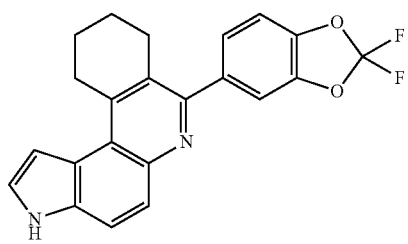
HSD-02-913
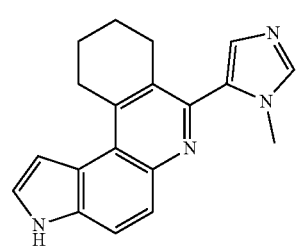
HSD-02-914
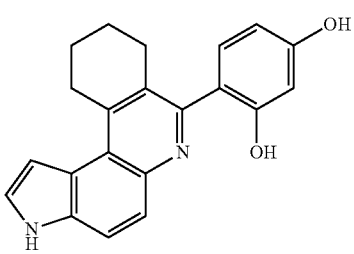
HSD915
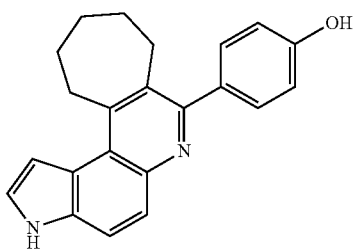
HSD916
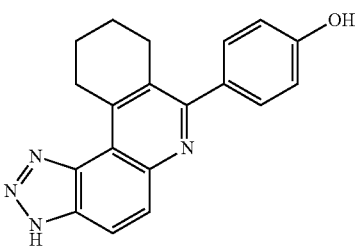
HSD917
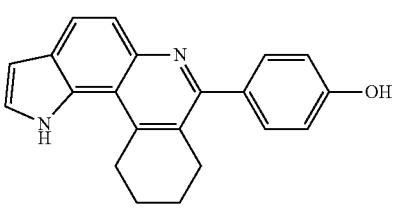
HSD918
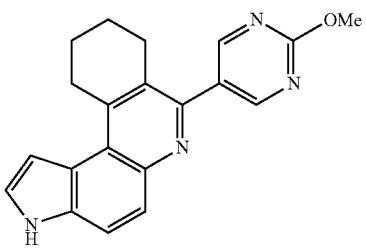
HSD919
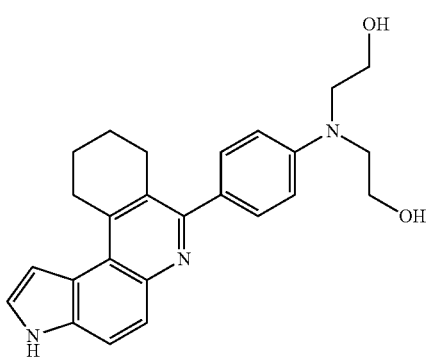

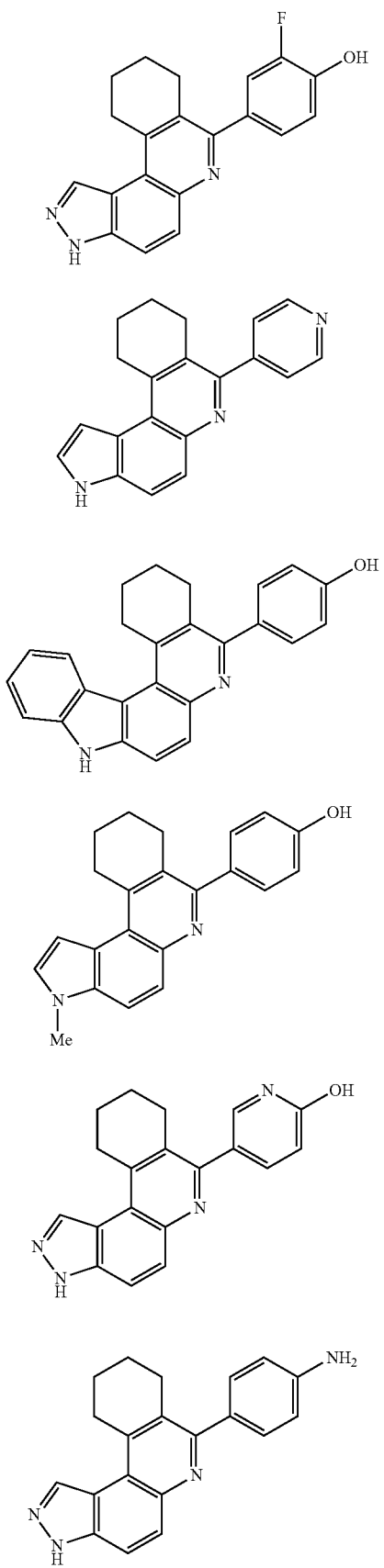
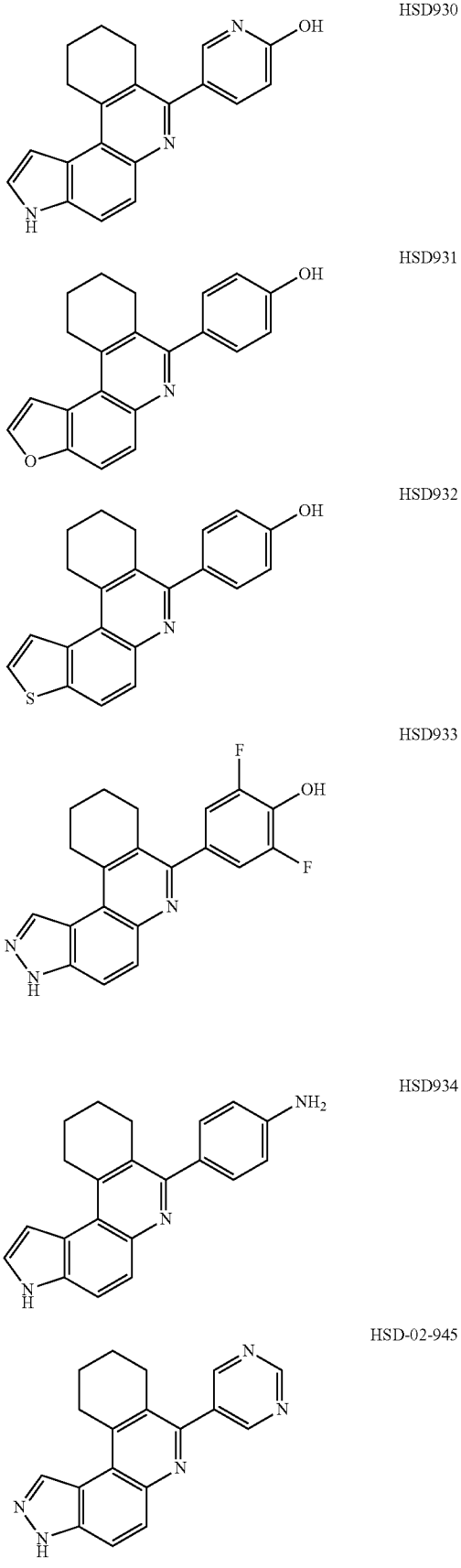

HSD-02-946
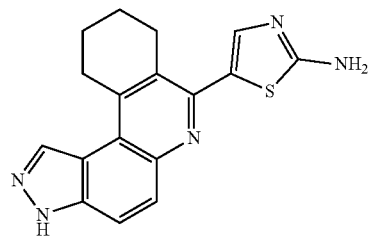
HSD-02-947
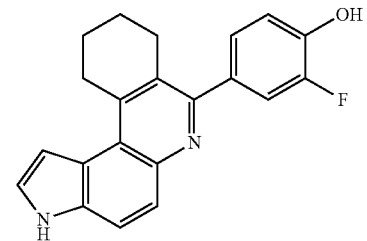
HSD-02-948
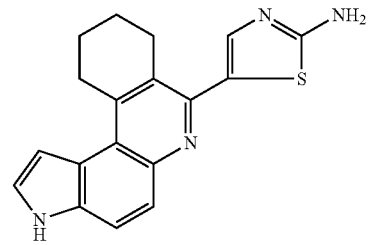
HSD-02-949
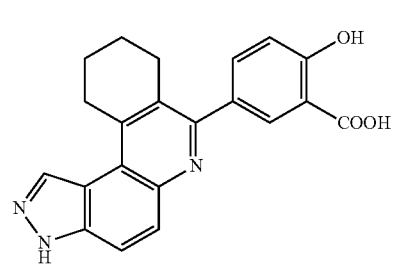
HSD-02-950
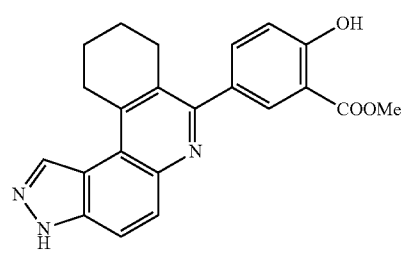
HSD-02-951
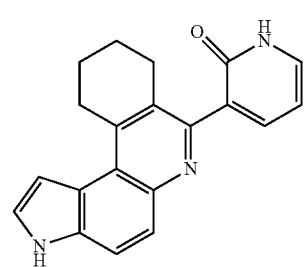
HSD-02-952
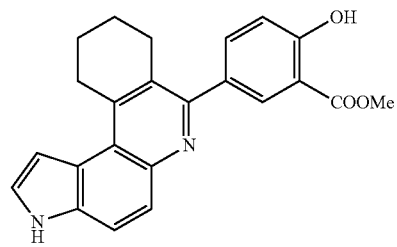
HSD-02-953
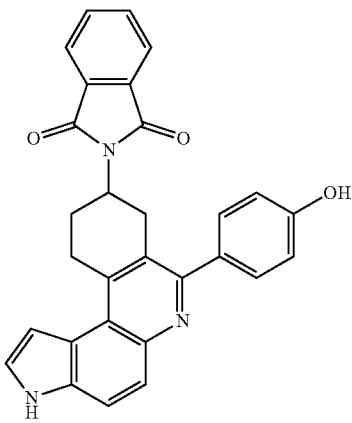
HSD-02-954
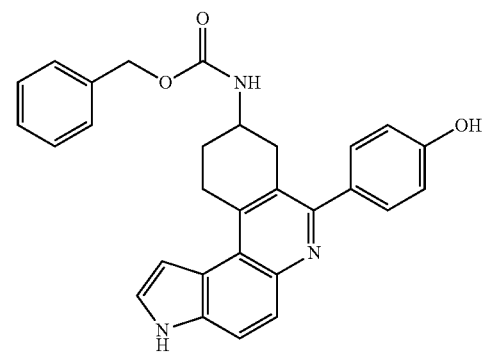
HSD-02-955
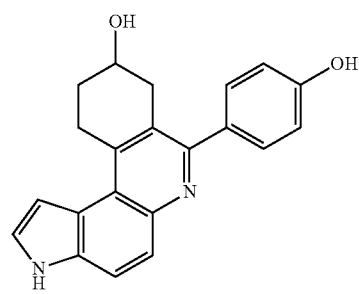
HSD-02-956
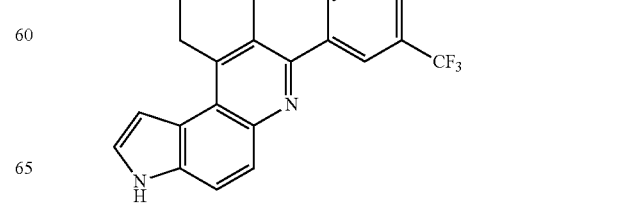

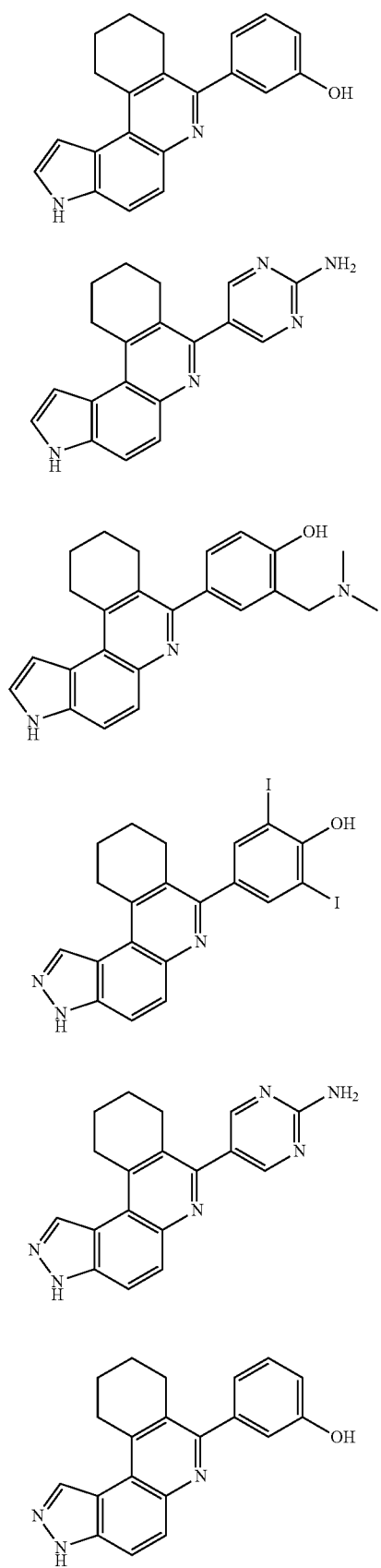
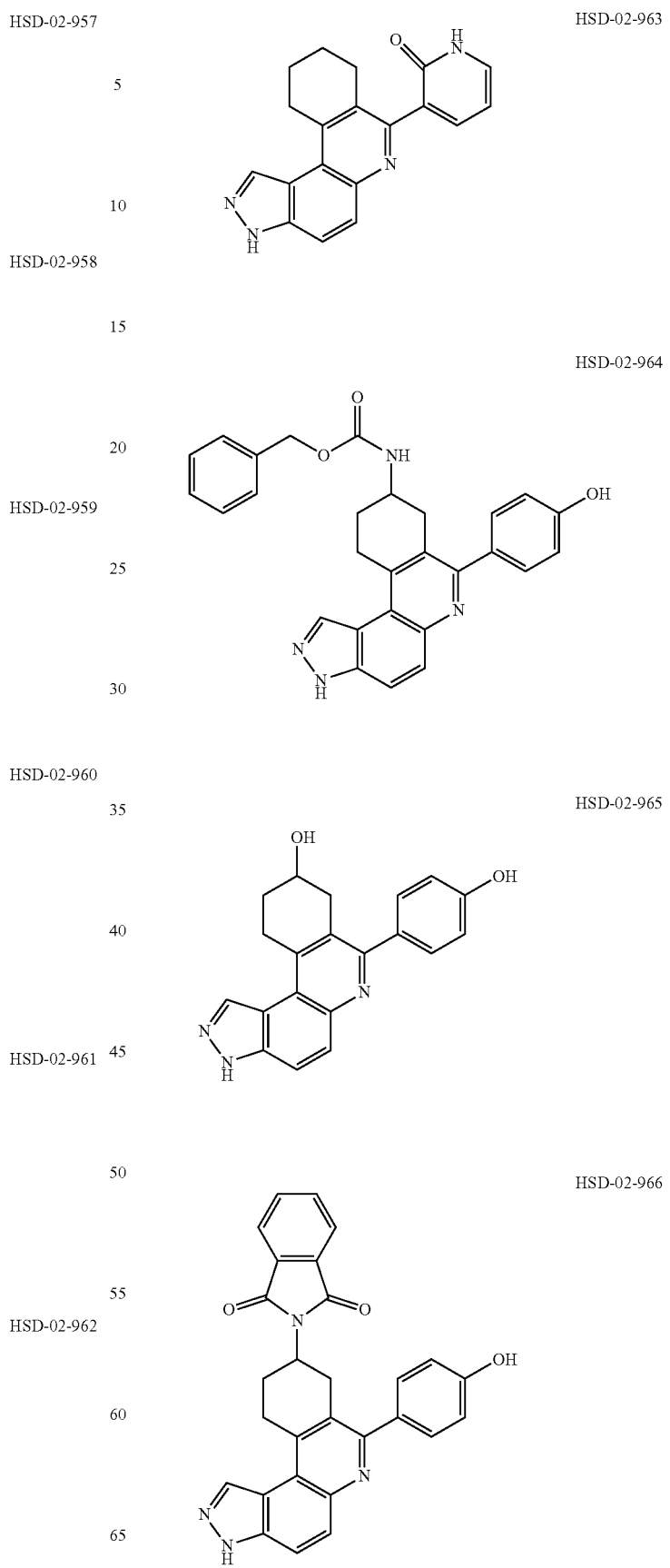

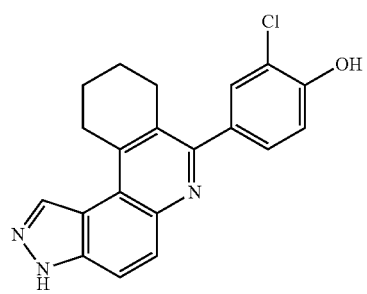 HSD-02-967
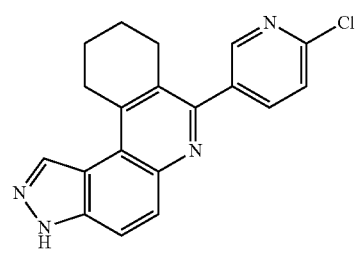 HSD-02-968
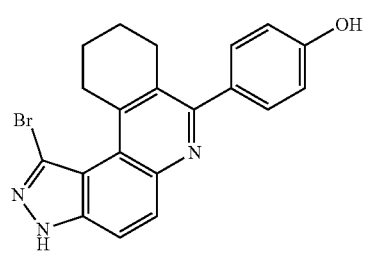 HSD-02-969
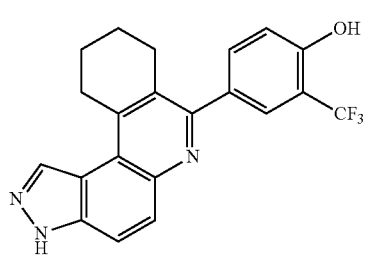 HSD-02-970
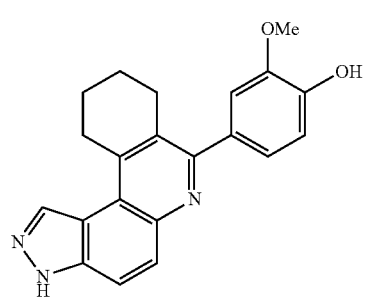 HSD-02-971
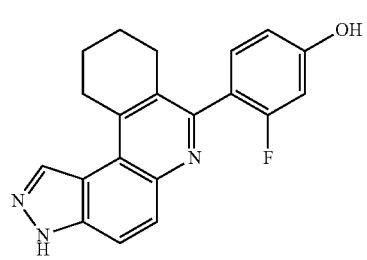 HSD-02-972
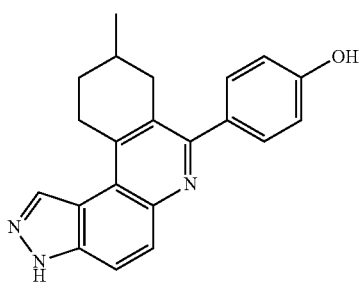 HSD-02-973
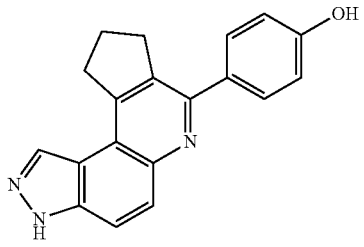 HSD-02-974
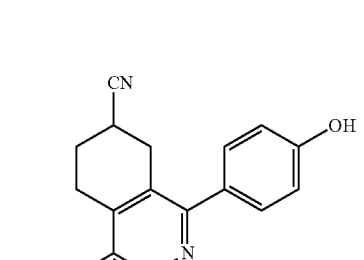 HSD-02-976
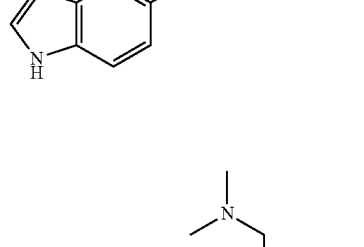 HSD-02-977
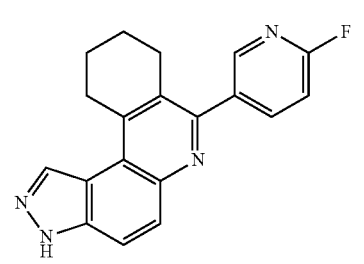 HSD-02-978

HSD-02-980
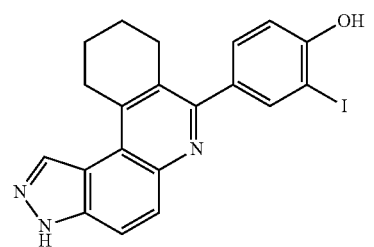
HSD-02-981
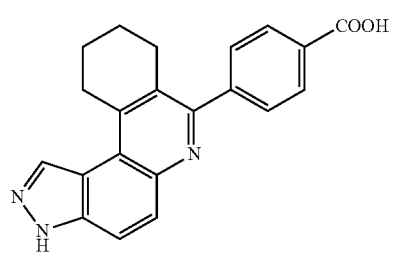
HSD-02-982
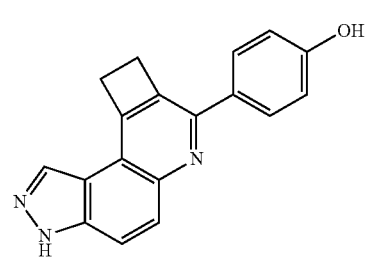
HSD-02-983
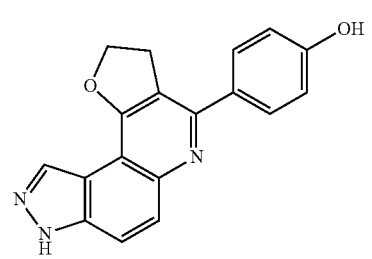
HSD-02-984
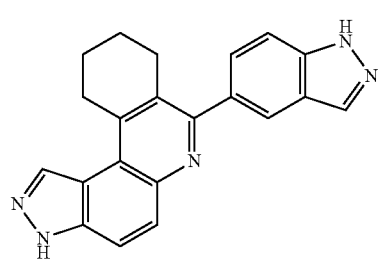
HSD-02-985
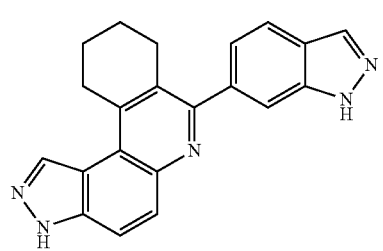
HSD-02-986
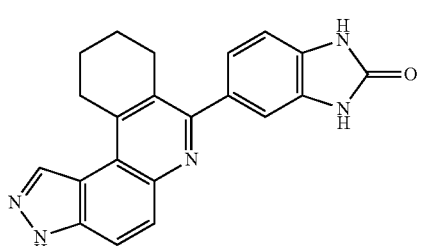
HSD-02-987
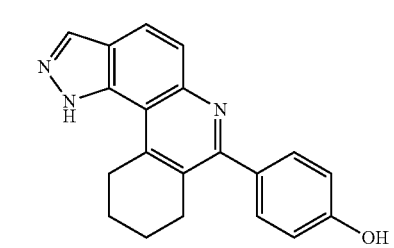
HSD-02-988
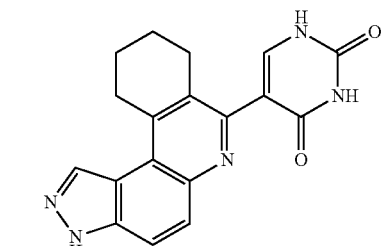
HSD-02-989
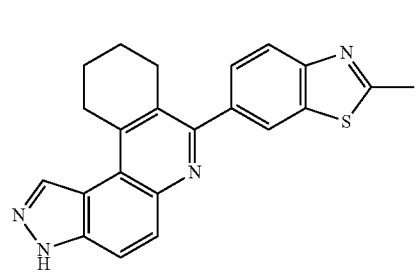
HSD-02-990
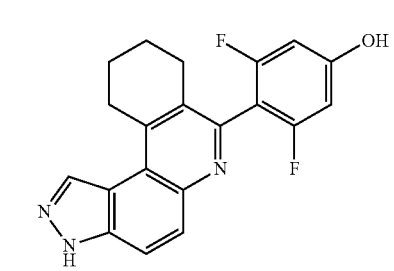
HSD-02-991
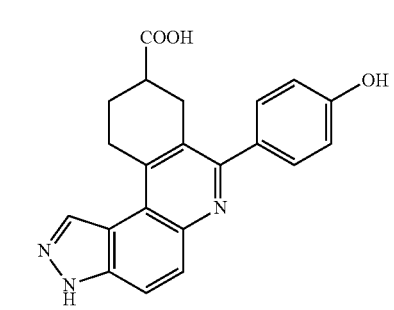

53
-continued
HSD-02-992
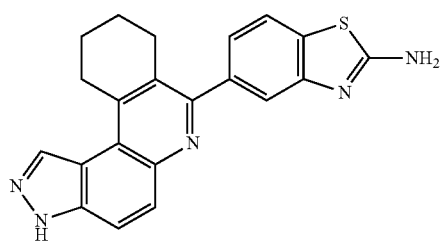
HSD-02-993
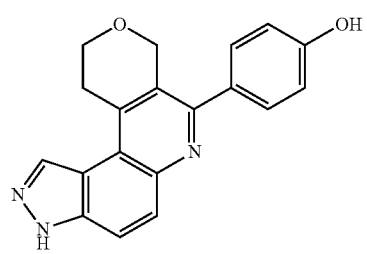
HSD-02-994
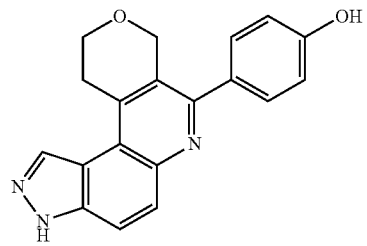
HSD-02-995
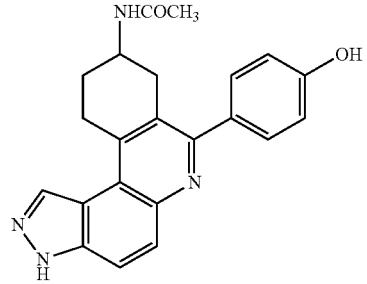
HSD-02-996
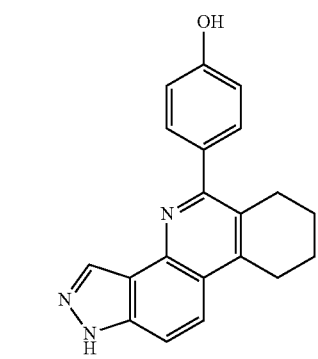
54
-continued
HSD-02-997
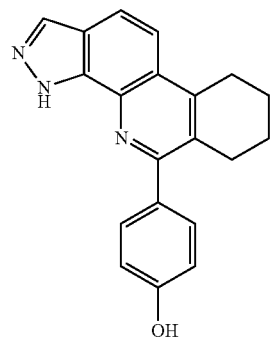
HSD-02-998
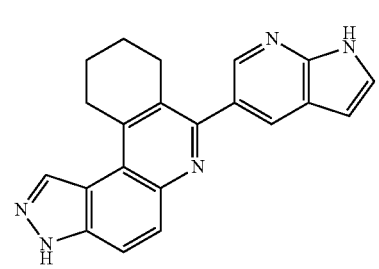
HSD-02-1001
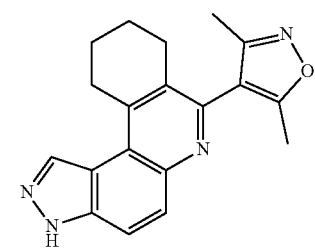
HSD1032
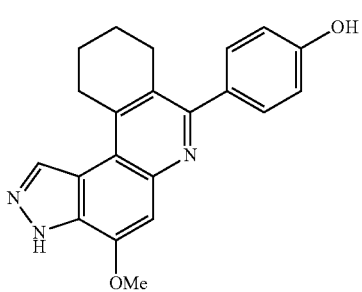
HSD1033
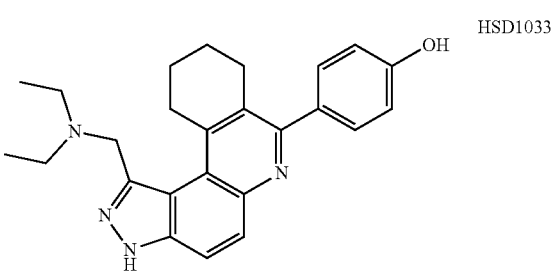

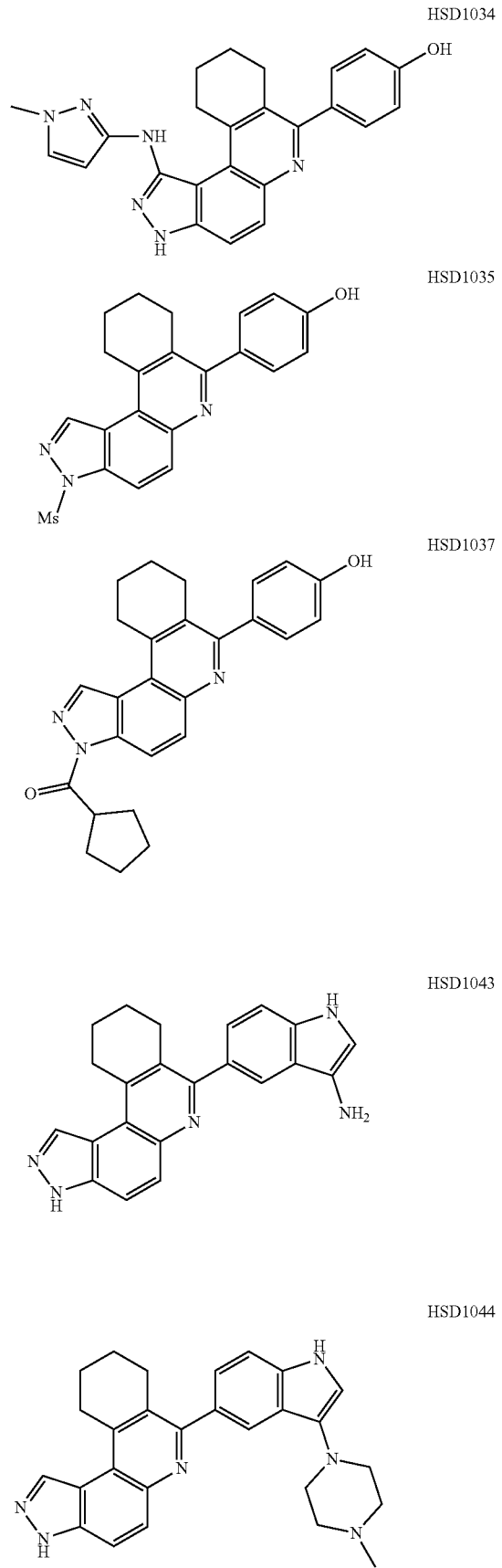
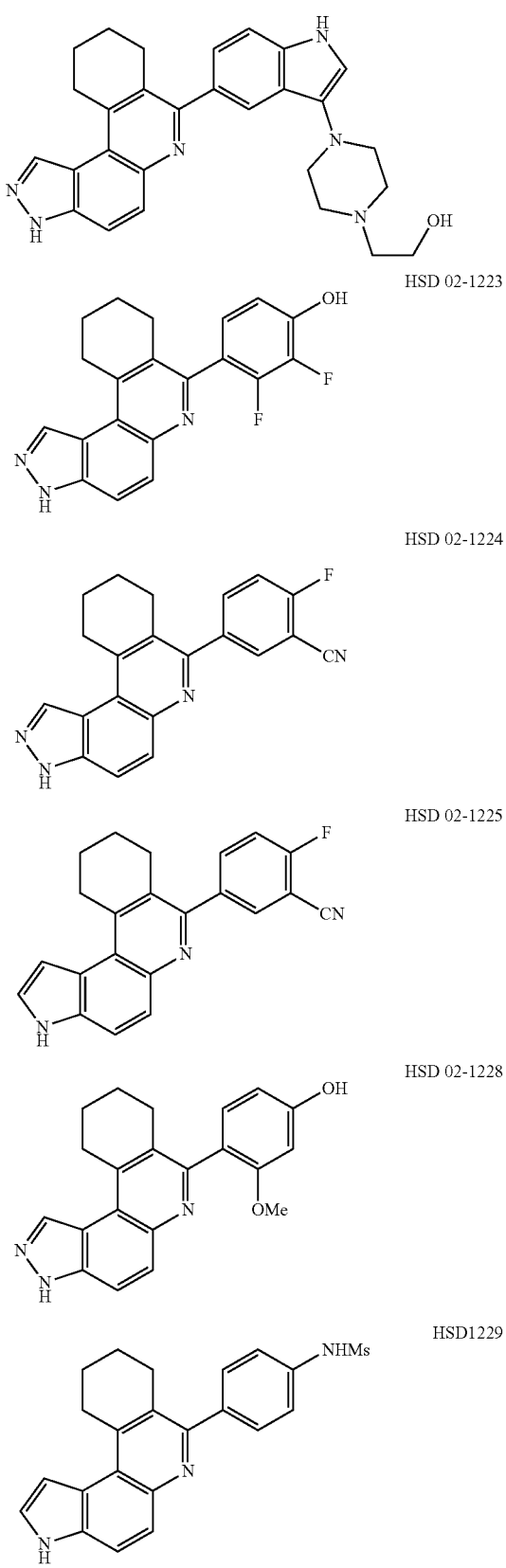

HSD1255
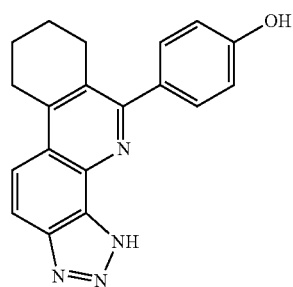
HSD-02-1005
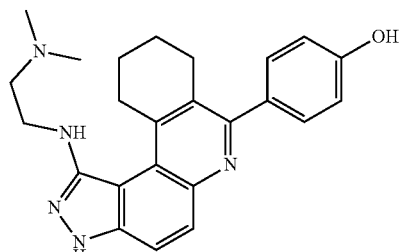
HSH205
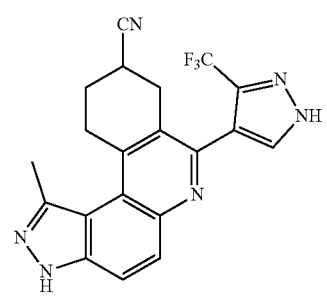
HSD-02-1006
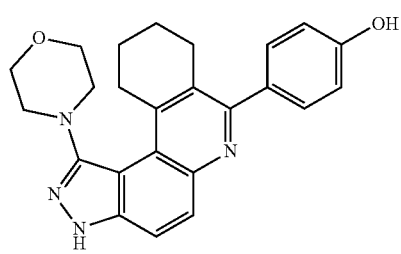
HSD-02-1002
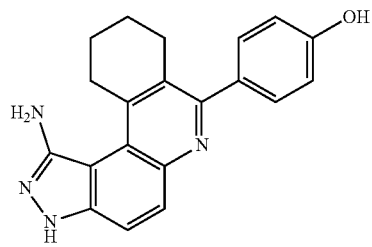
HSD-02-1007
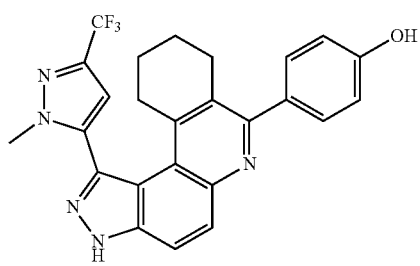
HSD-02-1003
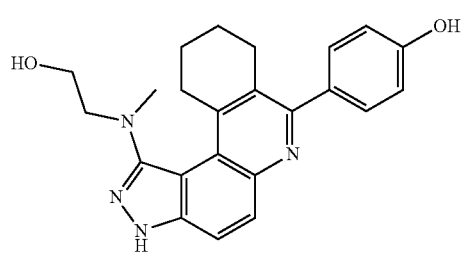
HSD-02-1008
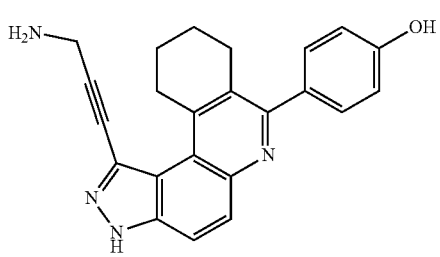
HSD-02-1004
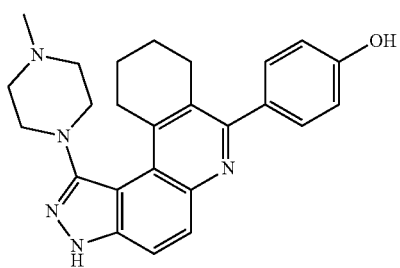
HSD-02-1009
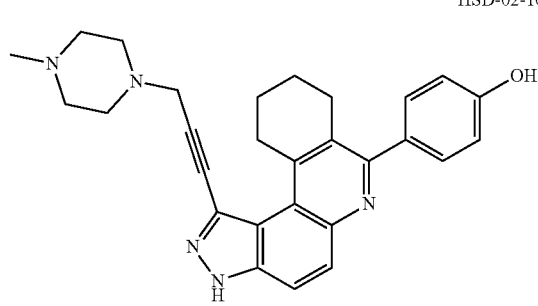

HSD-02-1010
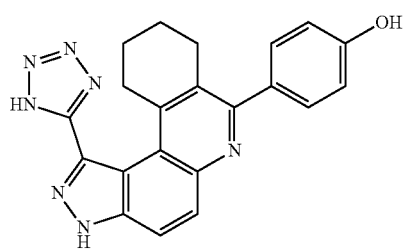
HSD-02-1011
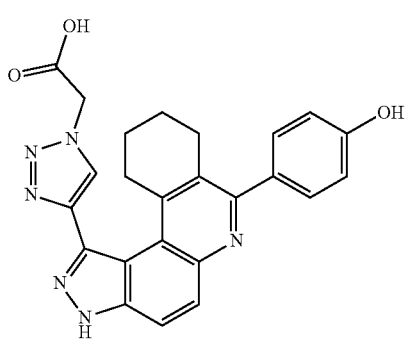
HSD-02-1012
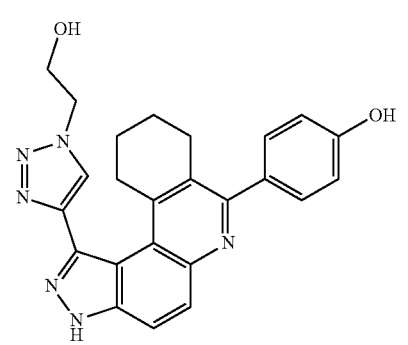
HSD-02-1013
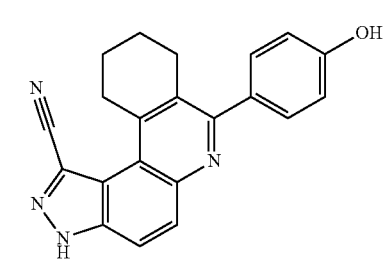
HSD-02-1014
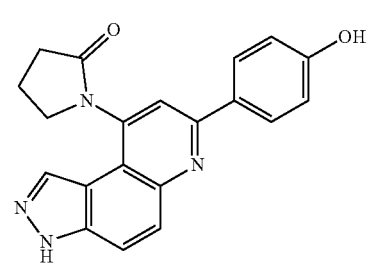
HSD-02-1015
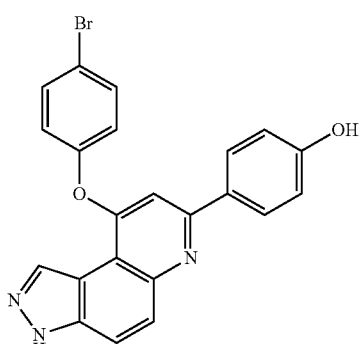
HSD-02-1016
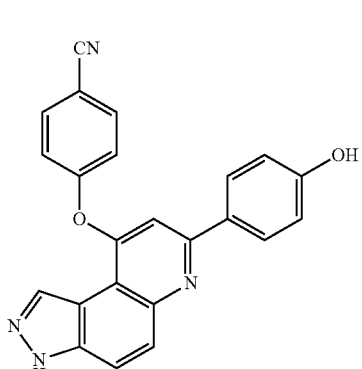
HSD-02-1017
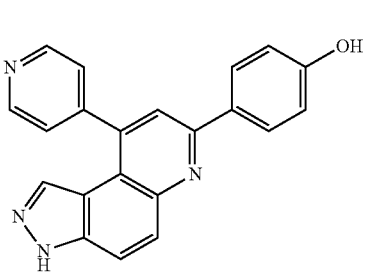
HSD-02-1018
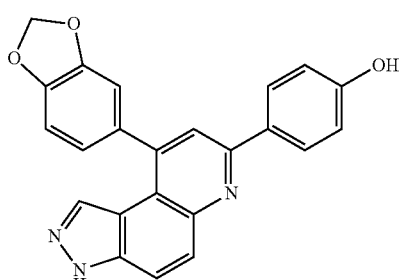
HSD-02-1019
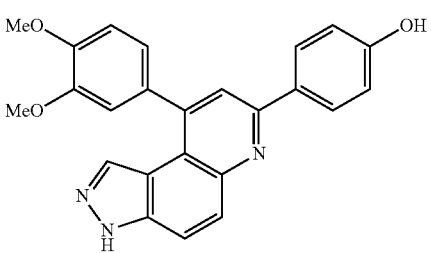

HSD-02-1020
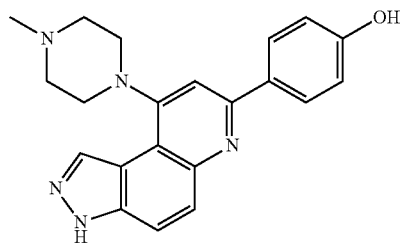
HSD-02-1021
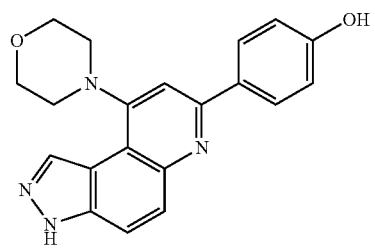
HSD-02-1022
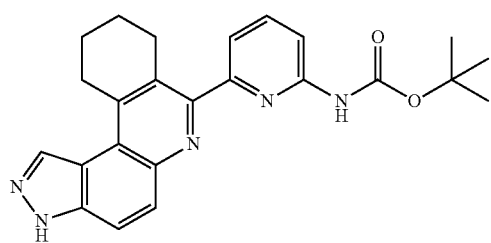
HSD-02-1023
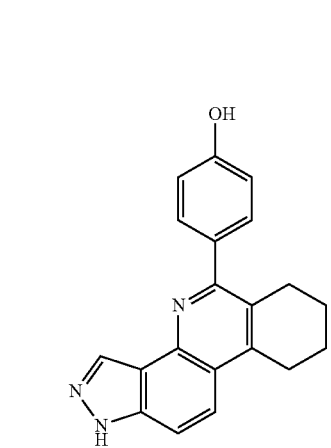
HSD-02-1024
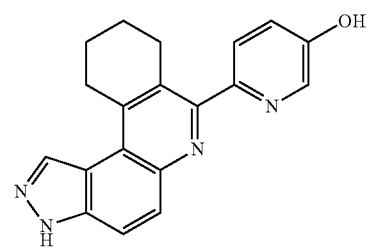
HSD-02-1025
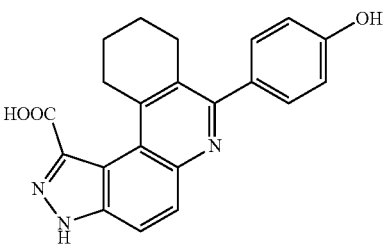
HSD-02-1026
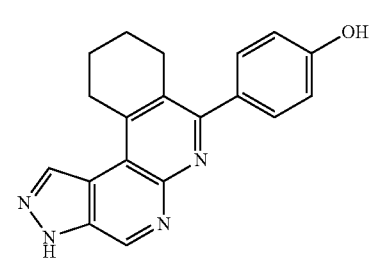
HSD-02-1027
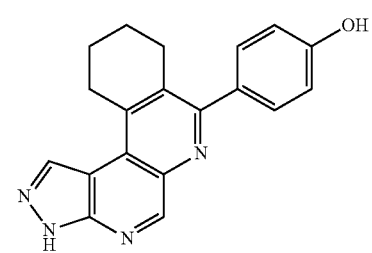
HSD-02-1031
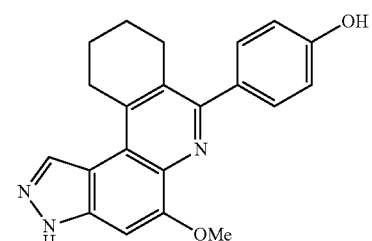
HSD-02-1036
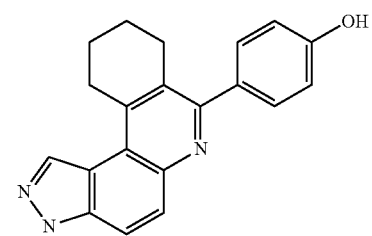
HSD-02-1071
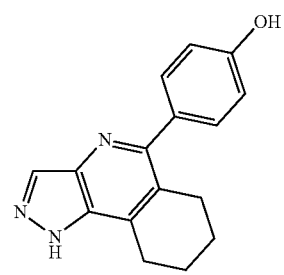

HSD-02-1077
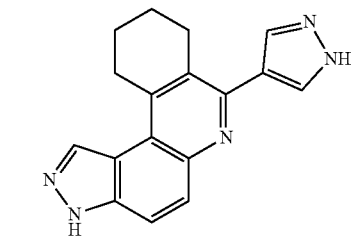
HSD-02-1079
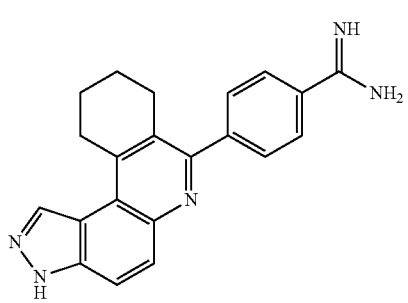
HSD-02-1046
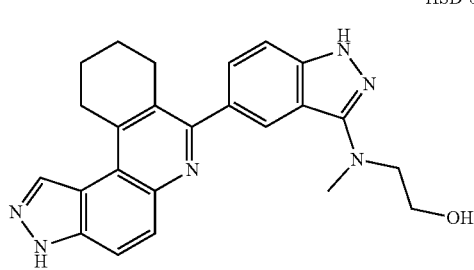
HSD-02-1047
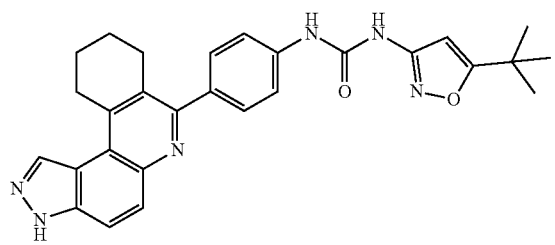
HSD-02-1048
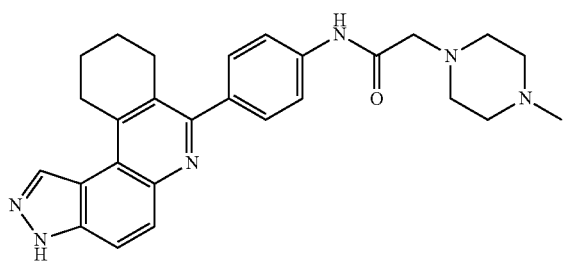
HSD-02-1049
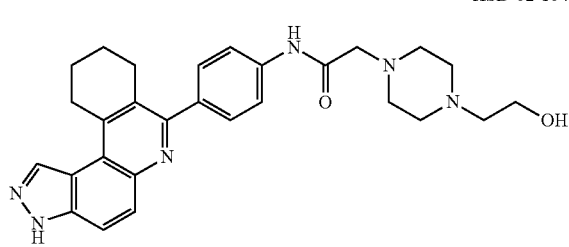
HSD-02-1050
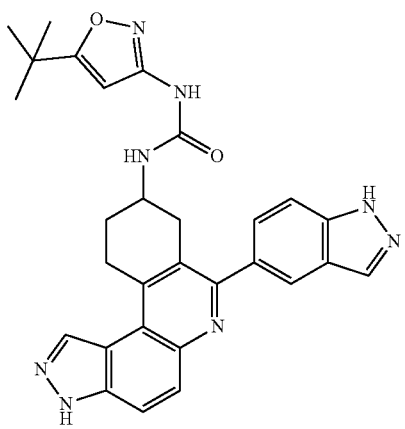
HSD-02-1051
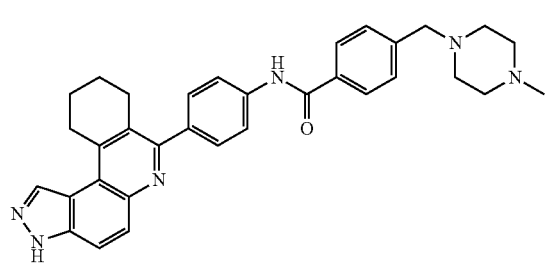
HSD-02-1052
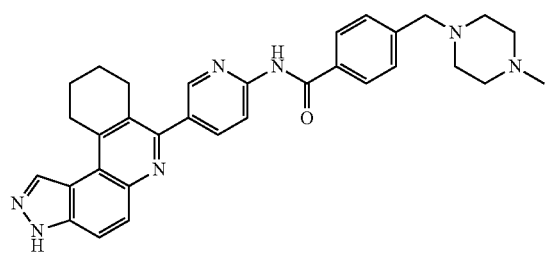
HSD-02-1053
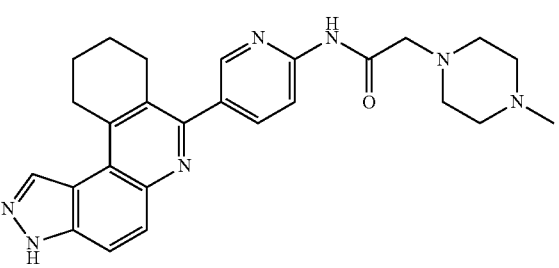

HSD-02-1054
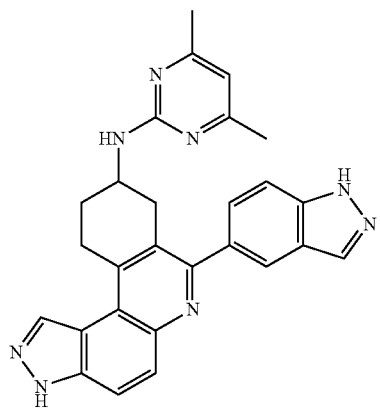
HSD-02-1055
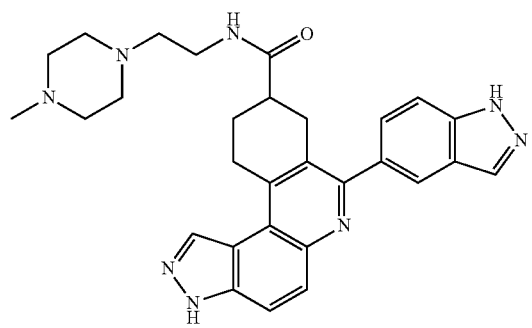
HSD-02-1056
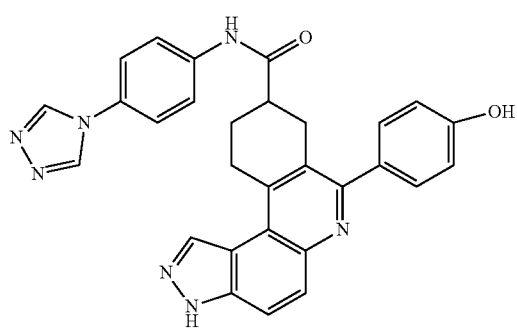
HSD-02-1057
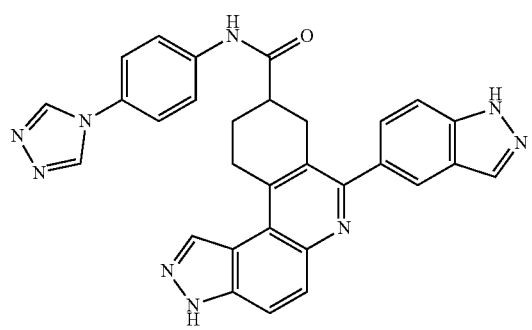
HSD-02-1058
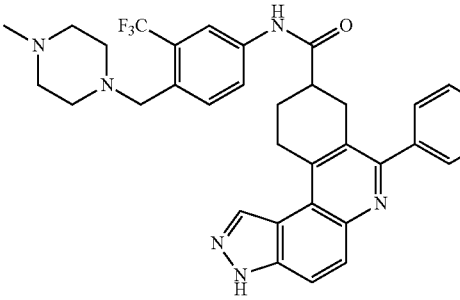
HSD-02-1059
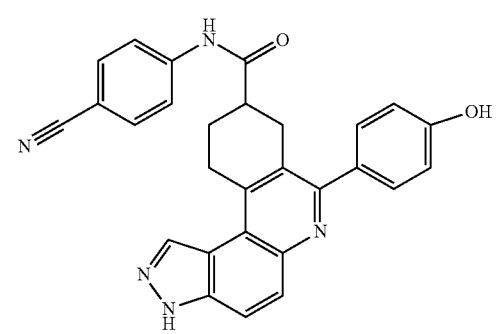
HSD-02-1060
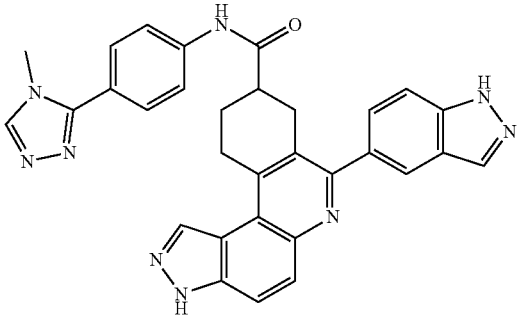
HSD-02-1061
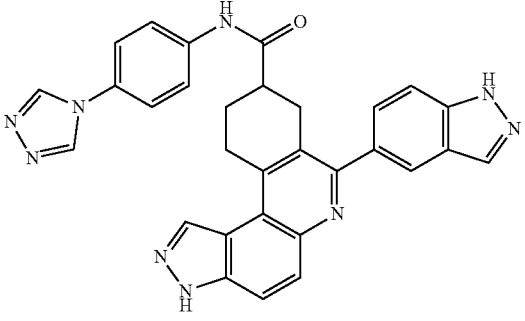

HSD-02-1062
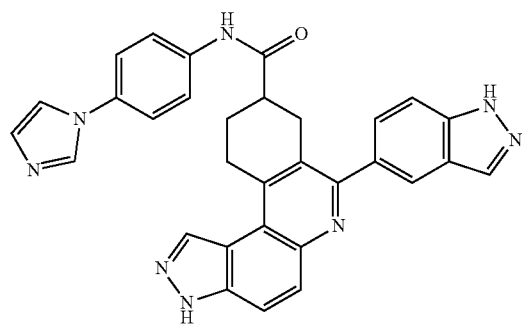
HSD-02-1063
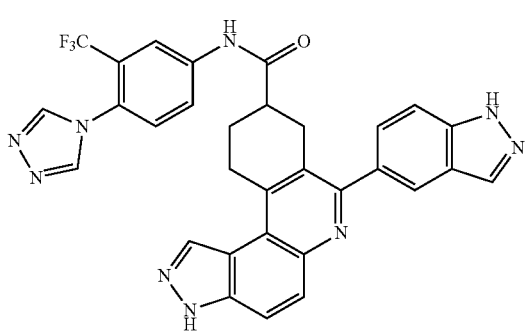
HSD-02-1081
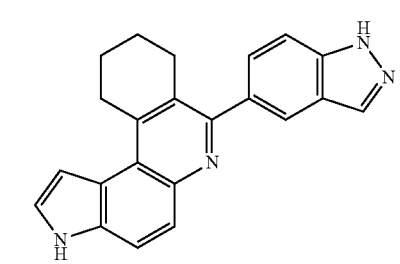
HSD-02-1082
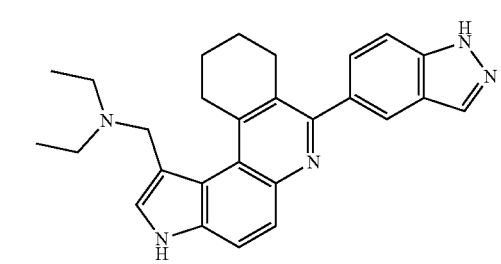
HSD-02-1083
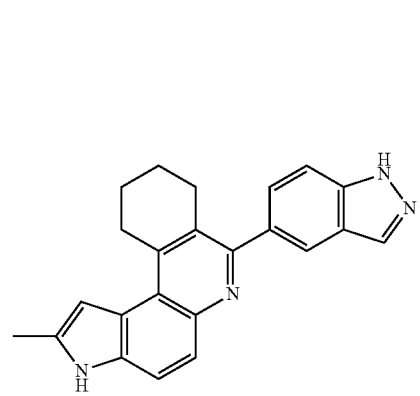
HSD-02-1084
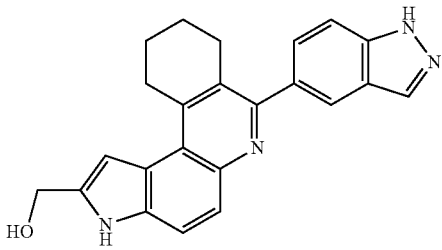
HSD-02-1085
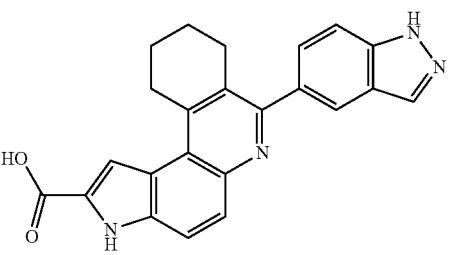
HSD-02-1086
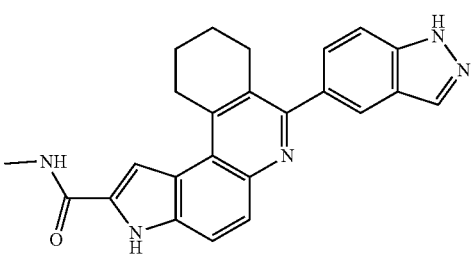
HSD-02-1087
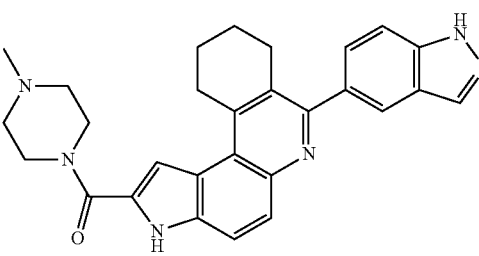
HSD-02-1088
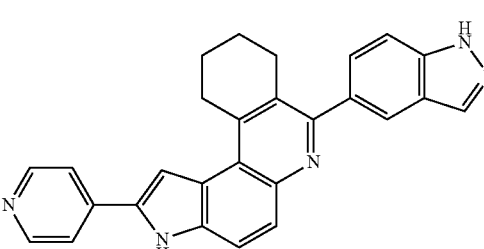
HSD-02-1089
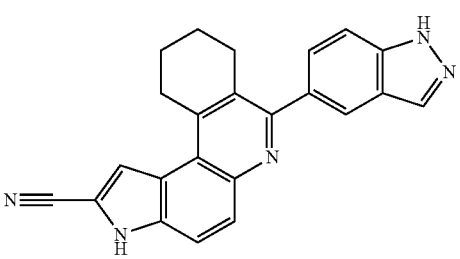

HSD-02-1090
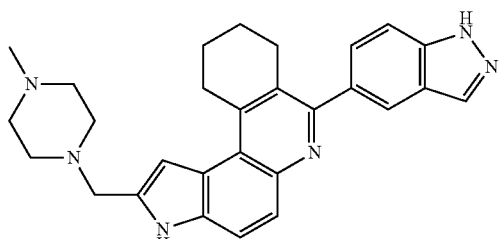
HSD-02-1091
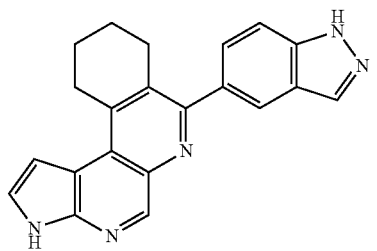
HSD-02-1092
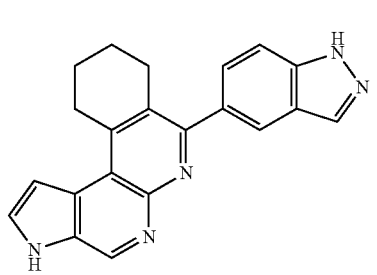
HSD-02-1093
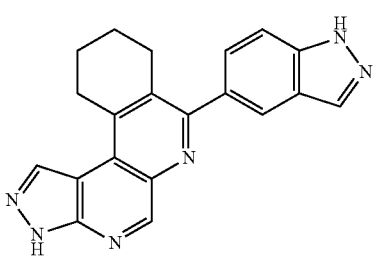
HSD-02-1094
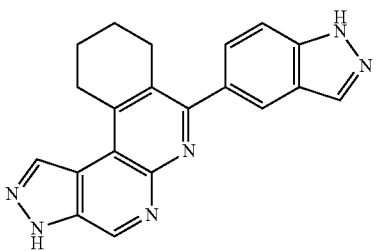
HSD-02-1095
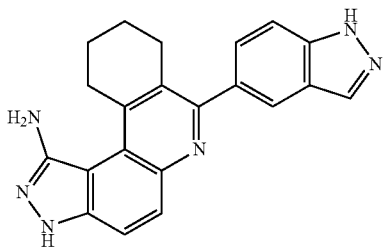
HSD-02-1096
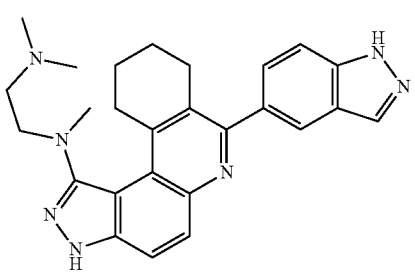
HSD-02-1097
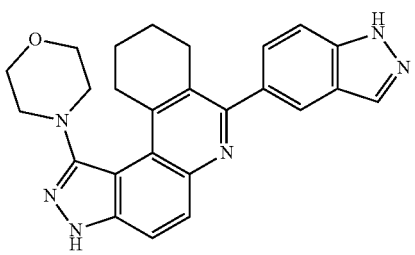
HSD-02-1098
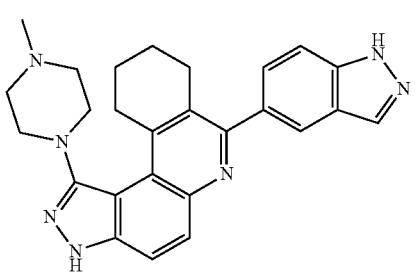
HSD-02-1099
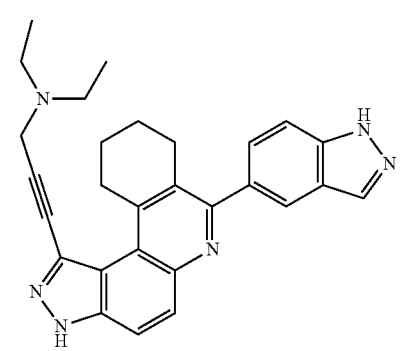
HSD-02-1100
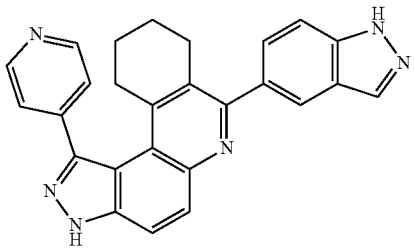

HSD-02-1101
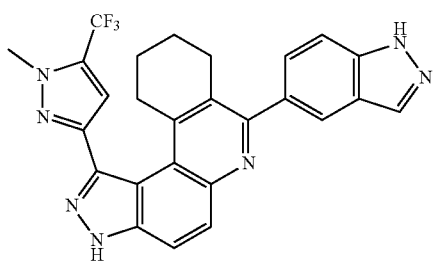
HSD-02-1102
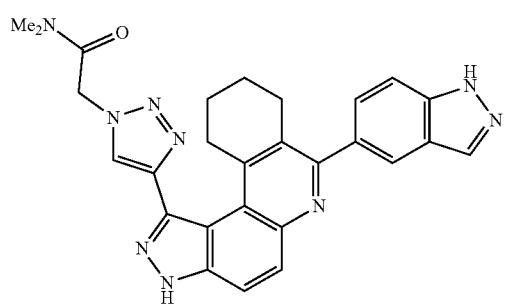
HSD-02-1103
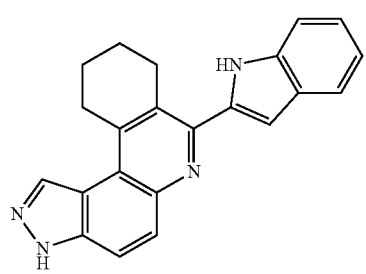
HSD-02-1104
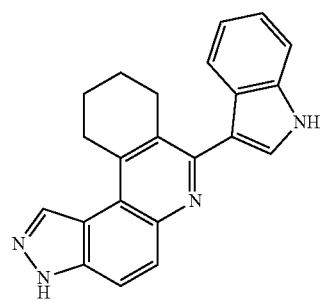
HSD-02-1105
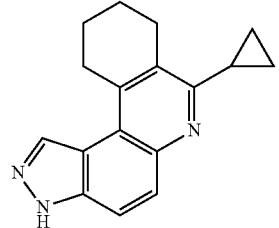
HSD-02-1106
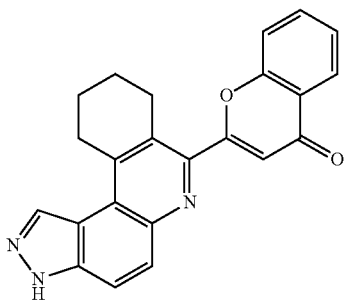
HSD-02-1107
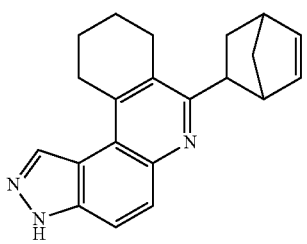
HSD-02-1108
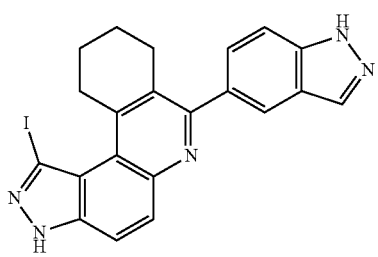
HSD-02-1109
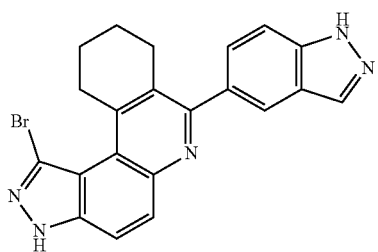
HSD-02-1110
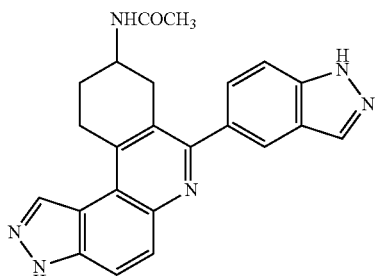
HSD-02-1111
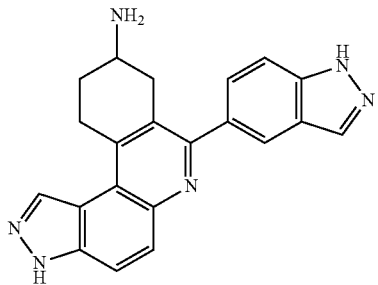

HSD-02-1112
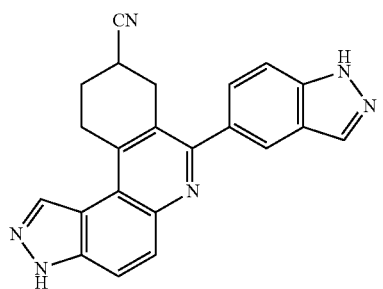
HSD-02-1113
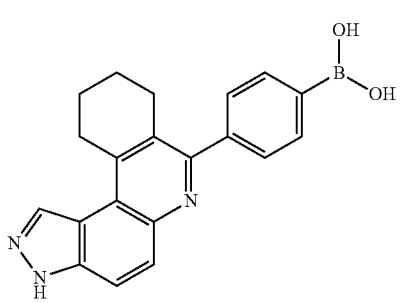
HSD-02-1114
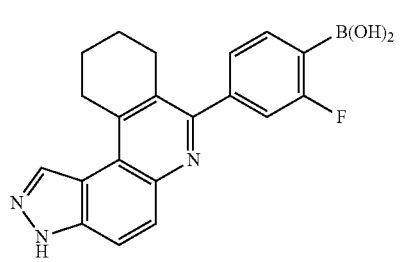
HSD1114A
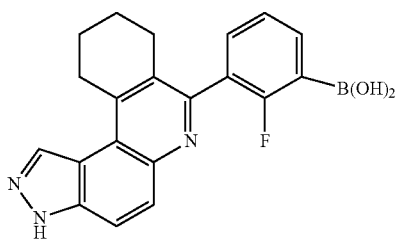
HSD-02-1115
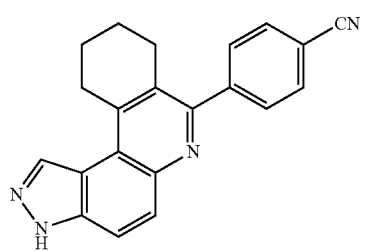
HSD-02-1116
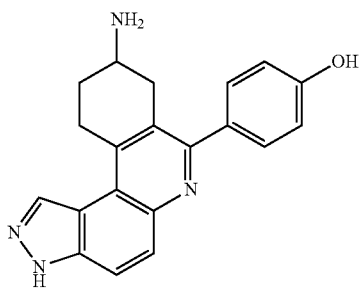
HSD1169
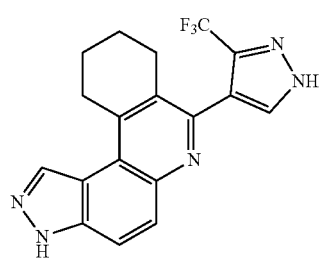
HSD1170
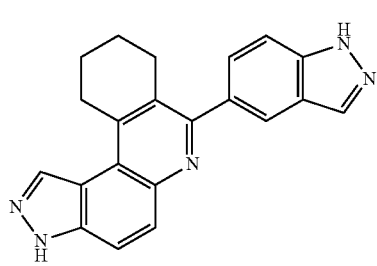
HSD-02-1276
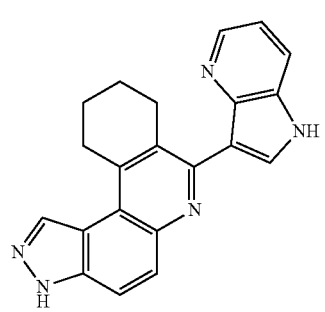
HSD-02-1279
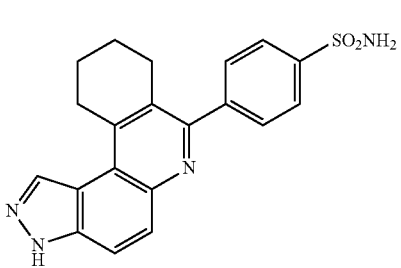

HSD-02-1280
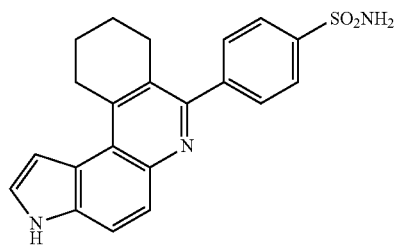
HSD-02-1281
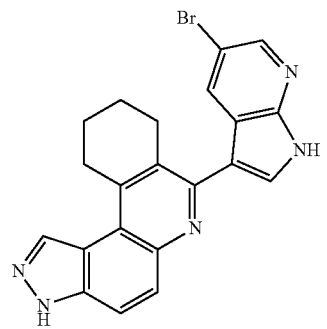
HSD-02-1282
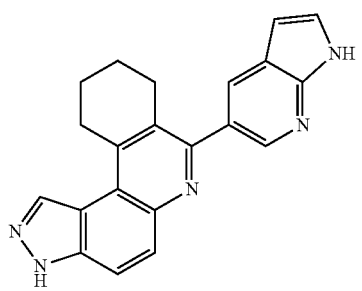
HSD1285
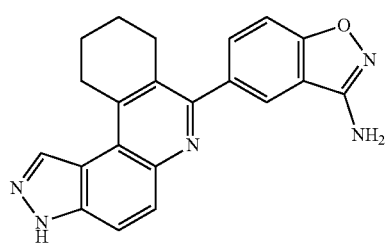
HSD1286
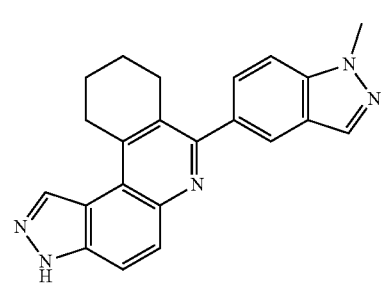
HSD1287
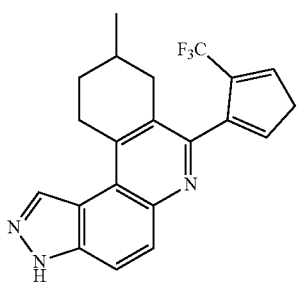
HSD-02-1117
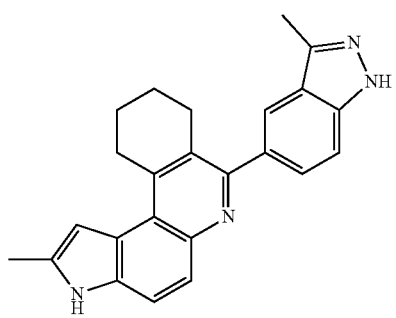
HSD-02-1118
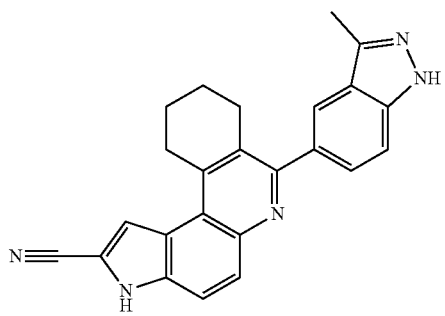
HSD-02-1119
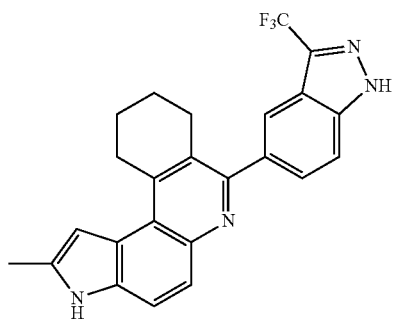
HSD-02-1120
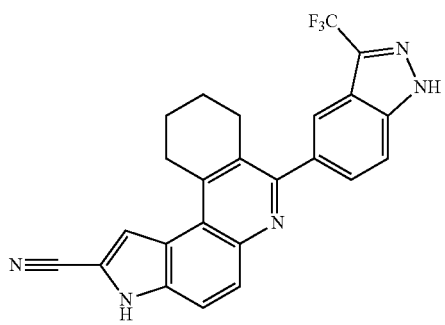

HSD-02-1121
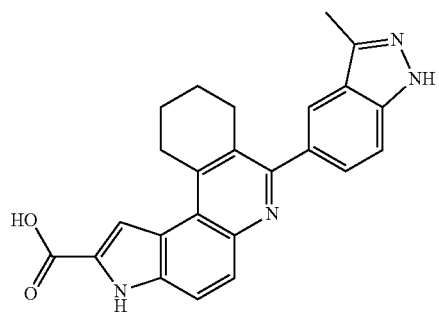
HSD-02-1125
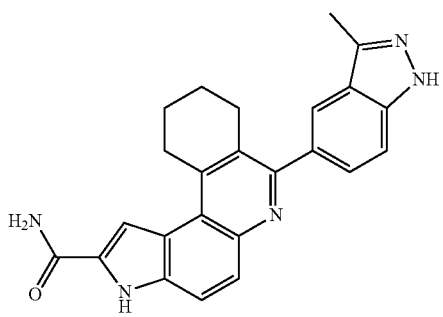
HSD-02-1122
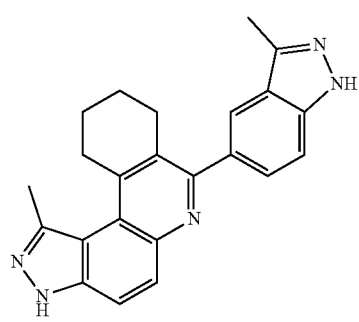
HSD-02-1126
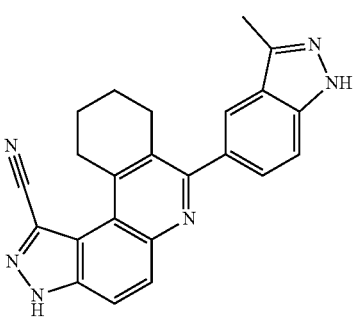
HSD-02-1123
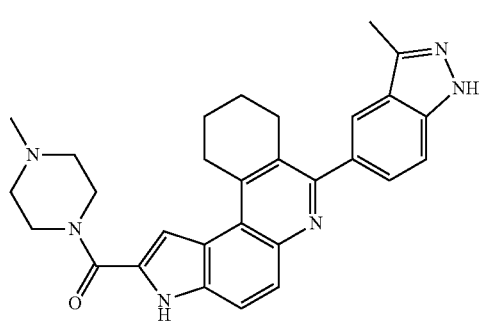
HSD-02-1127
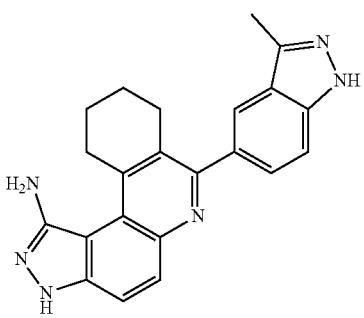
HSD-02-1124
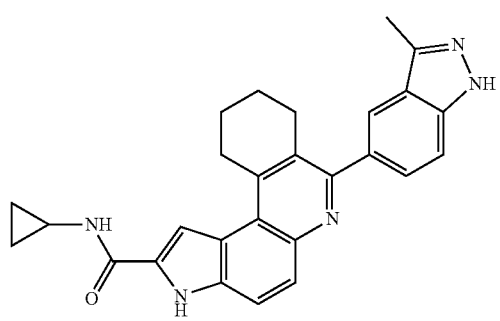
HSD-02-1128
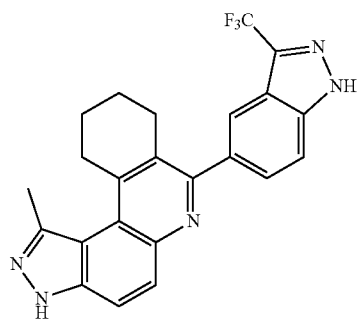

HSD-02-1129
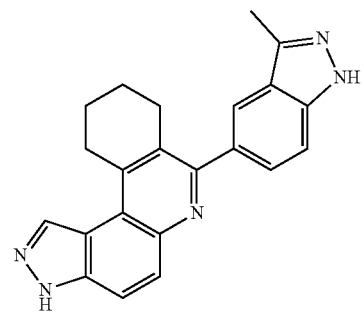
HSD-02-1143
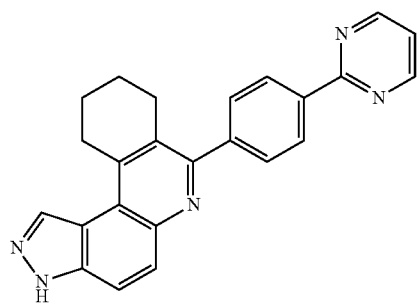
HSD-02-1144
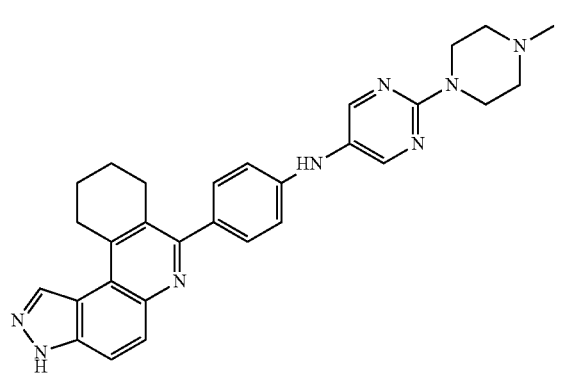
HSD-02-1145
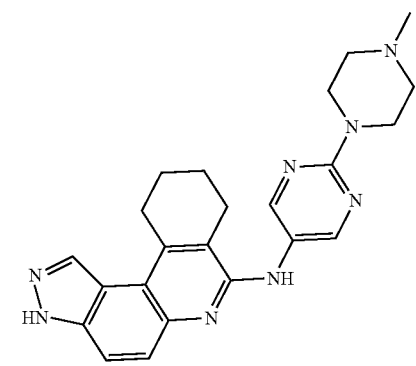
HSD-02-1146
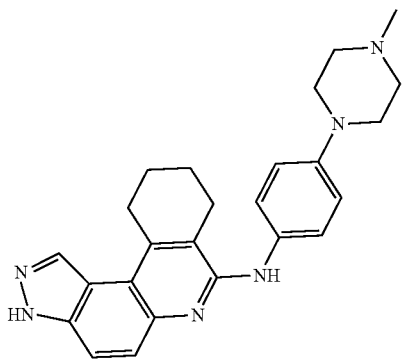
HSD-02-1147
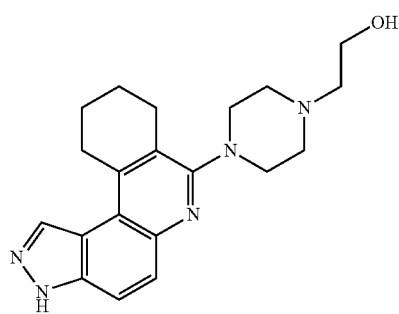
HSD-02-1148
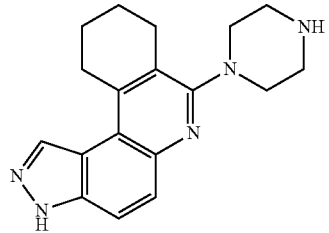
HSD-02-1149
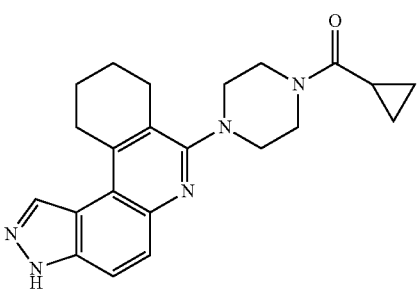
HSD-02-1150
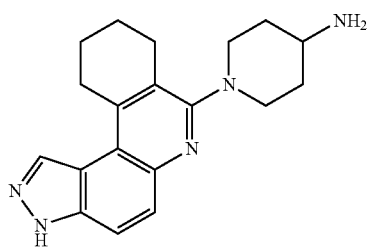

HSD-02-1151
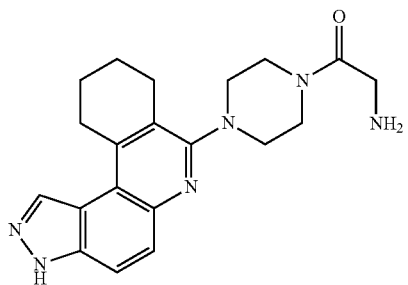
HSD-02-1152
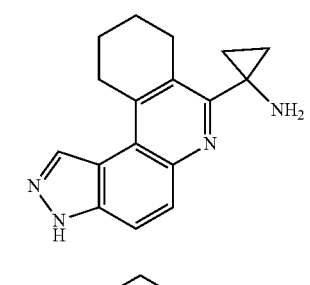
HSD-02-1153
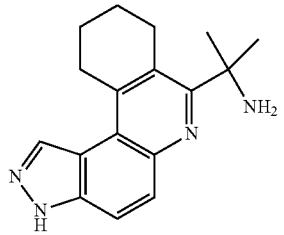
HSD-02-1154
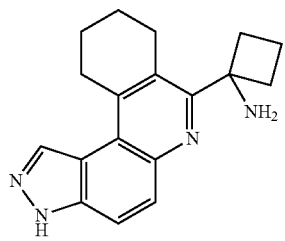
HSD-02-1155
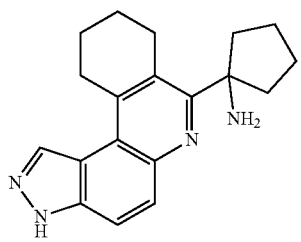
HSD-02-1156
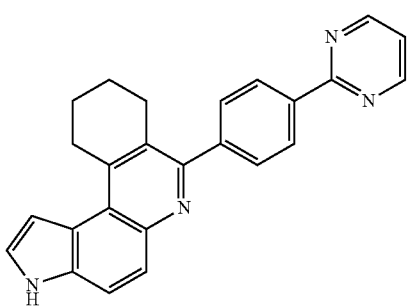
HSD-02-1157
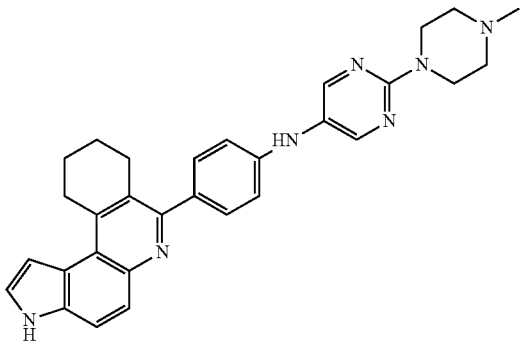
HSD-02-1158
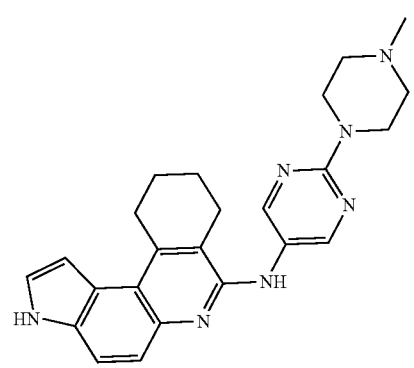
HSD-02-1159
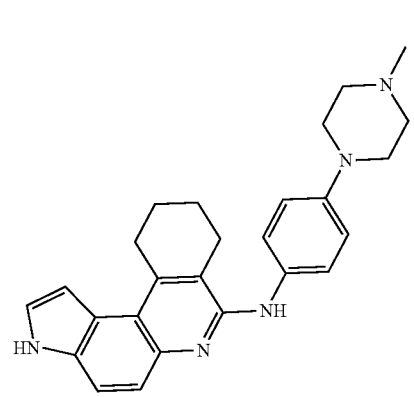
HSD-02-1160
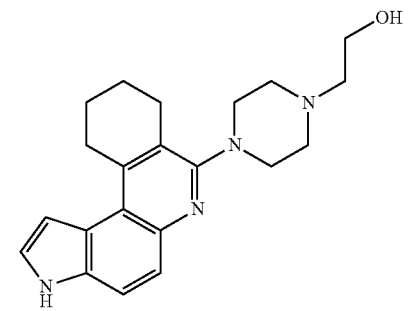

| HSD-02-1161 | HSD-02-1167 |
| HSD-02-1162 | HSD-02-1168 |
| HSD-02-1163 | HSD-02-1171 |
| HSD-02-1164 | HSD-02-1173 |
| HSD-02-1165 | HSD-02-1174 |
| HSD-02-1166 | HSD-02-1175 |

HSD-02-1176
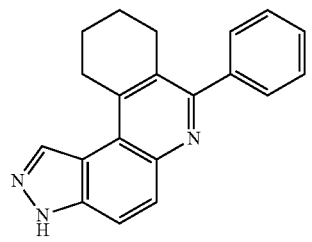
HSD-02-1177
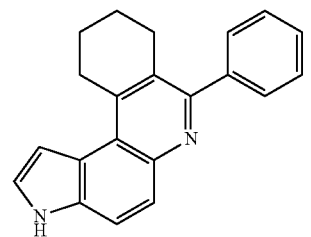
HSD-02-1178
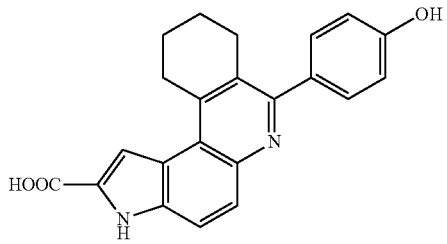
HSD-02-1180
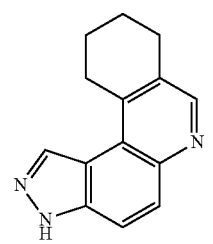
HSD-02-1181
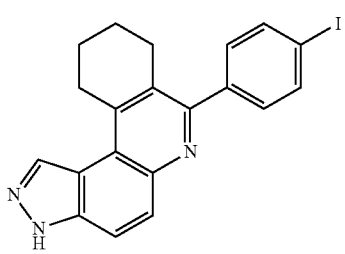
HSD-02-1182
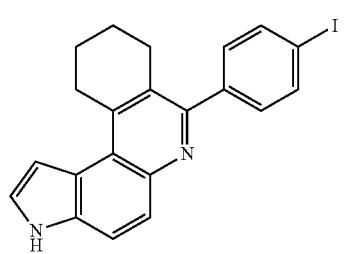
HSD-02-1183
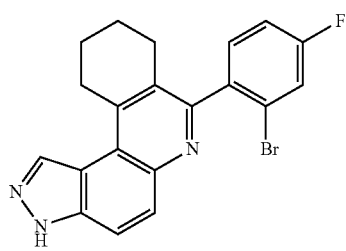
HSD-02-1184
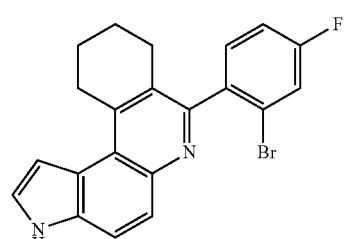
HSD-02-1185
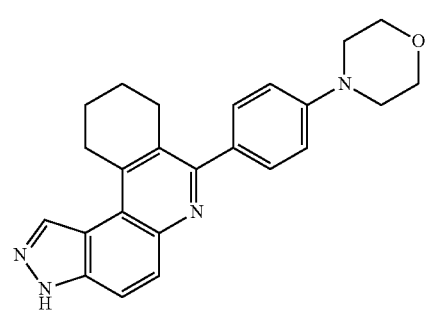
HSD-02-1186
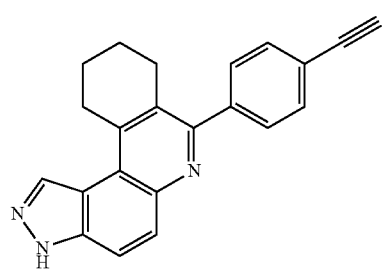
HSD-02-1188
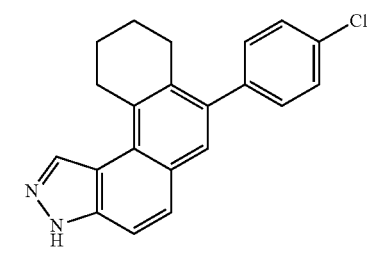
HSD-02-1189
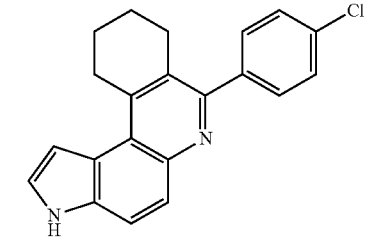

87
-continued
HSD-02-1190
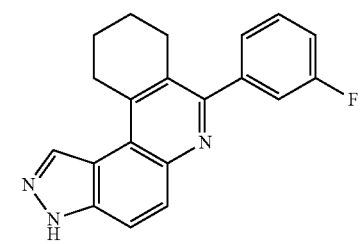
HSD-02-1191
HSD-02-1195
HSD-02-1196
HSD-02-1197
HSD-02-1198
88
-continued
HSD-02-1199
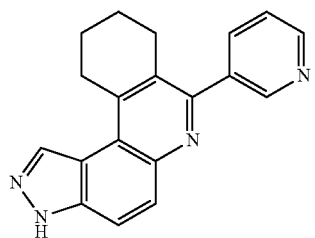
HSD-02-1200
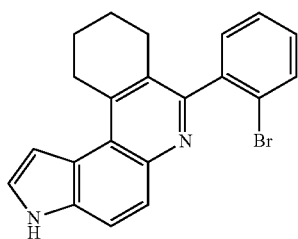
HSD-02-1202
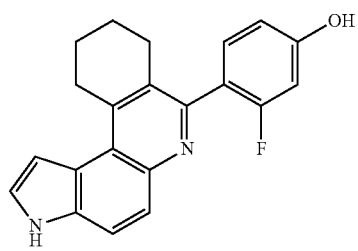
HSD 02-1203
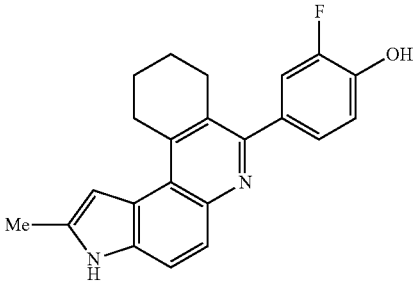
HSD 02-1204
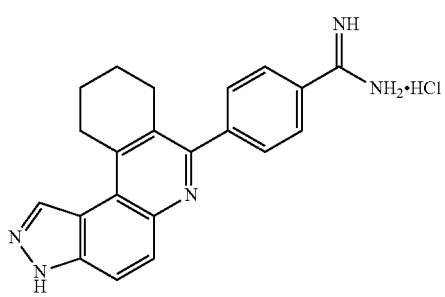
HSD 02-1205
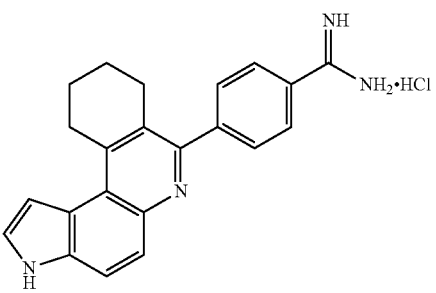

HSD 02-1207
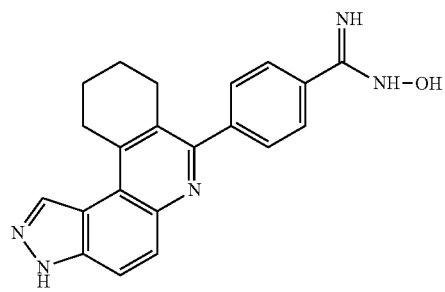
HSD 02-1208
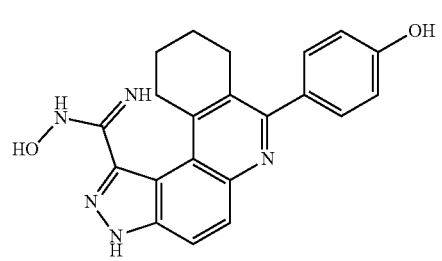
HSD 02-1209
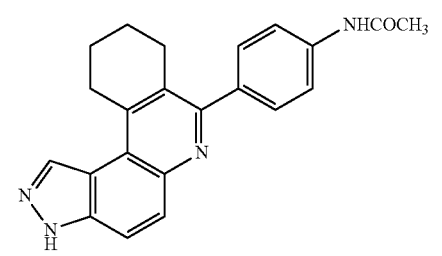
HSD 02-1210
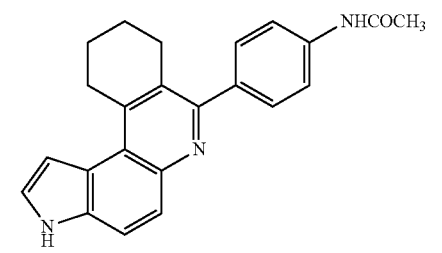
HSD 02-1211
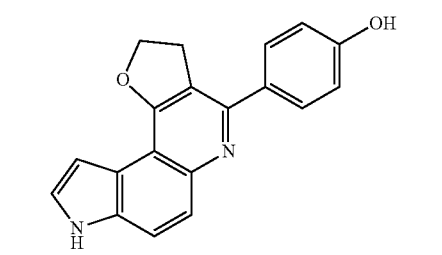
HSD 02-1213
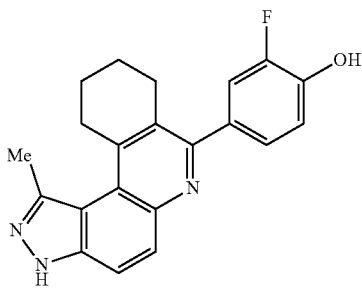
HSD 02-1214
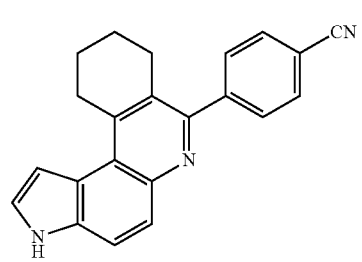
HSD 02-1215
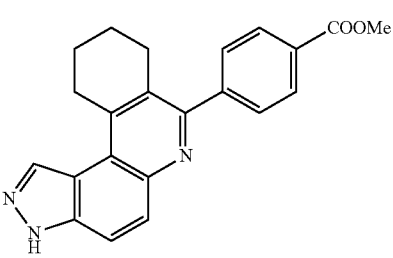
HSD 02-1217
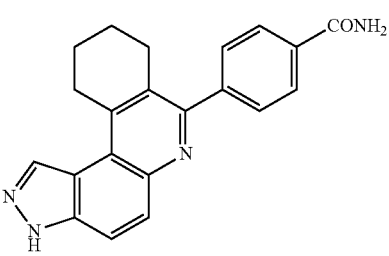
HSD 02-1218
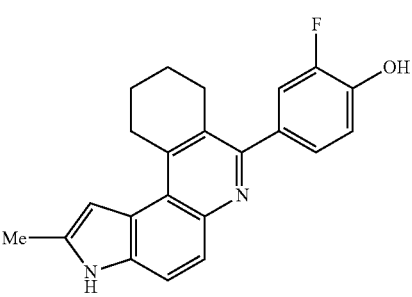

HSD 02-1219
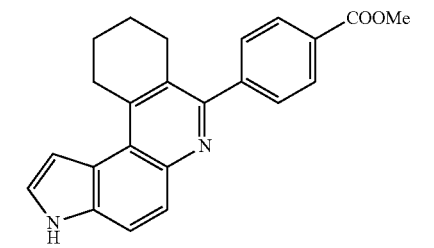
HSD 02-1220
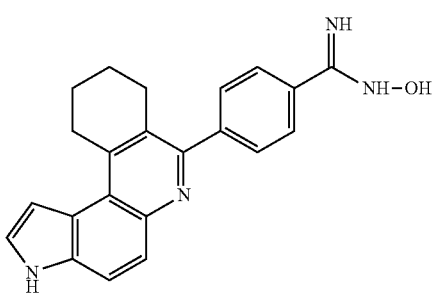
HSD 02-1221
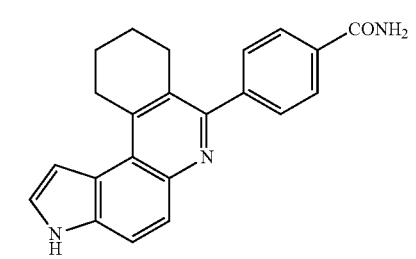
HSD 02-1222
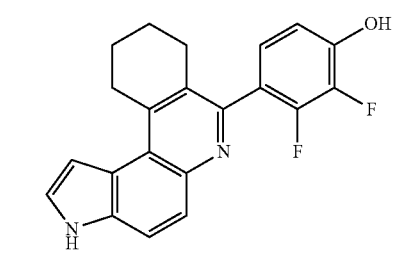
HSD1288
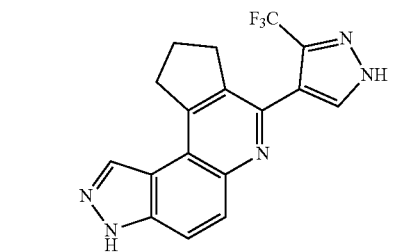
HSD1289
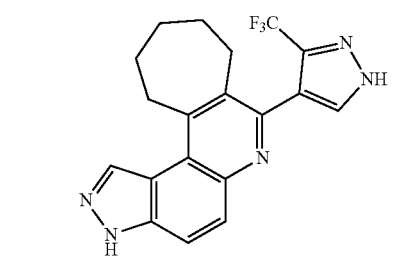
HSD290
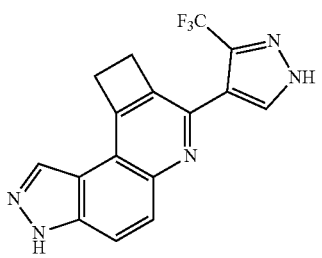
HSD1291
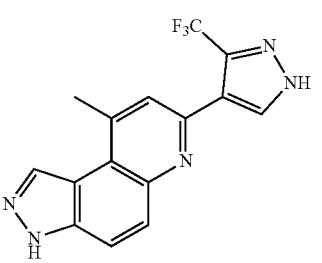
HSD1292
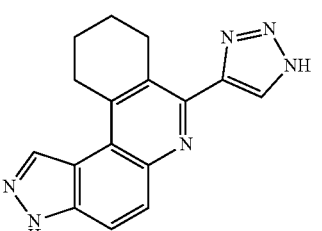
HSD1293
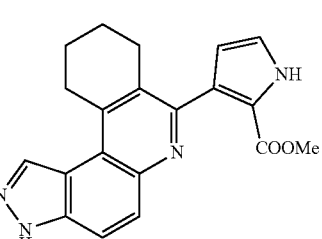
HSD1294
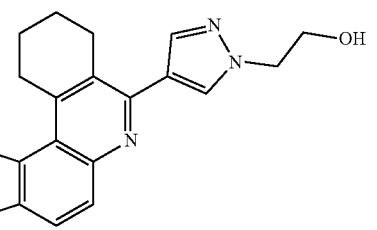
HSD1295
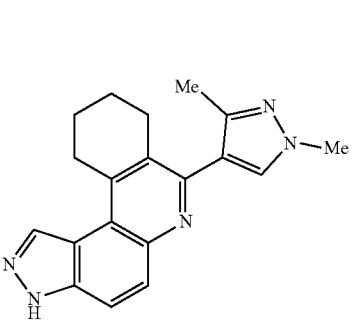

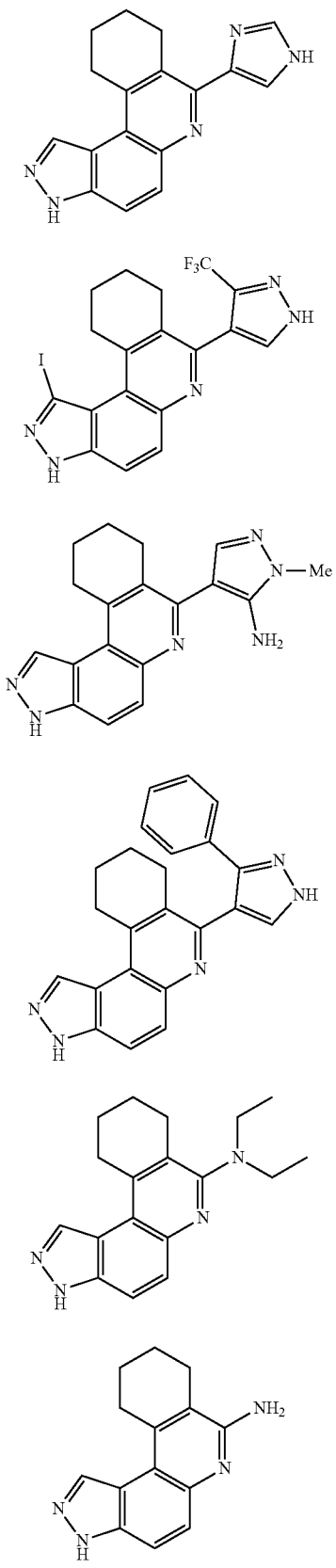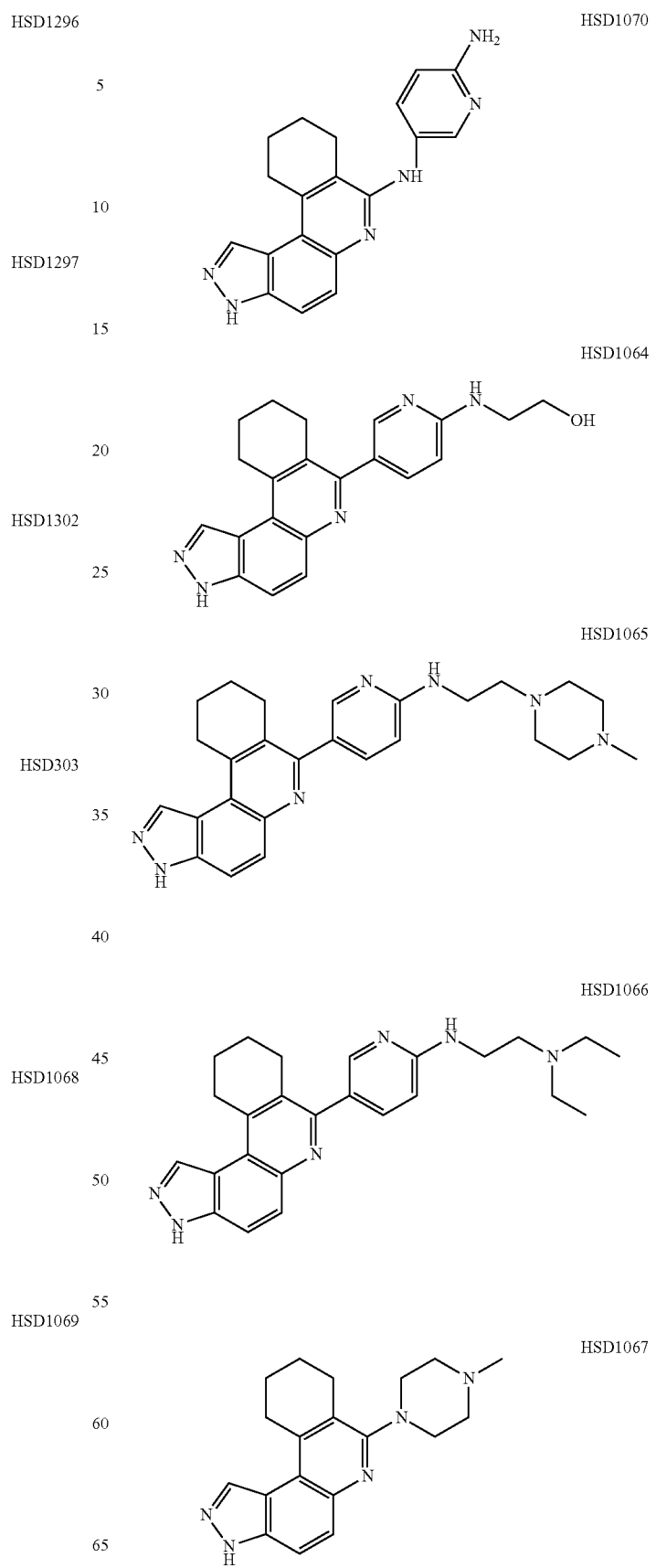

HSD1419
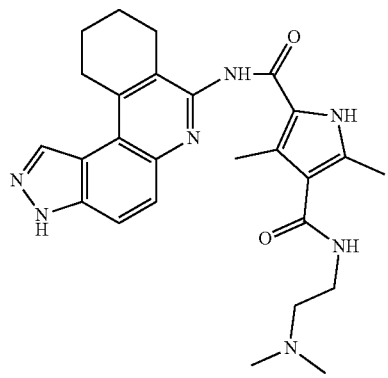
HSD1420
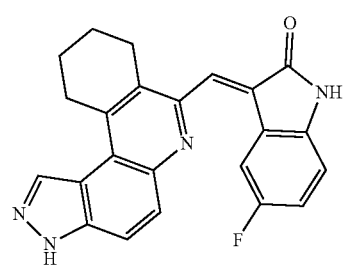
HSD1421
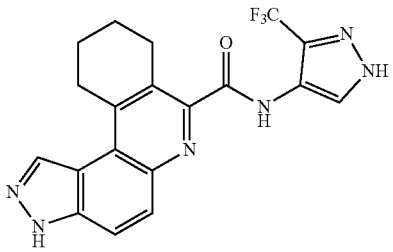
HSD1422
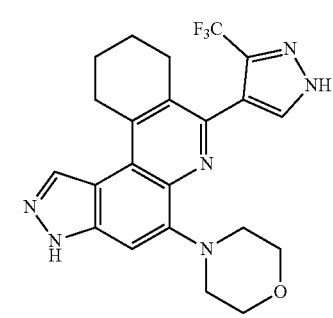
HSD1071
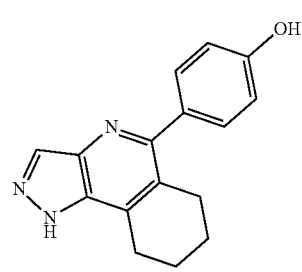
HSD1072
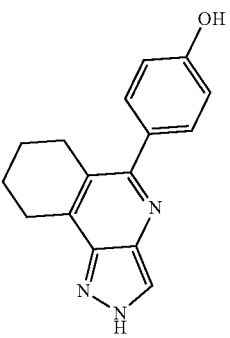
HSD1073
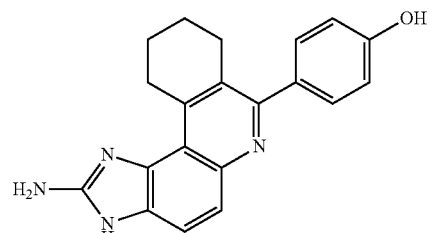
HSD1074
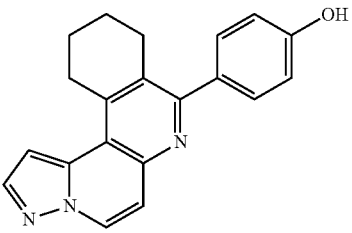
HSD1075
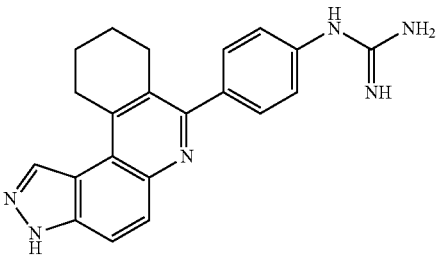
HSD1076
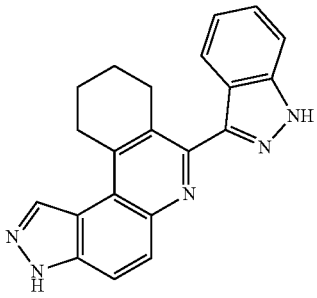

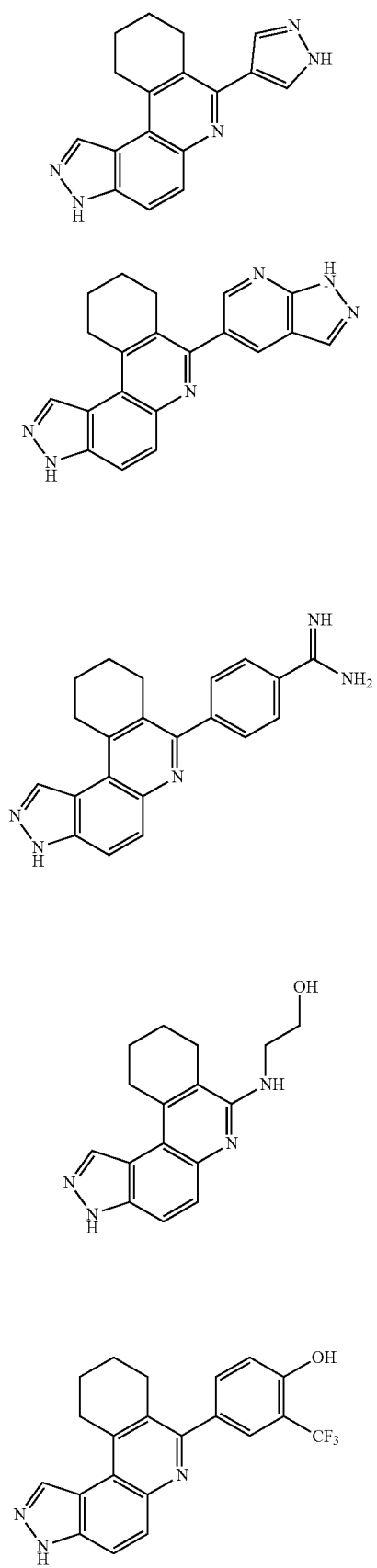
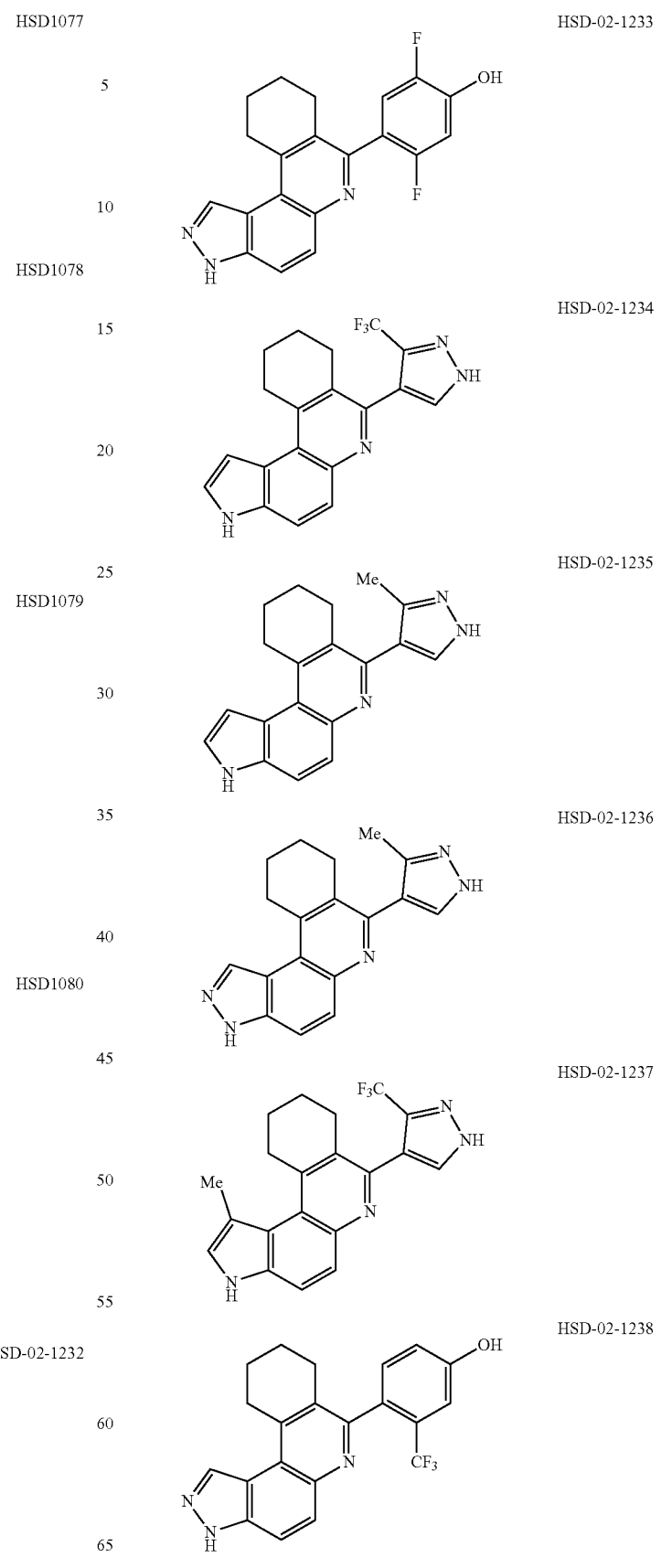

HSD-02-1239 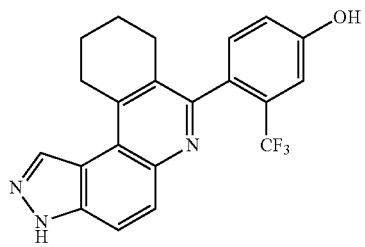
HSD-02-1240 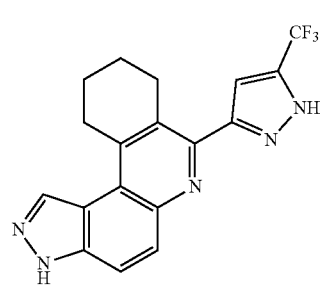
HSD-02-1243 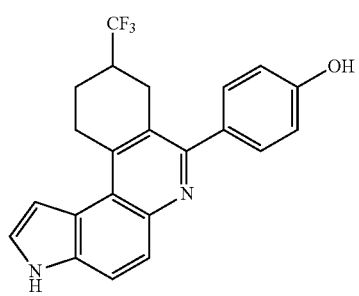
HSD-02-1242 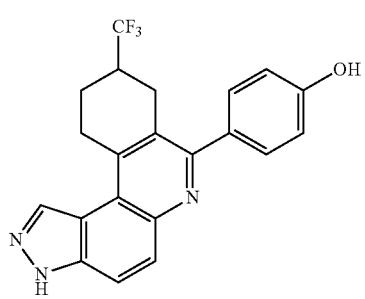
HSD-02-1243 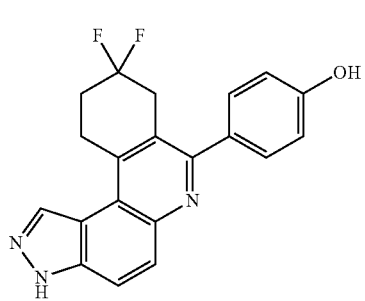
HSD-02-1244 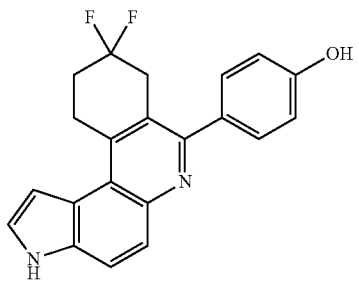
HSD-02-1245 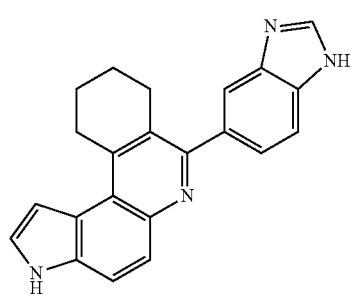
HSD-02-1246 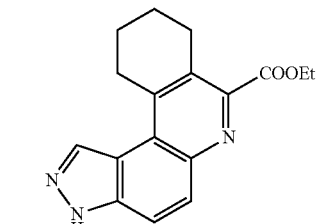
HSD-02-1247 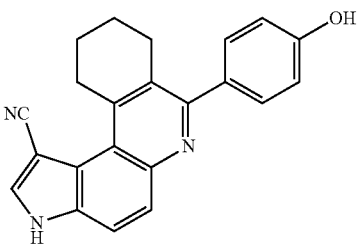
HSD-02-1248 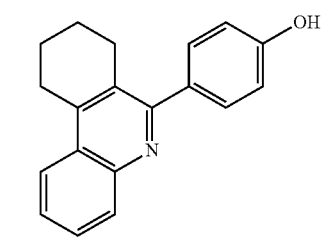
HSD-02-1252 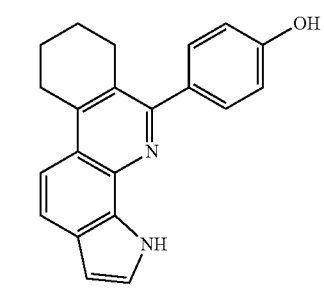

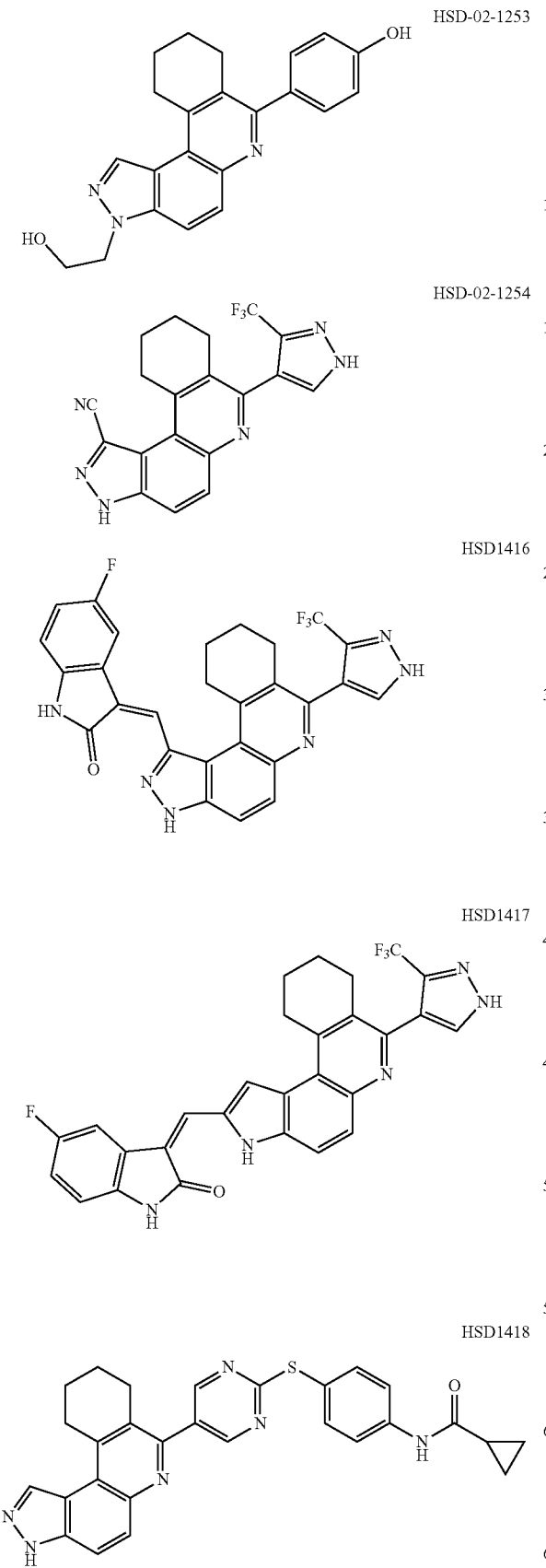
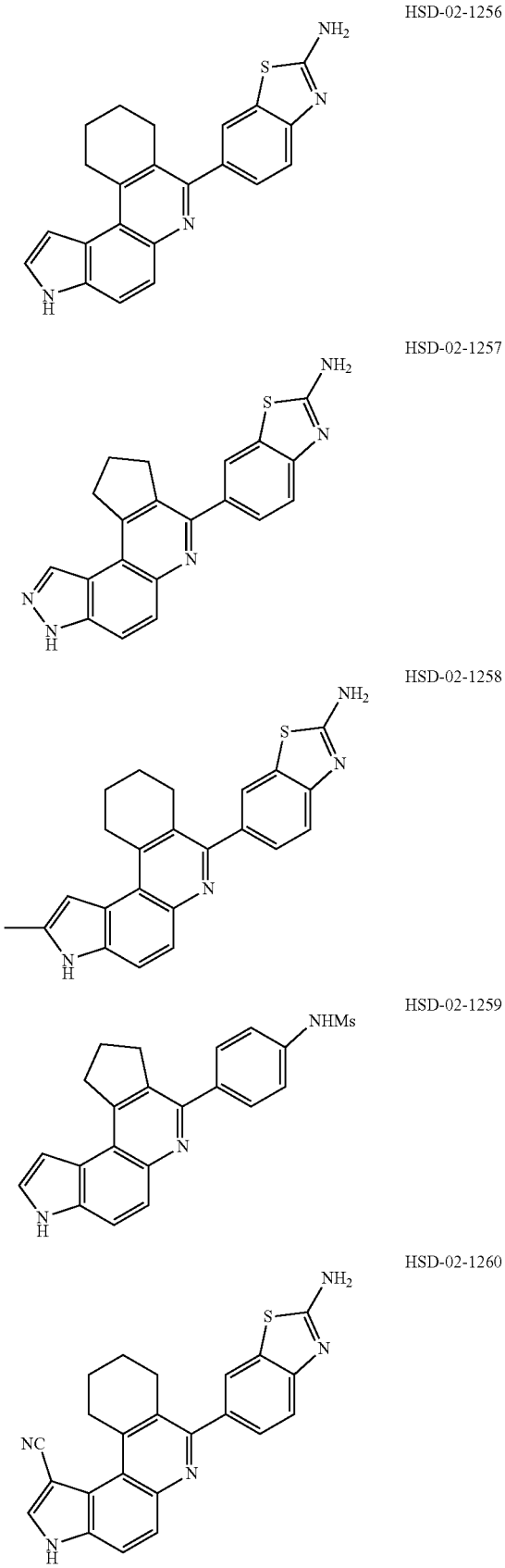

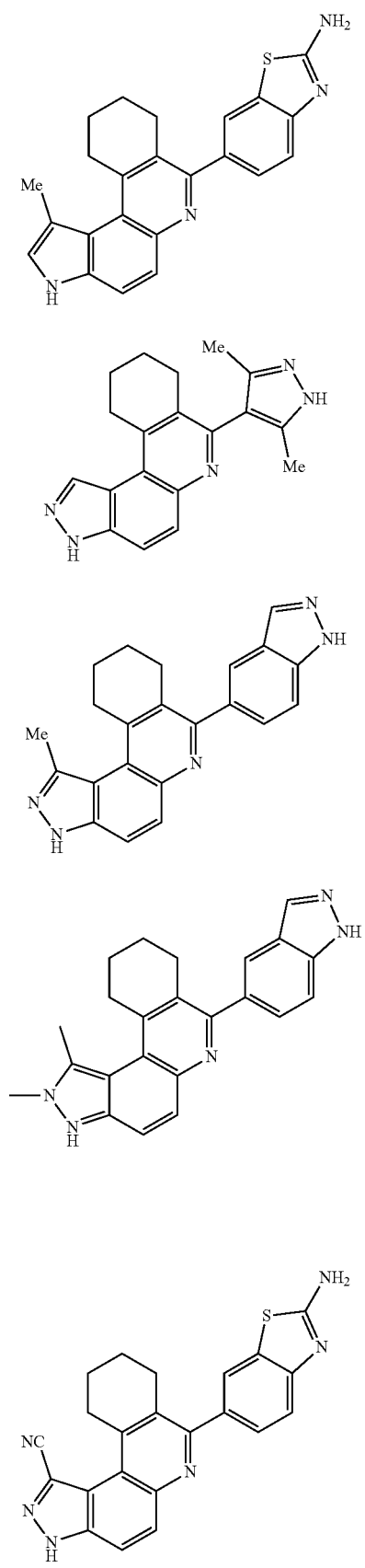
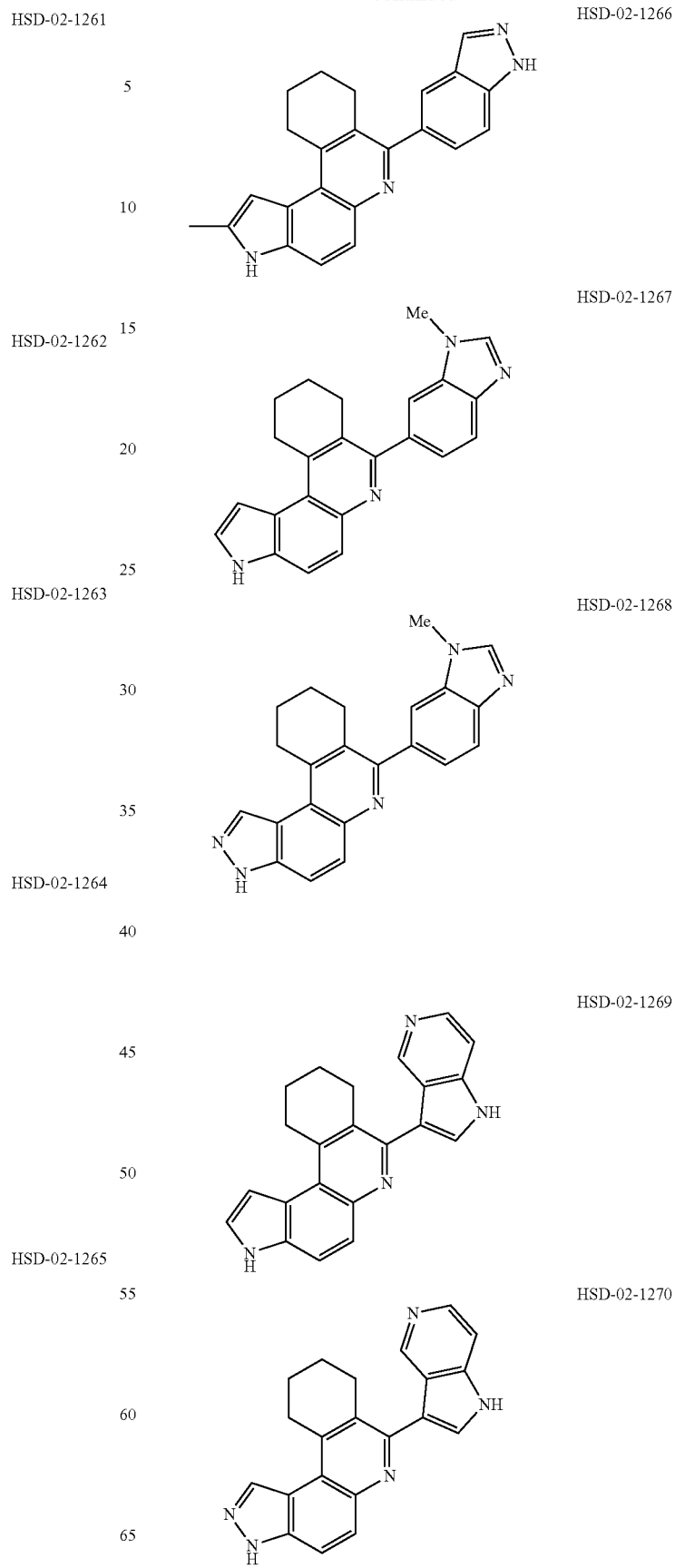

HSD-02-1271
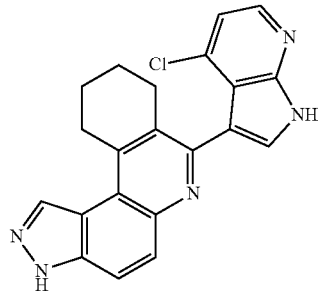
HSD-02-1272
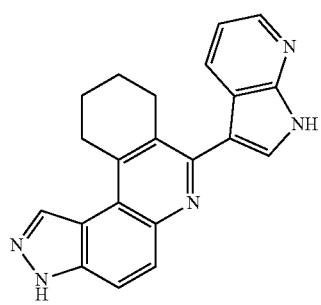
HSD-02-1273
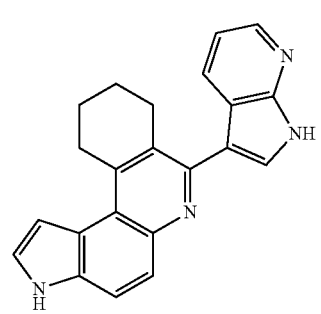
HSD-02-1274
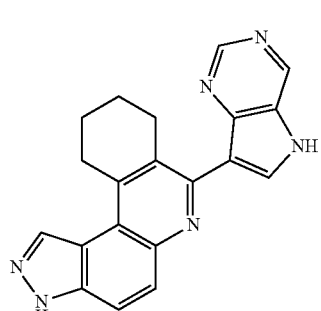
HSD-02-1275
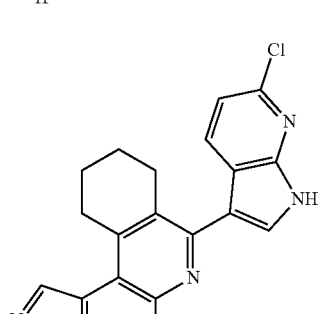
HSD1304
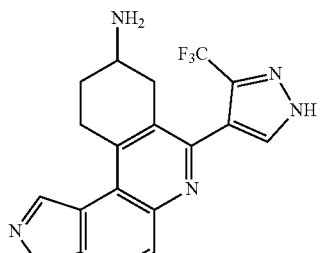
HSD1308
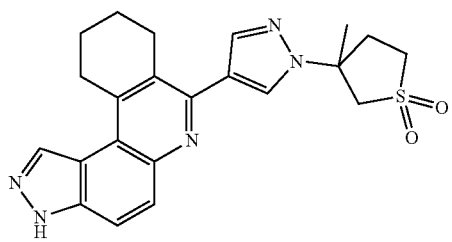
HSD1310
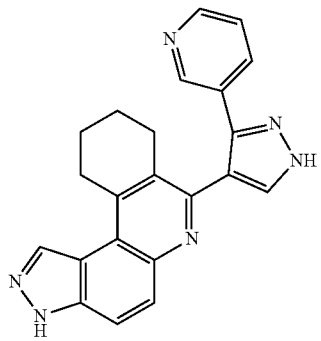
HSD311
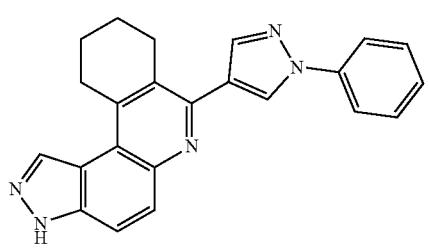
HSD312
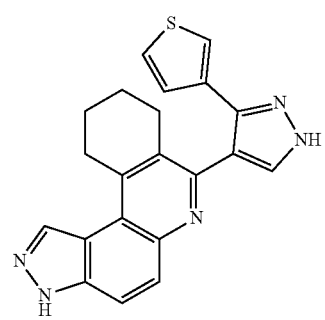

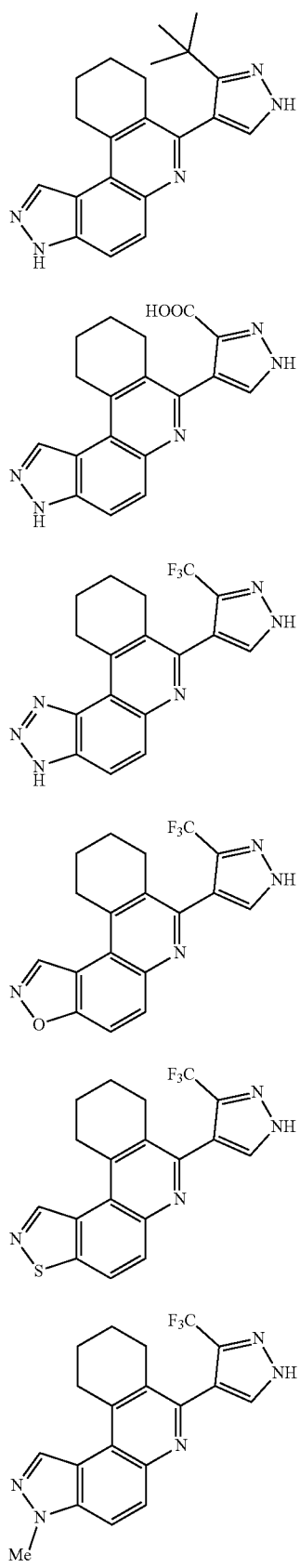
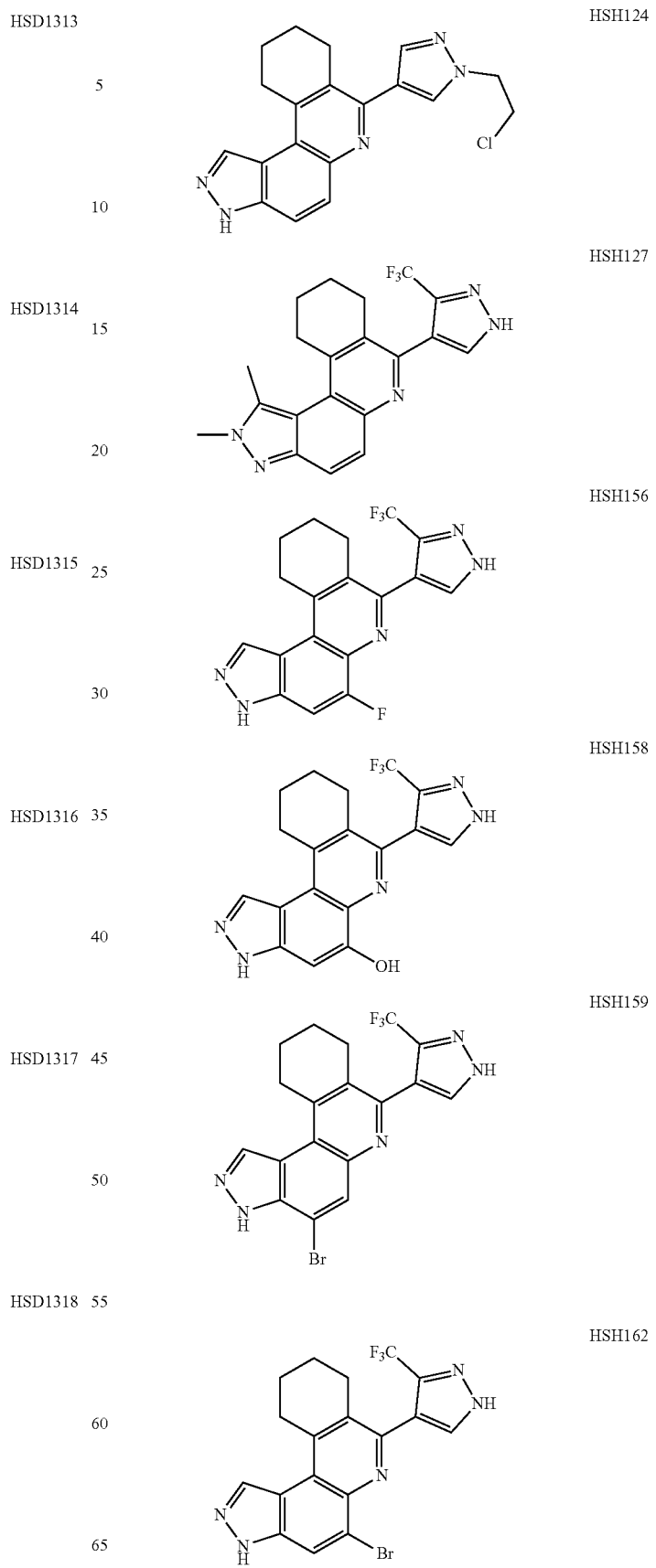

HSH163
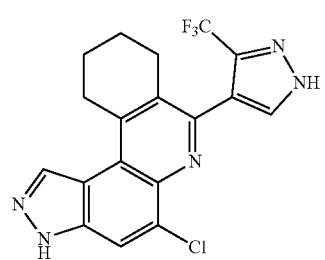
HSH164
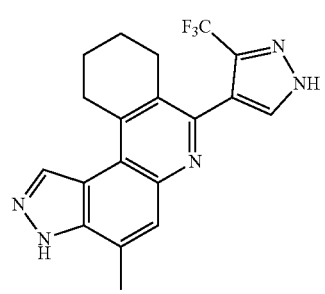
HSH165
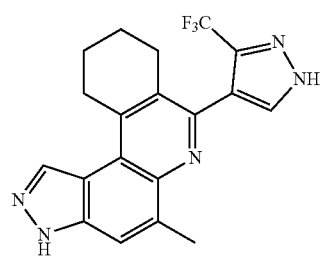
HSD1319
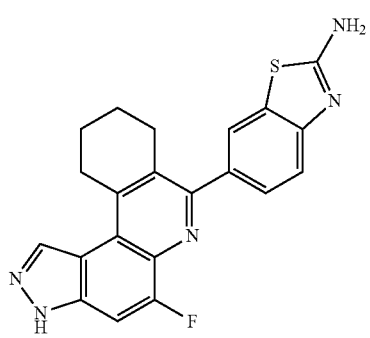
HSD1320
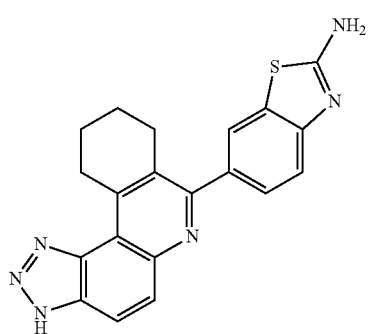
HSD1321
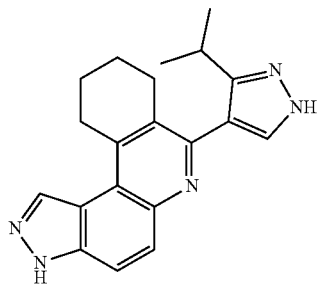
HSD1322
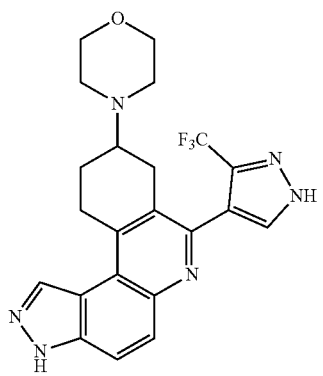
HSD1323
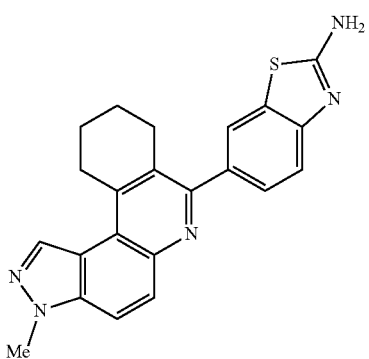
HSD1324
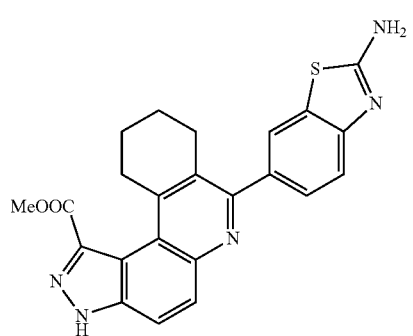

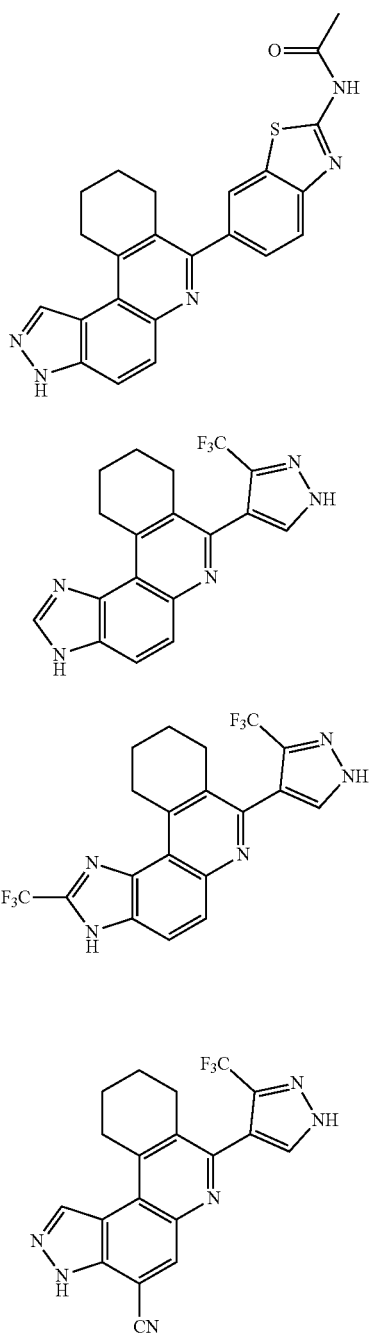
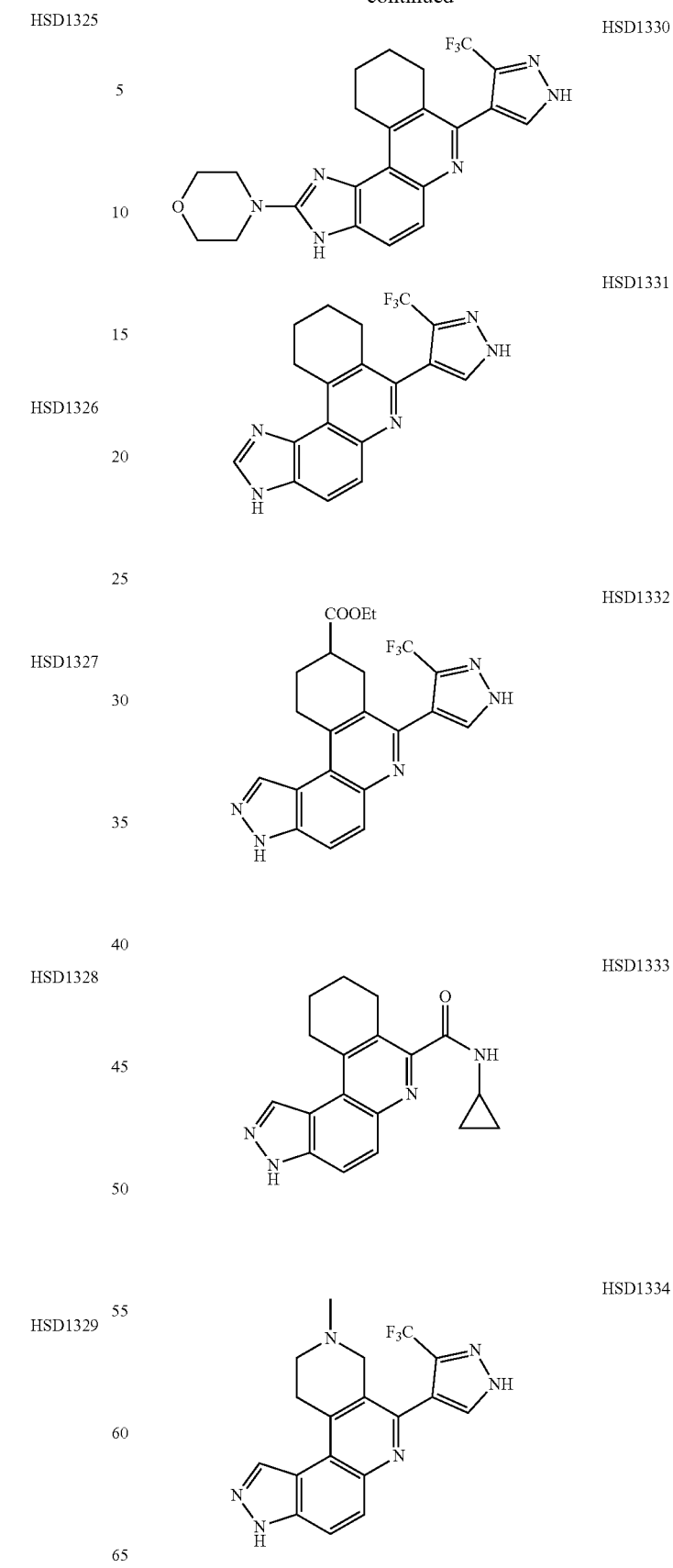

HSD1335
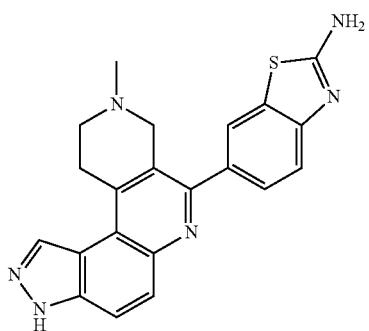
HSD1336
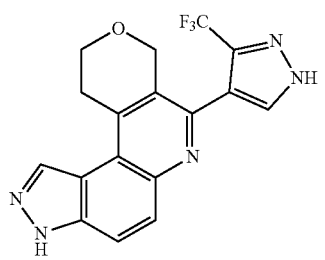
HSD1337
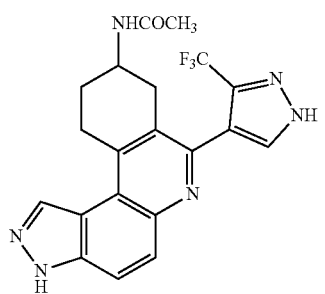
HSD1338
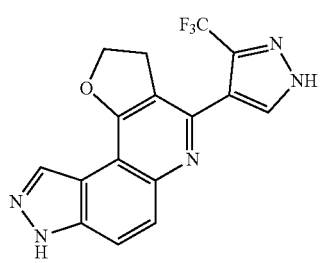
HSD1339
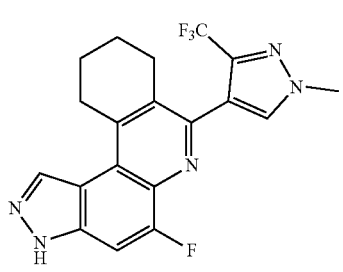
HSD1340
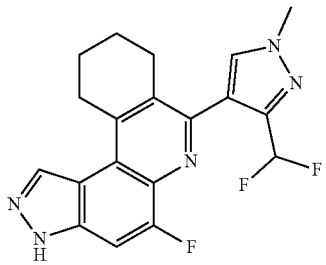
HSD1341
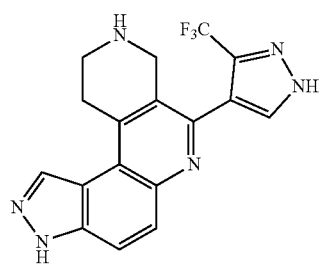
HSD1342
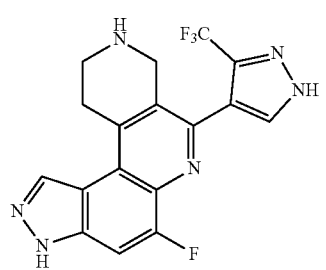
HSD1343
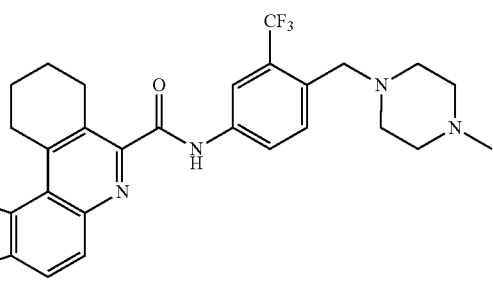
HSD1345
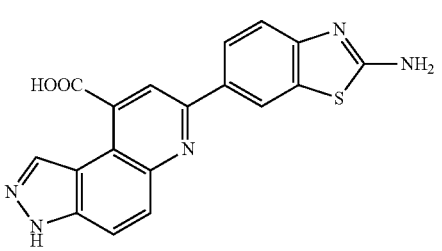
HSD1347
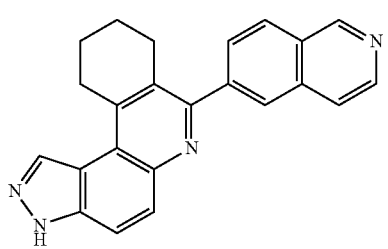

HSD1348
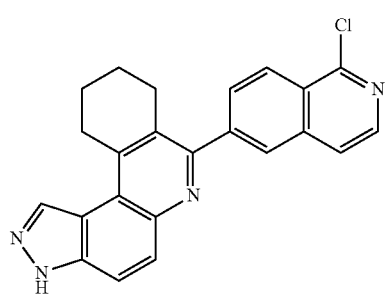
HSD1349
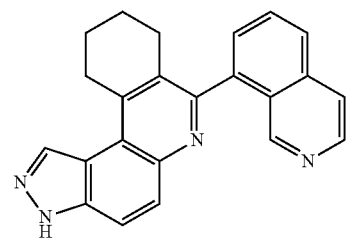
HSD1350
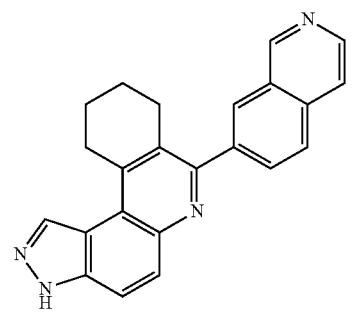
HSD1351
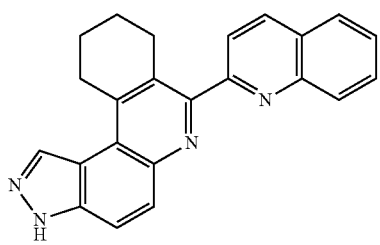
HSD1352
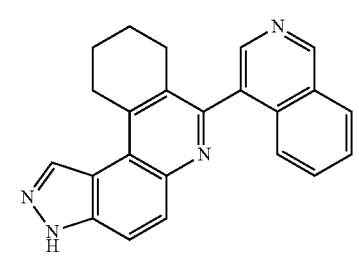
HSD1353B
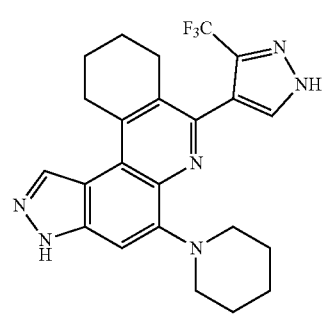
HSD1355
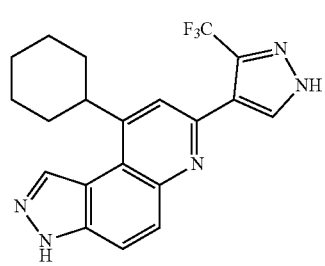
HSD1356
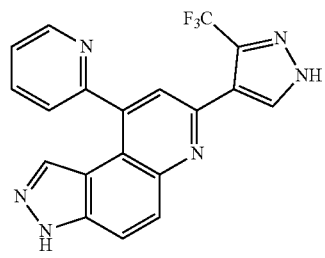
HSD1357
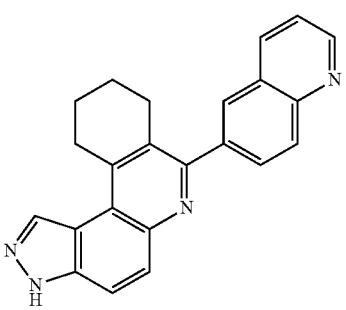
HSD1358
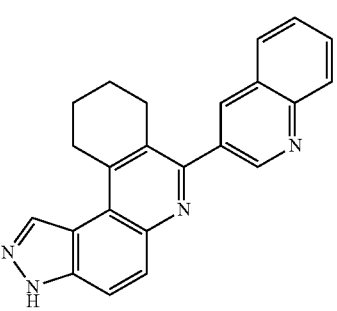
HSD1359
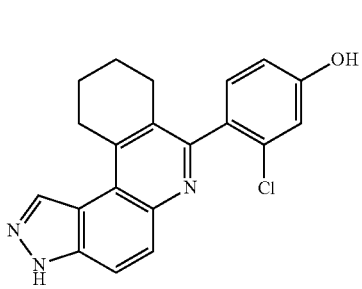

HSD1360 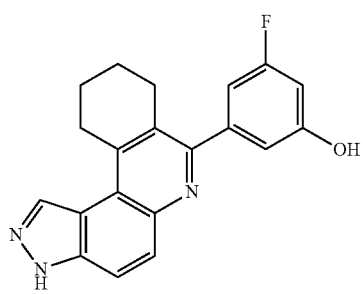
HSD1361 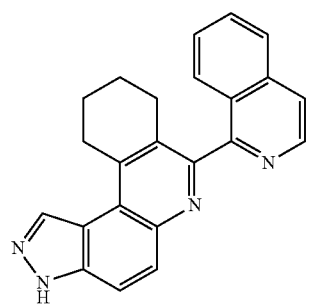
HSD1362 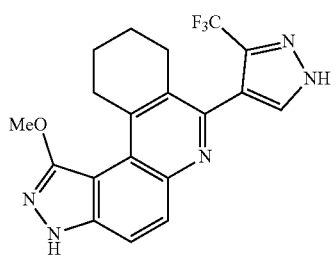
HSD1363 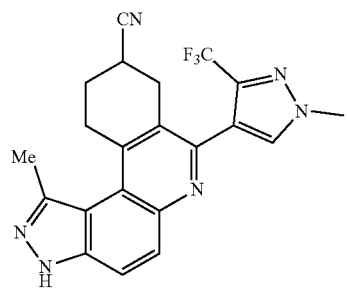
HSD1364 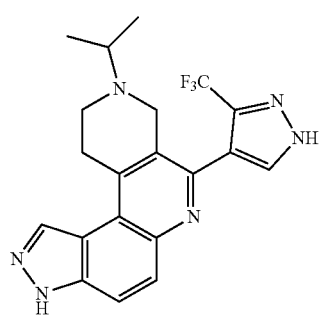
HSD1365 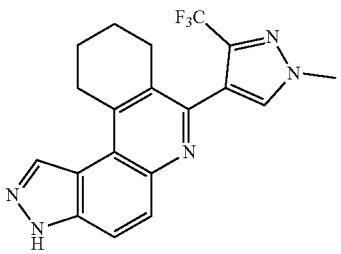
HSD1366 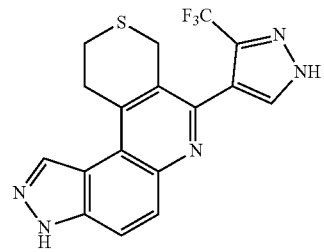
HSD1368 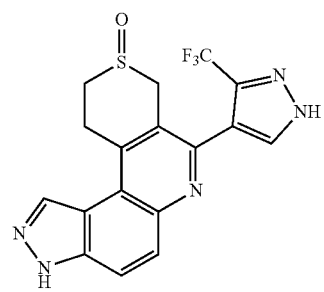
HSD1369 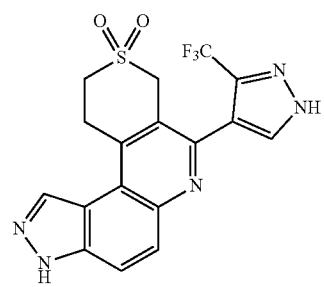
HSD1370 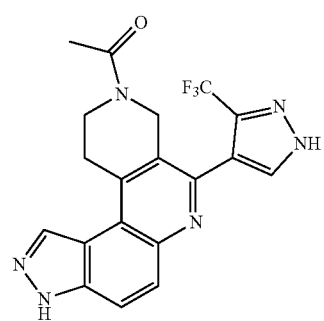

HSD1371 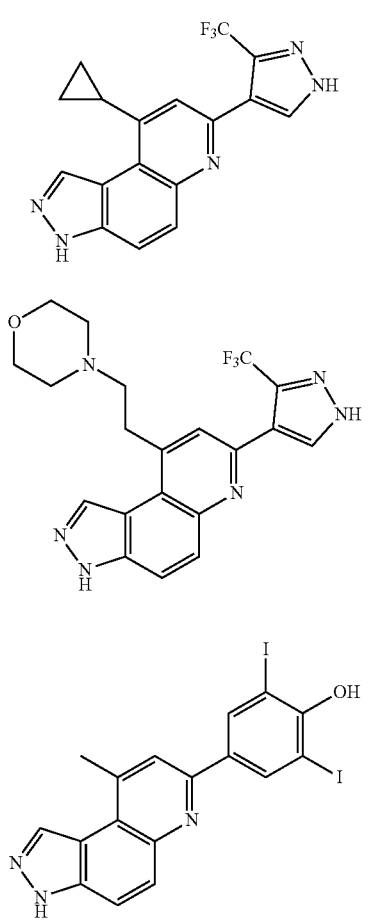
HSD1372
HSD1373
HSD1374
HSD1375
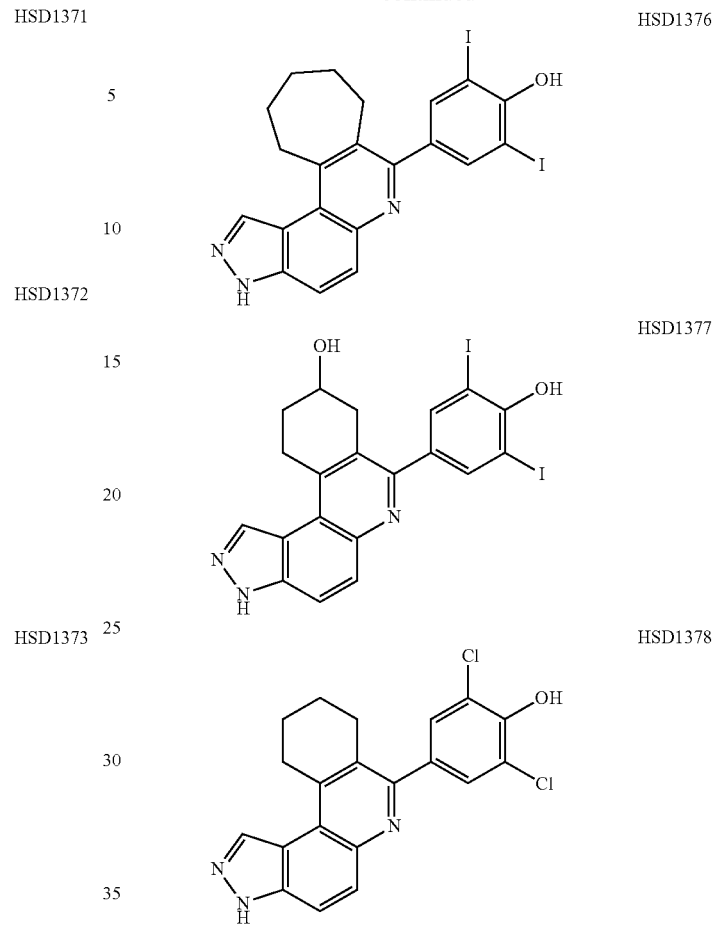
HSD1376
HSD1377
HSD1378
HSD1379
HSD1380

HSD1381
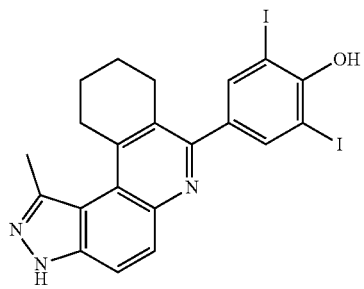
HSD1382
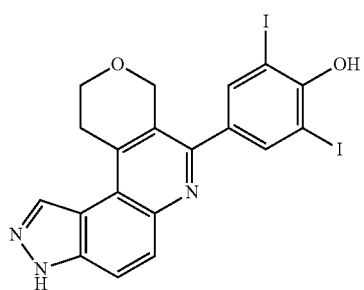
HSD1383
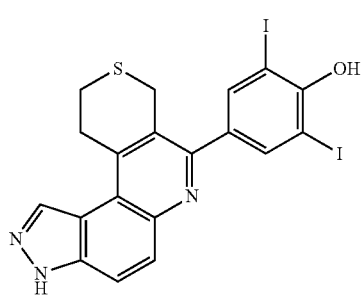
HSD1384
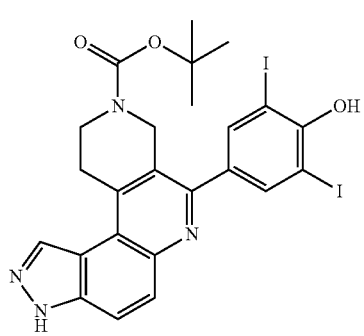
HSH-2-52
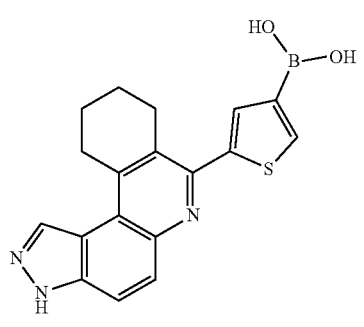
HSD1385
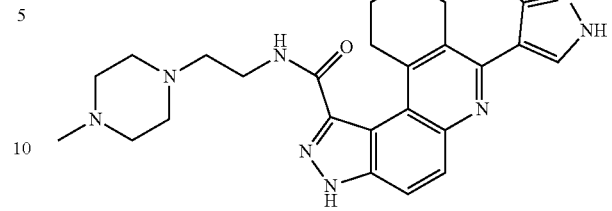
HSD1386
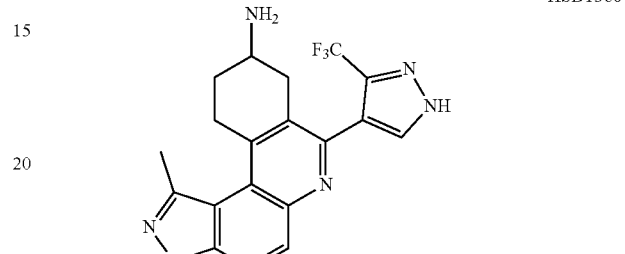
HSD1387
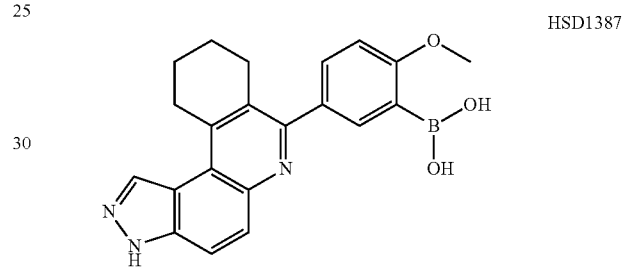
HSD1388
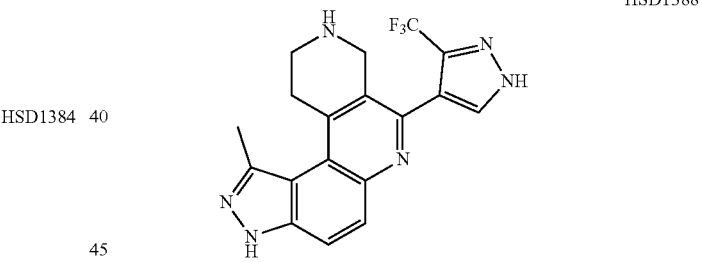
HSD1389
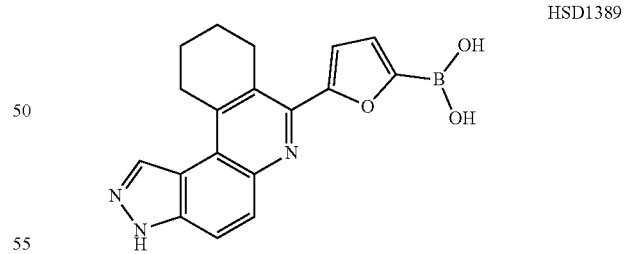
HSD1390
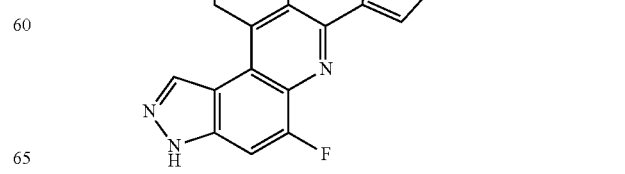

-continued
HSD1391
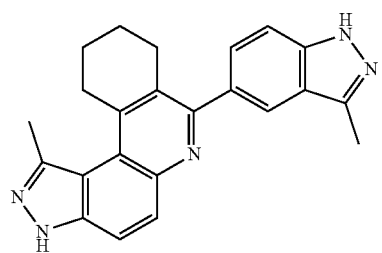
HSD1392
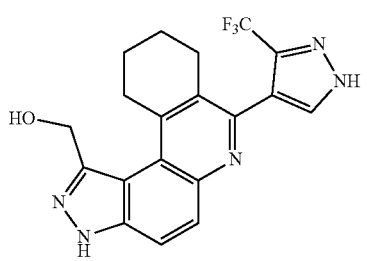
HSD1394
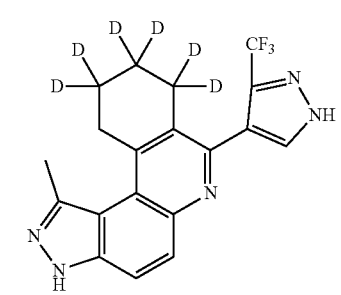
HSD1395
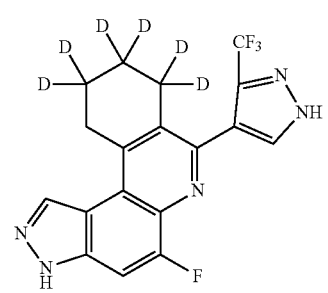
HSD1396
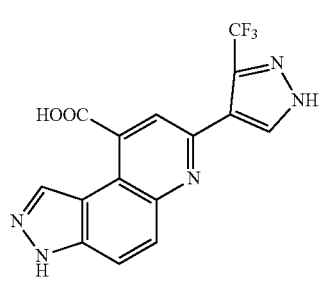
-continued
HSD1397
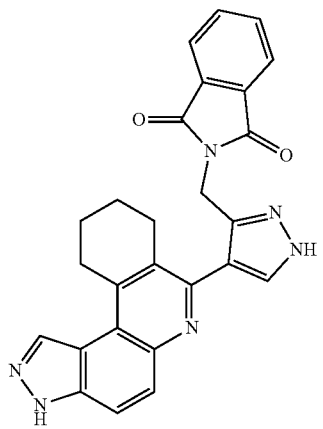
HSD1398
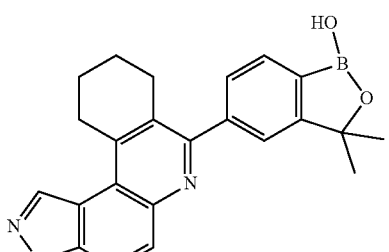
HSD1399
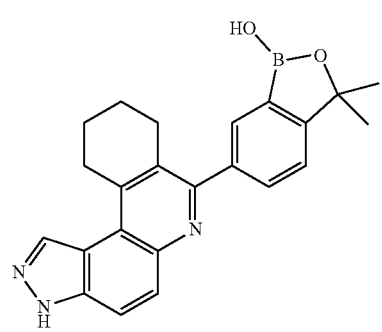
HSD1400
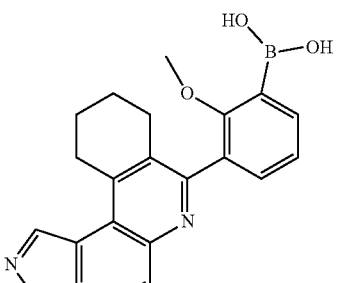
HSD1401
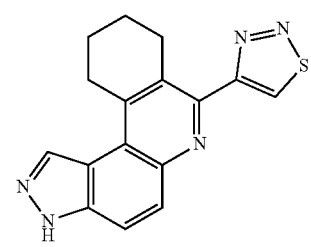

-continued
HSD1402
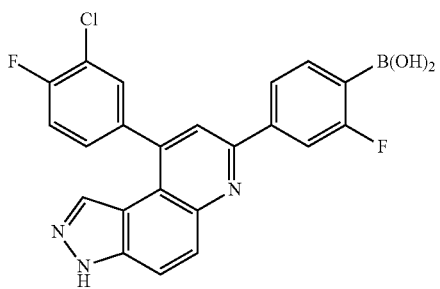
HSD1403
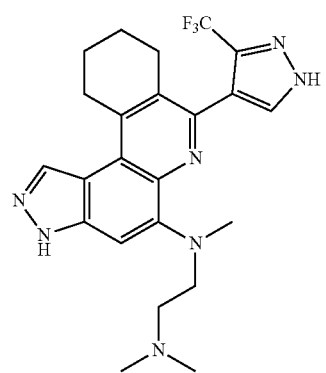
HSGN46
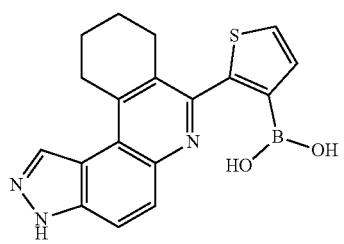
HSGN16
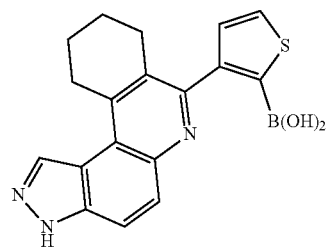
HSD1404
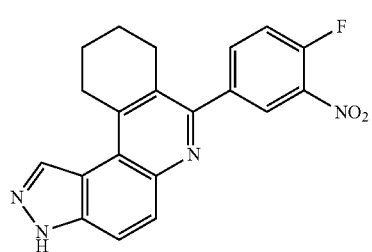
-continued
HSD1405
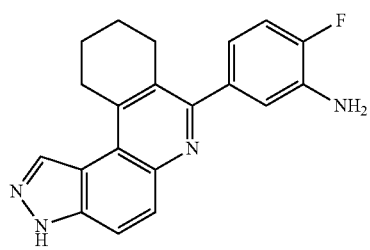
HSD1406
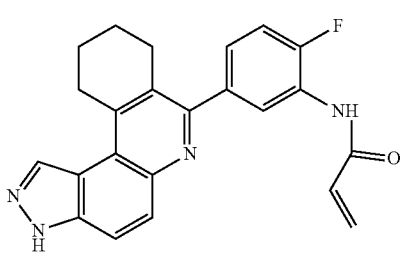
HSD1407
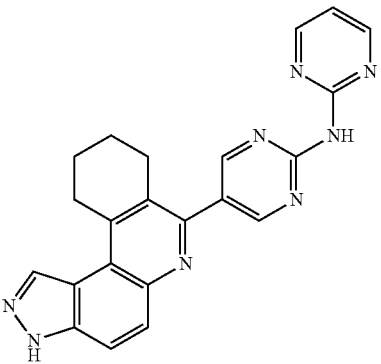
HSD1409
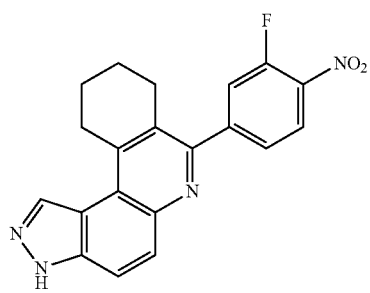
HSD1410
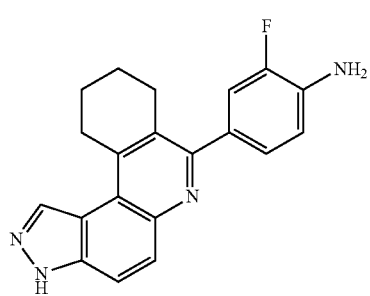

127
-continued
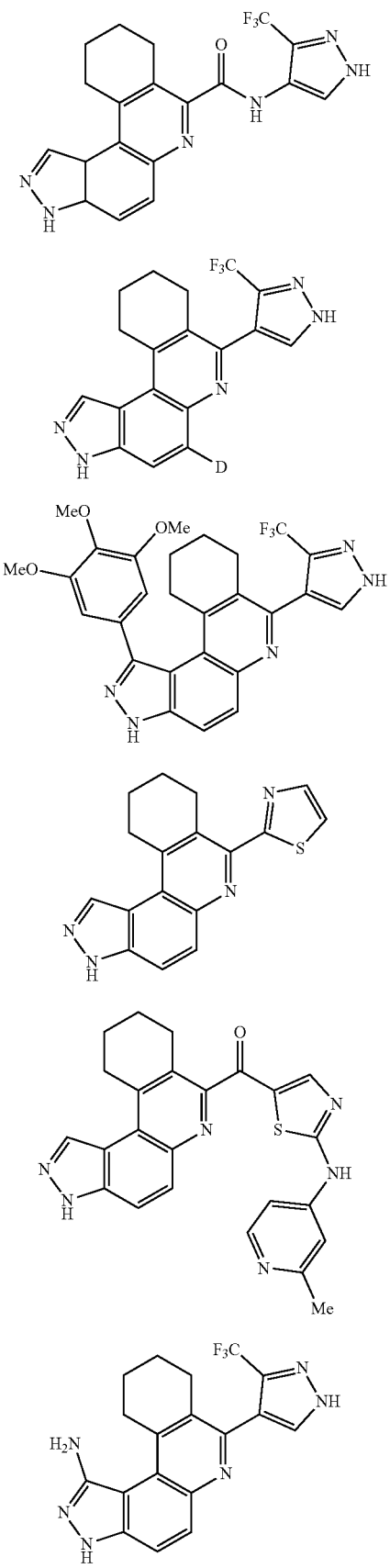
128
-continued
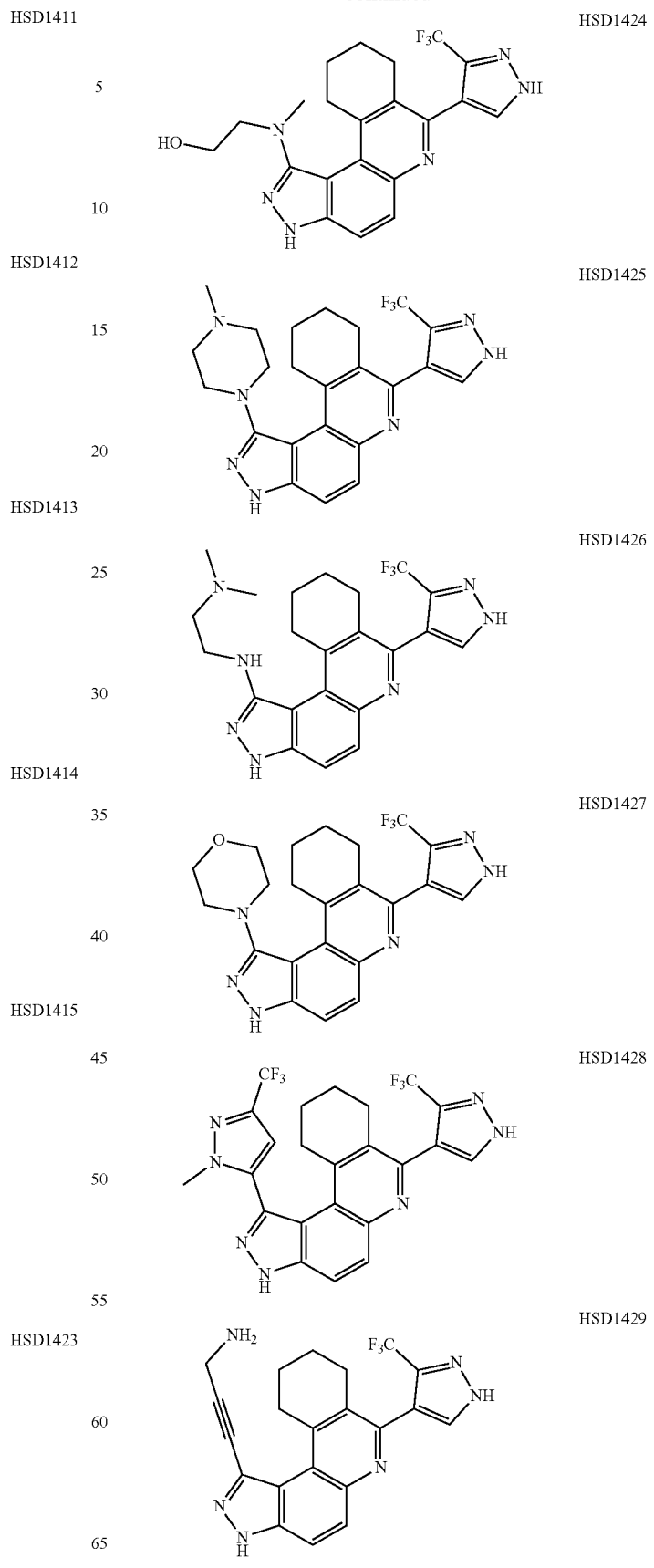

HSD1430
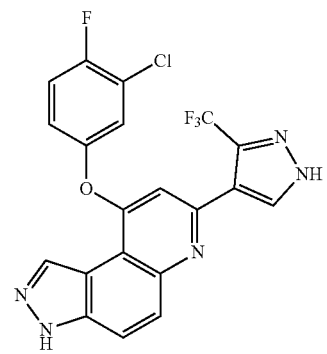
HSD1431
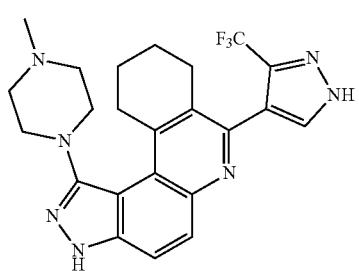
HSD1432
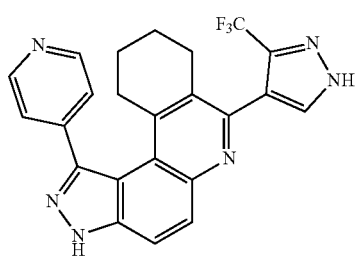
HSD1433
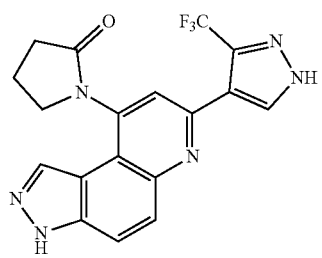
HSD1434
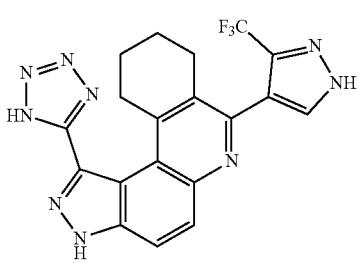
HSD1435
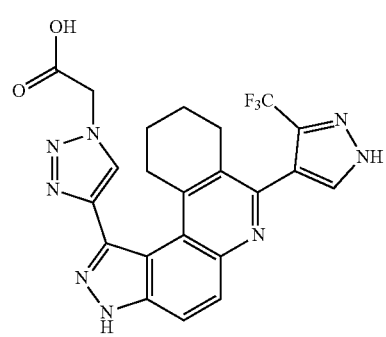
HSD1436
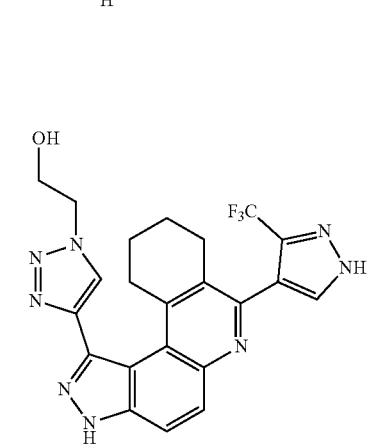
HSD1437
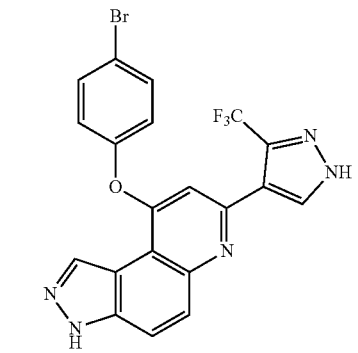
HSD1438
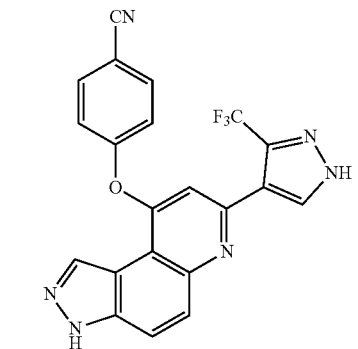

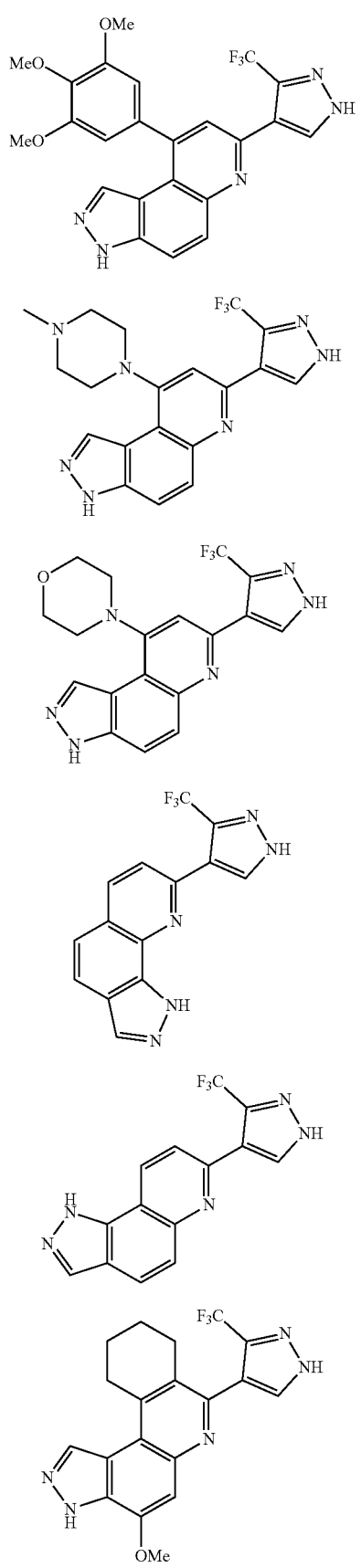
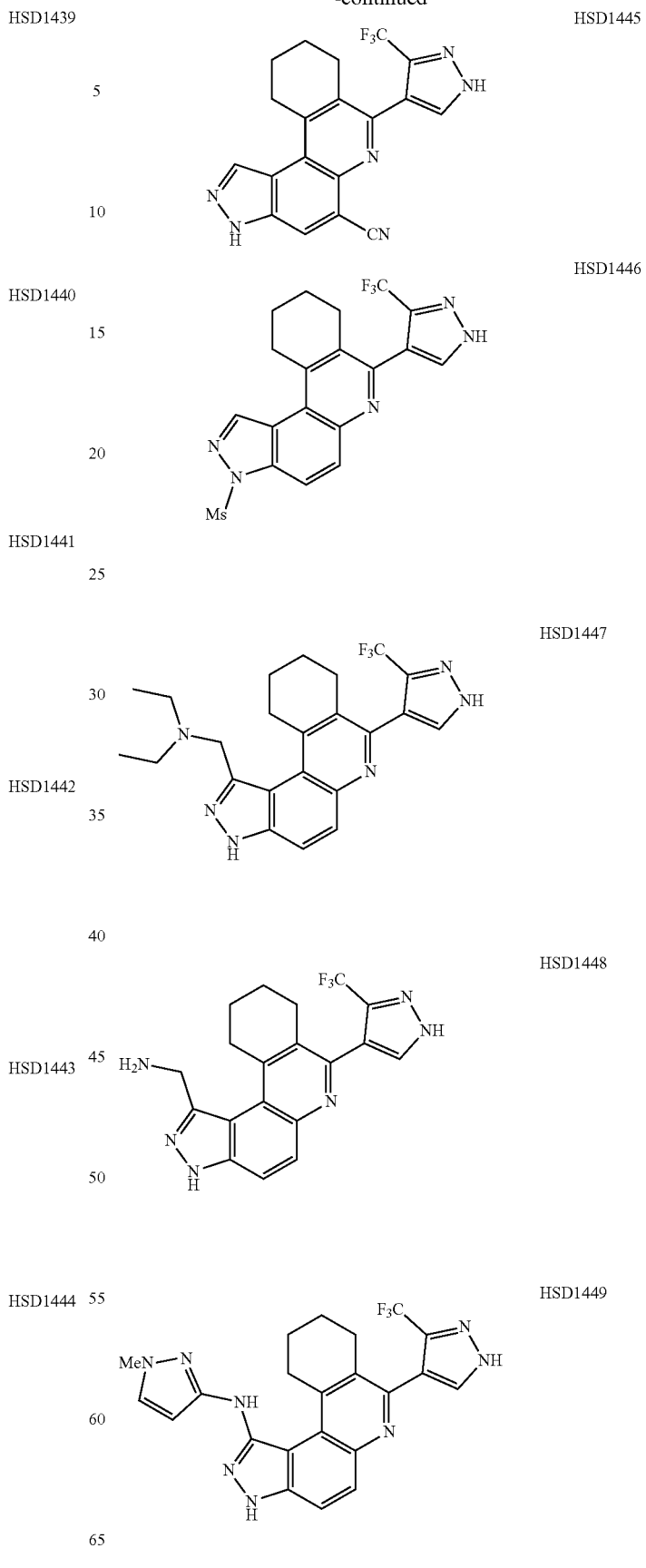

HSD1450 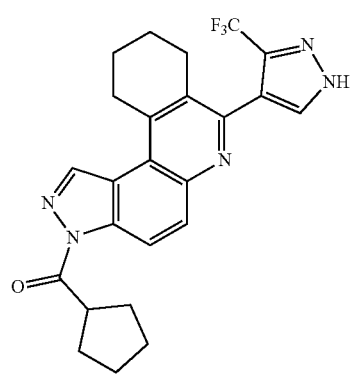
HSD1451 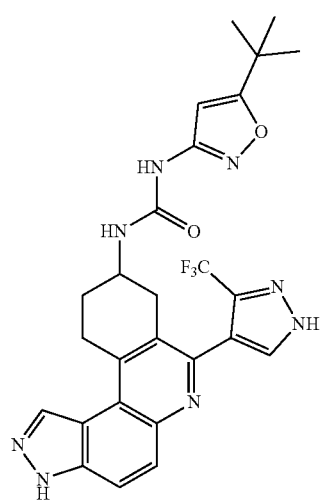
HSD1452 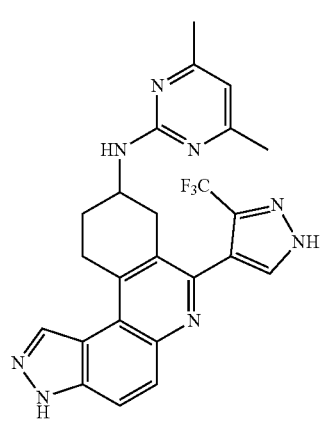
HSD1453 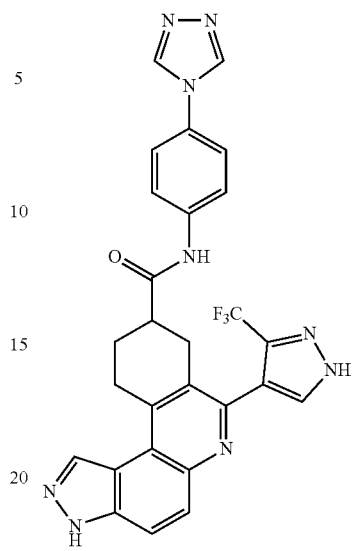
HSD1454 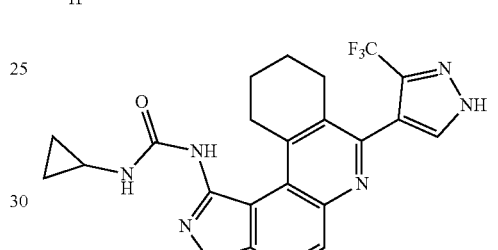
HSD1584 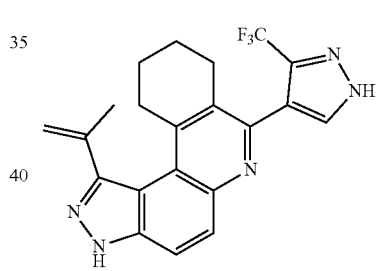
HSD1454 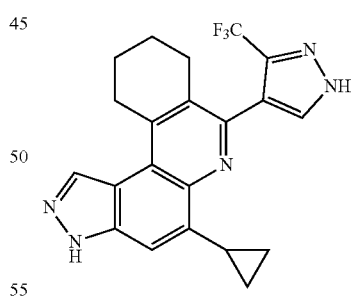
HSD1455 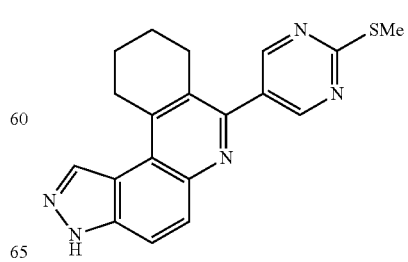

HSD1456
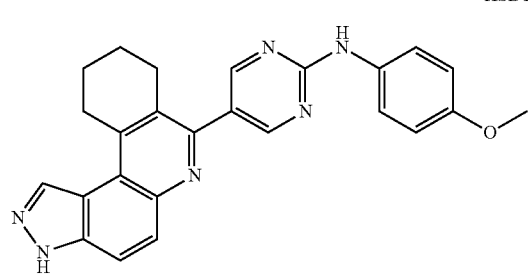
HSD1457
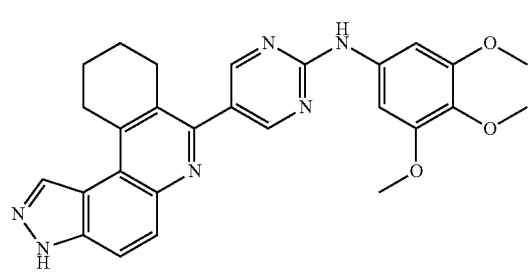
HSD1458
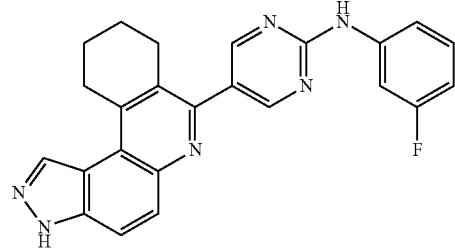
HSD1459
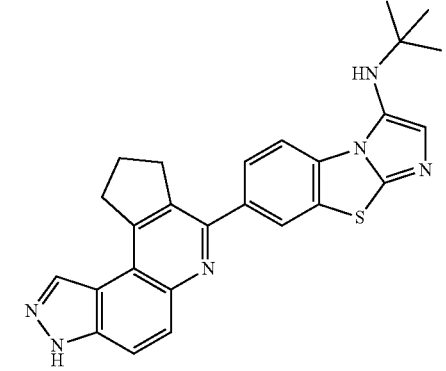
HSD1460
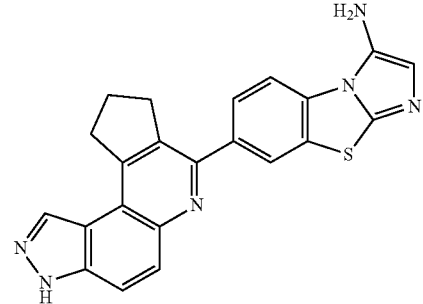
HSD1461
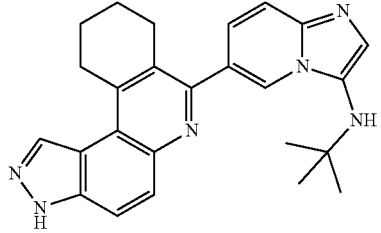
HSD1462
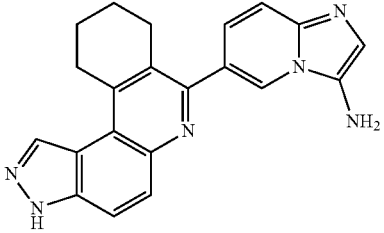
HSD1463
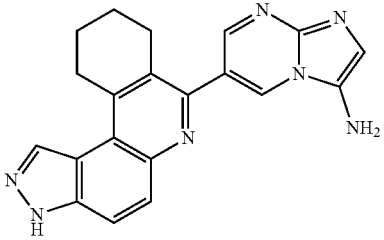
HSD1464
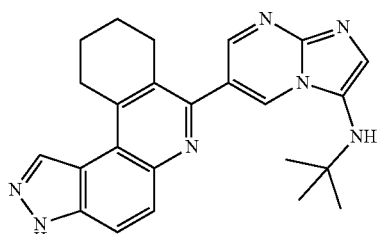
HSD1465
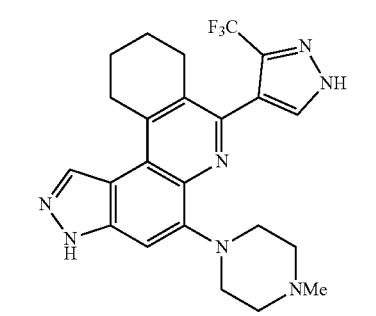
HSD1466
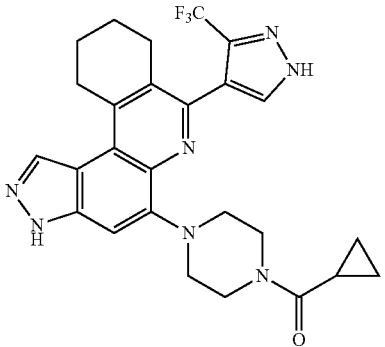

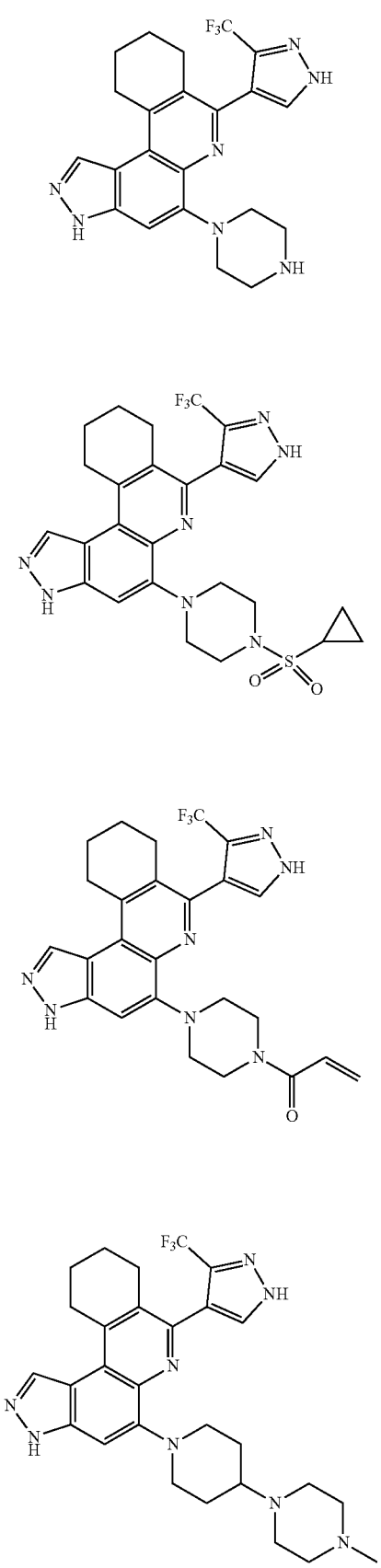
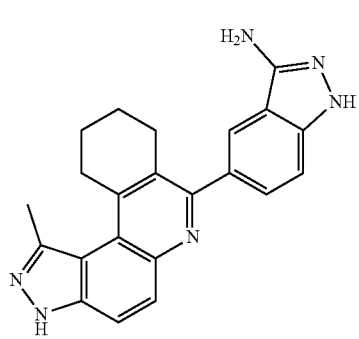
HSD1467
HSD1468
HSD1469
HSD1470
HSD1471
HSD1472
HSD1473
HSD1474
HSD1475

HSD1476 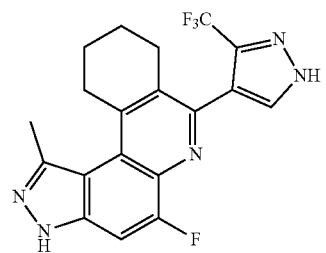
HSD1477 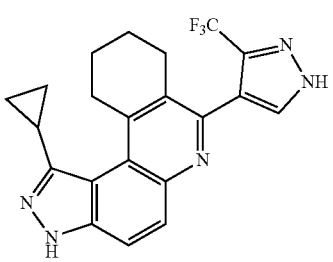
HSD1478 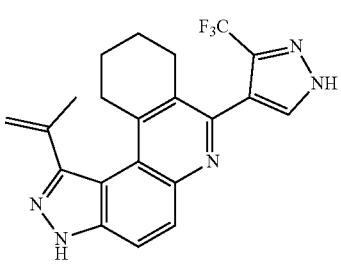
HSD1479 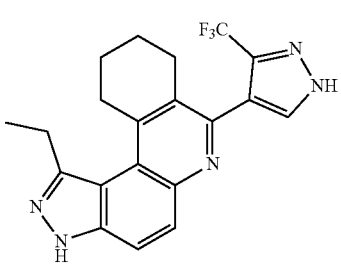
HSD1480 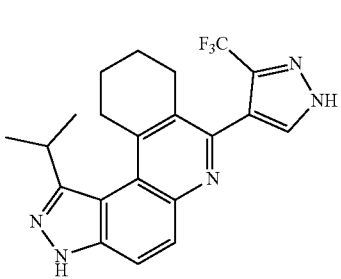
HSD1481 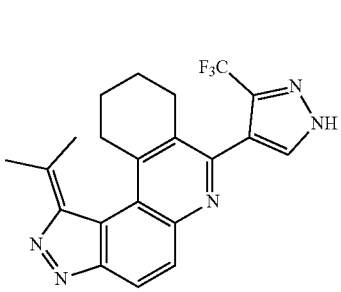
HSD1482 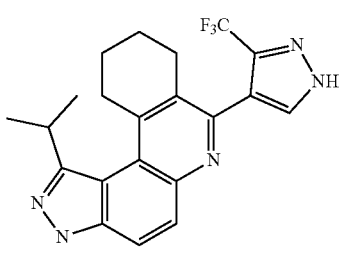
HSD1483 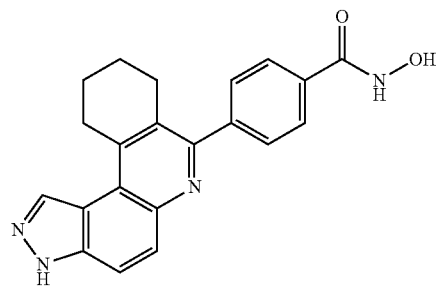
HSD1484 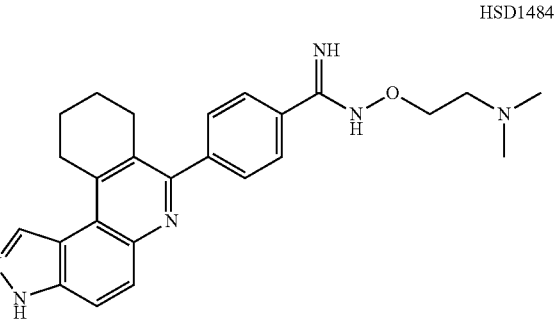
HSD1485 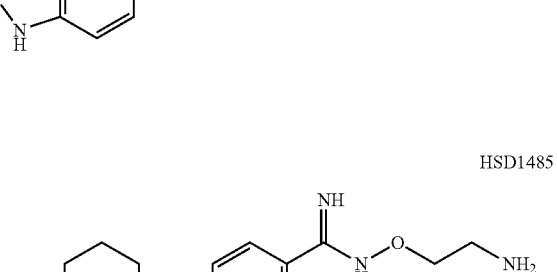
HSD1486 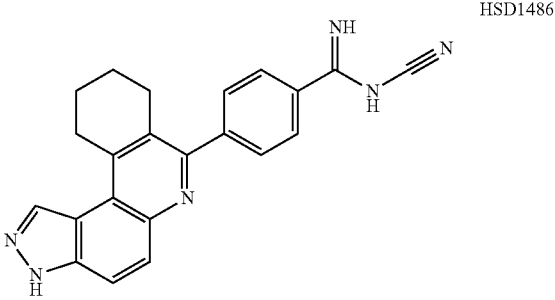

HSD1487
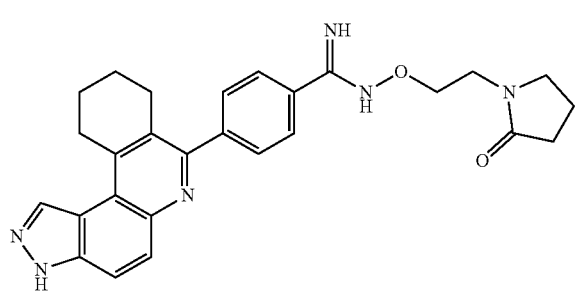
HSD1488
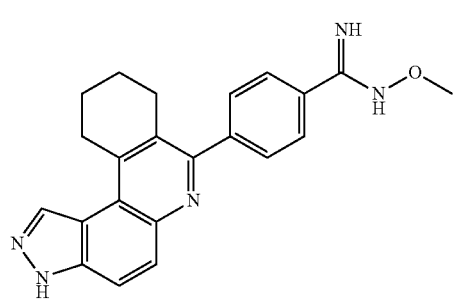
HSD1489
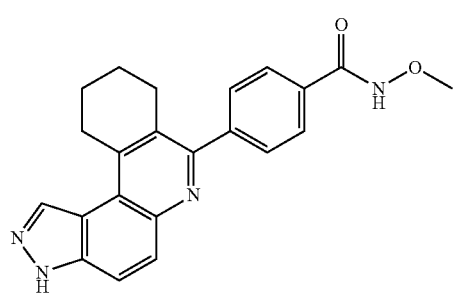
HSD1490
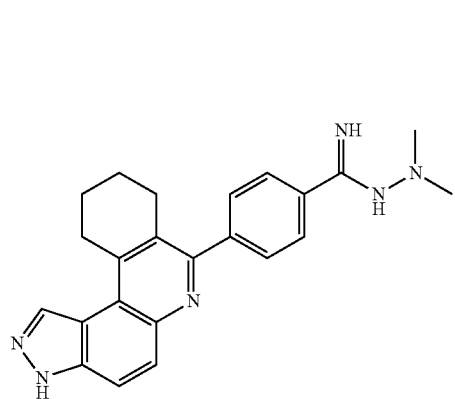
HSD1491
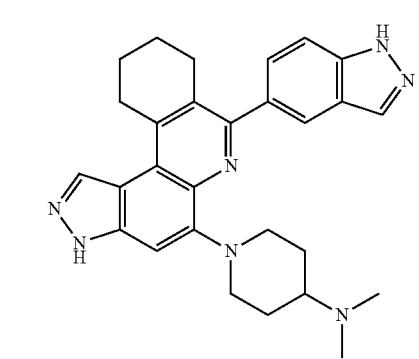
HSD1492
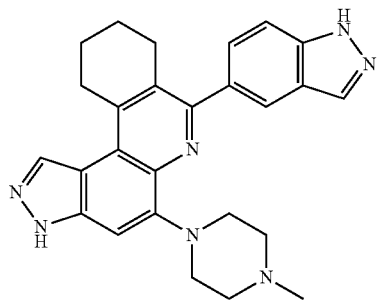
HSD1493
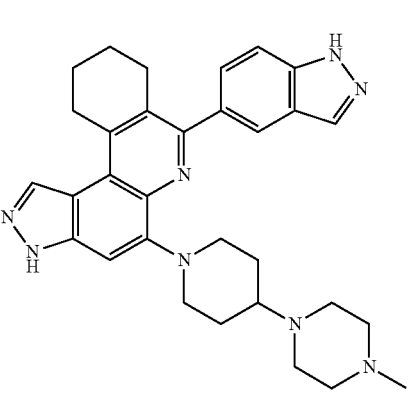
HSD1494
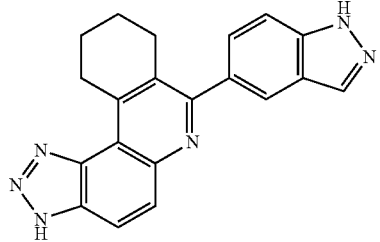
HSD1495
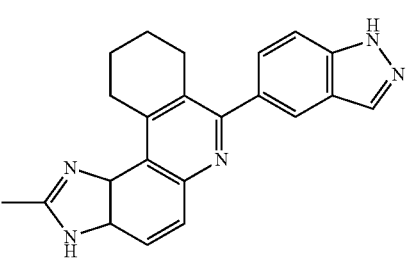
HSD1496
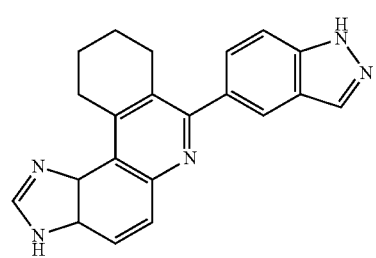

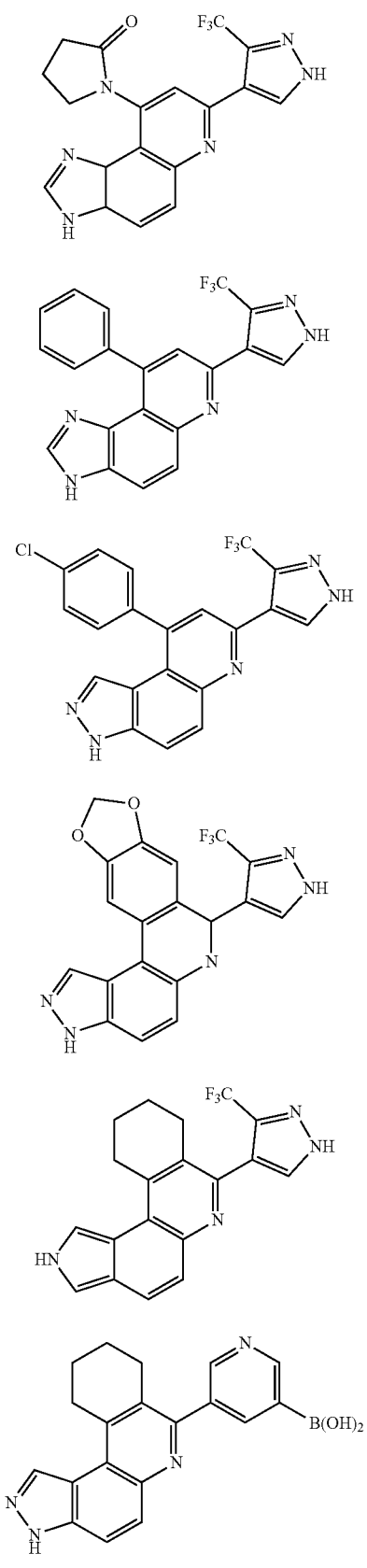
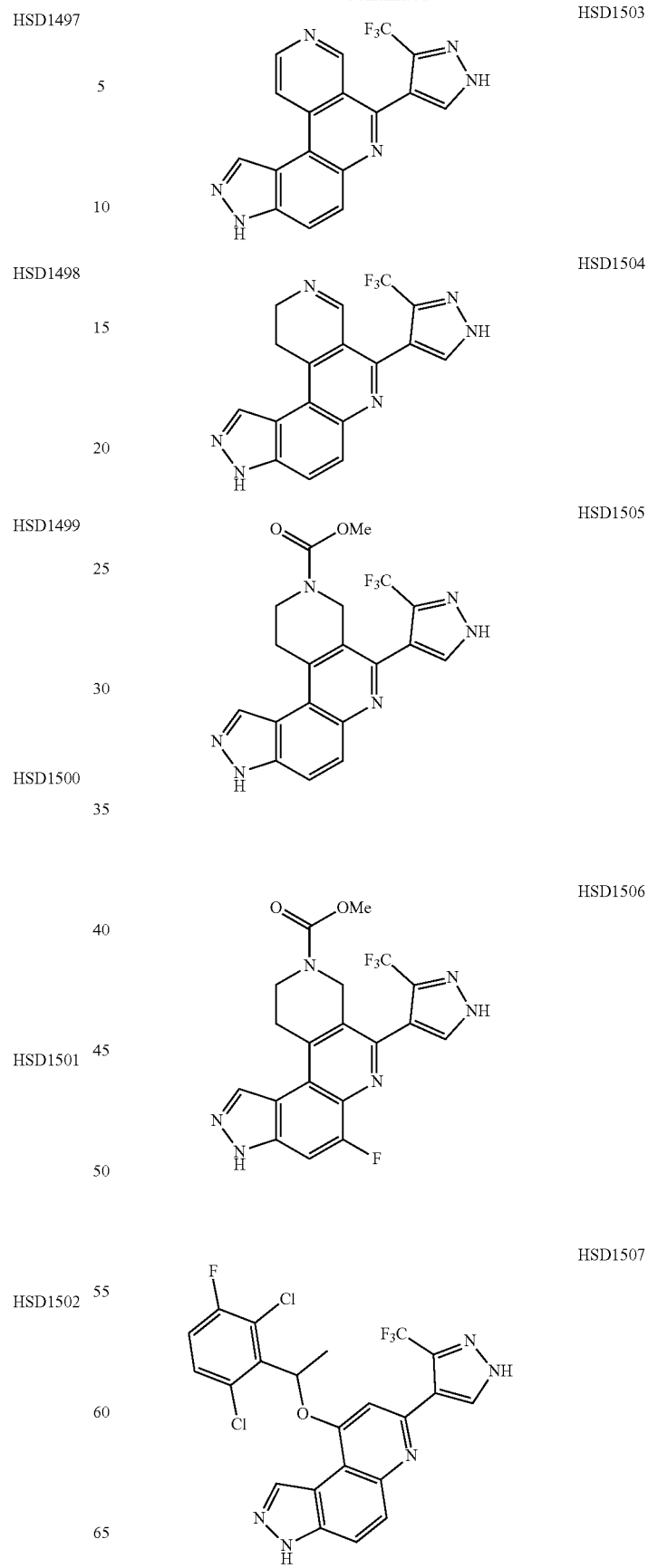

HSD1508 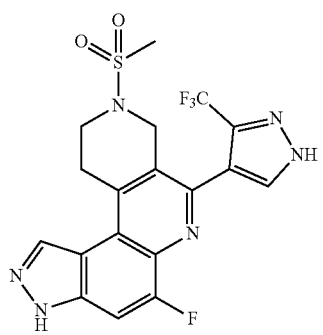
HSD1509 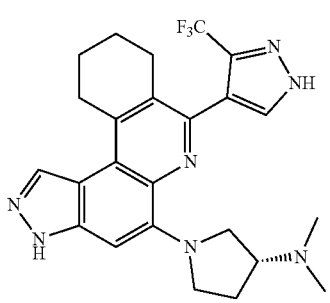
HSD1510 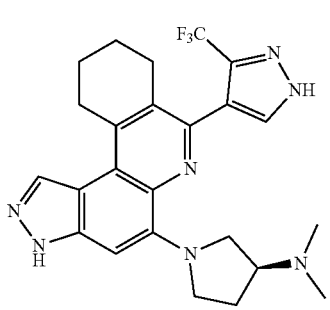
HSD1511 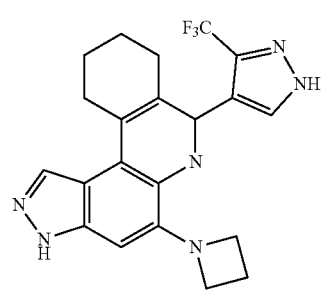
HSD1512 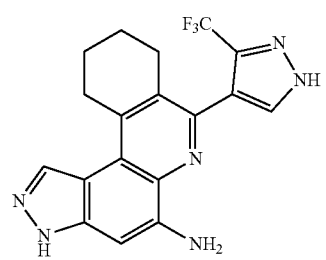
HSD1512 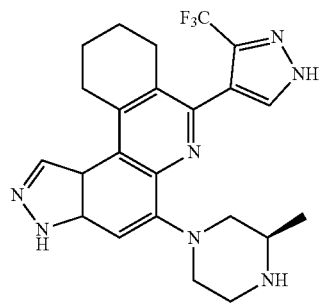
HSD1513 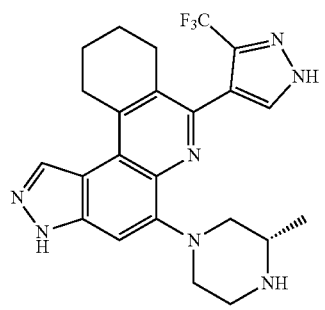
HSD1514 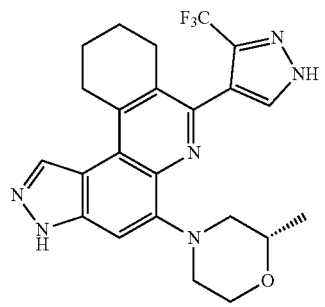
HSD1515 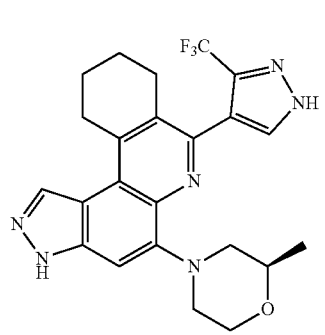
HSD1516 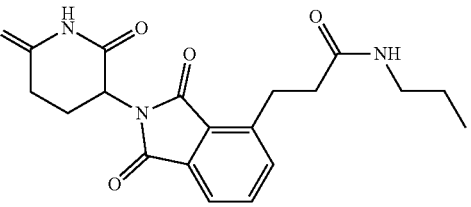

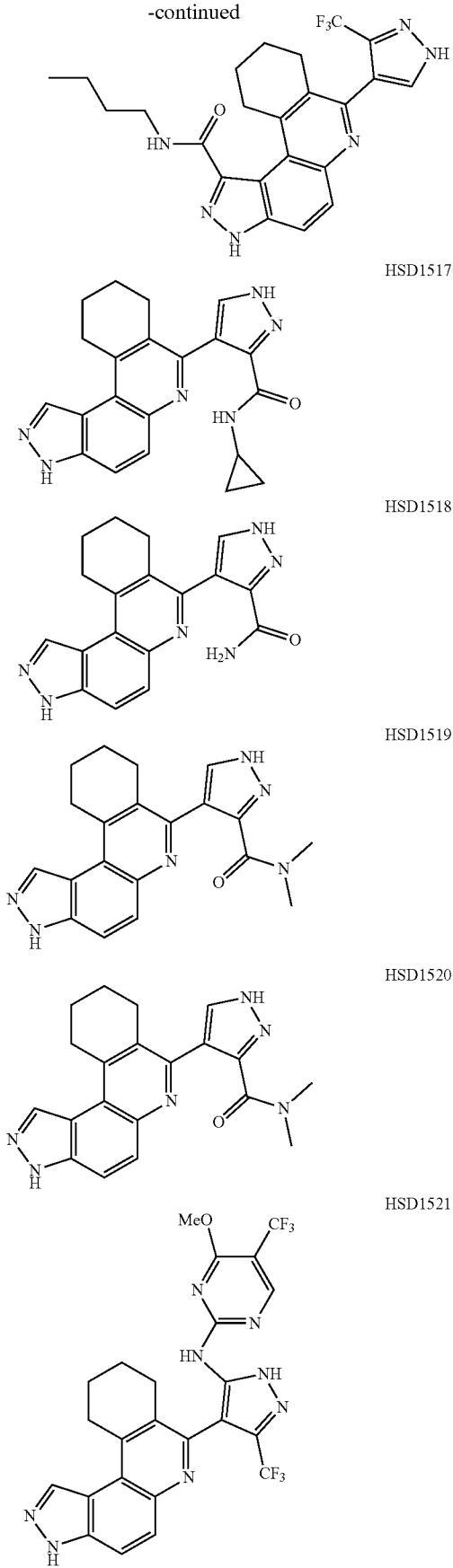
HSD1517
HSD1518
HSD1519
HSD1520
HSD1521
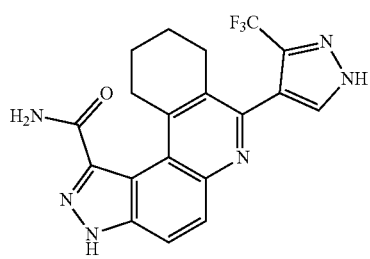
HSD1522
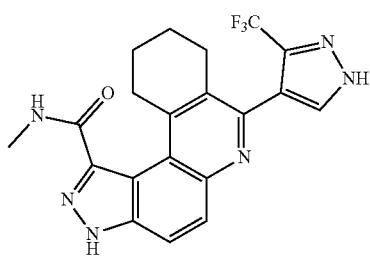
HSD1523
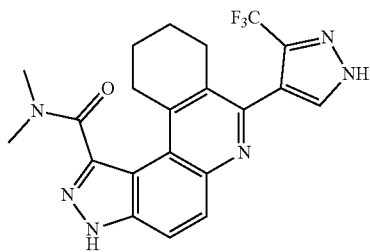
HSD1524
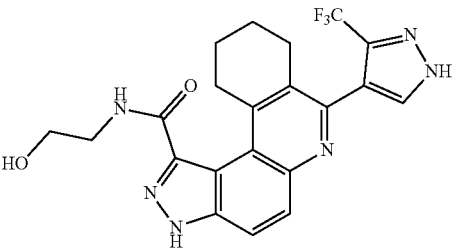
HSD1525
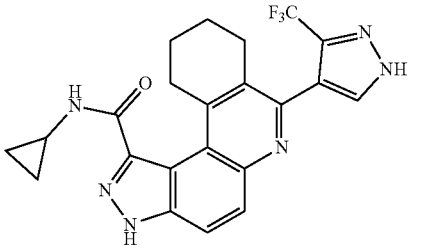
HSD1526
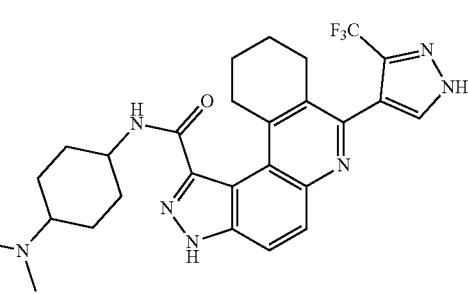
HSD1527

HSD1528
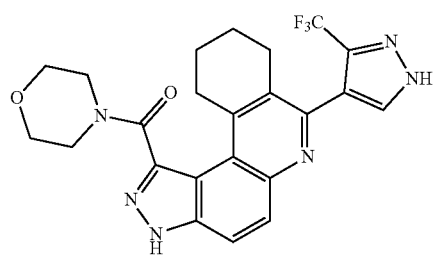
HSD1534
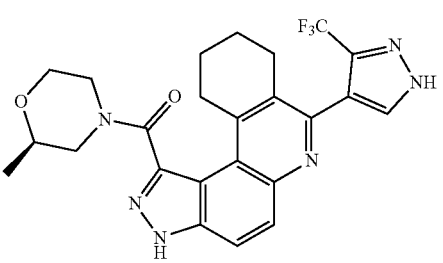
HSD1529
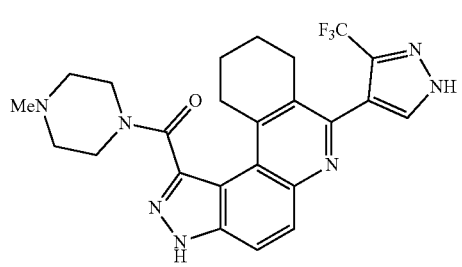
HSD1535
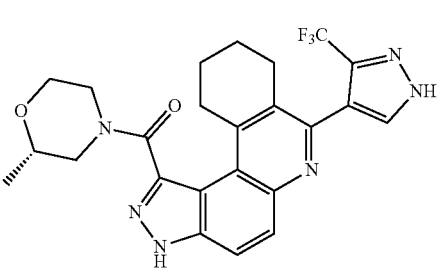
HSD1530
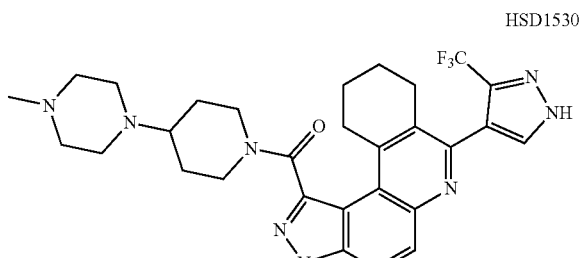
HSD1536
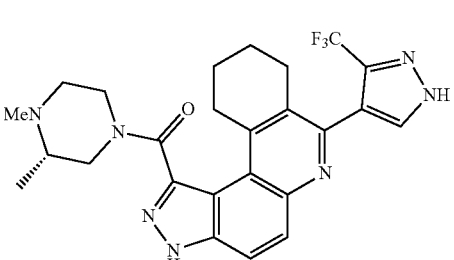
HSD1531
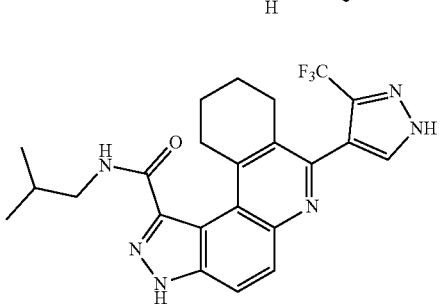
HSD1537
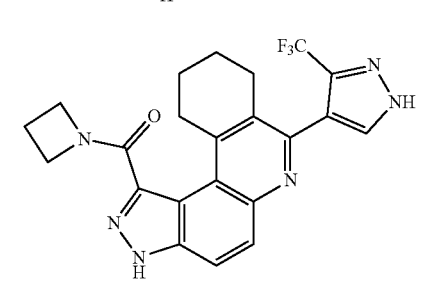
HSD1532
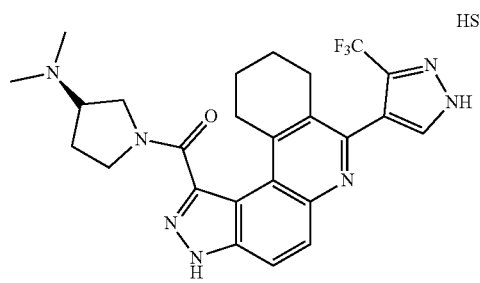
HSD1538
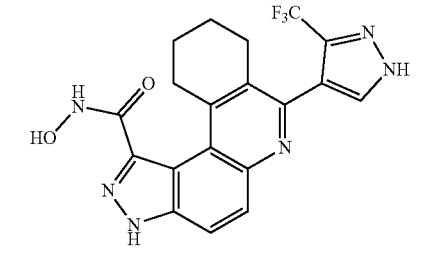
HSD1533
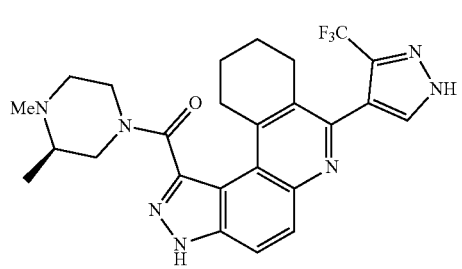
HSD1539
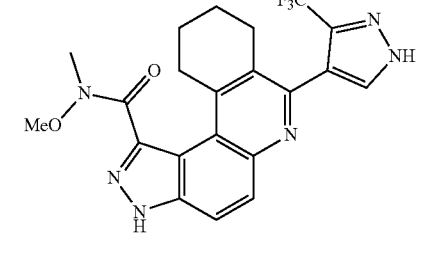

HSD1540
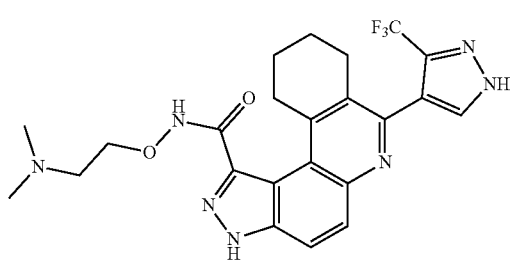
HSD1546
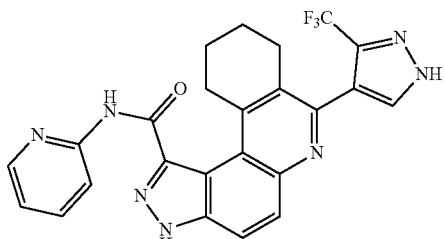
HSD1541
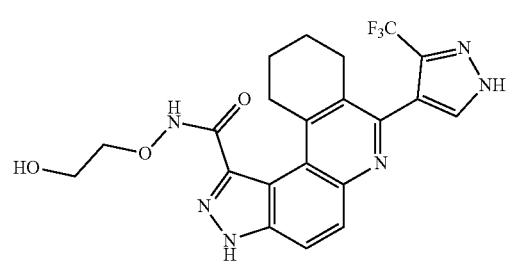
HSD1547
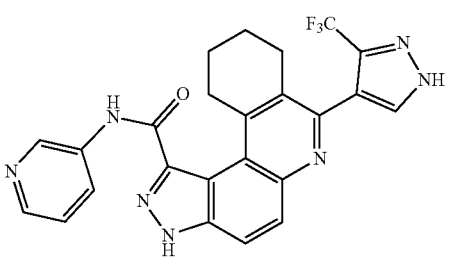
HSD1542
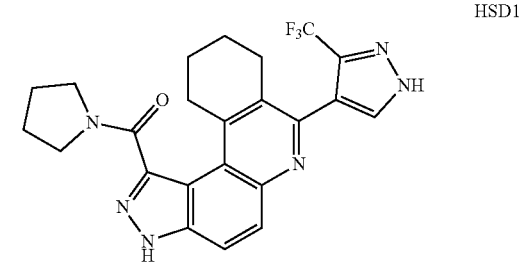
HSD1548
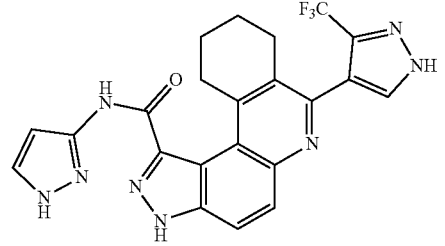
HSD1543
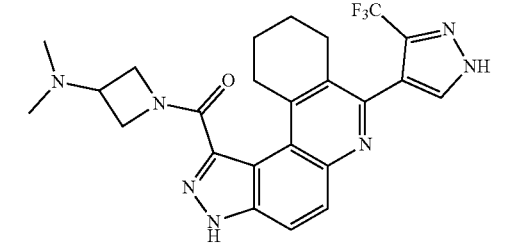
HSD1549
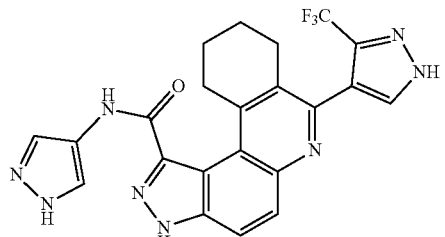
HSD1544
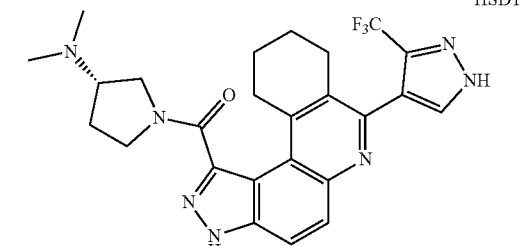
HSD1550
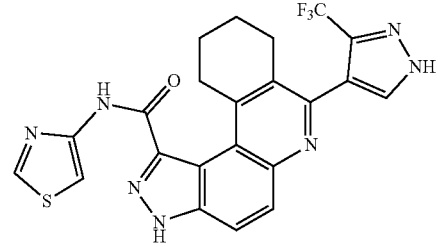
HSD1545
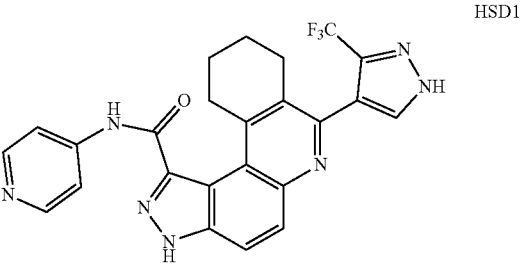
HSD1551
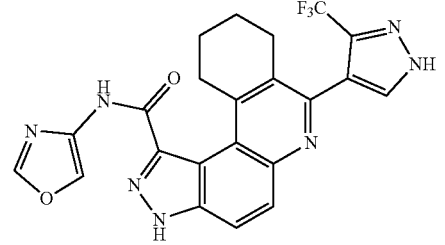

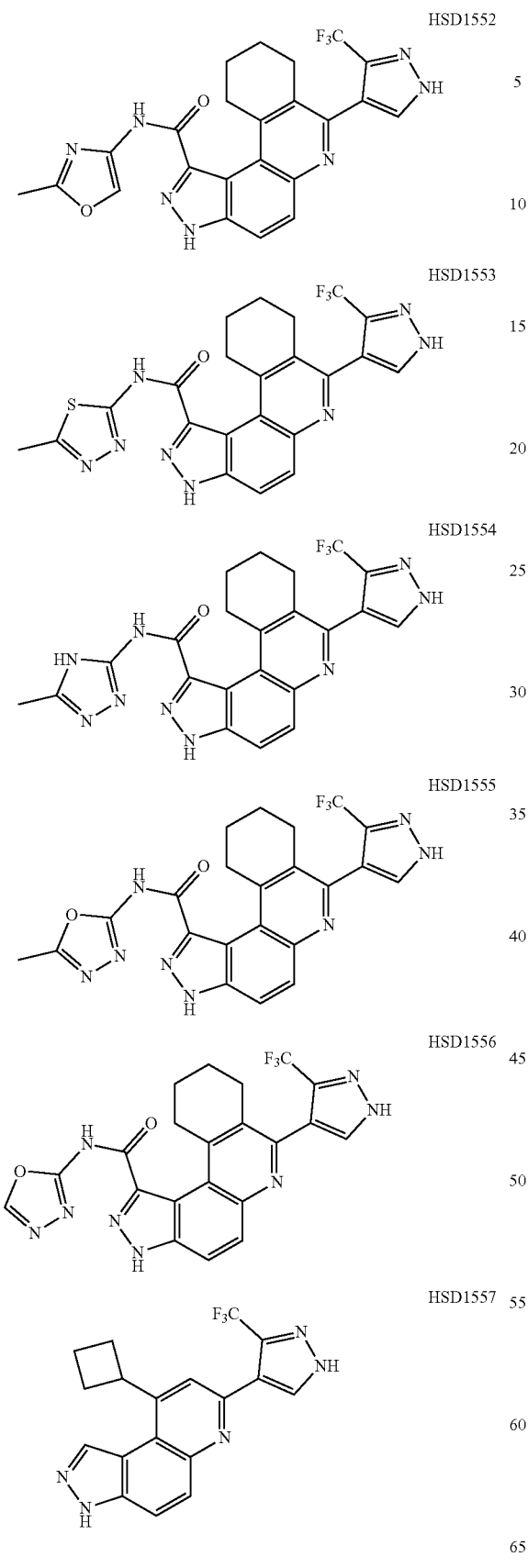
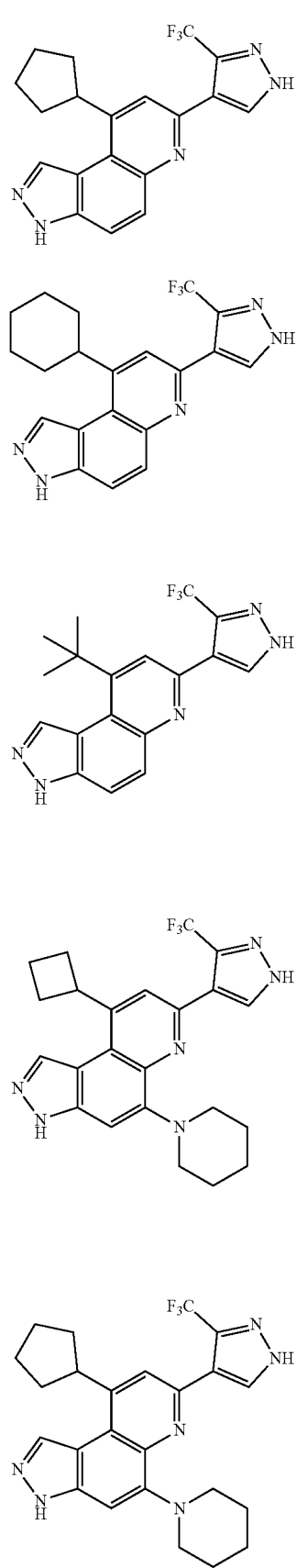

HSD1563
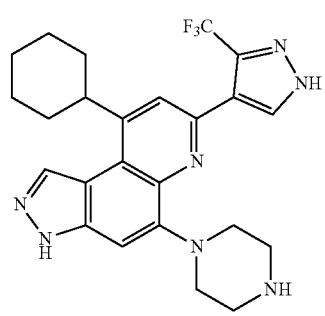
HSD1564
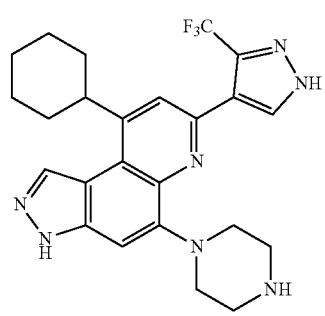
HSD1569
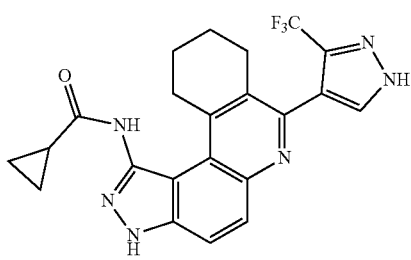
HSD1565
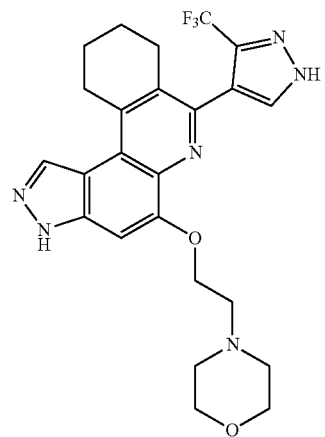
HSD1566
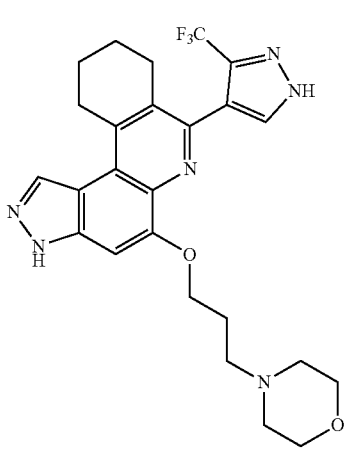
HSD1567
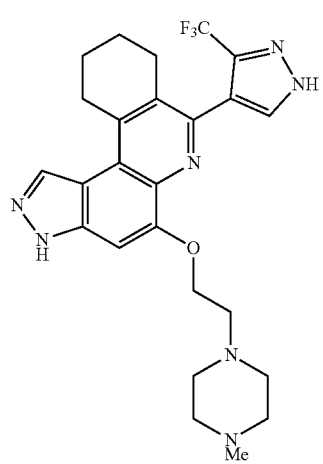
HSD1568
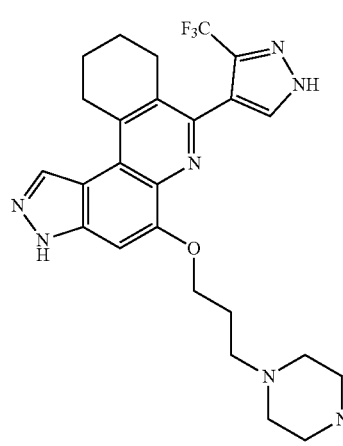
HSD1570
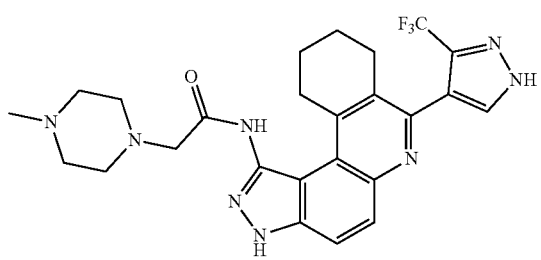

157
-continued
158
-continued
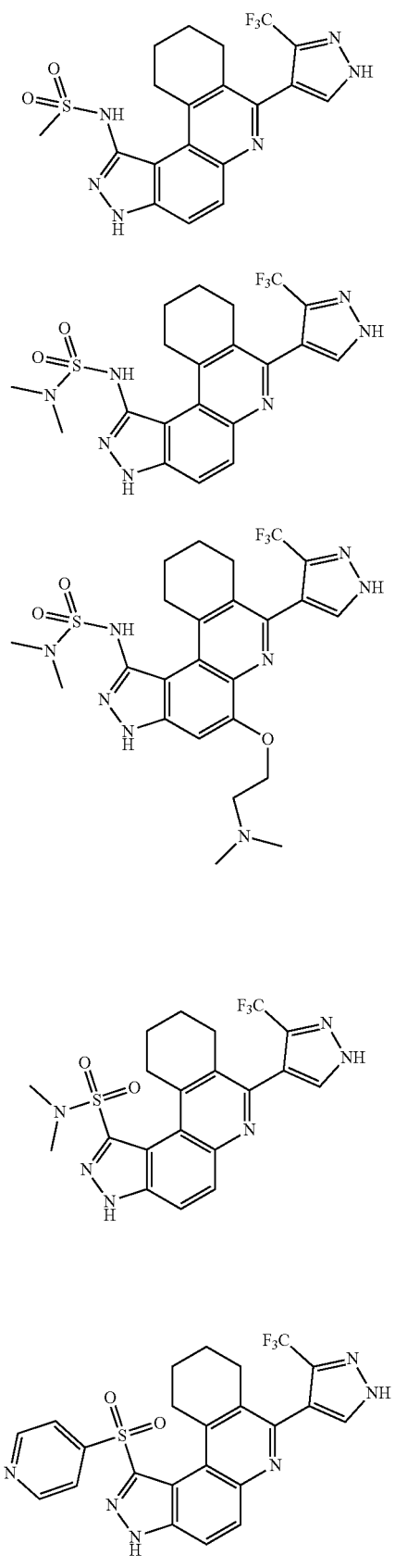
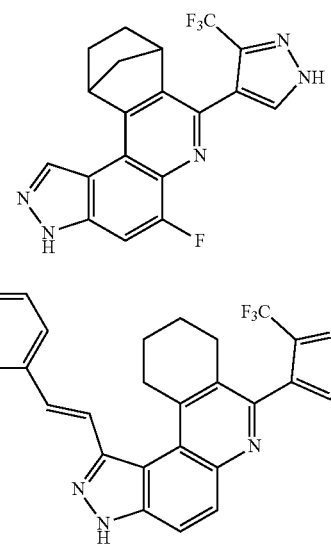
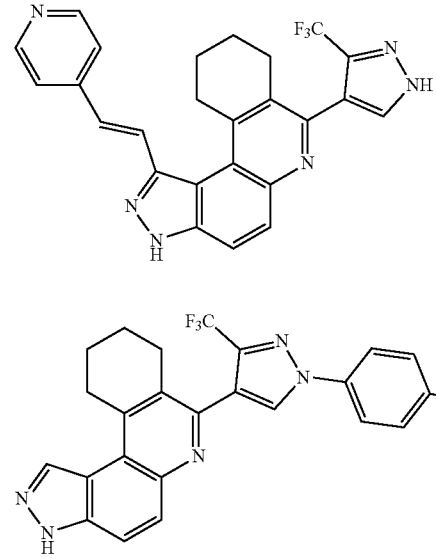
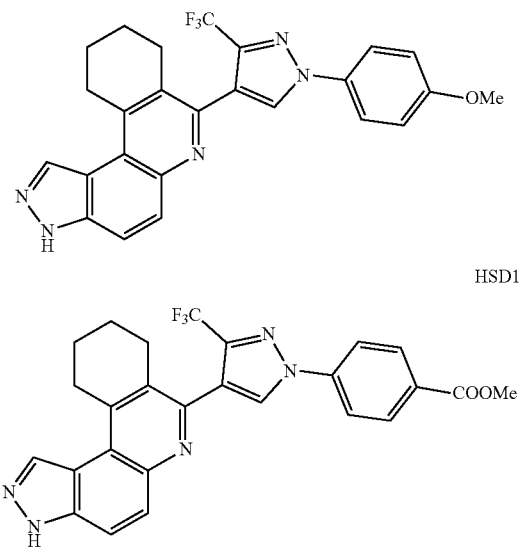
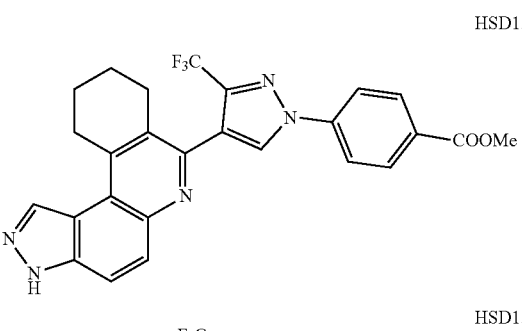
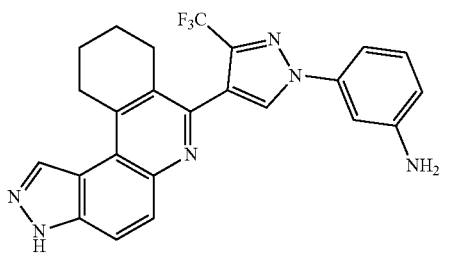

HSD1582

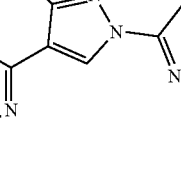

HSD1583

In some illustrative embodiments, the present invention relates to a pharmaceutical composition comprising one or more compounds disclosed herein, or a pharmaceutically acceptable salt thereof, together with one or more diluents, excipients or carriers.

In some illustrative embodiments, the present invention relates to a kinase inhibitor, wherein the kinase is selected from the group consisting of FLT3, MNK1/2, JAK1/2/3, Limk1/2, various CDKs, Haspin, ROCK1/2, TOPK, LRRK2, GSK3a/3b, RSK1-4, ERK, P70S6K, AKT, PI3K, p38, PKC, PKA, FGFR1-4, VEGFR1-3, ALK, AXL, LIMK1/2, Aurora A/B, ABL1, AKT, CSF1R, CSNK1D, DCAMKL1, CSNK1G2, EPHA2, ERBB2, IKK-alpha, IKK-beta, JNK1/2/3, MARK3, MEK1/2, MET, MLK1, PAK1/2/4, PDGFRa/b, PIM1/2/3, PLK1/2/3/4, PRKCE, PRKX, RET, TAOK2, TRKA/B/C, ULK2, and receptor-interacting protein kinase 4 (RIPK4).

In some illustrative embodiments, the present invention relates to a method for treating diseases mediated by a kinase and/or histone demethylases, including inflammation, cancer, viral and bacterial infections, gastrointestinal disorders, eye diseases, neurological, cardiovascular and immunological disorders, comprising the step of administering a therapeutically effective amount of one or more compounds disclosed herein, and one or more carriers, diluents, or excipients, to a patient in need of relief from said cancer.

In some illustrative embodiments, the present invention relates to a method for treating diseases mediated by a kinase and histone demethylases, including inflammation, cancer, viral and bacterial infections, gastrointestinal disorders, eye diseases, neurological, cardiovascular and immunological disorders, comprising the step of administering a therapeutically effective amount of a compound disclosed herein in combination with one or more other compounds of the same or different mode of action, and one or more carriers, diluents, or excipients, to a patient in need of relief from said cancer.

In some other illustrative embodiments, the present invention relates to a drug conjugate, either small molecule or biologic conjugate, comprising one or more compounds disclosed herein, wherein the conjugate confers cell-type or tissue type targeting or the conjugate targets another pathway that synergizes the action of the compounds.

In some illustrative embodiments, the present invention relates to a drug conjugate, either small molecule or biologic conjugate, comprising one or more compounds disclosed herein, wherein the conjugate confers aqueous solubility or low clearance.

In some illustrative embodiments, the present invention relates to a drug conjugate containing one or more compounds disclosed herein, and a moiety that aids the degradation of target proteins via systems including but not limited to the ubiquitin ligase/proteosome degradation system.

In some illustrative embodiments, the present invention relates to a pharmaceutical composition comprising nanoparticles of one or more compounds disclosed herein, together with one or more diluents, excipients or carriers.

In some illustrative embodiments, the present invention relates to a prodrug comprising one or more compounds disclosed herein, wherein the prodrug moiety is removed at specific location, such as gastrointestinal or in blood or in tissues or in cancer specific.

In some illustrative embodiments, the present invention relates to an analogs of compounds disclosed herein whereby specific metabolic hot spots are modified with groups such as deuterium or fluorine.

In addition, it is appreciated herein that the compounds described herein may be used in combination with other compounds that are administered to treat other symptoms of cancer, such as compounds administered to relieve pain, nausea, vomiting, and the like.

The following non-limiting exemplary embodiments are included herein to further illustrate the invention. These exemplary embodiments are not intended and should not be interpreted to limit the scope of the invention in any way. It is also to be understood that numerous variations of these exemplary embodiments are contemplated herein.

Experimental Section and Characterization

General Procedure for the Multicomponent Reaction:[10]
Method A:

A mixture of amine (1 mmol) and aldehyde (1 mmol) in 3 mL of absolute ethanol was refluxed for 2 h followed by addition of cyclic ketone or acetaldehyde (2.1 mmol) to the reaction mixture. A catalytic amount of conc. hydrochloric acid was added and the reaction was continued to reflux for 6-12 h. Reaction mixture concentrated and dissolved in DCM (50 mL), washed with brine solution (20 mL×2). The organic layer was dried ($Na_2SO_4$), concentrated under reduced pressure, and purified by silica gel chromatography (dichloromethane:methanol (99:01 to 80:20) to give the desired cyclized compound.

Method B:

A mixture of amine (1 mmol) and aldehyde (1 mmol) in 3 mL acetonitrile was refluxed for 2 h. The reaction mixture allowed to cool to room temperature followed by addition of alkene (2 mmol) and $Y(OTf)_3$ (30 mol %). The reaction continued to reflux for overnight. Reaction mixture concentrated and purified by silica gel chromatography dichloromethane:methanol (99:01) to give the desired cyclized compound.

Method C:

A mixture of amine (1 mmol), aldehyde (1 mmol) and cyclic ketone (2 mmol) in 6 mL tetrahydrofuran in presence of iodine (10 mol %) was refluxed for 6-12 h. After completion of reaction, reaction mixture was concentrated and purified by silica gel chromatography ethyl acetate:hexane (80:20) or dichloromethane:methanol (99:01) to give the desired cyclized compound. (Note: Sometime product may get precipitated out, which was filtered, washed with absolute ethanol and further purified by column chromatography).

Kinase Assay:

HotSpot kinase screening assay (Reaction Biology) was used to measure kinase/inhibitor interactions. Kinase and substrate were mixed in a buffer containing 20 mM HEPES pH 7.5, 10 mM $MgCl_2$, 1 mM EGTA, 0.02% Brij35, 0.02 mg/mL BSA, 0.1 mM $Na_3VO_4$, 2 mM DTT and 1% DMSO. Single-dose of compounds (500 nM) were then added to each reaction mixture. After 20-minute incubation, ATP (Sigma) and [γ-$^{33}$P] ATP (Perkin Elmer) were added at a final total concentration of 100 μM for addition 2 hours at room temperature, followed by spotting onto P81 ion exchange cellulose chromatography paper (Whatman, Inc.). Filter paper was washed in 0.75% phosphoric acid to remove unincorporated ATP. Percent remaining kinase activity of a vehicle (DMSO) containing kinase reaction was calculated for each kinase/inhibitor pair using Prism 5 (GraphPad).

LSD1 Assay:

The LSD1 Assay Kit was used to measure LSD1 activity of purified LSD1 enzyme. In a 96 well plate was added LSD1 buffer, 10 uM Histone H3(1-21)K4me2 peptide, and the test compound or DMSO control. The reaction was initiated with LSD1 enzyme. After 30 min incubation at room temperature, peroxidase and Amplex Red reagents are added and fluorescence (λex=530±13 nm, λem=590±18 nm) is measured after 5 min, using a plate reader. Percentage inhibition is calculated as fluorescence intensity in the presence of inhibitor divided by DMSO control times 100%.

$IC_{50}$ Proliferation Assay

Cell lines and primary cells were seeded into 96-well plates the afternoon prior to treatment. Approximately 18 hours later, compounds were semi-serially diluted in dimethyl sulfoxide (DMSO) and then growth medium, and added to cells. Plates were incubated for 72 hours prior to addition of Alamar Blue (Life Technologies, Carlsbad, CA). Plates were read after 4 additional hours of incubation at 37° C. using a Bio-Tek Synergy HT plate reader (Bio-Tek, Winooski, VT). Data was analyzed and graphed using GraphPad Prism Software (Graphpad, La Jolla, CA).

4-(8,9,10,11-Tetrahydro-3H-pyrrolo[3,2-a]phenanthridin-7-yl)phenol

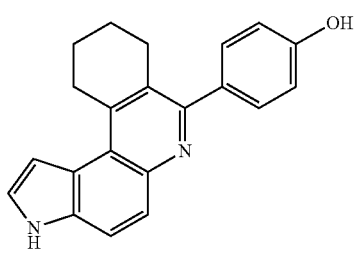

HSD-02-09

Yellow solid (195 mg, 62%). $^1$H NMR (500 MHz, DMSO-$d_6$) δ 10.35 (s, 1H), 8.20 (d, J=9.0 Hz, 1H), 8.02 (d, J=9.0 Hz, 1H), 7.79 (s, 1H), 7.58 (d, J=8.2 Hz, 2H), 7.31 (s, 1H), 7.05 (d, J=8.2 Hz, 2H), 3.56 (d, J=6.6 Hz, 2H), 2.80 (t, J=6.3 Hz, 2H), 2.02 (d, 1=8.4 Hz, 2H), 1.87-1.61 (m, 2H). $^{13}$C NMR (126 MHz, DMSO-$d_6$) δ 160.28, 150.26, 133.77, 131.92, 129.82, 127.07, 123.08, 121.33, 119.87, 115.98, 106.80, 31.35, 28.22, 22.01, 21.65; HRMS (ESI) m/z calcd for $C_{21}H_{19}N_2O$ [M+H]$^+$ 315.1497, found 315.1499.

4-(8,9,10,11-Tetrahydro-3H-pyrazolo[4,3-a]phenanthridin-7-yl)phenol

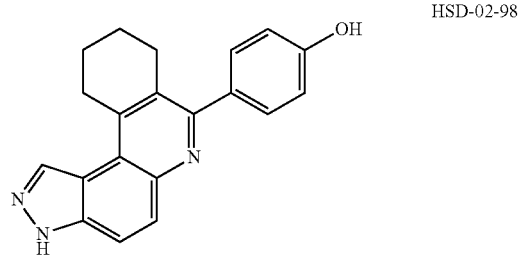 [SMILES: Oc1ccc(-c2nc3ccc4[nH]ncc4c3c3c2CCCC3)cc1]

HSD-02-98

Method A: Off white solid (189 mg, 60%). $^1$H NMR (500 MHz, DMSO-$d_6$) δ 10.46 (s, 1H), 8.67 (s, 1H), 8.16 (d, J=9.5 Hz, 1H), 7.60 (d, J=8.1 Hz, 2H), 7.06 (d, J=5 Hz, 1H), 3.31 (s, 1H), 2.80 (s, 1H), 2.00 (s, 1H), 1.74 (s, 1H); $^{13}$C NMR (126 MHz, DMSO-$d_6$) δ 160.40, 152.79, 151.09, 134.91, 132.09, 131.87, 122.67, 122.43, 119.96, 115.95, 114.66, 30.85, 28.21, 21.72, 21.66; HRMS (ESI) m/z calcd for $C_{20}H_{18}N_3O$ [M+H]$^+$ 316.1449, found 316.1458.

4-(8,9-Dihydro-3H-cyclobuta[c]pyrrolo[3,2-f]quinolin-7-yl)phenol

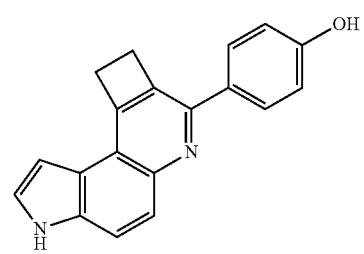

HSD-02-91

Method C: Yellow solid (166 mg, 58%). $^1$H NMR (500 MHz, Methanol-$d_4$) δ 8.12 (d, J=9.1 Hz, 1H), 8.00 (d, J=8.5 Hz, 2H), 7.97 (d, J=9.2 Hz, 2H), 7.65 (d, J=3.0 Hz, 1H), 7.14-7.04 (m, 2H), 3.92 (t, J=3.7 Hz, 2H), 3.85 (t, J=3.8 Hz, 2H); $^{13}$C NMR (126 MHz, DMSO) δ 161.86, 154.45, 143.71, 135.70, 134.66, 132.88, 131.33, 127.84, 123.68, 120.93, 119.32, 118.50, 116.87, 109.93, 103.31, 31.49. HRMS (ESI) m/z calcd for $C_{19}H_{15}N_2O$ [M+H]$^+$ 287.1184, found 287.1184.

4-(3,8,9,10-Tetrahydrocyclopenta[c]pyrrolo[3,2-f]quinolin-7-yl)phenol

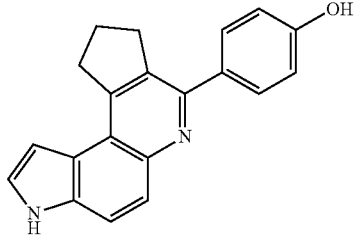

HSD-02-92

Method A: Yellow solid (181 mg, 60%). $^1$H NMR (500 MHz, Methanol-$d_4$) δ 8.18 (dd, J=9.0, 0.9 Hz, 1H), 7.92 (d, J=9.0 Hz, 1H), 7.79-7.72 (m, 2H), 7.70 (d, J=3.1 Hz, 1H), 7.27 (dd, J=3.1, 0.9 Hz, 1H), 7.11-7.04 (m, 2H), 3.92-3.79 (m, 2H), 3.37 (t, 1=7.6 Hz, 2H), 2.49 (p, J=7.7 Hz, 2H); $^{13}$C NMR (126 MHz, Methanol-$d_4$) δ 160.89, 146.91, 136.04, 135.25, 133.22, 130.80, 126.63, 122.44, 121.08, 120.85, 120.21, 115.78, 112.16, 104.20, 35.16, 31.66, 24.38; HRMS (ESI) m/z calcd for $C_{20}H_{17}N_2O$ [M+H]$^+$ 301.1340, found 301.1340.

4-(9-Methyl-8,9,10,11-tetrahydro-3H-pyrrolo[3,2-a]phenanthridin-7-yl)phenol

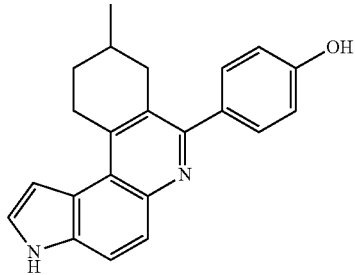

HSD-02-93

Method A: Yellow solid (236 mg, 72%). $^1$H NMR (500 MHz, Methanol-$d_4$) δ 8.17 (d, J=8.9 Hz, 1H), 7.84 (d, J=8.8 Hz, 1H), 7.71 (d, J=3.1 Hz, 1H), 7.55 (d, J=8.6 Hz, 2H), 7.40 (d, J=3.2 Hz, 1H), 7.07 (d, J=8.6 Hz, 2H), 3.86 (ddd, J=19.3, 5.9, 2.4 Hz, 1H), 3.69-3.50 (m, 1H), 2.89 (ddd, J=16.7, 4.5, 2.0 Hz, 1H), 2.62 (dd, J=16.9, 10.6 Hz, 1H), 2.30 (ddt, J=13.0, 7.0, 2.4 Hz, 1H), 1.98-1.83 (m, 1H), 1.71 (dtd, J=12.9, 10.9, 5.8 Hz, 1H), 1.14 (d, J=6.5 Hz, 3H); $^{13}$C NMR (126 MHz, Methanol-$d_4$) δ 160.12, 154.73, 150.23, 133.79, 130.78, 129.45, 126.06, 123.12, 122.70, 120.75, 120.16, 115.52, 112.48, 106.36, 36.01, 31.36, 29.62, 27.78, 20.23; HRMS (ESI) calcd for $C_{22}H_{21}N_2O$ [M+H]$^+$ 329.1653, found 329.1653.

2,6-Dibromo-4-(8,9,10,11-tetrahydro-3H-pyrrolo[3,2-a]phenanthridin-7-yl)phenol

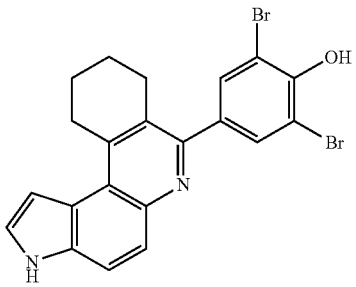

HSD-02-94

Method A: Yellow solid (277 mg, 59%). $^1$H NMR (500 MHz, DMSO-$d_6$) δ 11.80 (s, 1H), 10.10 (s, 1H), 7.80 (d, J=8.9 Hz, 0H), 7.73 (s, 1H), 7.64 (d, J=8.9 Hz, 0H), 7.51 (t, J=2.7 Hz, 0H), 7.13 (t, J=2.5 Hz, 1H), 3.37 (t, J=6.5 Hz, 1H), 2.79 (t, J=6.1 Hz, 1H), 2.03-1.89 (m, 1H), 1.74 (dq, J=6.3, 3.2 Hz, 1H); $^{13}$C NMR (126 MHz, DMSO) δ 152.61, 150.86, 142.79, 135.62, 133.32, 127.69, 124.22, 123.48, 122.70, 120.25, 116.95, 116.65, 111.87, 106.37, 30.09, 28.90, 22.72, 22.48; HRMS (ESI) m/z calcd for $C_{21}H_{17}Br_2N_2O$ [M+H]$^+$ 470.9707, found 470.9705.

7-(4-Bromophenyl)-8,9,10,11-tetrahydro-3H-pyrrolo[3,2-a]phenanthridine

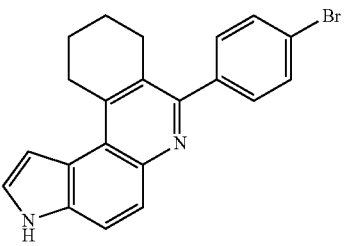

HSD-02-95

Method A: Off white solid (207 mg, 55%). $^1$H NMR (500 MHz, Methanol-$d_4$) δ 7.80 (dd, J=8.9, 0.9 Hz, 1H), 7.70 (d, J=8.9 Hz, 1H), 7.66 (d, J=8.4 Hz, 2H), 7.44-7.40 (m, 3H), 7.20 (dd, J=3.3, 0.9 Hz, 1H), 3.53-3.45 (m, 2H), 2.74 (t, J=6.2 Hz, 2H), 2.13-2.01 (m, 2H), 1.87-1.76 (m, 2H); $^{13}$C NMR (126 MHz, Methanol-$d_4$) δ 154.80, 143.92, 142.60, 140.03, 133.30, 131.01, 130.67, 127.22, 122.92, 122.85, 121.94, 121.71, 120.23, 116.08, 105.79, 29.93, 28.51, 22.43, 22.09; HRMS (ESI) m/z calcd for $C_{21}H_{18}BrN_2$ [M+H]$^+$ 377.0653, found 377.0653.

4-(9-Methyl-3H-pyrrolo[3,2-f]quinolin-7-yl)phenol

HSD-02-96

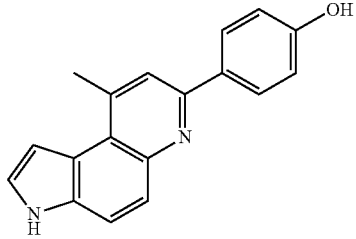

Method A: Yellow solid (173 mg, 63%). $^1$H NMR (500 MHz, DMSO-$d_6$) δ 10.57 (s, 1H), 8.24 (d, J=6.4 Hz, 3H), 8.09 (d, J=8.8 Hz, 1H), 7.80 (s, OH), 7.28 (s, 1H), 7.07 (d, J=8.8 Hz, 1H), 3.14 (s, 3H). $^{13}$C NMR (126 MHz, DMSO-$d_6$) δ 161.75, 149.00, 133.54, 131.40, 127.61, 122.28, 121.80, 121.28, 120.94, 116.69, 105.84, 24.33; HRMS (ESI) m/z calcd for $C_{18}H_{15}N_2O$ [M+H]$^+$ 275.1184, found 275.1192.

7-(3,4,5-Trimethoxyphenyl)-8,9,10,11-tetrahydro-3H-pyrrolo[3,2-a]phenanthridine

HSD-02-97

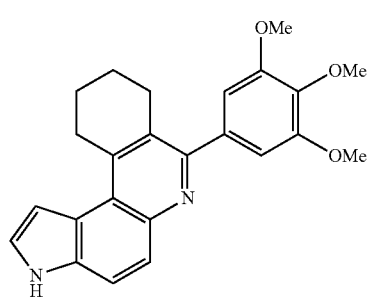

Method A: White crystalline solid (213 mg, 55%). $^1$H NMR (500 MHz, Methanol-$d_4$) δ 8.18 (dd, J=8.9, 0.8 Hz, 1H), 7.85 (d, J=8.9 Hz, 1H), 7.71 (d, J=3.1 Hz, 1H), 7.38 (dd, J=3.2, 0.9 Hz, 1H), 7.01 (s, 2H), 3.92 (s, 6H), 3.88 (s, 3H), 3.67 (t, J=6.6 Hz, 3H), 2.93 (t, J=6.2 Hz, 2H), 2.22-2.11 (m, 3H), 1.92 (ddd, J=9.1, 7.4, 4.5 Hz, 2H). $^{13}$C NMR (126 MHz, Methanol-$d_4$) δ 154.94, 153.66, 149.75, 139.80, 133.79, 133.67, 129.57, 127.67, 126.01, 123.58, 120.83, 120.04, 112.80, 106.71, 106.41, 59.88, 55.66, 31.23, 27.71, 21.56, 21.24; HRMS (ESI) m/z calcd for $C_{24}H_{25}N_2O_3$ [M+H]$^+$ 389.1865, found 389.1861.

4-(9,9-dimethyl-8,9,10,11-tetrahydro-3H-pyrrolo[3,2-a]phenanthridin-7-yl)phenol

HSD-02-99

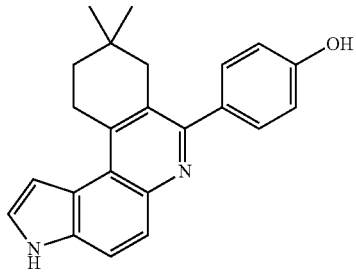

Method A: White crystalline solid (188 mg, 53%). $^1$H NMR (500 MHz, Methanol-$d_4$) δ 7.79 (d, J=8.9 Hz, 1H), 7.71 (d, J=8.9 Hz, 1H), 7.43 (d, J=3.1 Hz, 1H), 7.32 (d, J=8.1 Hz, 2H), 7.21 (d, J=3.1 Hz, 1H), 6.92 (d, J=8.1 Hz, 2H), 3.50 (t, J=6.8 Hz, 2H), 2.56 (s, 2H), 1.80 (t, J=6.7 Hz, 2H), 0.97 (s, 6H); $^{13}$C NMR (126 MHz, Methanol-$d_4$) δ 157.35, 156.02, 143.16, 141.88, 133.19, 131.52, 130.07, 126.84, 122.96, 122.26, 121.28, 120.30, 116.11, 114.60, 105.73, 48.11, 48.05, 47.94, 47.77, 47.60, 47.43, 47.26, 47.09, 42.06, 34.69, 28.29, 27.71, 26.60; HRMS (ESI) m/z calcd for $C_{23}H_{23}N_2O$ [M+H]$^+$ 343.1810, found 343.1808.

5-(8,9,10,11-Tetrahydro-3H-pyrrolo[3,2-a]phenanthridin-7-yl)benzene-1,2,3-triol

HSD-02-910

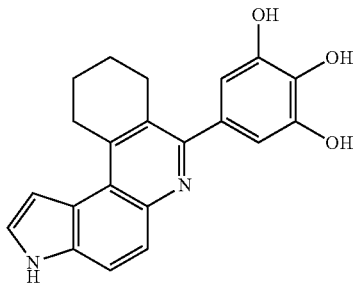

Method A: Yellow solid (246 mg, 71%). $^1$H NMR (500 MHz, DMSO-$d_6$) δ 9.52 (s, 2H), 9.01 (s, 1H), 8.17 (d, J=8.9 Hz, 1H), 7.95 (d, J=8.9 Hz, 1H), 7.78 (s, 1H), 7.27 (s, 1H), 6.65 (s, 2H), 3.50 (t, J=6.4 Hz, 2H), 2.80 (t, J=6.2 Hz, 2H), 2.03-1.98 (m, 2H), 1.83-1.73 (m, 2H). $^{13}$C NMR (126 MHz, DMSO-$d_6$) δ 154.17, 150.35, 146.76, 136.24, 133.69, 129.63, 127.03, 122.96, 122.04, 121.27, 119.85, 113.64, 109.26, 109.26, 106.74, 31.31, 28.26, 21.99, 21.58; HRMS (ESI) m/z calcd for $C_{21}H_{19}N_2O_3$ [M+H]$^+$ 347.1395, found 347.1390.

4-(6,7,8,9-Tetrahydro-1H-pyrrolo[2,3-c]phenanthridin-5-yl)phenol

HSD-02-911

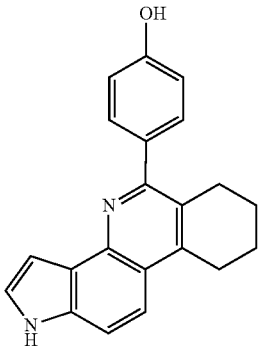

Method A: Yellow solid (163 mg, 52%). $^1$H NMR (500 MHz, Methanol-$d_4$) 8.05-7.92 (m, 2H), 7.58-7.52 (m, 3H), 7.48 (d, J=3.2 Hz, 1H), 7.07 (d, J=8.3 Hz, 2H), 3.51 (t, J=6.5 Hz, 2H), 2.82 (d, J=6.4 Hz, 2H), 2.06 (dd, J=7.7, 4.3 Hz, 2H), 1.92-1.77 (m, 2H). $^{13}$C NMR (126 MHz, Methanol-$d_4$) 160.10, 155.63, 152.51, 137.17, 131.84, 130.93, 128.03, 125.79, 122.79, 122.70, 116.47, 116.22, 115.74, 115.44, 101.89, 27.60, 27.36, 21.68, 21.30; HRMS (ESI) m/z calcd for $C_{21}H_{19}N_2O$ [M+H]$^+$ 315.1497, found 315.1495.

7-(2,2-Difluorobenzo[d][1,3]dioxol-5-yl)-8,9,10,11-tetrahydro-3H-pyrazolo[4,3-a]phenanthridine

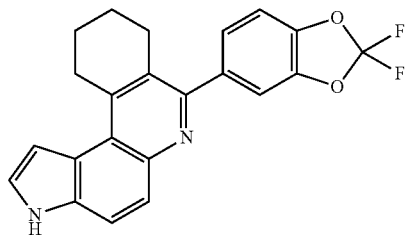

ND-02-912

Method A: Off-white solid (57 mg, 15%) $^1$H NMR (500 MHz, Methanol-d$_4$) δ 7.78 (dd, J=9.0, 3.6 Hz, 1H), 7.68 (dd, J=9.1, 3.6 Hz, 1H), 7.36 (dt, J=40.7, 3.0 Hz, 2H), 7.32-7.20 (m, 2H), 7.15 (d, J=3.5 Hz, 1H), 3.42 (q, J=5.7 Hz, 2H), 2.69 (q, J=5.4 Hz, 2H), 2.05-1.94 (m, 2H), 1.82-1.69 (m, 2H); $^{13}$C NMR (126 MHz, MeOD) δ 154.25, 144.03, 143.32, 143.22, 142.52, 137.40, 133.29, 131.73, 127.27, 124.87, 122.96, 122.87, 121.94, 120.19, 116.15, 110.39, 108.94, 105.81, 29.90, 28.49, 22.35, 22.03; HRMS (ESI) m/z calcd for $C_{21}H_{16}F_2N_3O_2$ [M+H]$^+$ 380.1211, found 380.1216.

7-(1-Methyl-1H-imidazol-5-yl)-8,9,10,11-tetrahydro-3H-pyrrolo[3,2-a]phenanthridine

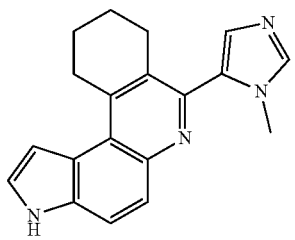

HSD-02-913

Method A: Off-white solid (151 mg, 50%). $^1$H NMR (500 MHz, Methanol-d$_4$) δ 7.79 (d, J=7.9 Hz, 2H), 7.66 (d, J=8.9 Hz, 1H), 7.40 (d, J=3.1 Hz, 1H), 7.18 (s, 1H), 7.12 (d, J=3.1 Hz, 1H), 3.60 (s, 3H), 3.38 (t, J=6.5 Hz, 2H), 2.75 (t, J=6.3 Hz, 2H), 2.00-1.94 (m, 2H), 1.81 (q, J=6.0, 5.6 Hz, 2H). $^{13}$C NMR (126 MHz, Methanol-d$_4$) δ 144.67, 144.01, 142.83, 138.47, 133.43, 130.97, 129.25, 128.07, 122.97, 122.14, 120.11, 116.34, 105.94, 31.45, 29.82, 27.83, 22.28, 21.90; HRMS (ESI) m/z calcd for $C_{19}H_{19}N_4$ [M+H]$^+$ 303.1609, found 303.1599.

4-(8,9,10,11-Tetrahydro-3H-pyrrolo[3,2-a]phenanthridin-7-yl)benzene-1,3-diol

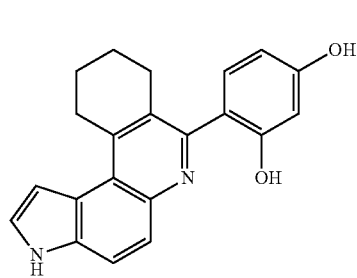

HSD-02-914

Method A: Yellow solid (142 mg, 43%). $^1$H NMR (500 MHz, Methanol-d$_4$) δ 7.77 (dd, J=8.9, 0.8 Hz, 1H), 7.68 (d, J=8.9 Hz, 1H), 7.42 (d, J=3.1 Hz, 1H), 7.19 (dd, J=3.2, 0.9 Hz, 1H), 7.09 (d, J=8.9 Hz, 1H), 6.46-6.42 (m, 2H), 3.49 (t, J=6.5 Hz, 2H), 2.80 (t, J=6.3 Hz, 2H), 2.09-2.02 (m, 2H), 1.87-1.78 (m, 2H). $^{13}$C NMR (126 MHz, Methanol-d$_4$) δ 158.65, 156.16, 154.02, 143.81, 141.57, 133.18, 130.73, 129.43, 122.78, 122.59, 121.13, 120.30, 118.60, 115.81, 106.34, 105.68, 102.35, 29.99, 27.42, 22.52, 22.05; HRMS (ESI) m/z calcd for $C_{21}H_{19}N_2O_2$ [M+H]$^+$ 331.1446, found 331.1440.

4-(3,8,9,10,11,12-Hexahydrocyclohepta[c]pyrrolo[3,2-f]quinolin-7-yl)phenol

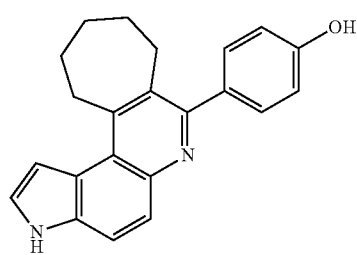

HSD-02-915

Method A: Off white solid (187 mg, 57%). $^1$H NMR (500 MHz, DMSO-d$_6$) δ 11.67 (s, 1H), 9.52 (s, 1H), 7.72 (s, 1H), 7.56 (d, J=8.9 Hz, 1H), 7.45 (d, J=2.8 Hz, 1H), 7.29 (d, J=8.1 Hz, 2H), 7.07 (d, J=3.1 Hz, 1H), 6.85 (s, 2H), 3.55 (dd, J=6.8, 3.3 Hz, 2H), 3.08-2.96 (m, 2H), 1.88 (dq, J=16.5, 4.5 Hz, 4H), 1.63 (p, J=5.1 Hz, 2H). $^{13}$C NMR (126 MHz, DMSO-d$_6$) δ 157.25, 157.11, 154.98, 148.20, 144.09, 133.98, 133.26, 133.10, 132.98, 130.91, 124.12, 123.99, 123.82, 121.64, 120.00, 116.78, 116.72, 115.09, 115.00, 105.09, 31.64, 30.68, 30.11, 27.75, 25.12; HRMS (ESI) m/z calcd for $C_{22}H_{21}N_2O$ [M+H]$^+$ 329.1653, found 329.1652.

4-(8,9,10,11-Tetrahydro-3H-[1,2,3]triazolo[4,5-a]phenanthridin-7-yl)phenol

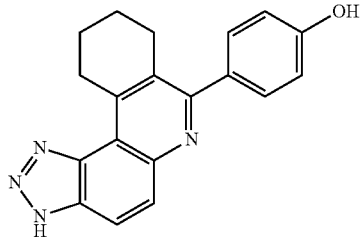

HSD-02-916

Method A: white solid (237 mg, 75%). $^1$H NMR (500 MHz, DMSO-$d_6$) δ 9.73 (s, 1H), 8.04 (d, J=9.1 Hz, 1H), 7.89 (d, J=9.1 Hz, 1H), 7.44 (d, J=8.3 Hz, 2H), 6.89 (d, J=8.4 Hz, 2H), 3.67 (s, 2H), 2.81 (s, 1H), 2.03-1.88 (m, 2H), 1.82-1.59 (m, 2H); $^{13}$C NMR (126 MHz, DMSO) δ 158.08, 143.69, 131.01, 130.34, 118.90, 115.25, 30.03, 28.96, 26.90, 24.76. HRMS (ESI) m/z calcd for $C_{19}H_{17}N_4O$ [M+H]$^+$ 317.1402, found 317.1408.

4-(2,3,4,8-Tetrahydro-1H-pyrrolo[3,2-b]phenanthridin-5-yl)phenol

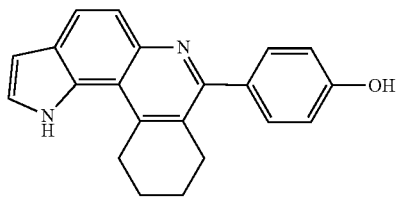

HSD-02-917

Method A: Off white solid (185 mg, 59%). $^1$H NMR (500 MHz, Methanol-$d_4$) δ 7.87 (d, J=8.7 Hz, 1H), 7.62 (d, J=8.7 Hz, 1H), 7.43 (d, J=3.1 Hz, 1H), 7.34 (d, J=8.5 Hz, 1H), 6.92 (d, J=8.5 Hz, 2H), 6.70 (d, J=3.1 Hz, 1H), 3.50 (t, J=6.5 Hz, 2H), 2.78 (t, J=6.3 Hz, 2H), 2.13-2.05 (m, 2H), 1.86-1.80 (m, 2H); $^{13}$C NMR (126 MHz, MeOD) δ 157.34, 156.57, 143.27, 141.29, 131.70, 130.00, 128.49, 127.57, 125.52, 124.19, 123.50, 119.83, 117.04, 114.57, 102.65, 29.32, 28.61, 22.41, 22.04; HRMS (ESI) m/z calcd for $C_{21}H_{19}N_2O$ [M+H]$^+$ 315.1497, found 315.1495.

4-(2,3,4,8-Tetrahydro-1H-pyrrolo[3,2-b]phenanthridin-5-yl)phenol

HSD-02-918

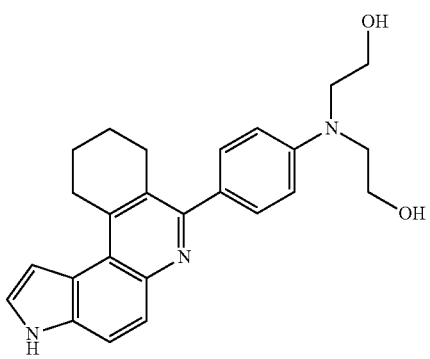

Method A: Off white solid (178 mg, 54%). $^1$H NMR (500 MHz, DMSO-$d_6$) δ 11.81 (s, 1H), 8.85 (s, 2H), 7.81 (d, J=8.8 Hz, 1H), 7.66 (d, J=8.8 Hz, 1H), 7.51 (t, J=2.8 Hz, 1H), 7.13 (t, J=2.5 Hz, 1H), 3.99 (s, 3H), 3.37 (t, J=6.5 Hz, 2H), 2.84 (t, J=6.2 Hz, 2H), 1.99-1.91 (m, 2H), 1.75 (dd, J=7.5, 4.3 Hz, 2H); $^{13}$C NMR (126 MHz, DMSO) δ 164.77, 159.82, 149.96, 143.68, 142.81, 133.37, 129.18, 127.97, 124.12, 124.09, 122.80, 120.25, 116.84, 106.43, 55.22, 29.96, 28.70, 22.75, 22.49; HRMS (ESI) m/z calcd for $C_{20}H_{19}N_4O$ [M+H]$^+$ 331.1558, found 331.1553.

2,2'-((4-(8,9,10,11-Tetrahydro-3H-pyrrolo[3,2-a]phenanthridin-7-yl)phenyl)azanediyl)diethanol

HSD-02-919

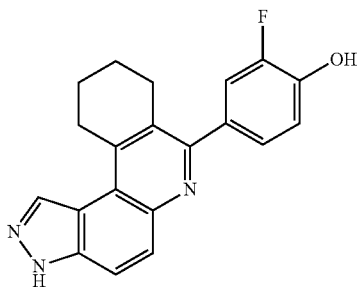

Method A: Yellow solid (209 mg, 70%). $^1$H NMR (500 MHz, Methanol-$d_4$) δ 8.00 (d, J=8.9 Hz, 1H), 7.77 (d, J=8.9 Hz, 1H), 7.59 (d, J=3.1 Hz, 1H), 7.48-7.43 (m, 2H), 7.28 (d, J=3.2 Hz, 1H), 6.95 (d, J=8.9 Hz, 2H), 3.79 (t, J=6.0 Hz, 4H), 3.65 (t, J=6.0 Hz, 4H), 2.90 (t, J=6.2 Hz, 2H), 2.12-2.06 (m, 2H), 1.84 (td, J=6.2, 3.2 Hz, 2H); $^{13}$C NMR (126 MHz, MeOD) δ 152.36, 151.09, 149.41, 136.32, 133.50, 130.36, 129.04, 124.91, 122.68, 121.37, 120.18, 118.91, 115.34, 111.33, 106.08, 58.85, 53.41, 30.85, 28.37, 21.94, 21.66; HRMS (ESI) m/z calcd for $C_{25}H_{28}N_3O_2$ [M+H]$^+$ 402.2181, found 402.2179.

2-Fluoro-4-(8,9,10,11-tetrahydro-3H-pyrazolo[4,3-a]phenanthridin-7-yl)phenol

HSD-02-920

Method A: Off white solid (207 mg, 62%). $^1$H NMR (500 MHz, DMSO-$d_6$) δ 10.81 (s, 1H), 8.83 (s, 1H), 8.26 (d, J=9.2 Hz, 1H), 8.21 (d, J=9.2 Hz, 1H), 7.66 (dd, J=11.8, 2.2 Hz, 1H), 7.42 (dd, J=8.4, 2.1 Hz, 1H), 7.26 (t, J=8.6 Hz, 1H), 3.49 (t, J=6.4 Hz, 2H), 2.83 (t, J=6.2 Hz, 2H), 2.07-2.00 (m, 2H), 1.85-1.76 (m, 2H); $^{13}$C NMR (126 MHz, DMSO) δ 151.89, 149.96, 147.88, 135.32, 132.02, 127.33, 123.16, 120.36, 118.65, 118.49, 118.29, 114.87, 30.92, 28.11, 21.80, 21.69; HRMS (ESI) m/z calcd for $C_{20}H_{17}FN_3O$ [M+H]$^+$ 334.1355, found 334.1352.

7-(Pyridin-4-yl)-8,9,10,11-tetrahydro-3H-pyrrolo[3,2-a]phenanthridine

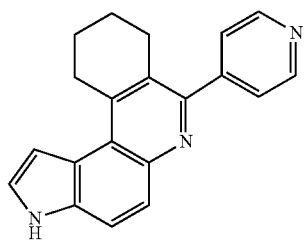

HSD-02-921

Method A: off white solid (183 mg, 61%). $^1$H NMR (500 MHz, DMSO-d$_6$) δ 11.81 (s, 1H), 8.67 (dt, J=4.4, 1.5 Hz, 2H), 7.81 (d, J=8.8 Hz, 1H), 7.65 (d, J=8.9 Hz, 1H), 7.60-7.55 (m, 2H), 7.54-7.48 (m, 1H), 7.14 (s, 1H), 3.40 (t, J=6.6 Hz, 2H), 2.77 (t, J=6.1 Hz, 2H), 2.01-1.94 (m, 2H), 1.75 (q, J=5.9 Hz, 2H); $^{13}$C NMR (126 MHz, DMSO) δ 153.34, 149.84, 149.10, 143.44, 142.78, 133.41, 127.19, 124.49, 124.16, 124.08, 122.90, 120.26, 116.87, 106.42, 29.94, 28.67, 22.76, 22.39; HRMS (ESI) m/z calcd for $C_{20}H_{18}N_3$ [M+H]$^+$ 300.1500, found 300.1508.

4-(2,3,4,9-Tetrahydro-1H-indolo[3,2-a]phenanthridin-5-yl)phenol

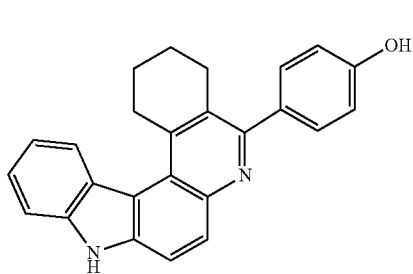

HSD-02-922

Method A: Brown solid (175 mg, 48%). $^1$H NMR (500 MHz, DMSO-d$_6$) δ 8.52 (d, J=8.5 Hz, 1H), 8.25 (dd, J=8.0, 3.7 Hz, 2H), 7.73 (dd, J=8.5, 4.1 Hz, 1H), 7.58 (ddd, J=8.3, 5.4, 2.6 Hz, 2H), 7.51 (td, J=7.7, 2.5 Hz, 1H), 7.33 (t, J=7.7 Hz, 1H), 7.09-7.00 (m, 2H), 3.86 (t, J=6.0 Hz, 2H), 2.89 (t, J=6.7 Hz, 2H), 1.91 (p, J=6.6 Hz, 2H), 1.81 (q, J=6.3 Hz, 2H); $^{13}$C NMR (126 MHz, DMSO) δ 159.66, 151.29, 145.82, 140.03, 139.23, 132.51, 131.70, 130.16, 128.83, 125.54, 125.33, 125.13, 123.01, 120.08, 116.30, 115.84, 113.14, 112.73, 110.76, 33.12, 26.84, 21.64, 21.36; HRMS (ESI) m/z calcd for $C_{25}H_{21}N_2O$ [M+H]$^+$ 365.1653, found 365.1647.

4-(3-Methyl-8,9,10,11-tetrahydro-3H-pyrrolo[3,2-a]phenanthridin-7-yl)phenol

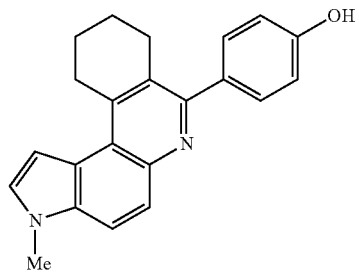

HSD-02-923

Method A: Yellow solid (246 mg, 75%). $^1$H NMR (500 MHz, Methanol-d$_4$) δ 8.23 (d, J=9.0 Hz, 1H), 7.89 (d, J=9.1 Hz, 1H), 7.66 (d, J=3.1 Hz, 1H), 7.54 (d, J=8.5 Hz, 2H), 7.35 (d, J=3.1 Hz, 1H), 7.06 (d, J=8.4 Hz, 2H), 4.08 (s, 3H), 3.65 (t, J=6.4 Hz, 2H), 2.92 (t, J=6.2 Hz, 2H), 2.14 (dq, J=8.6, 5.9, 4.6 Hz, 2H), 1.94-1.85 (m, 2H); $^{13}$C NMR (126 MHz, MeOD) δ 160.06, 154.70, 150.64, 134.12, 133.70, 130.78, 130.35, 129.85, 123.15, 122.88, 120.71, 118.64, 115.50, 112.77, 105.58, 32.40, 31.23, 27.96, 21.60, 21.28; HRMS (ESI) m/z calcd for $C_{22}H_{21}N_2O$ [M+H]$^+$ 329.1653, found 329.1645.

5-(8,9,10,11-Tetrahydro-3H-pyrazolo[4,3-a]phenanthridin-7-yl)pyridin-2-ol

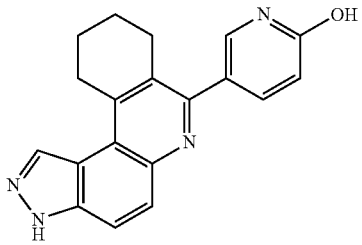

HSD-02-928

Method A: Off white solid (158 mg, 50%). H NMR (500 MHz, DMSO-d$_6$) δ 11.86 (s, 1H), 8.53 (s, 1H), 7.83 (d, J=9.0 Hz, 1H), 7.80-7.73 (m, 2H), 7.65 (d, J=2.6 Hz, 1H), 6.42 (d, J=9.4 Hz, 1H), 3.25 (t, J=6.6 Hz, 2H), 2.84 (t, J=6.1 Hz, 2H), 2.01-1.92 (m, 2H), 1.80-1.68 (m, 2H); $^{13}$C NMR (126 MHz, DMSO) δ 162.21, 152.68, 143.74, 142.84, 142.59, 136.37, 129.51, 129.43, 121.76, 119.38, 118.73, 116.21, 29.69, 28.78, 22.59, 22.54; HRMS (ESI) m/z calcd for $C_{19}H_{17}N_4O$ [M+H]$^+$ 317.1402, found 317.1403.

4-(8,9,10,11-Tetrahydro-3H-pyrazolo[4,3-a]phenanthridin-7-yl)aniline

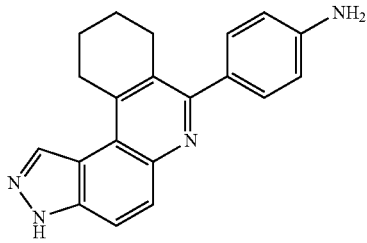

HSD-02-929

Method A: Orange solid (192 mg, 61%). ¹H NMR (500 MHz, DMSO-d₆) 8.73 (s, 1H), 8.16 (t, J=11.5 Hz, 2H), 7.45 (d, J=8.5 Hz, 2H), 6.79 (d, J=8.3 Hz, 2H), 3.46 (s, 2H), 2.98-2.78 (m, 2H), 2.09-1.92 (m, 2H), 1.82-1.63 (m, 2H); ¹³C NMR (126 MHz, DMSO) δ 162.75, 154.28, 150.08, 138.83, 136.20, 131.25, 130.62, 129.84, 124.50, 121.76, 115.68, 114.96, 113.80, 111.38, 30.33, 28.84, 22.22; HRMS (ESI) m/z calcd for $C_{20}H_{19}N_4$ [M+H]⁺ 315.1609, found 315.1619.

5-(8,9,10,11-Tetrahydro-3H-pyrrolo[3,2-a]phenanthridin-7-yl)pyridin-2-ol

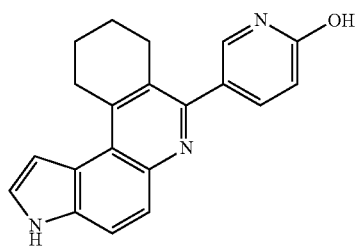

HSD-02-930

Method A: Off-white solid (170 mg, 54%). ¹H NMR (500 MHz, DMSO-d₆) δ 10.47 (s, 1H), 8.47 (d, J=2.1 Hz, 1H), 8.36 (q, J=9.2 Hz, 2H), 7.79 (d, J=2.2 Hz, 1H), 7.66-7.56 (m, 2H), 7.10-6.98 (m, 2H), 3.56 (t, J=6.4 Hz, 2H), 2.82 (t, J=6.2 Hz, 2H), 2.00 (dq, J=8.7, 5.8, 4.5 Hz, 2H), 1.85-1.65 (m, 2H); ¹³C NMR (126 MHz, DMSO) δ 160.63, 153.59, 153.01, 148.23, 132.05, 131.37, 122.86, 121.34, 119.47, 116.00, 110.37, 30.67, 28.32, 21.74, 21.57; HRMS (ESI) m/z calcd for $C_{20}H_{18}N_3O$ [M+H]⁺ 316.1449, found 316.1455.

4-(8,9,10,11-Tetrahydrofuro[3,2-a]phenanthridin-7-yl)phenol

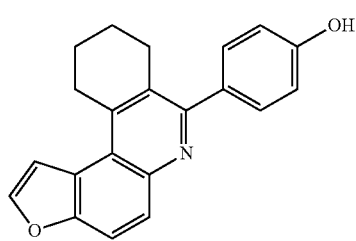

HSD-02-931

Method A: Off-white solid (218 mg, 69%). ¹H NMR (500 MHz, DMSO-d₆) δ 8.47 (d, J=2.1 Hz, 1H), 8.36 (q, J=9.2 Hz, 2H), 7.79 (d, J=2.2 Hz, 1H), 7.61 (d, J=8.6 Hz, 2H), 7.06 (d, J=8.6 Hz, 2H), 3.56 (t, J=6.4 Hz, 2H), 2.82 (t, J=6.2 Hz, 2H), 2.00 (dq, J=8.7, 5.8, 4.5 Hz, 2H), 1.86-1.65 (m, 2H); ¹³C NMR (126 MHz, DMSO) δ 160.63, 153.59, 153.01, 148.23, 132.05, 131.37, 122.86, 121.34, 119.47, 116.00, 110.37, 30.67, 28.32, 21.74, 21.57; HRMS (ESI) m/z calcd for $C_{21}H_{18}NO_2$ [M+H]⁺ 316.1337, found 316.1343.

4-(8,9,10,11-Tetrahydrothieno[3,2-a]phenanthridin-7-yl)phenol

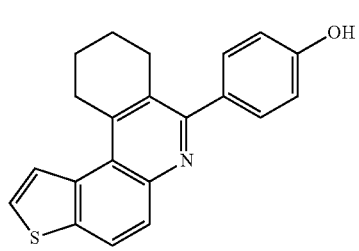

HSD-02-932

Method A: Off-white solid (245 mg, 74%). ¹H NMR (500 MHz, DMSO-d₆) δ 9.96 (s, 1H), 8.36 (d, J=8.9 Hz, 1H), 8.32 (d, J=5.6 Hz, 1H), 8.08 (d, J=5.5 Hz, 1H), 7.97 (d, J=8.9 Hz, 1H), 7.46 (d, J=8.5 Hz, 2H), 6.94 (d, J=8.5 Hz, 2H), 3.49 (q, J=6.5 Hz, 2H), 2.80 (t, J=6.2 Hz, 2H), 1.94 (dp, J=6.6, 4.6, 2.8 Hz, 2H), 1.79-1.65 (m, 2H); ¹³C NMR (126 MHz, DMSO) δ 158.82, 139.74, 133.74, 131.22, 130.02, 128.68, 127.46, 125.78, 123.88, 115.49, 31.70, 29.13, 22.58, 21.88; HRMS (ESI) m/z calcd for $C_{21}H_{18}NOS$ [M+H]⁺ 332.1109, found 332.1118.

2,6-Difluoro-4-(8,9,10,11-tetrahydro-3H-pyrazolo[4,3-a]phenanthridin-7-yl)phenol

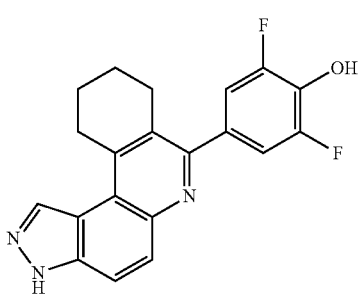

HSD-02-933

Method A: Off-white solid (221 mg, 63%). ¹H NMR (500 MHz, DMSO-d₆) δ 8.76 (s, 1H), 8.22 (s, 2H), 7.66-7.43 (m, 2H), 3.43 (t, J=6.4 Hz, 2H), 2.83 (t, J=6.1 Hz, 2H), 2.19-1.94 (m, 2H), 1.88-1.50 (m, 2H). ¹³C NMR (126 MHz, DMSO) δ 153.27, 151.34, 151.28, 136.31, 131.82, 123.22, 114.73, 114.52, 30.79, 27.97, 21.80, 21.69; HRMS (ESI) m/z calcd for $C_{20}H_{16}F_2N_3O$ [M+H]⁺ 352.1261, found 352.1260.

4-(8,9,10,11-Tetrahydro-3H-pyrrolo[3,2-a]phenanthridin-7-yl)aniline

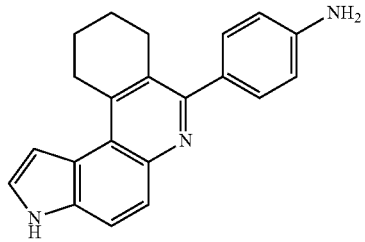

HSD-02-934

Method A: Bright yellow solid (194 mg, 62%). $^1$H NMR (500 MHz, DMSO-d$_6$) δ 8.09 (d, J=8.9 Hz, 1H), 7.93 (d, J=8.8 Hz, 1H), 7.72 (s, 1H), 7.40 (d, J=8.2 Hz, 2H), 7.26 (s, 1H), 6.75 (d, J=8.3 Hz, 2H), 5.79 (s, 2H), 3.51 (t, J=6.5 Hz, 2H), 3.32 (s, 2H), 2.85 (t, J=6.2 Hz, 2H), 2.09-1.95 (m, 2H), 1.81-1.68 (m, 2H); $^{13}$C NMR (126 MHz, DMSO) δ 151.31, 133.58, 133.58, 131.48, 129.37, 129.33, 127.94, 126.34, 122.49, 120.03, 118.73, 113.57, 106.60, 31.13, 28.60, 22.25, 21.94; HRMS (ESI) m/z calcd for C$_{21}$H$_{20}$N$_3$ [M+H]$^+$ 314.1657, found 314.1651.

2,6-Difluoro-4-(8,9,10,11-tetrahydro-3H-pyrrolo[3,2-a]phenanthridin-7-yl)phenol

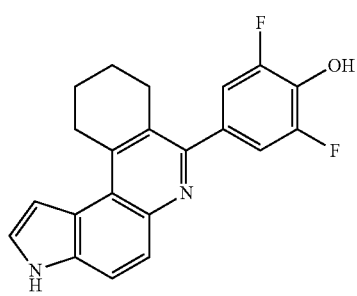

HSD-02-935

Method A: Yellow solid (161 mg, 46%). $^1$H NMR (500 MHz, DMSO-d$_6$) δ 12.43 (s, 1H), 10.91 (s, 1H), 8.13 (d, J=9.0 Hz, 1H), 7.95 (d, J=8.9 Hz, 1H), 7.73 (s, 1H), 7.50 (d, J=7.2 Hz, 2H), 7.28 (s, 1H), 3.52 (t, J=6.5 Hz, 2H), 2.81 (t, J=6.1 Hz, 2H), 2.03-1.99 (m, 2H), 1.78 (dd, J=6.2, 2.7 Hz, 2H); $^{13}$C NMR (126 MHz, DMSO) δ 153.28, 153.22, 151.35, 151.29, 148.78, 135.89, 133.70, 132.12, 129.36, 126.45, 123.30, 120.58, 119.86, 114.37, 106.78, 31.05, 28.08, 22.12, 21.76; HRMS (ESI) m/z calcd for C$_{21}$H$_{17}$F$_2$N$_2$O [M+H]$^+$ 351.1308, found 351.1302.

2-Methyl-4-(8,9,10,11-tetrahydro-3H-pyrrolo[3,2-a]phenanthridin-7-yl)phenol

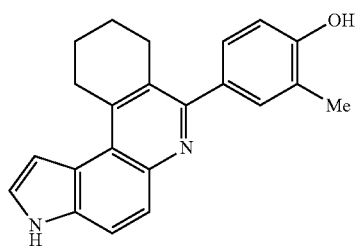

HSD-02-936

Method A: Yellow solid (260 mg, 79%). $^1$H NMR (500 MHz, DMSO-d$_6$) δ 10.31 (s, 1H), 8.19 (d, J=9.0 Hz, 1H), 8.03 (d, J=9.0 Hz, 1H), 7.78 (t, J 2.9 Hz, 1H), 7.47 (t, J=1.5 Hz, 1H), 7.41 (dd, J=8.3, 2.4 Hz, 1H), 7.29 (d, J=2.5 Hz, 1H), 7.10 (d, J=8.3 Hz, 1H), 3.54 (t, J=6.4 Hz, 2H), 2.82 (t, J=6.2 Hz, 2H), 2.06-1.97 (m, 2H), 1.78 (qd, J=6.2, 3.0 Hz, 2H); $^{13}$C NMR (126 MHz, DMSO) δ 158.45, 154.02, 150.34, 133.74, 132.54, 129.76, 129.19, 127.02, 124.97, 122.99, 122.46, 121.27, 119.85, 115.10, 113.79, 106.76, 31.34, 28.25, 22.01, 21.65, 16.42; HRMS (ESI) m/z calcd for C$_{22}$H$_{21}$N$_2$O [M+H]$^+$ 329.1653, found 329.1645.

2-Chloro-4-(8,9,10,11-tetrahydro-3H-pyrrolo[3,2-a]phenanthridin-7-yl)phenol

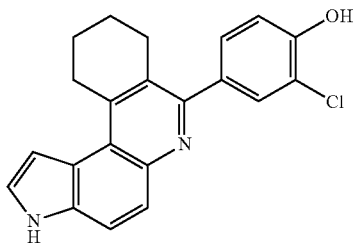

HSD-02-937

Method A: Yellow solid (226 mg, 65%). $^1$H NMR (500 MHz, DMSO-d$_6$) δ 11.74 (s, 1H), 7.77 (dd, J=8.9, 0.7 Hz, 1H), 7.62 (d, J=8.8 Hz, 1H), 7.50 (d, J=2.1 Hz, 1H), 7.48 (t, J=2.6 Hz, 1H), 7.34 (dd, J=8.3, 2.1 Hz, 1H), 7.13-7.10 (m, 1H), 7.04 (d, J=8.3 Hz, 1H), 3.37 (d, J=6.6 Hz, 2H), 2.78 (t, J=6.1 Hz, 2H), 1.97 (pd, J=6.1, 2.6 Hz, 2H), 1.77-1.68 (m, 2H); $^{13}$C NMR (126 MHz, DMSO) δ 154.51, 153.28, 143.38, 142.36, 133.59, 133.20, 130.91, 129.36, 127.54, 124.08, 123.92, 122.39, 120.33, 119.60, 116.47, 116.41, 106.27, 29.99, 29.17, 22.87, 22.60; HRMS (ESI) m/z calcd for C$_{21}$H$_{18}$ClN$_2$O [M+H]$^+$ 349.1107, found 349.1112.

7-(4-Hydroxyphenyl)-8,9,10,11-tetrahydro-3H-pyrrolo[3,2-a]phenanthridine-9-carbonitrile

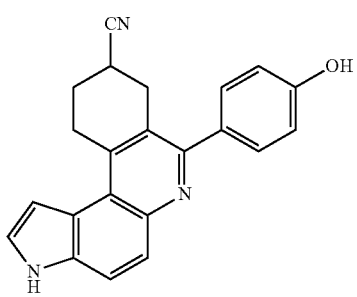

HSD-02-938

Method A: Yellow solid (190 mg, 56%). $^1$H NMR (500 MHz, DMSO-d$_6$) δ 10.46 (s, 1H), 8.21 (d, J=8.9 Hz, 1H), 8.05 (d, J=9.0 Hz, 1H), 7.81 (s, 1H), 7.62 (d, J=8.6 Hz, 2H), 7.29 (s, 1H), 7.08 (d, J=8.6 Hz, 2H), 3.63 (q, J=5.8 Hz, 2H), 3.40-3.36 (m, OH), 3.17 (qd, J=16.6, 6.4 Hz, 2H), 2.42-2.35 (m, 1H), 2.32-2.24 (m, 1H); $^{13}$C NMR (126 MHz, DMSO) δ 160.52, 151.84, 150.21, 134.27, 133.81, 132.07, 127.33, 126.12, 122.49, 122.38, 122.15, 121.66, 119.70, 116.10, 114.00, 106.64, 30.73, 29.32, 24.59, 23.97; HRMS (ESI) m/z calcd for $C_{22}H_8N_3O$ [M+H]$^+$ 340.1449, found 340.1445.

4-(1,2,4,9-Tetrahydropyrano[3,4-c]pyrrolo[3,2-1]quinolin-5-yl)phenol

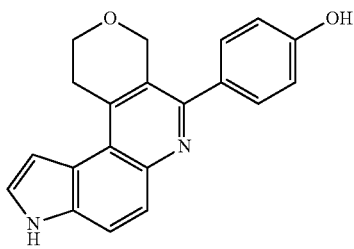

HSD-02-939

Method A: Yellow solid (193 mg, 61%). $^1$H NMR (500 MHz, DMSO-d$_6$) δ 10.36 (s, 1H), 8.22 (d, J=9.0 Hz, 1H), 8.03 (d, J=9.0 Hz, 1H), 7.81 (t, J=2.9 Hz, 1H), 7.59 (d, J=8.5 Hz, 2H), 7.30 (t, J=2.4 Hz, 1H), 7.03 (d, J=8.5 Hz, 2H), 4.17 (t, J=5.7 Hz, 2H), 3.61 (t, J=5.8 Hz, 2H), 3.42 (s, 2H); $^{13}$C NMR (126 MHz, DMSO) δ 159.90, 149.19, 133.51, 132.49, 131.49, 130.87, 127.07, 126.51, 122.13, 120.36, 119.93, 116.30, 115.93, 115.62, 105.92, 66.43, 64.15, 29.76; HRMS (ESI) m/z calcd for $C_{20}H_{17}N_2O_2$ [M+H]$^+$ 317.1290, found 317.1290.

6-(8,9,10,11-tetrahydro-3H-pyrrolo[3,2-a]phenanthridin-7-yl)pyridin-3-ol

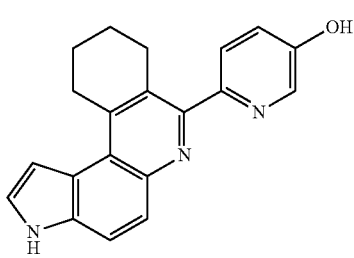

HSD-02-940

Method A: Yellow solid (98 mg, 31%). $^1$H NMR (500 MHz, DMSO-d$_6$) 11.74 (s, 1H), 10.03 (s, 1H), 8.18 (d, J=2.8 Hz, 1H), 7.77 (d, J=8.9 Hz, 1H), 7.64 (dd, J=12.0, 8.7 Hz, 2H), 7.49 (t, J=2.8 Hz, 1H), 7.29 (dd, J=8.5, 2.9 Hz, 1H), 7.12 (d, J=2.5 Hz, 1H), 3.40-3.35 (m, 2H), 2.95 (t, J=6.3 Hz, 2H), 1.96-1.92 (m, 2H), 1.78-1.69 (m, 2H); $^{13}$C NMR (126 MHz, DMSO) δ 153.80, 153.32, 151.06, 142.98, 142.40, 136.29, 133.31, 128.21, 125.55, 124.11, 123.92, 123.07, 122.67, 120.36, 116.37, 106.28, 30.10, 28.50, 22.89, 22.51; HRMS (ESI) m/z calcd for $C_{20}H_{18}N_3O$ [M+H]$^+$ 316.1450, found 316.1453.

4-(8,9,10,11-Tetrahydro-3H-pyrrolo[3,2-a]phenanthridin-7-yl)benzoic Acid

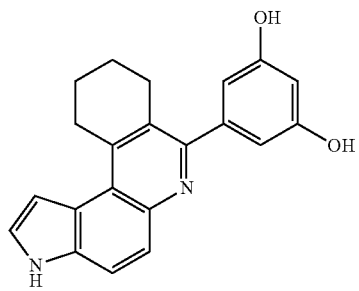

HSD-02-941

Method A: Yellow solid (212 mg, 62%). $^1$H NMR (500 MHz, Methanol-d$_4$) δ 8.17 (d, J=8.1 Hz, 2H), 7.87 (d, J=8.9 Hz, 1H), 7.73 (d, J=8.9 Hz, 1H), 7.62 (d, J=8.1 Hz, 2H), 7.49 (d, J=3.1 Hz, 1H), 7.24 (d, J=3.2 Hz, 1H), 3.53 (t, J=6.5 Hz, 2H), 2.76 (t, J=6.2 Hz, 2H), 2.11-2.04 (m, 2H), 1.88-1.79 (m, 2H); $^{13}$C NMR (126 MHz, MeOD) δ 153.85, 146.36, 142.90, 140.67, 133.41, 132.50, 129.30, 128.80, 127.65, 123.56, 123.12, 120.18, 119.96, 117.15, 105.96, 47.93, 30.20, 28.28, 22.22, 21.85; HRMS (ESI) m/z calcd for $C_{22}H_{19}N_2O_2$ [M+H]$^+$ 343.1446, found 343.1438.

5-(8,9,10,11-Tetrahydro-3H-pyrrolo[3,2-a]phenanthridin-7-yl)benzene-1,3-diol

HSD-02-943

Method A: Yellow solid (231 mg, 70%). $^1$H NMR (500 MHz, DMSO-d$_6$) δ 9.96 (s, 2H), 8.20 (d, J=8.9 Hz, 1H), 7.96 (d, J=9.0 Hz, 1H), 7.80 (s, 1H), 7.31 (d, J=2.4 Hz, 1H), 6.59-6.47 (m, 3H), 3.54 (t, J=6.5 Hz, 2H), 2.77 (t, J=6.2 Hz, 2H), 2.05-1.97 (m, 2H), 1.82-1.77 (m, 2H). $^{13}$C NMR (126 MHz, DMSO) δ 159.29, 154.49, 149.99, 133.76, 129.45, 127.13, 123.34, 121.54, 119.85, 113.69, 107.84, 106.82, 104.94, 40.48, 40.31, 40.14, 39.98, 39.81, 39.64, 39.48, 31.31, 27.91, 21.94, 21.44; HRMS (ESI) m/z calcd for $C_{21}H_{19}N_2O_2$ [M+H]$^+$ 331.1446, found 331.1450.

5-(8,9,10,11-Tetrahydro-3H-pyrazolo[4,3-a]phenanthridin-7-yl)pyridin-2-amine

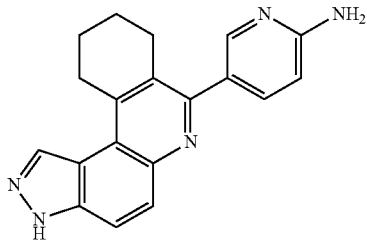

HSD-02-944

Method A: Yellow solid (205 mg, 65%). ¹H NMR (500 MHz, Methanol-d₄) δ 8.51 (s, 1H), 8.16 (d, J=2.1 Hz, 1H), 8.14 (dd, J=9.0, 2.2 Hz, 1H), 7.88 (d, J=9.1 Hz, 1H), 7.83 (d, J=9.2 Hz, 1H), 7.09 (d, J=9.0 Hz, 1H), 3.26 (t, J=6.6 Hz, 2H), 2.87 (t, J=6.1 Hz, 2H), 2.06 (ddt, J=9.2, 6.5, 3.2 Hz, 2H), 1.86 (dp, J=9.3, 3.1 Hz, 2H); ¹³C NMR (126 MHz, MeOD) δ 155.32, 150.42, 145.84, 143.67, 143.48, 141.93, 138.13, 130.19, 126.90, 123.86, 122.70, 119.27, 115.60, 111.95, 29.80, 28.11, 21.86, 21.86; HRMS (ESI) m/z calcd for $C_{19}H_{18}N_5$ [M+H]⁺ 316.1562, found 316.1555.

7-(Pyrimidin-5-yl)-8,9,10,11-tetrahydro-3H-pyrazolo[4,3-a]phenanthridine

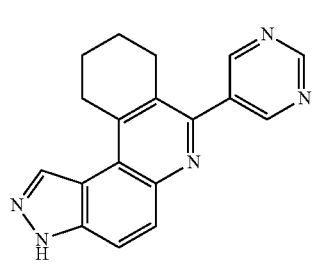

HSD-02-945

Method A: Yellow solid (144 mg, 48%). ¹H NMR (500 MHz, DMSO-d₆) δ ¹H NMR (500 MHz, DMSO-d₆) δ 9.26 (s, 1H), 9.07 (s, 2H), 8.55 (s, 1H), 7.89 (d, J=9.0 Hz, 1H), 7.84 (d, J=11.9 Hz, 2H), 3.31 (s, 4H), 2.84 (t, J=6.1 Hz, 2H), 2.03-1.94 (m, 2H), 1.80-1.71 (m, 2H); ¹³C NMR (126 MHz, DMSO) δ 158.00, 157.25, 150.89, 143.91, 142.97, 138.83, 136.49, 134.77, 129.84, 129.50, 122.42, 116.25, 114.94, 29.62, 28.44, 22.43, 22.38; HRMS (ESI) m/z calcd for $C_{19}H_{17}N_4$ [M+H]⁺ 301.1453, found 301.1457.

5-(8,9,10,11-Tetrahydro-3H-pyrazolo[4,3-a]phenanthridin-7-yl)thiazol-2-amine

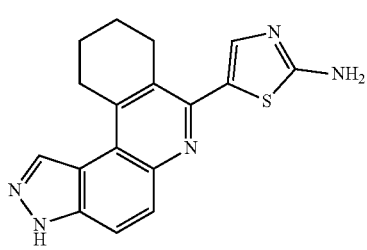

HSD-02-946

Method A: Yellow solid (166 mg, 52%). ¹H NMR (500 MHz, DMSO-d₆) δ 8.50 (s, 1H), 7.79 (d, J=9.1 Hz, 1H), 7.66 (d, J=9.4 Hz, 1H), 7.51 (s, 1H), 7.23 (s, 2H), 3.28-3.22 (m, 2H), 2.96 (t, J=6.2 Hz, 2H), 1.99-1.93 (m, 2H), 1.90-1.82 (m, 2H); ¹³C NMR (126 MHz, DMSO) δ 170.46, 148.47, 143.26, 142.39, 140.03, 138.39, 136.08, 129.21, 128.99, 128.03, 120.39, 116.44, 114.43, 29.95, 28.90, 22.52, 22.24; HRMS (ESI) m/z calcd for $C_{17}H_{16}N_5S$ [M+H]⁺ 322.1126, found 322.1127.

2-Fluoro-4-(8,9,10,11-tetrahydro-3H-pyrrolo[3,2-a]phenanthridin-7-yl)phenol

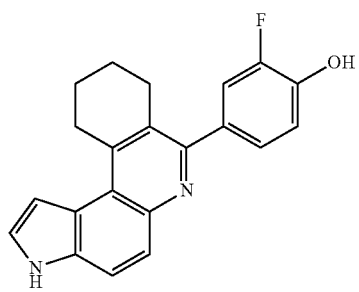

HSD-02-947

Method A: Yellow solid (196 mg, 59%). ¹H NMR (500 MHz, DMSO-d₆) δ 11.75 (s, 2H), 7.85-7.71 (m, 2H), 7.67-7.56 (m, 2H), 7.48 (t, J=2.8 Hz, 1H), 7.10 (t, J=2.4 Hz, 1H), 6.40 (d, J=9.4 Hz, 1H), 3.35 (t, J=6.6 Hz, 2H), 2.84 (t, J=6.1 Hz, 2H), 1.97 (td, J=8.6, 7.2, 4.5 Hz, 2H), 1.75 (tq, J=8.5, 5.4, 3.9 Hz, 2H). ¹³C NMR (126 MHz, DMSO) δ 162.16, 151.74, 143.46, 142.97, 142.51, 136.05, 133.19, 127.71, 123.97, 122.39, 120.28, 119.30, 116.56, 106.27, 30.00, 28.90, 22.83, 22.63; HRMS (ESI) m/z calcd for $C_{21}F_{18}FN_2O$ [M+H]⁺ 333.1405, found 333.1403.

5-(8,9,10,11-Tetrahydro-3H-pyrrolo[3,2-a]phenanthridin-7-yl)thiazol-2-amine

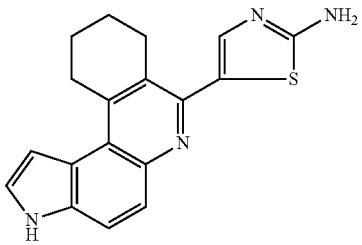

HSD-02-948

Method A: Yellow solid (112 mg, 35%). ¹H NMR (500 MHz, DMSO-d₆) δ 12.21 (s, 1H), 8.12 (d, J=9.0 Hz, 1H), 8.04-7.94 (m, 1H), 7.56-7.50 (m, 2H), 6.96 (s, 1H), 5.98 (t, J=2.4 Hz, 1H), 3.29 (t, J=6.4 Hz, 2H), 2.84 (s, 2H), 1.96-1.88 (m, 2H), 1.83 (q, J=6.0, 5.3 Hz, 2H); HRMS (ESI) m/z calcd for $C_{18}H_{17}N_4S$ [M+H]⁺ 321.1174, found 321.1177.

2-Hydroxy-5-(8,9,10,11-tetrahydro-3H-pyrazolo[4,3-a]phenanthridin-7-yl)benzoic Acid

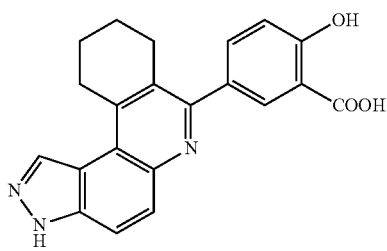

HSD-02-949

Method A: Yellow solid (187 mg, 52%). ¹H NMR (500 MHz, DMSO-d₆) δ 10.10 (s, 1H), 8.67 (s, 1H), 8.09 (d, J=9.8 Hz, 4H), 3.38-3.31 (m, 2H), 2.78 (t, J=6.2 Hz, 2H), 2.06-1.93 (m, 2H), 1.83-1.72 (m, 2H); HRMS (ESI) m/z calcd for $C_{21}H_{19}H_{18}N_3O_3$ [M+H]⁺ 360.1348, found 360.1351.

Methyl 2-hydroxy-5-(8,9,10,11-tetrahydro-3H-pyrazolo[4,3-a]phenanthridin-7-yl)benzoate

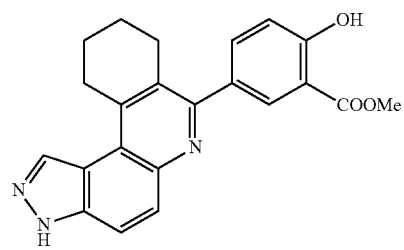

HSD-02-950

Method A: White solid (208 mg, 56%). ¹H NMR (500 MHz, DMSO-d₆) δ 10.93 (s, 1H), 8.73 (s, 1H), 8.20-8.12 (m, 2H), 8.09 (d, J=2.3 Hz, 1H), 7.87 (dd, J=8.6, 2.4 Hz, 1H), 7.24 (d, J=8.6 Hz, 1H), 3.89 (s, 3H), 3.40 (td, J=6.9, 4.0 Hz, 2H), 2.78 (t, J=6.1 Hz, 2H), 2.06-1.91 (m, 2H), 1.77 (tt, J=8.9, 5.5 Hz, 2H). ¹³C NMR (126 MHz, DMSO) δ 168.54, 168.54, 168.32, 161.15, 151.10, 150.72, 136.76, 132.49, 132.29, 131.52, 124.82, 122.96, 121.86, 118.10, 117.86, 115.02, 114.60, 53.03, 30.66, 28.23, 21.85, 21.79; HRMS (ESI) m/z calcd for $C_{22}H_{20}N_3O_3$ [M+H]⁺ 374.1505, found 374.1508.

3-(8,9,10,11-Tetrahydro-3H-pyrrolo[3,2-a]phenanthridin-7-yl)pyridin-2(1H)-one

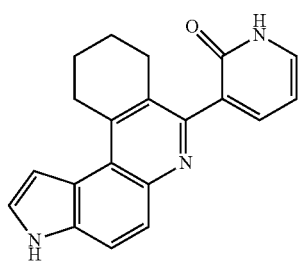

HSD-02-951

Method A: Yellow solid (204 mg, 65%). Yellow solid (217 mg, 70%). ¹H NMR (500 MHz, DMSO-d₆) δ 11.76 (s, 1H), 7.80-7.72 (m, 2H), 7.64-7.58 (m, 2H), 7.48 (t, J=2.7 Hz, 1H), 7.10 (t, J=2.3 Hz, 1H), 6.41 (d, J=9.4 Hz, 1H), 3.36 (d, J=6.6 Hz, 2H), 2.84 (t, J=6.2 Hz, 2H), 2.02-1.94 (m, 2H), 1.75 (dp, J=9.3, 3.4, 2.9 Hz, 2H); ¹³C NMR (126 MHz, DMSO) δ 162.19, 151.74, 143.47, 142.98, 142.52, 136.07, 133.20, 127.72, 123.98, 122.40, 120.30, 119.29, 116.56, 106.28, 30.01, 28.91, 22.83, 22.63; HRMS (ESI) m/z calcd for $C_{20}H_{18}N_3O$ [M+H]⁺ 316.1450, found 316.1459.

Methyl 2-hydroxy-5-(8,9,10,11-tetrahydro-3H-pyrrolo[3,2-a]phenanthridin-7-yl)benzoate

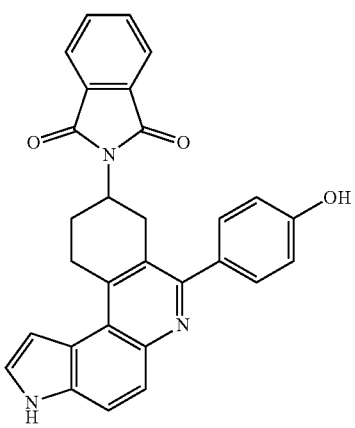

HSD-02-952

Method A: White solid (189 mg, 51%). ¹H NMR (500 MHz, Methanol-d₄) δ 8.01 (d, J=2.3 Hz, 1H), 7.79 (d, J=8.9 Hz, 1H), 7.71 (d, J=8.8 Hz, 1H), 7.66 (dt, J=8.5, 2.1 Hz, 1H), 7.43 (d, J=3.1 Hz, 1H), 7.20 (d, J=3.2 Hz, 1H), 7.09 (dd, J=8.3, 2.4 Hz, 1H), 3.96 (s, 3H), 3.49 (t, J=6.5 Hz, 2H), 2.77 (t, J=6.2 Hz, 2H), 2.11-2.03 (m, 2H), 1.83 (dp, J=9.4, 3.0 Hz, 2H); ¹³C NMR (126 MHz, MeOD) δ 170.24, 161.08, 154.60, 143.93, 142.64, 136.22, 133.26, 132.11, 130.33, 127.42, 122.82, 121.91, 120.24, 116.86, 116.03, 111.93, 105.77, 51.58, 48.10, 29.95, 28.67, 22.45, 22.16; HRMS (ESI) m/z calcd for $C_{23}H_{21}N_2O_3$ [M+H]⁺ 373.1552, found 373.1557.

2-(7-(4-Hydroxyphenyl)-8,9,10,11-tetrahydro-3H-pyrrolo[3,2-a]phenanthridin-9-yl)isoindoline-1,3-dione 12.11

HSD-02-953

Method A: Yellow solid (197 mg, 43%). ¹H NMR (500 MHz, DMSO-d₆) δ 11.85 (s, 1H), 7.81 (tt, J=4.4, 1.9 Hz, 5H), 7.64 (d, J=8.9 Hz, 1H), 7.50 (d, J=3.1 Hz, 1H), 7.37-7.29 (m, 2H), 7.12 (d, J=3.3 Hz, 1H), 6.85-6.78 (m, 2H), 4.44-4.33 (m, 1H), 3.78-3.69 (m, 1H), 3.69-3.57 (m, 1H), 3.54-3.44 (m, 1H), 2.89-2.81 (m, 1H), 2.79-2.68 (m, 1H), 2.34-2.26 (m, 1H); $^{13}$C NMR (126 MHz, DMSO) δ 168.40, 157.71, 155.84, 143.60, 141.02, 134.77, 133.23, 132.00, 130.64, 125.66, 124.08, 123.99, 123.38, 121.75, 120.41, 116.72, 115.24, 106.26, 47.58, 32.31, 30.31, 26.40; HRMS (ESI) m/z calcd for $C_{29}H_{22}N_3O_3$ [M+H]$^+$ 460.1661, found 460.1665.

Benzyl (7-(4-hydroxyphenyl)-8,9,10,11-tetrahydro-3H-pyrrolo[3,2-a]phenanthridin-9-yl)carbamate

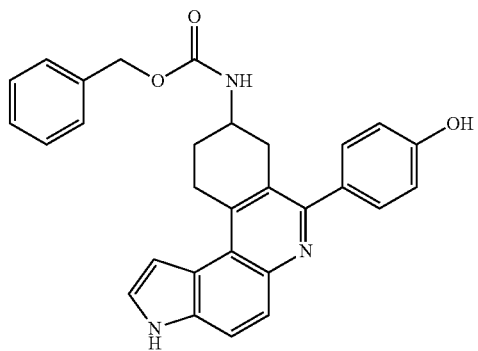

HSD-02-954

Method A: Yellow solid (240 mg, 52%). $^1$H NMR (500 MHz, DMSO-d$_6$) δ 10.46 (s, 1H), 8.20 (d, J=9.0 Hz, 1H), 8.07 (d, J=8.9 Hz, 1H), 7.78 (d, J=3.0 Hz, 1H), 7.55 (d, J=8.4 Hz, 2H), 7.37-7.19 (m, 611), 7.08 (s, 1H), 4.97 (d, J=3.2 Hz, 2H), 3.84 (t, J=7.4 Hz, 1H), 3.69 (dt, J=19.6, 5.6 Hz, 1H), 3.56 (dt, J=19.2, 7.4 Hz, 1H), 3.01 (dd, J=16.9, 4.6 Hz, 1H), 2.81 (dd, J=16.6, 8.4 Hz, 1H), 2.31-2.18 (m, 1H), 2.06-1.95 (m, 1H). $^{13}$C NMR (126 MHz, DMSO) δ 160.39, 156.05, 153.02, 150.33, 137.46, 133.91, 133.75, 131.95, 128.79, 128.27, 127.75, 127.12, 122.61, 122.34, 121.41, 119.89, 116.02, 113.72, 106.77, 65.77, 45.47, 33.92, 29.80, 27.29; HRMS (ESI) m/z calcd for $C_{29}H_{26}N_3O_3$ [M+H]$^+$ 4, 64.1974 found 464.1970.

7-(4-Hydroxyphenyl)-8,9,10,11-tetrahydro-3H-pyrrolo[3,2-a]phenanthridin-9-ol

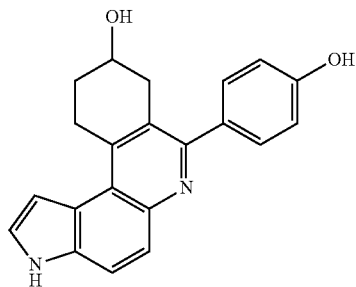

HSD-02-955

Method A: Yellow solid (172 mg, 52%). $^1$H NMR (500 MHz, DMSO-d$_6$) δ 10.43 (s, 1H), 8.19 (d, J=8.9 Hz, 1H), 8.04 (d, J=8.9 Hz, 1H), 7.78 (t, J=2.9 Hz, 1H), 7.65-7.51 (m, 2H), 7.29 (t, J=2.4 Hz, 1H), 7.12-7.00 (m, 211), 4.05 (tt, J=7.0, 3.1 Hz, 1H), 3.70-3.60 (m, 1H), 3.52 (dt, J=19.2, 6.8 Hz, 1H), 2.99 (dd, J=16.6, 4.1 Hz, 1H), 2.75 (dd, J=16.6, 6.7 Hz, 1H), 2.19-2.09 (m, 1H), 1.99 (dq, J=13.9, 7.0 Hz, 1H). $^{13}$C NMR (126 MHz, DMSO) 160.37, 153.53, 150.30, 133.89, 133.72, 132.01, 127.94, 127.08, 122.53, 121.38, 119.84, 115.99, 113.73, 106.74, 63.25, 36.67, 29.46, 29.03; HRMS (ESI) m/z calcd for $C_{21}F_{19}N_2O_2$ [M+H]$^+$ 331.1447, found 331.1452.

4-(8,9,10,11-Tetrahydro-3H-pyrrolo[3,2-a]phenanthridin-7-yl)-2-(trifluoromethoxy)phenol

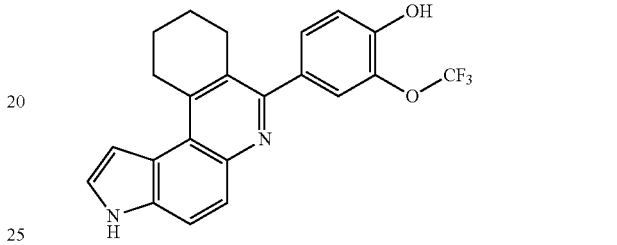

HSD-02-956

Method A: off-white solid (242 mg, 61%). $^1$H NMR (500 MHz, DMSO-d$_6$) δ 11.16 (s, 1H), 8.22 (d, J=8.9 Hz, 1H), 8.01 (d, J=9.0 Hz, 1H), 7.86-7.75 (m, 2H), 7.60 (dd, J=8.4, 2.2 Hz, 1H), 7.41-7.29 (m, 2H), 3.57 (t, J=6.4 Hz, 2H), 2.79 (t. J=6.2 Hz, 2H), 2.09-1.97 (m, 1.83-1.76 (m, 2H). $^{13}$C NMR (126 MHz, DMSO) δ 152.73, 148.65, 136.08, 134.20, 133.76, 130.85, 129.77, 126.94, 125.54, 123.93 (q, J=257 Hz), 123.31, 121.29, 119.80, 118.25, 114.31, 106.81, 31.29, 28.01, 21.96, 21.63; HRMS (ESI) m/z calcd for $C_{22}H_{18}F_3N_2O$ [M+H]$^+$ 399.1320, found 399.1321.

3-(8,9,10,11-Tetrahydro-3H-pyrrolo[3,2-a]phenanthridin-7-yl)phenol

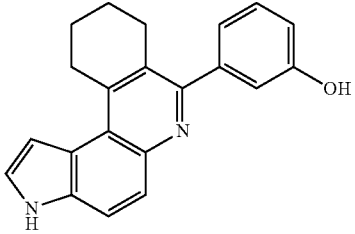

HSD-02-957

Method A: Yellow solid (188 mg, 60%). $^1$H NMR (500 MHz, DMSO-d$_6$) δ 10.28 (s, 1H), 8.17 (d, J=8.9 Hz, 1H), 7.97 (d, J=8.9 Hz, 1H), 7.77 (t, J=2.9 Hz, 1H), 7.43 (t, J=7.9 Hz, 1H), 7.27-7.16 (m, 2H), 7.09 (td, J=5.2, 2.2 Hz, 2H), 3.45 (t, J=6.5 Hz, 2H), 2.73 (t, J=6.2 Hz, 2H), 2.03-1.95 (m, 2H), 1.81-1.72 (m, 2H). $^{13}$C NMR (126 MHz, DMSO) δ 158.18, 154.01, 149.81, 133.69, 130.40, 129.35, 126.95, 123.26, 121.30, 120.36, 119.72, 118.04, 116.76, 113.98, 106.74, 31.22, 27.99, 21.92, 21.47; HRMS (ESI) m/z calcd for $C_{21}H_{19}N_2O$ [M+H]$^+$ 315.1497, found 315.1499.

5-(8,9,10,11-tetrahydro-3H-pyrrolo[3,2-a]phenanthridin-7-yl)pyrimidin-2-amine

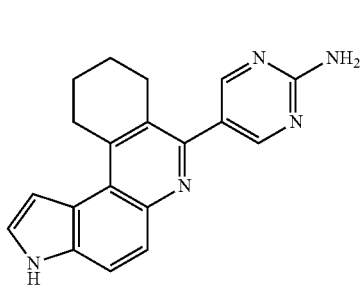

HSD-02-958

Method A: Pale yellow solid (185 mg, 59%). ¹H NMR (500 MHz, Methanol-d₄) δ 8.07 (dd, J=2.4, 0.9 Hz, 1H), 7.77 (dd, J=8.9, 0.9 Hz, 1H), 7.69 (d, J=8.9 Hz, 1H), 7.63 (dd, J=8.5, 2.4 Hz, 1H), 7.40 (d, J=3.1 Hz, 1H), 7.14 (dd, J=3.2, 0.9 Hz, 1H), 6.70 (dd, J=8.5, 0.8 Hz, 1H), 3.42 (t, J=6.4 Hz, 2H), 2.78 (t, J=6.2 Hz, 2H), 2.05-1.96 (m, 2H), 1.83-1.75 (m, 2H); ¹³C NMR (126 MHz, DMSO) δ 163.22, 158.63, 158.15, 152.27, 144.04, 142.51, 134.14, 129.66, 129.58, 123.56, 123.39, 121.80, 116.22, 29.69, 28.81, 22.63, 22.56; HRMS (ESI) m/z calcd for $C_{19}H_{18}N_5$ [M+H]⁺ 316.1562, found 316.1565.

2-((Dimethylamino)methyl)-4-(8,9,10,11-tetrahydro-3H-pyrrolo[3,2-a]phenanthridin-7-yl)phenol

HSD-02-959

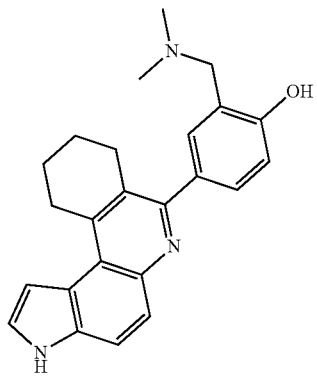

Method A: Pale yellow solid (170 mg, 46%). ¹H NMR (500 MHz, Methanol-d₄) δ 7.77 (d, J=8.9 Hz, 1H), 7.69 (d, J=9.0 Hz, 1H), 7.41 (s, 1H), 7.33 (dd, J=8.2, 2.2 Hz, 1H), 7.26 (d, J=2.2 Hz, 1H), 7.19-7.15 (m, 1H), 6.92 (d, J=8.2 Hz, 1H), 3.88 (s, 2H), 3.46 (t, J=6.5 Hz, 2H), 2.75 (t, J=6.2 Hz, 2H), 2.05-2.01 (m, 2H), 1.82-1.76 (m, 2H); HRMS (ESI) m/z calcd for $C_{24}H_{26}N_3O$ [M+H]⁺ 372.2076, found 372.2082.

2,6-Diiodo-4-(8,9,10,11-tetrahydro-3H-pyrazolo[4,3-a]phenanthridin-7-yl)phenol

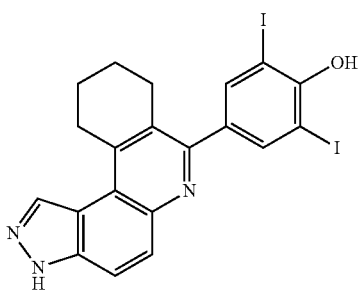

HSD-02-960

Method A: Yellow solid (272 mg, 48%). ¹H NMR (500 MHz, DMSO-d₆) δ 9.79 (s, 1H), 8.57 (s, 1H), 7.94 (s, 2H), 7.92-7.78 (m, 3H), 3.29 (s, 2H), 2.03-1.95 (m, 2H), 1.78-1.70 (m, 2H); HRMS (ESI) m/z calcd for $C_{20}H_{16}I_2N_3O$ [M+H]⁺ 567.9383, found 567.9388.

3-(8,9,10,11-Tetrahydro-3H-pyrazolo[4,3-a]phenanthridin-7-yl)phenol

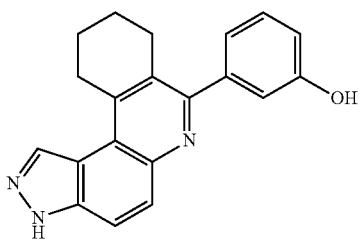

HSD-02-962

Method A: White solid (195 mg, 62%). ¹H NMR (500 MHz, DMSO-d₆) δ 10.18 (s, 1H), 8.72 (s, 1H), 8.13 (dd, J=37.4, 8.8 Hz, 2H), 7.42 (t, J=7.9 Hz, 1H), 7.17-7.03 (m, 3H), 3.37 (q, J=8.2, 6.3 Hz, 2H), 2.75 (t, J=6.2 Hz, 2H), 2.00 (p, J=6.5, 6.1 Hz, 2H), 1.76 (dd, J=11.3, 5.9 Hz, 2H). ¹³C NMR (126 MHz, DMSO) δ 158.08, 152.26, 151.41, 135.68, 134.33, 131.45, 130.29, 123.05, 120.90, 120.40, 117.83, 116.79, 114.86, 30.73, 28.07, 21.77, 21.59; HRMS (ESI) m/z calcd for $C_{19}H_{18}N_5$ [M+H]⁺ 316.1562, found 316.1555.

3-(8,9,10,11-Tetrahydro-3H-pyrazolo[4,3-a]phenanthridin-7-yl)pyridin-2(1H)-one

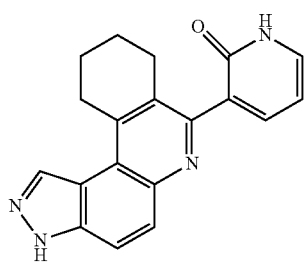

HSD-02-963

Method A: Off-white solid (214 mg, 67%). $^1$H NMR (500 MHz, DMSO-d$_6$) δ 8.53 (s, 1H), 7.83 (d, J=9.0 Hz, 1H), 7.81-7.73 (m, 2H), 7.65 (d, J=2.7 Hz, 1H), 6.42 (d, J=9.4 Hz, 1H), 3.25 (t, J=6.5 Hz, 2H), 2.84 (t, J=6.0 Hz, 2H), 1.97 (dq, J=8.4, 5.7 Hz, 2H), 1.78-1.69 (m, 2H); $^{13}$C NMR (126 MHz, DMSO) δ 162.24, 152.74, 143.82, 142.86, 142.53, 140.86, 139.70, 136.38, 134.04, 129.50, 121.76, 119.36, 118.81, 116.19, 115.37, 29.69, 28.79, 22.61, 22.55; HRMS (ESI) m/z calcd for C$_{19}$F$_{17}$N$_4$O [M+H]$^+$ 317.1402, found 317.1411.

Benzyl (7-(4-hydroxyphenyl)-8,9,10,11-tetrahydro-3H-pyrazolo[4,3-a]phenanthridin-9-yl)carbamate

HSD-02-964

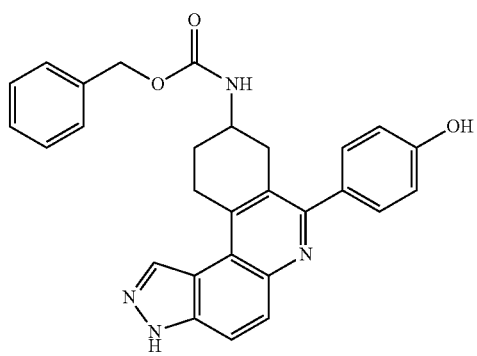

Method A: Off-white solid (241 mg, 52%). $^1$H NMR (500 MHz, Methanol-d$_4$) δ 8.66 (d, J=9.1 Hz, 1H), 8.08 (dd, J=9.2, 6.3 Hz, 1H), 7.93 (dd, J=9.3, 5.3 Hz, 1H), 7.50 (d, J=8.2 Hz, 2H), 7.29-7.20 (m, 5H), 7.02 (d, J=8.2 Hz, 2H), 5.01 (s, 2H), 3.97-3.84 (m, 1H), 3.67-3.56 (m, 1H), 3.54-3.41 (m, 1H), 3.18-3.08 (m, 1H), 2.95-2.82 (m, 1H), 2.42-2.29 (m, 1H), 2.11-2.01 (m, 1H). $^{13}$C NMR (126 MHz, MeOD) δ 161.72, 159.87, 156.89, 152.70, 150.63, 139.58, 136.84, 136.35, 130.82, 129.46, 128.03, 127.56, 127.34, 123.73, 122.33, 120.83, 119.33, 118.00, 115.47, 114.97, 66.04, 48.13, 48.08, 47.96, 47.79, 47.62, 47.45, 47.28, 47.11, 45.66, 33.71, 29.28, 26.87; HRMS (ESI) m/z calcd for C$_{28}$H$_{25}$N$_4$O$_3$ [M+H]$^+$ 465.1927, found 465.1927.

7-(4-Hydroxyphenyl)-8,9,10,11-tetrahydro-3H-pyrazolo[4,3-a]phenanthridin-9-ol

HSD-02-965

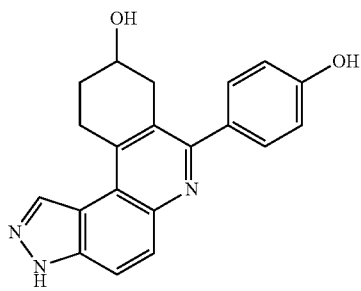

Method A: Off-white solid (211 mg, 64%). $^1$H NMR (500 MHz, DMSO-d$_6$) δ 9.87 (s, 1H), 8.57 (s, 1H), 7.97-7.80 (m, 2H), 7.45 (d, J=8.1 Hz, 2H), 6.93 (d, J=8.1 Hz, 2H), 4.92 (s, 1H), 3.95 (a, J=7.8, 3.3 Hz, 1H), 3.41 (dt, J=20.7, 4.7 Hz, 1H), 3.27 (p, J=7.1 Hz, 1H), 2.96 (dd, J=16.6, 4.2 Hz, 1H), 2.74 (dd, J=16.5, 7.4 Hz, 1H), 2.13 (dt, J=13.1, 6.2 Hz, 1H), 1.90 (dq, J=15.0, 7.8 Hz, 1H). $^{13}$C NMR (126 MHz, DMSO) δ 158.44, 155.40, 144.50, 141.23, 138.96, 136.06, 131.24, 129.27, 128.15, 126.83, 121.32, 115.90, 115.38, 64.42, 37.63, 30.18, 28.16; HRMS (ESI) m/z calcd for C$_{20}$H$_{18}$N$_3$O$_2$ [M+H]$^+$ 332.1399, found 332.1402.

2-(7-(4-Hydroxyphenyl)-8,9,10,11-tetrahydro-3H-pyrazolo[4,3-a]phenanthridin-9-yl)isoindoline-1,3-dione

HSD-02-966

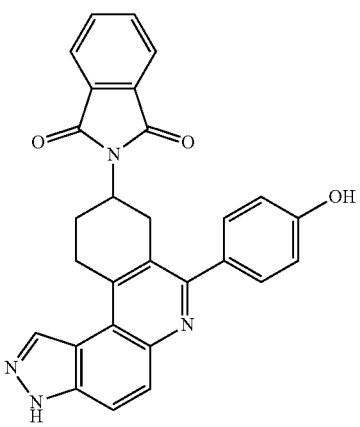

Method A: Off-white solid (239 mg, 52%). $^1$H NMR (500 MHz, DMSO-d$_6$) δ 9.56 (s, 1H), 8.57 (s, 1H), 7.89-7.84 (m, 2H), 7.83-7.78 (m, 4H), 7.36 (d, J=8.6 Hz, 1H), 6.82 (d, J=8.6 Hz, 1H), 4.45-4.33 (m, 1H), 3.73-3.59 (m, 2H), 3.53-3.39 (m, 1H), 2.92-2.85 (m, 1H), 2.82-2.69 (m, 1H), 2.36-2.26 (m, 1H); $^{13}$C NMR (126 MHz, DMSO) δ 168.38, 157.66, 156.88, 143.84, 141.13, 138.66, 136.38, 134.76, 132.01, 131.67, 130.75, 129.58, 127.50, 123.38, 121.10, 116.54, 115.25, 114.60, 47.46, 32.19, 31.15, 26.15; HRMS (ESI) m/z calcd for C$_{28}$H$_{21}$N$_4$O$_3$ [M+H]$^+$ 461.1614, found 461.1619.

2-Chloro-4-(8,9,10,11-tetrahydro-3H-pyrazolo[4,3-a]phenanthridin-7-yl)phenol

HSD-02-967

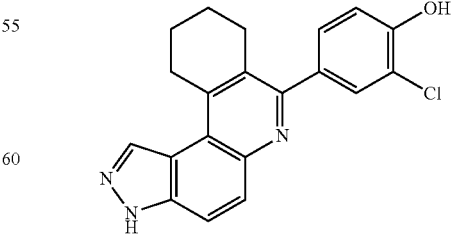

Method A: Off-white solid (191 mg, 55%). $^1$H NMR (500 MHz, DMSO-d$_6$) δ 11.20 (s, 1H), 8.74 (s, 1H), 8.25-8.12 (m, 2H), 7.80 (d, J=2.1 Hz, 1H), 7.56 (dd, J=8.4, 2.2 Hz, 1H), 7.30 (d, J=8.4 Hz, 1H), 3.40 (d, J=6.7 Hz, 2H), 2.81 (t, J=6.1 Hz, 2H), 2.07-1.98 (m, 2H), 1.81-1.75 (m, 2H). ¹³C NMR (126 MHz, DMSO) δ 155.92, 152.58, 149.60, 135.00, 131.94, 131.83, 130.50, 123.67, 122.81, 120.32, 120.19, 116.98, 114.53, 30.78, 28.06, 21.65, 21.61; HRMS (ESI) m/z calcd for $C_{20}H_{17}ClN_3O$ [M+H]⁺ 350.1060, found 350.1066.

4-(1-Bromo-8,9,10,11-tetrahydro-3H-pyrazolo[4,3-a]phenanthridin-7-yl)phenol Method A

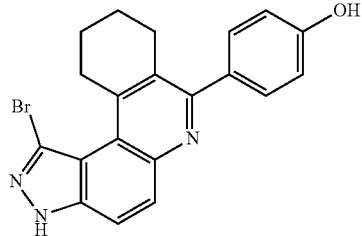

HSD-02-968

Method A: Yellow solid (110 mg, 28%). Off-white solid (153 mg, 39%). ¹H NMR (500 MHz, Methanol-d₄) δ 8.18 (d, J=9.1 Hz, 1H), 8.06 (d, J=9.2 Hz, 1H), 7.57 (d, J=8.3 Hz, 2H), 7.07 (d, J=8.3 Hz, 2H), 3.99 (s, 2H), 2.97 (s, 2H), 1.97 (t, J=3.5 Hz, 4H). ¹³C NMR (126 MHz, MeOD) 160.37, 155.96, 151.79, 141.59, 135.37, 132.94, 130.83, 123.46, 121.93, 120.38, 119.36, 115.60, 114.56, 36.01, 27.02, 20.91, 20.80. ¹³C NMR (126 MHz, MeOD) δ 160.37, 155.96, 154.60, 151.79, 141.55, 135.37, 132.94, 130.83, 127.59, 123.46, 121.93, 120.38, 119.25, 115.60, 114.56, 36.01, 27.02, 20.91, 20.80; HRMS (ESI) m/z calcd for $C_{20}H_{17}BrN_3O$ [M+H]⁺ 394.0555, found 394.0556.

7-(6-Chloropyridin-3-yl)-8,9,10,11-tetrahydro-3H-pyrazolo[4,3-a]phenanthridine

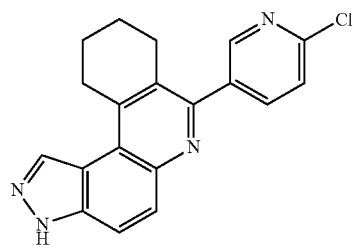

HSD-02-969

Method A: White solid (210 mg, 63%). ¹H NMR (500 MHz, DMSO-d₆) 8.69 (d, J=2.4 Hz, 1H), 8.64 (s, 1H), 8.17 (dd, J=8.2, 2.5 Hz, 1H), 8.02-7.91 (m, 2H), 7.70 (d, J=8.2 Hz, 1H), 3.33 (t, J=6.6 Hz, 2H), 2.78 (t, J=6.2 Hz, 2H), 2.02-1.97 (m, 2H), 1.80-1.73 (m, 2H); HRMS (ESI) m/z calcd for $C_{19}H_{16}ClN_4$ [M+H]⁺ 335.1063, found 335.1063.

4-(8,9,10,11-Tetrahydro-3H-pyrazolo[4,3-a]phenanthridin-7-yl)-2-(trifluoromethyl)phenol

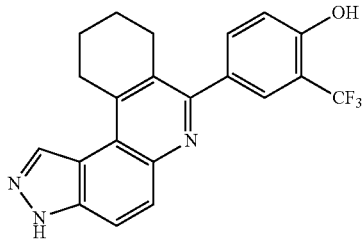

HSD-02-970

Method A: white solid (233 mg, 61%). ¹H NMR (500 MHz, DMSO-d₆) δ 10.77 (s, 1H), 8.52 (s, 1H), 7.82 (d, J=2.2 Hz, 2H), 7.72-7.64 (m, 2H), 7.12 (d, J=8.3 Hz, 1H), 3.32-3.25 (m, 2H), 2.78 (t, J=6.1 Hz, 2H), 2.02-1.92 (m, 2H), 1.77-1.67 (m, 2H); ¹³C NMR (126 MHz, DMSO) δ 155.93, 155.43, 143.63, 142.52, 138.66, 136.33, 134.92, 131.78, 129.60, 129.39, 127.78, 127.73, 125.63 (q, J=273.42 Hz), 121.78, 116.87, 116.43, 115.61 (q, J=30.24 Hz), 114.39, 29.69, 29.00, 22.55; HRMS (ESI) m/z calcd for $C_{21}H_{17}F_3N_3O$ [M+H]⁺ 384.1324, found 384.1329.

2-Methoxy-4-(8,9,10,11-tetrahydro-3H-pyrazolo[4,3-a]phenanthridin-7-yl)phenol

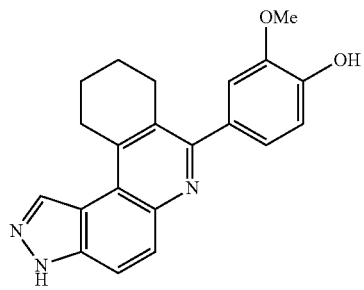

HSD-02-971

Method A: White solid (231 mg, 67%). ¹H NMR (500 MHz, DMSO-d₆) 9.57 (s, 1H), 8.63 (s, 1H), 8.03 (s, 2H), 7.24 (d, J=2.1 Hz, 1H), 7.08 (dd, J=8.0, 2.0 Hz, 1H), 6.98 (d, J=8.0 Hz, 1H), 3.83 (s, 3H), 3.35 (s, 2H), 2.82 (t, J=6.2 Hz, 2H), 2.04-1.98 (m, 2H), 1.79-1.71 (m, 2H); ¹³C NMR (126 MHz, DMSO) δ 148.62, 147.81, 138.57, 135.55, 131.11, 126.48, 123.12, 122.31, 115.71, 114.34, 56.35, 30.47, 28.55, 22.05; HRMS (ESI) m/z calcd for $C_{21}H_{20}N_3O_2$ [M+H]⁺ 346.1556, found 346.1562.

191

3-Fluoro-4-(8,9,10,11-tetrahydro-3H-pyrazolo[4,3-a]phenanthridin-7-yl)phenol

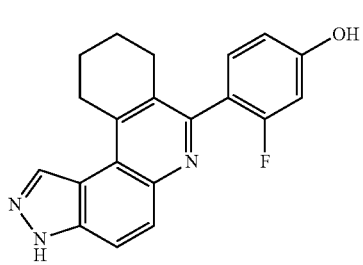

HSD-02-972

Method A: White solid (186 mg, 56%). $^1$H NMR (500 MHz, DMSO-$d_6$) δ 8.57 (s, 1H), 7.84 (dd, J=9.0, 0.9 Hz, 1H), 7.79 (d, J=9.1 Hz, 1H), 7.22 (t, J=8.6 Hz, 1H), 6.72 (dd, J=8.3, 2.3 Hz, 1H), 6.66 (dd, J=11.8, 2.3 Hz, 1H), 3.30 (t, J=6.6 Hz, 2H), 2.61 (t, J=6.0 Hz, 2H), 2.00-1.91 (m, 2H), 1.79-1.69 (m, 2H); $^{13}$C NMR (126 MHz, DMSO) δ 161.25 (J=245.11 Hz), 159.59, 159.50, 152.73, 143.80, 142.04, 132.20, 132.16, 130.53, 129.53, 122.03, 119.48, 119.35, 116.25, 112.08, 102.89, 102.70, 29.48, 27.50, 22.64, 22.24; HRMS (ESI) m/z calcd for $C_{20}H_{17}FN_3O$ [M+H]$^+$ 334.1356, found 334.1360.

4-(9-Methyl-8,9,10,11-tetrahydro-3H-pyrazolo[4,3-a]phenanthridin-7-yl)phenol

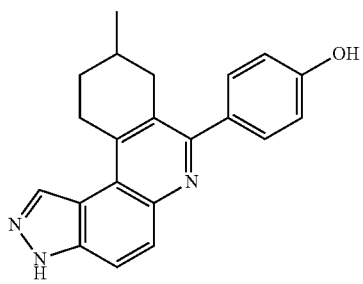

HSD-02-973

Method A: Off-white solid (223 mg, 68%). $^1$H NMR (500 MHz, Methanol-$d_4$) δ 8.81 (s, 1H), 8.22 (d, J=9.3 Hz, 1H), 8.02 (d, J=9.3 Hz, 1H), 7.58 (dd, J=8.5, 1.9 Hz, 2H), 7.07 (dd, J=8.6, 1.9 Hz, 2H), 3.75-3.68 (m, 1H), 3.56 (dt, J=18.6, 8.3 Hz, 1H), 2.91 (dt, J=17.3, 2.7 Hz, 1H), 2.65 (dd, J=17.1, 10.6 Hz, 1H), 2.38-2.21 (m, 1H), 1.99-1.85 (m, 1H), 1.79-1.64 (m, 1H), 1.14 (dd, J=6.5, 1.8 Hz, 3H); $^{13}$C NMR (126 MHz, MeOD) δ 160.23, 153.67, 151.60, 134.75, 132.00, 130.90, 124.14, 123.00, 123.00, 122.62, 121.61, 119.36, 119.08, 116.55, 115.54, 115.03, 35.98, 30.99, 29.34, 27.83, 20.20; HRMS (ESI) m/z calcd for $C_{21}H_{30}N_3O$ [M+H]$^+$ 330.1606, found 330.1609.

192

4-(3,8,9,10-Tetrahydrocyclopenta[c]pyrazolo[4,3-t]quinolin-7-yl)phenol

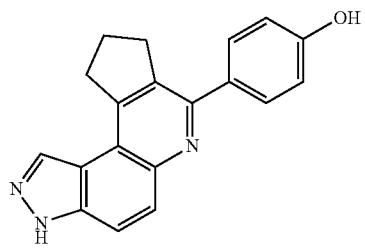

HSD-02-974

Method A: Off-white solid (168 mg, 56%). $^1$H NMR (500 MHz, DMSO-$d_6$) δ 8.42 (s, 1H), 7.85 (d, J=9.2 Hz, 1H), 7.81 (dd, J=9.1, 0.9 Hz, 1H), 7.74 (d, J=8.6 Hz, 2H), 6.89 (d, J=8.6 Hz, 2H), 3.41 (t, J=7.6 Hz, 2H), 3.21 (t, J=7.4 Hz, 2H), 2.21 (p, J=7.6 Hz, 2H); $^{13}$C NMR (126 MHz, DMSO) δ 158.20, 152.26, 149.32, 144.91, 135.59, 131.44, 130.38, 129.22, 118.73, 116.70, 115.46, 33.48, 33.40, 24.97; HRMS (ESI) m/z calcd for $C_{19}H_{16}N_3O$ [M+H]$^+$ 302.1293, found 302.1295.

7-(4-Hydroxyphenyl)-8,9,10,11-tetrahydro-3H-pyrazolo[4,3-a]phenanthridine-9-carbonitrile

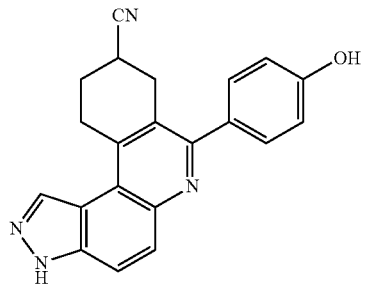

HSD-02-976

Method A: Yellow solid (207 mg, 61%). $^1$H NMR (500 MHz, DMSO-$d_6$) δ 10.41 (s, 1H), 8.76 (s, 1H), 8.21 (d, J=9.2 Hz, 1H), 8.17 (d, J=9.2 Hz, 1H), 7.62 (d, J=8.2 Hz, 2H), 7.07 (d, J=8.2 Hz, 2H), 3.58-3.48 (m, 2H), 3.45-3.36 (m, 1H), 3.28-3.12 (m, 2H), 2.43-2.34 (m, 1H), 2.34-2.24 (m, 1H). $^{13}$C NMR (126 MHz, DMSO) δ 157.87, 156.56, 144.05, 140.61, 138.62, 136.16, 131.33, 130.95, 129.54, 125.63, 122.86, 120.97, 116.21, 115.29, 114.74, 31.73, 27.64, 25.08, 24.57; HRMS (ESI) m/z calcd for $C_{21}H_{17}N_4O$ [M+H]$^+$ 341.1402, found 341.1410.

2-((Dimethylamino)methyl)-4-(8,9,10,11-tetrahydro-3H-pyrazolo[4,3-a]phenanthridin-7-yl)phenol

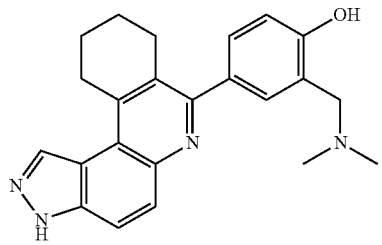

HSD-02-977

Method A: Yellow solid (148 mg, 40%). $^1$H NMR (500 MHz, Methanol-d$_4$) δ 8.63 (s, 1H), 7.92 (s, 2H), 7.61-7.55 (m, 2H), 7.12 (d, J=8.1 Hz, 1H), 4.42 (s, 2H), 3.43 (d, J=6.2 Hz, 2H), 2.93 (s, 6H), 2.85 (t, J=6.2 Hz, 2H), 2.13-2.08 (m, 2H), 1.91-1.82 (m, 2H); HRMS (ESI) m/z calcd for C$_{23}$H$_{25}$N$_4$O [M+H]$^+$ 373.2028, found 373.2033.

7-(6-Fluoropyridin-3-yl)-8,9,10,11-tetrahydro-3H-pyrazolo[4,3-a]phenanthridine

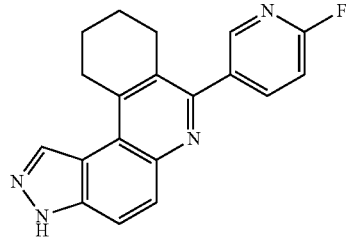

HSD-02-978

Method A: Pale yellow solid (181 mg, 57%). $^1$H NMR (500 MHz, Methanol-d$_4$) δ 8.51 (s, 1H), 8.40 (d, J=2.4 Hz, 1H), 8.16 (td, J=8.0, 2.5 Hz, 1H), 7.83 (s, 2H), 7.22 (dd, J=8.4, 2.4 Hz, 1H), 3.27 (t, J=6.6 Hz, 2H), 2.76 (t, J=6.2 Hz, 2H), 2.09-2.02 (m, 2H), 1.86-1.78 (m, 2H); $^{13}$C NMR (126 MHz, MeOD) δ 164.30, 162.39, 152.26, 147.56, 147.45, 144.47, 142.82, 142.68, 142.61, 133.99, 129.83, 127.94, 122.52, 115.69, 108.96, 108.67, 29.58, 28.25, 21.91, 21.87; HRMS (ESI) m/z calcd for C$_{19}$H$_{16}$FN$_4$ [M+H]$^+$ 319.1359, found 319.1366.

2-Iodo-4-(8,9,10,11-tetrahydro-3H-pyrazolo[4,3-a]phenanthridin-7-yl)phenol

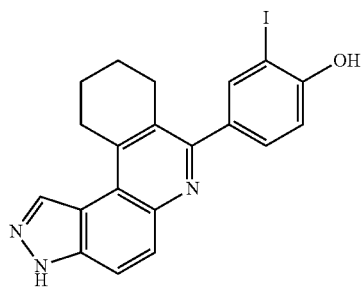

HSD-02-980

Method A: White solid (198 mg, 45%). $^1$H NMR (500 MHz, Methanol-d$_4$) δ 8.87 (s, 1H), 8.28 (d, J=9.2 Hz, 1H), 8.11 (d, J=2.2 Hz, 1H), 8.06 (d, J=9.2 Hz, 1H), 7.60 (dd, J=8.4, 2.2 Hz, 1H), 7.10 (d, J=8.4 Hz, 1H), 3.65 (t, J=6.4 Hz, 2H), 2.95 (t, J=6.2 Hz, 2H), 2.31-2.09 (m, 2H), 2.03-1.69 (m, 2H); $^{13}$C NMR (126 MHz, MeOD) δ 159.64, 154.77, 153.68, 149.57, 140.11, 134.50, 132.47, 130.75, 129.17, 123.97, 123.61, 118.95, 114.86, 114.28, 109.63, 83.68, 30.98, 27.82, 21.28, 21.20; HRMS (ESI) m/z calcd for C$_{20}$H$_{17}$IN$_3$O [M+H]$^+$ 442.0416, found 442.0416.

4-(8,9,10,11-Tetrahydro-3H-pyrazolo[4,3-a]phenanthridin-7-yl)benzoic Acid

HSD-02-981

Method A: Yellow solid (172 mg, 50%). $^1$H NMR (500 MHz, DMSO-d$_6$) δ 8.62 (s, 1H), 8.12-8.08 (m, 2H), 8.02 (d, J=9.1 Hz, 1H), 7.95 (d, J=9.1 Hz, 1H), 7.80-7.73 (m, 2H), 3.29 (t, J=6.5 Hz, 2H), 2.75-2.68 (m, 2H), 2.00-1.94 (m, 2H), 1.76-1.66 (m, 2H). $^{13}$C NMR (126 MHz, DMSO) δ 167.42, 152.75, 148.00, 140.96, 139.42, 135.00, 131.73, 130.39, 130.19, 129.66, 129.59, 124.86, 122.74, 118.09, 115.38, 30.20, 28.32, 22.04, 21.92; HRMS (ESI) m/z calcd for C$_{21}$H$_{18}$N$_3$O$_2$ [M+H]$^+$ 344.1399, found 344.1401.

4-(8,9-Dihydro-3H-cyclobuta[c]pyrazolo[4,3-f]quinolin-7-yl)phenol

HSD-02-982

Method A: Off-white solid (152 mg, 53%). $^1$H NMR (500 MHz, DMSO-d$_6$) δ 9.80 (s, 1H), 8.32 (s, 1H), 8.01 (dd, J=8.6, 1.4 Hz, 2H), 7.82 (d, J=9.5 Hz, 1H), 7.78 (d, J=9.1 Hz, 1H), 6.91 (dd, J=8.6, 1.4 Hz, 2H), 3.73-3.64 (m, 2H), 3.62-3.54 (m, 2H); $^{13}$C NMR (126 MHz, DMSO) δ 159.12, 149.75, 148.04, 144.97, 137.96, 136.56, 134.42, 130.02, 129.03, 128.87, 116.88, 116.11, 115.24, 114.32, 32.33, 30.24; HRMS (ESI) m/z calcd for C$_{18}$H$_{14}$N$_3$O [M+H]$^+$ 288.1137, found 288.1139.

4-(3,8-Dihydro-2H-furo[3,2-c]pyrazolo[4,3-f]quinolin-4-yl)phenol

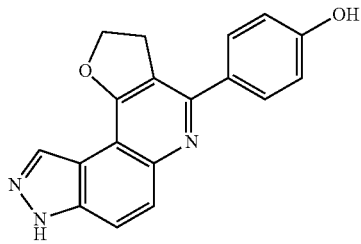

HSD-02-983

Method B: Off-white solid (127 mg, 42%). $^1$H NMR (500 MHz, Methanol-$d_4$) δ 8.72 (s, 1H), 8.61 (s, 1H), 7.90 (d, J=9.2 Hz, 1H), 7.84 (d, J=9.2 Hz, 1H), 7.40 (d, J=8.5 Hz, 2H), 6.94 (d, J=8.5 Hz, 2H), 3.74 (t, J=7.0 Hz, 2H), 3.10 (t, J=7.0 Hz, 2H); HRMS (ESI) m/z calcd for $C_{18}H_{14}N_3O_2$ [M+H]$^+$ 304.1086, found 304.1087.

7-(1H-Indazol-5-yl)-8,9,10,11-tetrahydro-3H-pyrazolo[4,3-a]phenanthridine

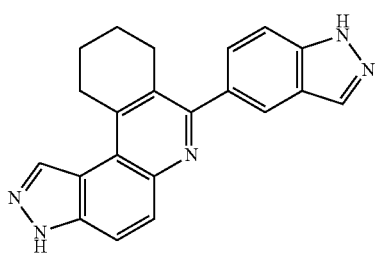

HSD-02-984

Method A: Off-white solid (224 mg, 65%). $^1$H NMR (500 MHz, DMSO-$d_6$) δ 8.56 (s, 1H), 8.12 (s, 1H), 7.92 (s, 1H), 7.83 (d, J=5.8 Hz, 2H), 7.61 (d, J=8.6 Hz, 1H), 7.55 (d, J=8.6 Hz, 1H), 3.32-3.26 (m, 2H), 2.78 (t, J=6.1 Hz, 2H), 2.01-1.92 (m, 2H), 1.74-1.65 (m, 2H); $^{13}$C NMR (126 MHz, DMSO) δ 157.30, 143.71, 142.28, 139.80, 138.66, 136.27, 134.45, 133.55, 129.66, 129.54, 128.17, 123.07, 121.71, 121.43, 116.44, 114.31, 109.93, 29.69, 29.22, 22.64, 22.59; HRMS (ESI) m/z calcd for $C_{21}H_{18}N_5$ [M+H]$^+$ 340.1562, found 340.1565.

7-(1H-Indazol-6-yl)-8,9,10,11-tetrahydro-3H-pyrazolo[4,3-a]phenanthridine

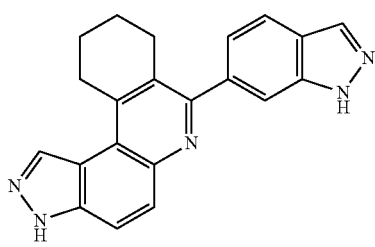

HSD-02-985

Method A: Off-white solid (176 mg, 52%). $^1$H NMR (500 MHz, DMSO-$d_6$) δ 8.52 (s, 1H), 7.87-7.77 (m, 2H), 7.61 (d, J=1.6 Hz, 1H), 7.48 (d, J=8.2 Hz, 1H), 7.38 (dd, J=8.2, 1.7 Hz, 1H), 3.27 (d, J=7.7 Hz, 2H), 2.75 (t, J=6.0 Hz, 2H), 1.97 (qd, J=6.5, 4.2, 2.9 Hz, 2H), 1.79-1.67 (m, 2H); $^{13}$C NMR (126 MHz, DMSO) δ 155.27, 143.48, 142.61, 138.71, 138.01, 136.36, 133.74, 131.74, 129.55, 129.36, 125.92, 122.00, 116.36, 114.53, 111.49, 110.02, 29.64, 28.80, 22.52, 22.44; HRMS (ESI) m/z calcd for $C_{21}H_{18}N_5$ [M+H]$^+$ 340.1562, found 340.1565.

5-(8,9,10,11-Tetrahydro-3H-pyrazolo[4,3-a]phenanthridin-7-yl)-1H-benzo[d]imidazol-2(3H)-one

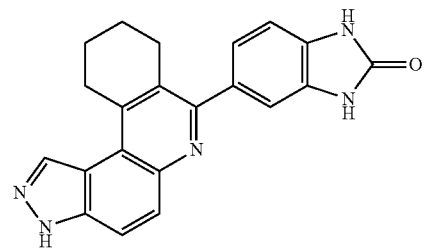

HSD-02-986

Method A: Off-white solid (178 mg, 50%). $^1$H NMR (500 MHz, DMSO-$d_6$) δ 8.55 (s, 1H), 7.84 (d, J=9.1 Hz, 1H), 7.78 (d, J=9.1 Hz, 1H), 7.16-7.09 (m, 2H), 7.00 (d, J=7.8 Hz, 1H), 3.28 (t, J=6.5 Hz, 2H), 2.77 (t, J=6.1 Hz, 2H), 2.00-1.95 (m, 2H), 1.73-1.66 (m, 2H); $^{13}$C NMR (126 MHz, DMSO) δ 157.16, 156.09, 143.72, 142.21, 139.73, 134.99, 133.77, 130.00, 129.94, 129.53, 129.35, 122.16, 121.65, 116.30, 115.27, 109.89, 108.18, 29.70, 29.28, 22.65, 22.62; HRMS (ESI) m/z calcd for $C_{22}H_{17}N_4O_2$ [M+H]$^+$ 369.1352, found 369.1352.

4-(8,9,10,11-Tetrahydro-1H-pyrazolo[3,4-a]phenanthridin-7-yl)phenol

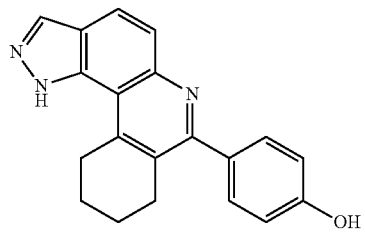

HSD-02-987

Method A: Off-white solid (126 mg, 40%). $^1$H NMR (500 MHz, DMSO-$d_6$) δ 9.63 (s, 1H), 8.14 (s, 1H), 7.77 (d, J=8.9 Hz, 1H), 7.58 (d, J=9.0 Hz, 1H), 7.43 (d, J=8.5 Hz, 2H), 6.88 (d, J=8.6 Hz, 2H), 3.17 (t, J=6.6 Hz, 2H), 2.73 (t, J=6.1 Hz, 2H), 1.88 (qd, J=7.8, 6.4, 4.5 Hz, 2H), 1.73-1.63 (m, 2H); $^{13}$C NMR (126 MHz, DMSO) δ 158.72, 157.79, 142.88, 138.02, 134.71, 134.54, 131.87, 130.95, 129.09, 124.62, 121.76, 119.80, 116.13, 115.13, 28.93, 26.48, 22.74, 22.32; HRMS (ESI) m/z calcd for $C_{20}H_{18}N_3O$ [M+H]$^+$ 316.1449, found 316.1458.

5-(8,9,10,11-Tetrahydro-3H-pyrazolo[4,3-a]phenanthridin-7-yl)pyrimidine-2,4(1H,3H)-dione

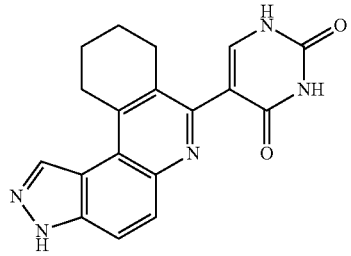

HSD-02-988

Method A: Off-white solid (173 mg, 52%). ¹H NMR (500 MHz, Methanol-d₄) δ 8.77 (s, 1H), 8.18-8.10 (m, 1H), 8.02-7.85 (m, 1H), 7.74-7.17 (m, 2H), 3.60-3.48 (m, 2H), 3.02-2.89 (m, 2H), 2.20-2.09 (m, 1H), 2.04-1.90 (m, 1H); HRMS (ESI) m/z calcd for $C_{18}H_{16}N_5O_2$ [M+H]⁺ 334.1304, found 334.1305.

2-Methyl-6-(8,9,10,11-tetrahydro-3H-pyrazolo[4,3-a]phenanthridin-7-yl)benzo[d]thiazole

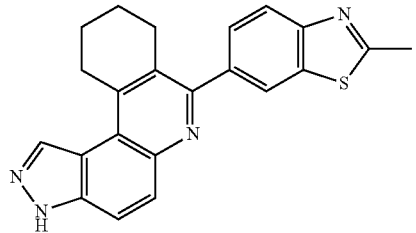

HSD-02-989

Method A: Off-white solid (207 mg, 56%). ¹H NMR (500 MHz, DMSO-d₆) δ 8.59 (s, 1H), 8.22 (d, J=1.6 Hz, 1H), 7.97 (d, J=8.3 Hz, 1H), 7.86 (dd, J=9.0, 0.9 Hz, 1H), 7.82 (d, J=9.1 Hz, 1H), 7.65 (dd, J=8.3, 1.7 Hz, 1H), 3.36-3.33 (m, 3H), 2.83 (s, 3H), 2.81-2.78 (m, 2H), 2.04-1.98 (m, 2H), 1.78-1.70 (m, 2H); ¹³C NMR (126 MHz, DMSO) δ 168.24, 156.38, 152.90, 143.77, 142.53, 137.87, 135.52, 129.61, 129.48, 127.80, 122.99, 121.99, 121.67, 118.44, 116.26, 29.71, 29.02, 22.62, 22.54, 20.33; HRMS (ESI) m/z calcd for $C_{22}H_{19}N_4S$ [M+H]⁺ 371.1330, found 371.1333.

3,5-Difluoro-4-(8,9,10,11-tetrahydro-3H-pyrazolo[4,3-a]phenanthridin-7-yl)phenol

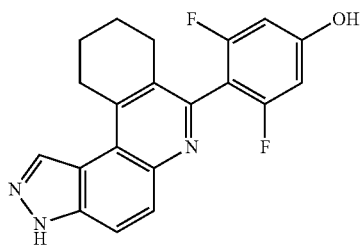

HSD-02-990

Method A: White solid (168 mg, 48%). ¹H NMR (500 MHz, DMSO-d₆) 8.52 (s, 1H), 7.84 (d, J=9.0 Hz, 1H), 7.80 (d, J=9.5 Hz, 1H), 7.61 (d, J=1.6 Hz, 1H), 7.48 (d, J=8.2 Hz, 1H), 7.38 (dd, J=8.2, 1.7 Hz, 1H), 3.27 (d, J=7.7 Hz, 2H), 2.75 (t, J=6.0 Hz, 2H), 1.99-1.92 (m, 2H), 1.76-1.65 (m, 2H); ¹³C NMR (126 MHz, DMSO) δ 155.27, 143.48, 142.96, 142.76, 142.61, 138.71, 138.01, 136.36, 133.74, 131.74, 129.55, 129.36, 125.92, 122.00, 116.36, 114.53, 111.49, 110.02, 29.64, 28.80, 22.52, 22.44; HRMS (ESI) m/z calcd for $C_{20}H_{16}FN_3O$ [M+H]⁺ 352.1261, found 352.1266.

7-(4-Hydroxyphenyl)-8,9,10,11-tetrahydro-3H-pyrazolo[4,3-a]phenanthridine-9-carboxylic Acid

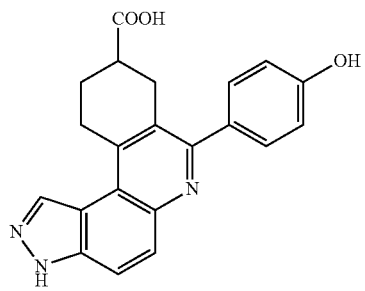

HSD-02-991

Method A: Off-white solid (180 mg, 50%). ¹H NMR (500 MHz, DMSO-d₆) δ 8.56 (s, 1H), 7.83 (d, J=9.1 Hz, 1H), 7.78 (d, J=9.1 Hz, 1H), 7.38 (d, J=8.5 Hz, 2H), 6.87 (d, J=8.5 Hz, 2H), 3.48-3.39 (m, 1H), 3.36-3.23 (m, H), 3.05-2.97 (m, 1H), 2.95-2.87 (m, 1H), 2.62-2.56 (m, 1H), 2.38-2.30 (m, 1H), 2.01-1.91 (m, 1H); ¹³C NMR (126 MHz, DMSO) δ 177.11, 157.71, 156.96, 143.77, 141.52, 131.87, 130.83, 129.55, 128.25, 121.22, 116.27, 115.19, 31.66, 29.18, 25.49; HRMS (ESI) m/z calcd for $C_{21}H_{18}N_3O_3$ [M+H]⁺ 360.1348, found 360.1351.

5-(8,9,10,11-Tetrahydro-3H-pyrazolo[4,3-a]phenanthridin-7-yl)benzo[d]thiazol-2-amine

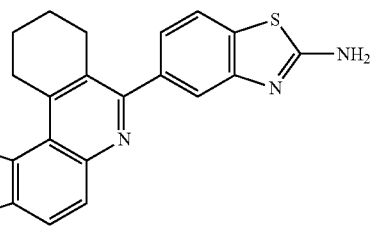

HSD-02-992

Method A: Pale yellow solid (137 mg, 37%). ¹H NMR (500 MHz, DMSO-d₆) δ 8.55 (s, 1H), 7.88-7.78 (m, 3H), 7.55 (s, 2H), 7.45-7.36 (m, 2H), 3.32 (s, 2H), 2.82 (t, J=6.1 Hz, 2H), 1.99 (qq, J=5.2, 2.7 Hz, 2H), 1.74 (dp, J=9.1, 3.2, 2.8 Hz, 2H); ¹³C NMR (126 MHz, DMSO) δ 167.61, 156.90, 152.94, 143.53, 142.39, 138.63, 136.32, 133.93, 131.17, 129.60, 127.25, 122.13, 121.64, 117.32, 116.50, 114.34, 29.75, 29.18, 22.66, 22.62; HRMS (ESI) m/z calcd for $C_{21}H_{18}N_5S$ [M+H]⁺ 372.1283, found 372.1285.

4-(3,8,10,11-Tetrahydropyrano[3,4-c]pyrazolo[4,3-f]quinolin-7-yl)phenol

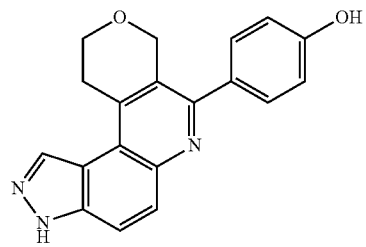

HSD-02-993

Method A: Off-white solid (206 mg, 65%). $^1$H NMR (500 MHz, DMSO-d$_6$) δ 9.69 (s, 1H), 8.52 (s, 1H), 7.85 (q, J=9.2 Hz, 2H), 7.40 (d, J=8.5 Hz, 2H), 6.87 (d, J=8.6 Hz, 2H), 4.77 (s, 2H), 4.11 (t, J=5.9 Hz, 2H), 3.34 (d, J=6.8 Hz, 2H); $^{13}$C NMR (126 MHz, DMSO) δ 158.09, 153.88, 144.20, 139.12, 138.55, 135.81, 130.66, 130.59, 129.53, 127.54, 120.80, 116.34, 115.40, 114.82, 67.17, 64.45, 28.70; HRMS (ESI) m/z calcd for C$_{19}$H$_{16}$N$_3$O$_2$ [M+H]$^+$ 318.1243, found 318.1244.

N-(7-(4-Hydroxyphenyl)-8,9,10,11-tetrahydro-3H-pyrazolo[4,3-a]phenanthridin-9-yl)acetamide

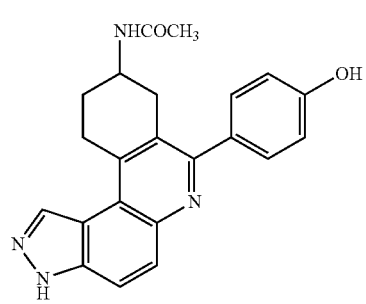

HSD-02-994

Method A: Pale brownish solid (220 mg, 59%). $^1$H NMR (500 MHz, DMSO-d$_6$) δ 8.57 (s, 1H), 7.97 (d, J=7.2 Hz, 1H), 7.84 (dd, J=9.0, 0.9 Hz, 1H), 7.79 (d, J=9.1 Hz, 1H), 7.40-7.35 (m, 2H), 6.89-6.80 (m, 2H), 3.96-3.88 (m, 1H), 3.52-3.46 (m, 1H), 3.34-3.29 (m, 1H), 2.98-2.90 (m, 1H), 2.75 (dd, J=16.6, 9.0 Hz, 1H), 2.24-2.16 (m, 1H), 1.95-1.83 (m, 1H), 1.77 (s, 3H); $^{13}$C NMR (126 MHz, DMSO) δ 169.29, 157.68, 157.02, 143.86, 141.35, 131.82, 130.82, 129.56, 127.39, 121.15, 116.35, 115.20, 44.69, 35.05, 28.48, 28.02, 23.15; HRMS (ESI) m/z calcd for C$_{22}$H$_{21}$N$_4$O$_2$ [M+H]$^+$ 373.1665, found 373.1670.

4-(6,7,8,9-Tetrahydro-1H-pyrazolo[3,4-c]phenanthridin-5-yl)phenol

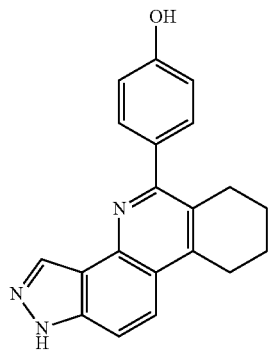

HSD-02-995

Method A: Pale brownish solid (132 mg, 42%). $^1$H NMR (500 MHz, Methanol-d$_4$) δ 8.90 (s, 1H), 8.28 (dd, J=11.6, 5.5 Hz, 2H), 8.05 (t, J=8.7 Hz, 2H), 7.62-7.54 (m, 2H), 7.11-7.05 (m, 2H), 3.57 (t, J=6.4 Hz, 2H), 2.88 (t, J=6.2 Hz, 2H), 2.14-2.05 (m, 2H), 1.93-1.85 (m, 2H); $^{13}$C NMR (126 MHz, MeOD) δ 160.37, 156.23, 153.72, 132.09, 130.99, 130.27, 123.52, 122.38, 122.21, 115.50, 111.83, 27.76, 27.47, 21.48, 21.18; HRMS (ESI) m/z calcd for C$_{20}$H$_{18}$N$_3$O [M+H]$^+$ 316.1449, found 316.1456.

4-(6,7,8,9-Tetrahydro-3H-pyrazolo[4,3-c]phenanthridin-5-yl)phenol

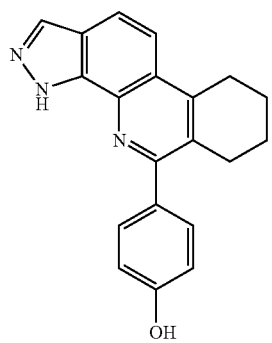

HSD-02-997

Method A: Pale yellow solid (161 mg, 51%). $^1$H NMR (500 MHz, Methanol-d$_4$) δ 8.49 (s, 1H), 8.11 (d, J=9.2 Hz, 1H), 7.89 (d, J=9.2 Hz, 1H), 7.65-7.56 (m, 2H), 7.12-7.03 (m, 2H), 3.53 (t, J=6.5 Hz, 2H), 2.92 (t, J=6.3 Hz, 2H), 2.14-2.05 (m, 2H), 1.95-1.83 (m, 2H); $^{13}$C NMR (126 MHz, DMSO) δ 162.75, 159.17, 154.29, 147.97, 140.25, 139.21, 136.17, 134.68, 130.81, 128.84, 127.83, 124.74, 122.97, 122.65, 122.32, 115.57, 110.49, 110.49, 30.27, 28.70, 22.16, 22.08; HRMS (ESI) m/z calcd for C$_{20}$H$_{18}$N$_3$O [M+H]$^+$ 316.1449, found 316.1459.

7-(1H-Pyrrolo[2,3-b]pyridin-5-yl)-8,9,10,11-tetra-hydro-3H-pyrazolo[4,3-a]phenanthridine

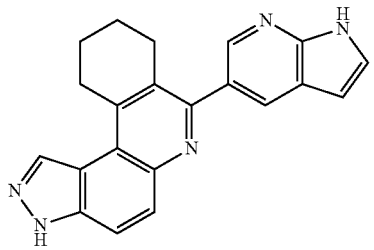

HSD-02-998

Method A: Off-white solid (203 mg, 60%). $^1$H NMR (500 MHz, DMSO-$d_6$) δ 12.09 (s, 1H), 8.78 (s, 1H), 8.54 (d, J=2.1 Hz, 1H), 8.37 (d, J=2.1 Hz, 1H), 8.17 (q, J=9.2 Hz, 2H), 7.65 (t, J=3.0 Hz, 1H), 6.61 (dd, J=3.5, 1.8 Hz, 1H), 3.51-3.44 (m, 2H), 2.86 (t, J=6.2 Hz, 2H), 2.09-2.01 (m, 2H), 1.86-1.73 (m, 2H); $^{13}$C NMR (126 MHz, DMSO) δ 151.20, 149.00, 143.45, 136.93, 132.02, 130.20, 128.42, 122.92, 122.10, 119.30, 115.16, 115.08, 101.14, 30.71, 28.46, 21.95, 21.88; HRMS (ESI) m/z calcd for $C_{21}H_{18}N_5$ [M+H]$^+$ 340.1562, found 340.1569.

4-(8,9,10,11-Tetrahydro-1H-pyrazolo[3,4-a]phenanthridin-7-yl)phenol

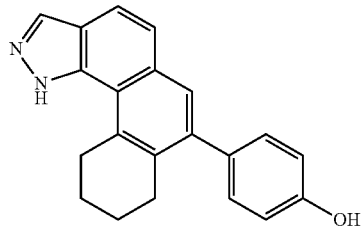

HSD-02-999

Method A: Off-white solid (182 mg, 58%). $^1$H NMR (500 MHz, DMSO-$d_6$) δ 8.31 (s, 1H), 7.87 (d, J=8.9 Hz, 1H), 7.51 (d, J=8.9 Hz, 1H), 7.39 (d, J=8.5 Hz, 2H), 6.85 (d, J=8.5 Hz, 2H), 3.50 (t, J=6.6 Hz, 2H), 2.79 (t, J=6.1 Hz, 2H), 1.97-1.92 (m, 2H), 1.77-1.70 (m, 2H); $^{13}$C NMR (126 MHz, DMSO) δ 158.40, 157.95, 146.70, 142.55, 131.73, 130.87, 128.50, 124.50, 122.19, 119.87, 116.93, 115.17, 29.97, 29.12, 22.56; HRMS (ESI) m/z calcd for $C_{20}H_{18}N_3O$ [M+H]$^+$ 316.1449, found 316.1458.

3,5-Dimethyl-4-(8,9,10,11-tetrahydro-3H-pyrazolo[4,3-a]phenanthridin-7-yl)isoxazole

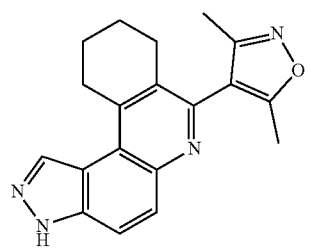

HSD-02-1001

Method A: White solid (229 mg, 72%). $^1$H NMR (500 MHz, Methanol-$d_4$) δ 8.92 (s, 1H), 8.35 (d, J=9.3 Hz, 1H), 8.06 (dd, J=9.2, 2.4 Hz, 1H), 3.71-3.64 (m, 2H), 2.86-2.77 (m, 2H), 2.45 (s, 3H), 2.25-2.20 (m, 5H), 2.06-1.98 (m, 2H); $^{13}$C NMR (126 MHz, MeOD) δ 170.18, 158.64, 155.86, 140.72, 140.00, 135.64, 134.42, 134.28, 124.70, 121.79, 118.93, 114.70, 108.54, 30.94, 26.68, 21.17, 20.88, 10.39, 8.99; HRMS (ESI) m/z calcd for $C_{19}H_{19}N_4O$ [M+H]$^+$ 319.1559, found 319.1563.

7-(4-Hydroxyphenyl)-8,9,10,11-tetrahydro-3H-pyrazolo[4,3-a]phenanthridine-1-carbonitrile

HSD-02-1013

Method A: White solid (210 mg, 61%). $^1$H NMR (500 MHz, Methanol-$d_4$) δ 8.32 (d, J=9.3 Hz, 1H), 8.20 (d, J=9.2 Hz, 1H), 7.62 (d, J=8.6 Hz, 2H), 7.09 (d, J=8.5 Hz, 2H), 3.91 (t, J=6.3 Hz, 2H), 3.00 (t, J=6.3 Hz, 2H), 2.24-2.09 (m, 2H), 2.01-1.90 (m, 2H). $^{13}$C NMR (126 MHz, MeOD) δ 160.62, 155.55, 153.29, 139.97, 135.54, 133.16, 130.98, 122.63, 121.71, 121.08, 119.18, 115.88, 115.65, 115.28, 33.30, 27.88, 20.92, 20.63; HRMS (ESI) m/z calcd for $C_{21}H_{21}N_4O$ [M+H]$^+$ 345.1715, found 345.1720.

tert-Butyl (6-(8,9,10,11-tetrahydro-3H-pyrazolo[4,3-a]phenanthridin-7-yl)pyridin-2-yl)carbamate

HSD-02-1022

Method A: White solid (270 mg, 65%). $^1$H NMR (500 MHz, Methanol-$d_4$) δ 8.79 (s, 1H), 8.23 (d, J=9.3 Hz, 1H), 8.12-8.05 (m, 3H), 7.65 (dd, J=5.7, 2.6 Hz, 1H), 3.53 (d, J=6.0 Hz, 2H), 3.08 (t, J=6.1 Hz, 2H), 2.21-2.14 (m, 2H), 1.99-1.91 (m, 2H), 1.58 (s, 9H); $^{13}$C NMR (126 MHz, MeOD) δ 154.62, 153.09, 153.05, 147.37, 146.93, 140.49, 139.57, 134.87, 134.39, 132.10, 124.03, 120.98, 119.75, 119.68, 114.62, 114.29, 80.98, 30.97, 27.41, 27.15, 21.16, 21.06.

4-(5-Methoxy-8,9,10,11-tetrahydro-3H-pyrazolo[4,3-a]phenanthridin-7-yl)phenol

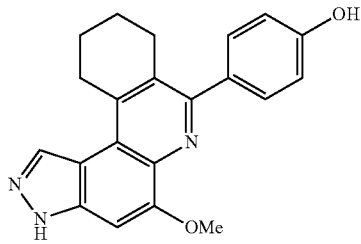

HSD-02-1031

Method A: White solid (145 mg, 42%). $^1$H NMR (500 MHz, DMSO-d$_6$) δ 10.16 (s, 1H), 8.60 (s, 1H), 7.53-7.39 (m, 3H), 7.03-6.92 (m, 2H), 4.05 (s, 3H), 3.37 (t, J=6.5 Hz, 2H), 2.75 (t, J=6.2 Hz, 2H), 1.99 (pd, J=6.4, 4.3, 2.6 Hz, 2H), 1.75 (dq, 1=6.0, 2.9, 2.5 Hz, 2H); $^{13}$C NMR (126 MHz, DMSO) δ 159.52, 152.70, 150.67, 150.36, 140.21, 132.48, 131.68, 130.23, 125.17, 123.07, 121.30, 115.56, 109.83, 96.56, 56.90, 30.79, 28.48, 21.93, 21.80; HRMS (ESI) m/z calcd for C$_{21}$H$_{20}$N$_3$O$_2$ [M+H]$^+$ 346.1556, found 346.1559.

4-(3-Methyl-8,9,10,11-tetrahydro-3H-pyrazolo[4,3-a]phenanthridin-7-yl)phenol

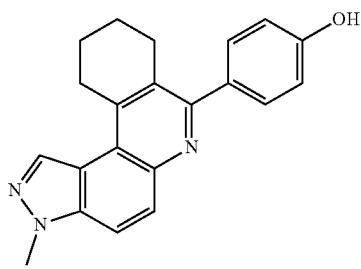

HSD-02-1036

Method A: Off-white solid (208 mg, 63%). $^1$H NMR (500 MHz, Methanol-d$_4$) δ 8.74 (s, 1H), 8.34 (d, J=9.2 Hz, 1H), 8.11 (d, J=9.3 Hz, 1H), 7.63-7.56 (m, 2H), 7.10-7.03 (m, 2H), 4.30 (s, 3H), 3.64 (t, J=6.4 Hz, 2H), 2.96 (t, J=6.2 Hz, 2H), 2.23-2.14 (m, 2H), 1.98-1.88 (m, 2H); $^{13}$C NMR (126 MHz, MeOD) δ 160.36, 154.36, 151.77, 138.31, 134.95, 134.11, 132.57, 130.94, 123.00, 122.30, 118.94, 118.25, 116.10, 115.57, 35.20, 30.96, 27.98, 21.33, 21.26.

7-(1H-Pyrazol-4-yl)-8,9,10,11-tetrahydro-3H-pyrazolo[4,3-a]phenanthridine

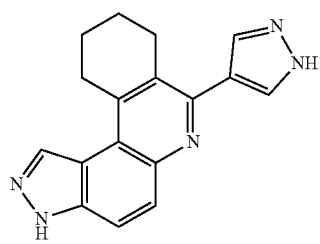

HSD-02-1077

Method A: White solid (220 mg, 76%). $^1$H NMR (500 MHz, DMSO-d$_6$) δ 8.52 (s, 1H), 8.14 (s, 2H), 7.79 (d, J=5.4 Hz, 2H), 3.28 (d, J=6.7 Hz, 2H), 2.99 (t, J=6.1 Hz, 2H), 1.98 (ddt, J=9.0, 6.4, 3.2 Hz, 2H), 1.84 (dp, J=9.2, 3.4, 2.9 Hz, 2H); $^{13}$C NMR (126 MHz, DMSO) δ 149.72, 143.79, 142.11, 138.53, 136.11, 129.61, 128.83, 121.65, 121.03, 116.45, 114.22, 29.85, 28.67, 22.64, 22.48; HRMS (ESI) m/z calcd for C$_{17}$H$_{16}$N$_5$ [M+H]$^+$ 290.1406, found 290.1406.

7-(1H-Indazol-5-yl)-8,9,10,11-tetrahydro-3H-pyrrolo[3,2-a]phenanthridine

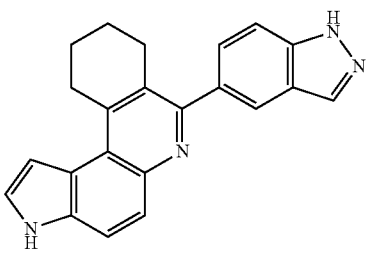

HSD-02-1081

Method A: white solid (173 mg, 51%). $^1$H NMR (500 MHz, DMSO-d$_6$) δ 11.76 (s, 1H), 8.12 (s, 1H), 7.91 (s, 1H), 7.80 (d, J=8.8 Hz, 1H), 7.66 (d, J=8.8 Hz, 1H), 7.61 (d, J=8.5 Hz, 1H), 7.54 (dd, J=8.5, 1.5 Hz, 1H), 7.48 (t, J=2.8 Hz, 1H), 7.11 (t, J=2.6 Hz, 1H), 3.37 (d, J=6.9 Hz, 2H), 2.77 (t, J=6.2 Hz, 2H), 1.99-1.91 (m, 2H), 1.73-1.64 (m, 2H); $^{13}$C NMR (126 MHz, DMSO) δ 156.34, 143.43, 142.27, 139.73, 134.40, 134.08, 133.20, 128.24, 127.74, 124.12, 123.87, 123.10, 122.38, 121.28, 120.41, 116.42, 109.84, 106.27, 30.01, 29.35, 22.91, 22.62; HRMS (ESI) m/z calcd for C$_{22}$H$_{19}$N$_4$ [M+H]$^+$ 339.1610, found 339.1618.

7-(1H-Indol-2-yl)-8,9,10,11-tetrahydro-3H-pyrazolo[4,3-a]phenanthridine

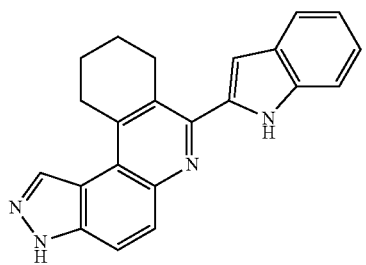

HSD-02-1103

Method A: Yellow solid (264 mg, 78%). $^1$H NMR (500 MHz, DMSO-d$_6$) δ 12.12 (s, 1H), 8.76 (s, 1H), 8.38-8.08 (m, 2H), 7.70 (d, J=8.0 Hz, 1H), 7.57 (dd, J=8.2, 1.0 Hz, 1H), 7.30-7.21 (m, 2H), 7.09 (td, J=7.4, 6.9, 1.0 Hz, 1H), 3.45 (t, J=6.4 Hz, 2H), 3.18-3.15 (m, 2H), 2.11-1.99 (m, 2H), 1.92-1.81 (m, 2H); $^{13}$C NMR (126 MHz, DMSO) δ 143.78, 137.55, 134.89, 131.22, 130.49, 128.14, 124.23, 122.63, 121.72, 120.53, 119.45, 115.27, 112.54, 108.05, 30.84, 28.26, 21.91, 21.86; HRMS (EST) m/z calcd for C$_{22}$H$_{19}$N$_4$ [M+H]$^+$ 339.1610, found 339.1618.

7-(1H-indol-3-yl)-8,9,10,11-tetrahydro-3H-pyrazolo[4,3-a]phenanthridine

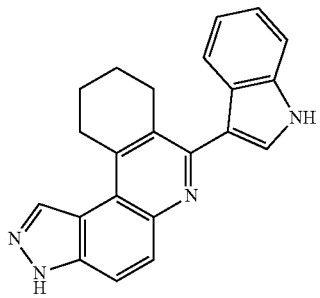

HSD-02-1104

Method A: white solid (183 mg, 54%). $^1$H NMR (500 MHz, Methanol-$d_4$) δ 8.72 (s, 1H), 8.14 (d, J=8.7 Hz, 1H), 8.04-7.93 (m, 2H), 7.61-7.52 (m, 2H), 7.30-7.16 (m, 2H), 3.49 (t, J=6.2 Hz, 2H), 2.99 (t, J=6.1 Hz, 2H), 2.22-2.10 (m, 2H), 1.87 (q, J=5.7 Hz, 2H); $^{13}$C NMR (126 MHz, MeOD) δ 152.83, 147.51, 136.55, 135.07, 132.76, 128.62, 125.73, 122.77, 122.39, 120.99, 119.61, 118.86, 115.08, 112.11, 107.22, 30.80, 27.71, 21.46, 21.29; HRMS (ESI) m/z calcd for $C_{22}H_{19}N_4$ [M+H]$^+$ 339.1610, found 339.1618.

7-Cyclopropyl-8,9,10,11-tetrahydro-3H-pyrazolo[4,3-a]phenanthridine

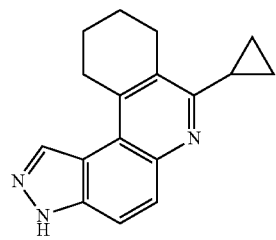

HSD-02-1105

Method A: Off-white solid (181 mg, 69%). $^1$H NMR (500 MHz, DMSO-$d_6$) δ 8.45 (s, 1H), 7.73 (d, J=9.0 Hz, 1H), 7.64 (d, J=9.1 Hz, 1H), 3.18 (q, J=5.3, 4.6 Hz, 2H), 2.94 (t, J=6.2 Hz, 2H), 2.21 (tt, J=8.1, 4.9 Hz, 1H), 1.96-1.88 (m, 2H), 1.86-1.81 (m, 2H), 1.10-0.99 (m, 2H), 0.97-0.87 (m, 2H); $^{13}$C NMR (126 MHz, DMSO) δ 157.71, 143.33, 140.97, 138.28, 135.75, 129.57, 129.38, 120.82, 116.55, 113.67, 29.49, 26.38, 22.40, 22.37, 13.67, 9.14; HRMS (ESI) m/z calcd for $C_{17}H_{18}N_3$ [M+H]$^+$ 264.1501, found 264.1509.

2-(8,9,10,11-Tetrahydro-3H-pyrazolo[4,3-a]phenanthridin-7-yl)-4H-chromen-4-one

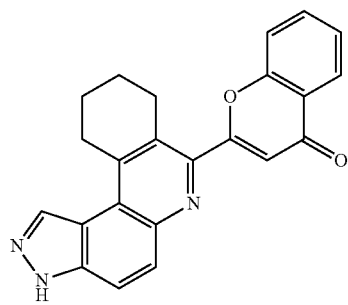

HSD-02-1106

Method A: Off-white solid (96 mg, 25%). $^1$H NMR (500 MHz, DMSO-$d_6$) δ 8.88 (s, 1H), 8.85 (s, 1H), 8.26 (d, J=9.2 Hz, 1H), 8.23 (d, J=9.2 Hz, 1H), 8.17 (dd, J=8.0, 1.7 Hz, 1H), 7.95 (dt, J=8.7, 7.1 Hz, 1H), 7.85-7.83 (d, J=8.2 Hz, 1H), 7.62 (t, J=8.0 Hz 1H), 3.52 (t, J=6.4 Hz, 2H), 2.87 (t, J=6.3 Hz, 2H), 2.08-1.98 (m, 2H), 1.82 (dp, J=9.8, 3.9, 3.1 Hz, 2H); HRMS (ESI) m/z calcd for $C_{23}H_{18}N_3O_2$ [M+H]$^+$ 368.1399, found 368.1400.

7-(Bicyclo[2.2.1]hept-5-en-2-yl)-8,9,10,11-tetrahydro-3H-pyrazolo[4,3-a]phenanthridine

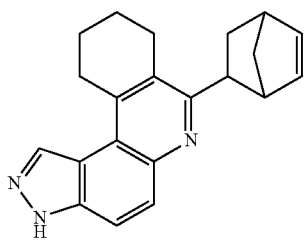

HSD-02-1107

Method A: Off-white solid (110 mg, 34%). $^1$H NMR (500 MHz, Methanol-$d_4$) δ 8.82 (s, 1H), 8.34 (d, J=9.3 Hz, 1H), 8.23 (d, J=9.2 Hz, 1H), 6.71 (dd, J=5.8, 3.2 Hz, 1H), 6.44-6.36 (m, 1H), 5.68 (dd, J=5.7, 2.9 Hz, 1H), 4.34-4.28 (m, 1H), 3.64-3.59 (m, 2H), 3.43 (s, 1H), 3.24 (d, J=4.8 Hz, 2H), 2.42 (ddd, J=12.9, 9.3, 3.6 Hz, 1H), 2.24-2.16 (m, 1H), 2.14-2.03 (m, 4H), 1.76 (d, J=8.4 Hz, 1H), 1.74-1.66 (m, 2H); HRMS (ESI) m/z calcd for $C_{21}H_{22}N_3$ [M+H]$^+$ 316.1814, found 316.1819.

7-(1H-Indazol-5-yl)-1-iodo-8,9,10,11-tetrahydro-3H-pyrazolo[4,3-a]phenanthridine

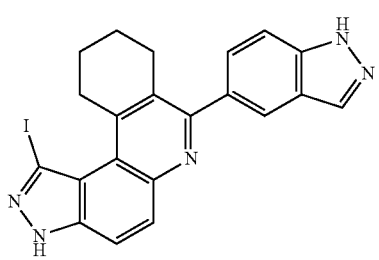

HSD-02-1108

Method A: Yellow solid (302 mg, 65%). $^1$H NMR (500 MHz, DMSO-$d_6$) δ 8.13 (s, 1H), 7.94 (t, J=1.1 Hz, 1H), 7.79 (d, J=9.1 Hz, 1H), 7.76 (d, J=9.0 Hz, 1H), 7.62 (d, J=8.6 Hz, 1H), 7.55 (dd, J=8.6, 1.6 Hz, 1H), 3.70 (t, J=5.9 Hz, 2H), 2.82 (t, J=6.3 Hz, 2H), 1.76-1.72 (m, 4H); $^{13}$C NMR (126 MHz, DMSO) δ 157.35, 144.29, 143.76, 141.32, 139.91, 134.39, 133.08, 130.70, 129.56, 129.31, 128.08, 123.10, 121.70, 121.50, 120.04, 114.80, 110.12, 37.07, 27.57, 22.22, 22.04; HRMS (ESI) m/z calcd for $C_{21}H_{17}IN_5$ [M+H]$^+$ 466.0529, found 466.0535.

207
1-Bromo-7-(1H-indazol-5-yl)-8,9,10,11-tetrahydro-3H-pyrazolo[4,3-a]phenanthridine

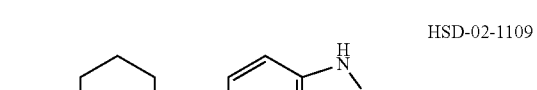

HSD-02-1109

Method A: Off-white solid (234 mg, 56%). $^1$H NMR (500 MHz, DMSO-d$_6$) δ 8.13 (d, J=1.0 Hz, 1H), 7.94-7.92 (m, 1H), 7.83-7.76 (m, 2H), 7.62 (dt, J=8.6, 1.0 Hz, 1H), 7.54 (dd, J=8.6, 1.6 Hz, 1H), 3.60 (t, J=5.9 Hz, 2H), 2.81 (t, J=6.2 Hz, 2H), 1.79-1.70 (m, 4H); $^{13}$C NMR (126 MHz, DMSO) δ 157.76, 144.25, 143.42, 141.60, 139.90, 134.39, 133.10, 131.25, 129.53, 128.02, 123.10, 121.51, 121.45, 115.33, 114.67, 110.13, 34.34, 27.88, 22.29, 22.10; HRMS (ESI) m/z calcd for C$_{19}$H$_{18}$N$_5$ [M+H]$^+$ 316.1562, found 316.1555.

N-(7-(1H-Indazol-5-yl)-8,9,10,11-tetrahydro-3H-pyrazolo[4,3-a]phenanthridin-9-yl)acetamide

HSD-02-1110

Method A: Off-white solid (277 mg, 70%). $^1$H NMR (500 MHz, DMSO-d$_6$) δ 8.71 (s, 1H), 8.23 (s, 1H), 8.09 (q, J=7.1, 5.1 Hz, 4H), 7.74 (d, J=8.6 Hz, 1H), 7.63 (dd, J=8.6, 1.6 Hz, 1H), 4.04-3.93 (m, 1H), 3.57 (dt, J=18.7, 5.5 Hz, 1H), 3.45 (dt, J=17.9, 7.4 Hz, 1H), 2.96 (dd, J=16.8, 4.7 Hz, 1H), 2.80 (dd, J=16.7, 8.7 Hz, 1H), 2.27-2.18 (m, 1H), 2.04-1.91 (m, 1H), 1.75 (s, 3H); $^{13}$C NMR (126 MHz, DMSO) δ 169.40, 153.72, 140.39, 138.50, 134.76, 129.36, 127.67, 122.94, 122.22, 115.46, 110.75, 44.11, 34.25, 29.21, 27.36, 23.11; HRMS (ESI) m/z calcd for C$_{23}$H$_{21}$N$_6$O [M+H]$^+$ 397.1777, found 397.1778.

208
7-(1H-Indazol-5-yl)-8,9,10,11-tetrahydro-3H-pyrazolo[4,3-a]phenanthridin-9-amine

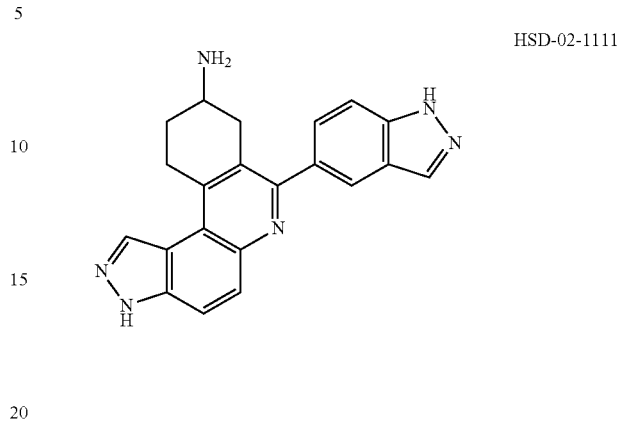

HSD-02-1111

Method A: Pale yellow solid (227 mg, 64%). $^1$H NMR (500 MHz, DMSO-d$_6$) δ 8.80 (s, 1H), 8.60-8.51 (m, 3H), 8.27 (s, 1H), 8.24 (s, 2H), 8.16 (s, 1H), 7.80 (d, J=8.5 Hz, 1H), 7.65 (dd, J=8.6, 1.6 Hz, 1H), 3.74-3.65 (m, 1H), 3.54 (q, J=9.8, 9.2 Hz, 2H), 3.15-3.09 (m, 2H), 2.55-2.51 (m, 1H), 2.20-2.10 (m, 1H); $^{13}$C NMR (126 MHz, DMSO) δ 157.40, 143.77, 141.82, 139.88, 139.65, 135.14, 134.42, 133.51, 133.35, 129.58, 128.37, 128.18, 123.04, 121.43, 121.35, 116.32, 115.26, 110.08, 46.76, 38.61, 31.48, 29.03; HRMS (ESI) m/z calcd for C$_{21}$H$_{19}$N$_6$ [M+H]$^+$ 355.1671, found 355.1673.

(4-(8,9,10,11-Tetrahydro-3H-pyrazolo[4,3-a]phenanthridin-7-yl)phenyl)boronic Acid

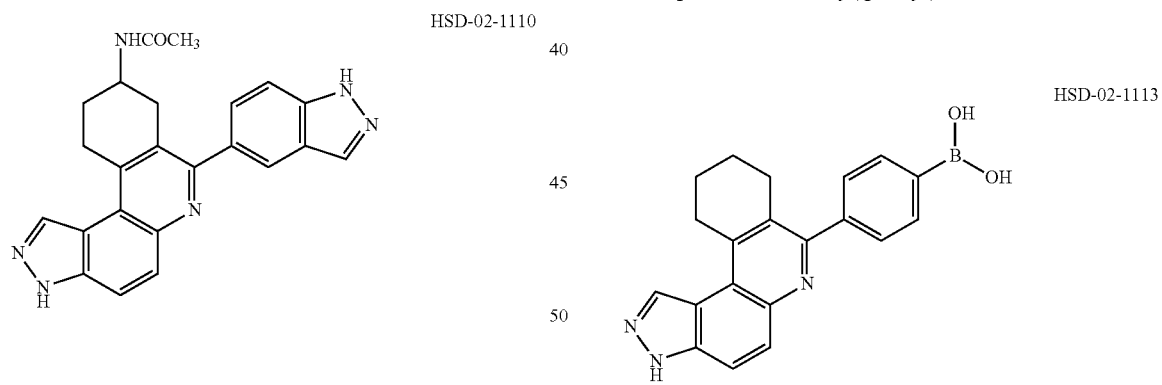

HSD-02-1113

Method A: Off-white solid (151 mg, 44%). $^1$H NMR (500 MHz, Methanol-d$_4$) δ 8.84 (s, 1H), 8.25 (dd, J=9.3, 3.1 Hz, 1H), 8.04 (dd, J=9.2, 3.2 Hz, 2H), 7.95 (s, 1H), 7.68 (d, J=7.5 Hz, 2H), 3.67-3.59 (m, 2H), 2.96-2.85 (m, 2H), 2.24-2.13 (m, 2H), 1.95-1.89 (m, 2H); $^{13}$C NMR (126 MHz, MeOD) δ 154.13, 151.37, 135.10, 134.26, 134.02, 133.60, 132.07, 128.01, 123.67, 119.63, 114.91, 30.85, 27.73, 21.31, 21.16; HRMS (ESI) m/z calcd for C$_{20}$H$_{19}$BN$_3$O$_2$ [M+H]$^+$ 344.1570, found 344.1577.

4-(8,9,10,11-Tetrahydro-3H-pyrazolo[4,3-a]phenanthridin-7-yl)benzonitrile

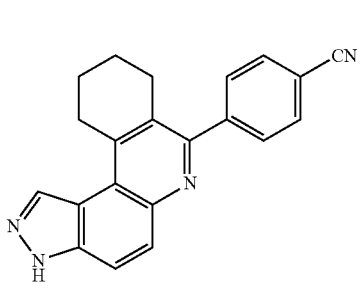

HSD-02-1115

Method A: Off-white solid (182 mg, 56%). $^1$H NMR (500 MHz, DMSO-$d_6$) δ 8.78 (s, 1H), 8.20 (t, J=7.4 Hz, 2H), 8.10 (d, J=8.1 Hz, 2H), 7.94 (d, J=8.2 Hz, 2H), 3.48-3.44 (m, 2H), 2.73 (t, J=6.2 Hz, 2H), 2.07-1.97 (m, 2H), 1.84-1.72 (m, 2H); $^{13}$C NMR (126 MHz, DMSO) δ 150.26, 140.30, 138.64, 136.93, 135.01, 132.87, 131.23, 130.97, 123.45, 122.31, 119.99, 118.89, 115.01, 113.13, 30.63, 28.01, 21.85, 21.68; HRMS (ESI) m/z calcd for $C_{21}H_{17}N_4$ [M+H]$^+$ 325.1453, found 325.1455.

4-(9-Amino-8,9,10,11-tetrahydro-3H-pyrazolo[4,3-a]phenanthridin-7-yl)phenol

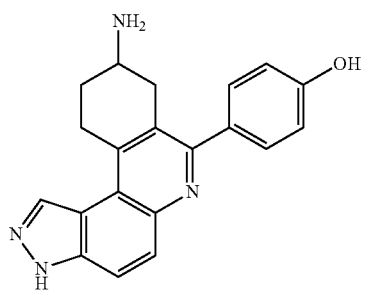

HSD-02-1116

Method A: Off-white solid (205 mg, 62%). $^1$H NMR (500 MHz, Methanol-$d_4$) δ 8.60-8.56 (m, 1H), 7.89 (d, J=9.2 Hz, 1H), 7.83 (dd, J=9.2, 0.9 Hz, 1H), 7.37 (d, J=8.6 Hz, 1H), 6.92 (d, J=8.6 Hz, 1H), 3.62-3.55 (m, 1H), 3.45-3.35 (m, 1H), 3.14-3.08 (m, 1H), 3.03-2.98 (m, 1H), 2.74-2.66 (m, 1H), 2.37-2.29 (m, 1H), 1.89-1.78 (m, 1H). $^{13}$C NMR (126 MHz, MeOD) δ 157.83, 157.59, 143.24, 142.36, 139.52, 134.57, 131.18, 130.07, 128.37, 128.06, 121.39, 116.01, 114.78, 114.55, 46.29, 37.35, 30.57, 28.84; HRMS (ESI) m/z calcd for $C_{20}H_{19}N_4O$ [M+H]$^+$ 331.1559, found 331.1561.

(2-Fluoro-3-(8,9,10,11-tetrahydro-3H-pyrazolo[4,3-a]phenanthridin-7-yl)phenyl)boronic Acid

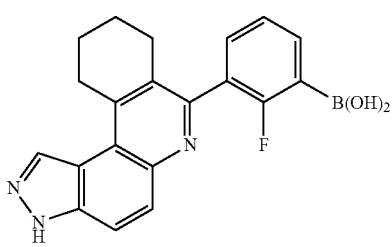

HSD114A

Method A: Off-white solid (163 mg, 45%). $^1$H NMR (500 MHz, Methanol-$d_4$) δ 8.77 (s, 1H), 8.10 (s, 1H), 7.94 (d, J=7.3 Hz, 1H), 7.77-7.55 (m, 2H), 7.52-7.34 (m, 1H), 3.52 (s, 2H), 2.77 (s, 2H), 2.13 (s, 2H), 1.91 (s, 2H); $^{13}$C NMR (126 MHz, MeOD) δ 150.62, 147.92, 138.23, 136.61, 132.21, 132.13, 131.10, 124.78, 124.63, 123.70, 122.50, 122.02, 115.93, 115.76, 30.40, 26.98, 21.61, 21.26.

7-(3-(Trifluoromethyl)-1H-pyrazol-4-yl)-8,9,10,11-tetrahydro-3H-pyrazolo[4,3-a]phenanthridine

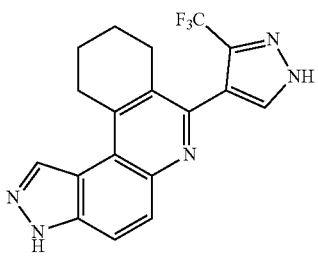

HSD-02-1169

Method A: Off-white solid (161 mg, 45%). $^1$H NMR (500 MHz, DMSO-$d_6$) δ 8.55 (s, 1H), 8.22 (s, 1H), 7.85 (d, J=9.1 Hz, 1H), 7.77 (d, J=9.1 Hz, 1H), 3.26 (t, J=6.4 Hz, 2H), 2.68 (t, J=6.2 Hz, 2H), 1.98-1.86 (m, 2H), 1.80-1.69 (m, 2H); $^{13}$C NMR (126 MHz, DMSO) δ 148.52, 143.61, 141.99, 139.65, 139.37 (q, J=35.28 Hz), 135.14, 131.28, 130.36, 129.53, 123.56 (q, J=269.64 Hz), 121.99, 119.73, 116.21, 115.24, 29.48, 28.17, 22.51, 22.29; HRMS (ESI) m/z calcd for $C_{18}H_{15}F_3N_5$ [M+H]$^+$ 358.1280, found 358.1286.

7-(1H-Benzo[d]imidazol-5-yl)-8,9,10,11-tetrahydro-3H-pyrazolo[4,3-a]phenanthridine

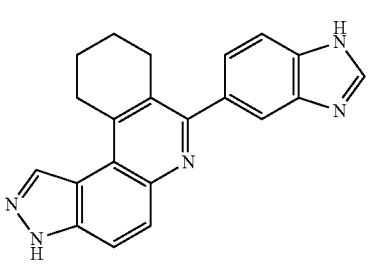

HSD-02-1170

Method A: Off-white solid (238 mg, 70%). $^1$H NMR (500 MHz, DMSO-$d_6$) δ 8.58 (s, 1H), 8.28 (s, 1H), 7.85 (d, J=9.0, 0.8 Hz, 1H), 7.81 (d, J=9.1 Hz, 1H), 7.74 (s, 1H), 7.66 (d, J=8.3 Hz, 1H), 7.38 (dd, J=8.2, 1.6 Hz, 1H), 3.33 (t, J=6.6 Hz, 2H), 2.80 (t, J=6.1 Hz, 2H), 2.00 (td, J=9.0, 7.4, 4.6 Hz, 2H), 1.72 (ddt, J=9.2, 6.3, 3.8 Hz, 2H). $^{13}$C NMR (126 MHz, DMSO) δ 157.66, 143.73, 143.21, 142.24, 135.19, 129.71, 129.58, 123.77, 121.72, 116.34, 29.72, 29.29, 22.67, 22.62; HRMS (ESI) m/z calcd for $C_{21}H_{18}N_5$ [M+H]$^+$ 340.1562, found 340.1570.

4-(1-Methyl-8,9,10,11-tetrahydro-3H-pyrazolo[4,3-a]phenanthridin-7-yl)phenol

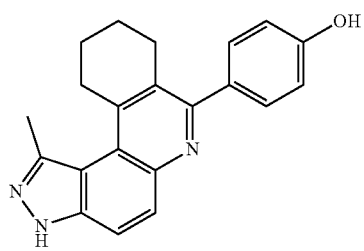

HSD-02-1171

Method A: off-white solid (132 mg, 40%). $^1$H NMR (500 MHz, DMSO-$d_6$) δ 10.37 (s, 1H), 8.24-8.03 (m, 2H), 7.56 (d, J=8.6 Hz, 2H), 7.04 (d, J=8.6 Hz, 2H), 3.62 (t, J=5.9 Hz, 2H), 2.94 (s, 3H), 2.81 (t, J=6.2 Hz, 2H), 1.93-1.73 (m, 4H); $^{13}$C NMR (126 MHz, DMSO) δ 163.50, 160.27, 153.31, 150.55, 135.81, 135.11, 131.86, 131.49, 125.28, 122.45, 119.96, 116.00, 112.81, 32.79, 27.62, 21.69, 21.32; HRMS (ESI) m/z calcd for $C_{21}H_{20}N_3O$ [M+H]$^+$ 330.1606, found 330.1606.

Methyl 7-(4-hydroxyphenyl)-8,9,10,11-tetrahydro-3H-pyrrolo[3,2-a]phenanthridine-2-carboxylate

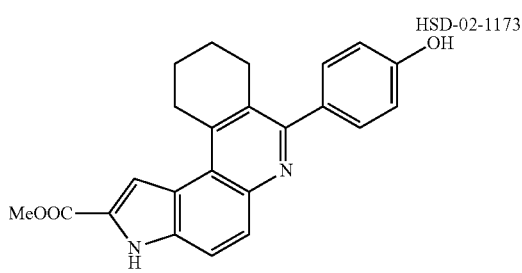 [SMILES: COC(=O)c1cc2c(ccc3nc(-c4ccc(O)cc4)c4c(c32)CCCC4)[nH]1]

HSD-02-1173

Method A: Yellow solid (146 mg, 39%). $^1$H NMR (500 MHz, DMSO-$d_6$) δ 9.79 (s, 1H), 7.83 (t, J=7.1 Hz, 2H), 7.71 (d, J=2.3 Hz, 1H), 7.42 (dd, J=8.6, 2.3 Hz, 2H), 6.90 (dd, J=8.4, 2.2 Hz, 2H), 3.35-3.32 (m, 8H), 2.77 (t, J=6.1 Hz, 2H), 2.02-1.92 (m, 2H), 1.78-1.65 (m, 2H); $^{13}$C NMR (126 MHz, DMSO) δ 161.47, 158.28, 155.16, 135.67, 131.12, 129.38, 126.63, 122.76, 119.77, 118.05, 115.31, 112.07, 30.25, 29.02, 22.48, 22.24; HRMS (ESI) m/z calcd for $C_{23}H_{23}N_2O_3$ [M+H]$^+$ 375.1709, found 375.1711.

7-(4-Fluorophenyl)-8,9,10,11-tetrahydro-3H-pyrazolo[4,3-a]phenanthridine

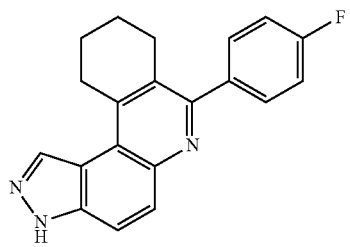

HSD-02-1174

Method A: Off-white solid (190 mg, 59%). $^1$H NMR (500 MHz, DMSO-$d_6$) δ 8.80 (s, 1H), 8.24 (d, J=9.1 Hz, 1H), 8.20 (d, J=9.2 Hz, 1H), 7.85-7.77 (m, 2H), 7.52-7.44 (m, 2H), 3.47 (t, J=6.4 Hz, 2H), 2.76 (t, J=6.2 Hz, 2H), 2.07-1.98 (m, 2H), 1.83-1.71 (m, 2H); $^{13}$C NMR (126 MHz, DMSO) δ 164.66, 162.69, 150.54, 132.78, 132.71, 131.76, 129.72, 123.29, 121.12, 116.26, 116.08, 114.93, 111.46, 101.25, 30.79, 28.10, 21.80, 21.67; HRMS (ESI) m/z calcd for $C_{20}H_{21}FN_3$ [M+H]$^{+1}$ 322.1720, found 322.1724.

7-(4-Fluorophenyl)-8,9,10,11-tetrahydro-3H-pyrrolo[3,2-a]phenanthridine

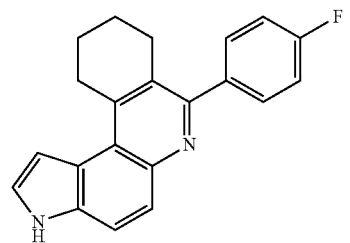

HSD-02-1175

Method A: Off-white solid (144 mg, 45%). $^1$H NMR (500 MHz, DMSO-$d_6$) δ 11.76 (s, 1H), 7.78 (dd, J=8.9, 0.8 Hz, 1H), 7.63 (d, J=8.8 Hz, 1H), 7.61-7.54 (m, 2H), 7.49 (t, J=2.8 Hz, 1H), 7.32-7.24 (m, 2H), 7.12 (ddd, J=3.1, 2.0, 0.9 Hz, 1H), 3.38 (t, J=6.5 Hz, 2H), 2.74 (t, J=6.1 Hz, 2H), 2.01-1.92 (m, 2H), 1.72 (ddd, J=9.0, 7.1, 4.1 Hz, 2H); $^{13}$C NMR (126 MHz, DMSO) δ 163.08, 161.14, 154.88, 143.35, 142.44, 138.19, 133.25, 131.61, 131.54, 127.45, 124.06, 123.98, 122.53, 120.32, 116.56, 115.24, 115.07, 106.29, 29.96, 29.06, 22.84, 22.53; HRMS (ESI) m/z calcd for $C_{21}H_{22}FN_2$ [M+H]$^+$ 321.1767, found 321.1768.

7-Phenyl-8,9,10,11-tetrahydro-3H-pyrrolo[3,2-a]phenanthridine

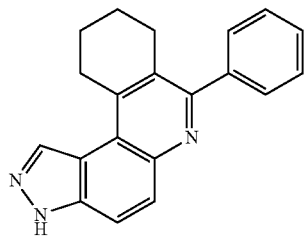

HSD-02-1176

Method A: Off-white solid (235 mg, 78%). ¹H NMR (500 MHz, DMSO-d₆) δ 8.56 (s, 1H), 7.84 (dd, J=9.1, 0.9 Hz, 1H), 7.80 (d, J=9.1 Hz, 1H), 7.54-7.51 (m, 2H), 7.48-7.44 (m, 2H), 7.44-7.39 (m, 1H), 3.29 (t, J=6.5 Hz, 2H), 2.74 (t, J=6.1 Hz, 2H), 2.02-1.91 (m, 2H), 1.77-1.64 (m, 2H); ¹³C NMR (126 MHz, DMSO) δ 156.89, 143.73, 142.34, 141.33, 139.70, 135.12, 129.62, 129.45, 129.22, 128.39, 128.15, 121.89, 116.26, 115.24, 29.64, 28.95, 22.59, 22.49; HRMS (ESI) m/z calcd for C₂₀H₁₈N₃ [M+H]⁺ 300.1501, found 300.1501.

7-Phenyl-8,9,10,11-tetrahydro-3H-pyrrolo[3,2-a]phenanthridine

HSD-02-1177

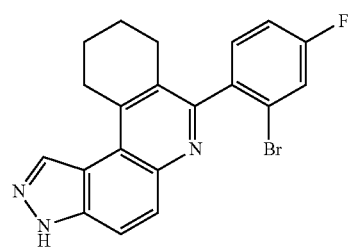

Method A: Yellow solid (180 mg, 60%). ¹H NMR (500 MHz, Methanol-d₄) δ 8.19 (d, J=8.9 Hz, 1H), 7.84 (d, J=8.9 Hz, 1H), 7.72 (d, J=3.2 Hz, 1H), 7.69 (s, 5H), 7.42 (d, J=3.1 Hz, 1H), 3.71 (t, J=6.5 Hz, 2H), 2.87 (t, J=6.3 Hz, 2H), 2.16 (p, J=6.3 Hz, 3H), 1.92 (p, J=6.1 Hz, 2H). ¹³C NMR (126 MHz, MeOD) δ 154.99, 150.08, 133.99, 133.82, 132.55, 130.58, 129.45, 128.93, 128.81, 126.02, 123.68, 120.84, 120.09, 112.92, 106.45, 31.23, 27.74, 21.57, 21.19; HRMS (ESI) m/z calcd for C₂₁H₁₉N₂ [M+H]⁺ 301.1705, found 301.1713.

7-(4-Hydroxyphenyl)-8,9,10,11-tetrahydro-3H-pyrrolo[3,2-a]phenanthridine-2-carboxylic Acid

HSD-02-1178

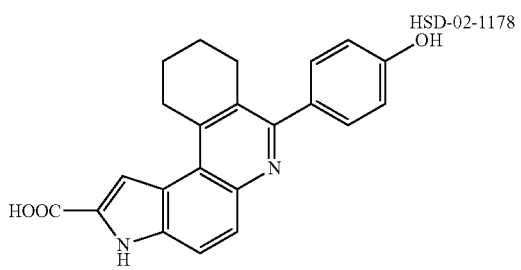 [SMILES: O=C(O)c1cc2c(ccc3nc(-c4ccc(O)cc4)c4c(c32)CCCC4)[nH]1]

Method A: Yellow solid (220 mg, 61%). ¹H NMR (500 MHz, DMSO-d₆) δ 10.44 (s, 1H), 8.29-7.84 (m, 2H), 7.77-7.44 (m, 3H), 7.06 (d, J=8.2 Hz, 2H), 3.56-3.32 (m, 2H), 2.94-2.62 (m, 2H), 2.14-1.89 (m, 2H), 1.75-1.55 (m, 2H); ¹³C NMR (126 MHz, DMSO) δ 162.48, 160.31, 153.04, 150.98, 135.29, 131.99, 130.84, 129.33, 123.31, 122.54, 121.26, 121.09, 119.04, 117.85, 115.91, 111.63, 31.11, 28.30, 21.81, 21.55; HRMS (ESI) m/z calcd for C₂₂H₂₁N₂O₃ [M+]⁺ 361.1552, found 361.1552.

7-(2-Bromo-4-fluorophenyl)-8,9,10,11-tetrahydro-3H-pyrazolo[4,3-a]phenanthridine

HSD-02-1183

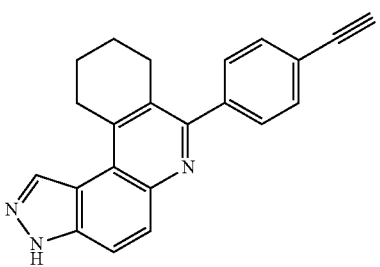

Method A: Off-white solid (163 mg, 41%). ¹H NMR (500 MHz, Methanol-d₄) δ 8.56 (s, 1H), 7.84 (s, 2H), 7.55 (dd, J=8.5, 2.6 Hz, 1H), 7.42 (dd, J=8.5, 5.9 Hz, 1H), 7.29 (td, J=8.4, 2.6 Hz, 1H), 3.36-3.29 (m, 1H), 2.66-2.44 (m, 2H), 2.06-1.98 (m, 2H), 1.89-1.79 (m, 2H); ¹³C NMR (126 MHz, MeOD) δ 163.31 (J=250.74 Hz), 155.51, 143.71, 142.87, 137.54, 135.92, 131.53, 131.46, 130.07, 128.21, 122.77, 122.69, 122.62, 119.51, 119.32, 114.72, 114.55, 29.42, 27.22, 22.02, 21.75; HRMS (ESI) m/z calcd for C₂₀H₁₈BrFN₃ [M+H]⁺ 398.0668, found 398.0673.

7-(4-Ethynylphenyl)-8,9,10,11-tetrahydro-3H-pyrazolo[4,3-a]phenanthridine

HSD-02-1186

Method A: Off-white solid (160 mg, 49%). ¹H NMR (500 MHz, DMSO-d₆) δ 8.54 (d, J=1.0 Hz, 1H), 7.88-7.84 (m, 1H), 7.79 (d, J=9.1 Hz, 1H), 7.64 (t, J=1.7 Hz, 1H), 7.58 (dt, J=7.6, 1.5 Hz, 1H), 7.54 (dt, J=7.7, 1.4 Hz, 1H), 7.47 (t, J=7.7 Hz, 1H), 4.21 (s, 1H), 3.25 (t, J=6.6 Hz, 2H), 2.73 (t, J=6.2 Hz, 2H), 1.99-1.92 (m, 2H), 1.70 (tdd, J=9.0, 5.6, 2.8 Hz, 2H); ¹³C NMR (126 MHz, DMSO) δ 155.63, 143.76, 142.49, 141.73, 139.83, 135.09, 132.65, 131.45, 130.16, 129.47, 129.13, 128.86, 122.07, 121.97, 116.19, 115.47, 83.85, 81.41, 29.63, 28.83, 22.52, 22.45; HRMS (ESI) m/z calcd for C₂₂H₂₀N₃ [M+H]⁺ 326.1657, found 326.1659.

7-(4-Chlorophenyl)-8,9,10,11-tetrahydro-3H-naphtho[1,2-e]indazole

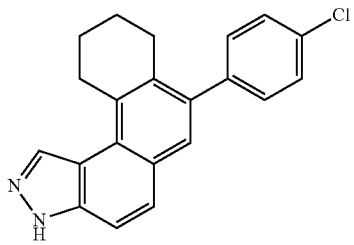

HSD-02-1188

Method A: Off-white solid (171 mg, 51%). $^1$H NMR (500 MHz, DMSO-$d_6$) δ 8.54 (s, 1H), 7.85 (d, J=9.1 Hz, 1H), 7.81 (d, J=9.1 Hz, 1H), 7.61-7.55 (m, 2H), 7.55-7.47 (m, 2H), 3.30 (t, J=6.5 Hz, 2H), 2.74 (t, J=6.1 Hz, 2H), 2.01-1.91 (m, 2H), 1.76-1.66 (m, 2H); $^{13}$C NMR (126 MHz, DMSO) δ 155.62, 143.60, 143.11, 142.56, 140.08, 138.71, 136.38, 134.90, 133.05, 131.42, 129.61, 129.49, 129.30, 128.62, 128.43, 121.95, 116.41, 114.51, 29.67, 28.86, 22.54, 22.47; HRMS (ESI) m/z calcd for $C_{20}H_{19}ClN_3$ [M+H]$^+$ 336.1268, found 336.1271.

7-(4-Chlorophenyl)-8,9,10,11-tetrahydro-3H-pyrrolo[3,2-a]phenanthridine

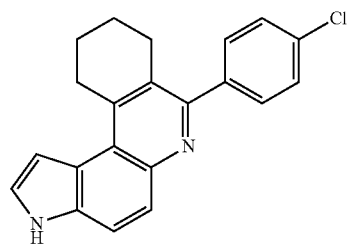

HSD-02-1189

Method A: Off-white solid (180 mg, 54%). $^1$H NMR (500 MHz, Methanol-$d_4$) δ 7.75 (d, J=45.8 Hz, 2H), 7.46 (d, J=32.4 Hz, 5H), 7.20 (s, 1H), 3.50 (s, 214), 2.74 (s, 2H), 2.06 (s, 2H), 1.83 (s, 2H); $^{13}$C NMR (126 MHz, MeOD) δ 154.78, 143.91, 142.58, 139.60, 133.67, 133.29, 130.38, 127.99, 127.27, 122.84, 121.93, 120.21, 116.07, 105.77, 29.93, 28.51, 22.42, 22.09; HRMS (ESI) m/z calcd for $C_{21}H_{20}ClN_2$ [M+H]$^+$ 335.1315, found 335.1322.

7-(3-Fluorophenyl)-8,9,10,11-tetrahydro-3H-pyrazolo[4,3-a]phenanthridine

HSD-02-1190

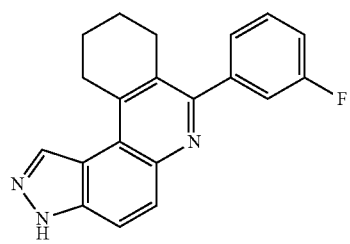

Method A: Off-white solid (195 mg, 61%). $^1$H NMR (500 MHz, DMSO-$d_6$) δ 8.56 (s, 1H), 7.85 (dd, J=9.1, 0.9 Hz, 1H), 7.79 (d, J=9.1 Hz, 1H), 7.50 (td, J=8.0, 6.1 Hz, 1H), 7.42-7.36 (m, 2H), 7.30-7.22 (m, 1H), 3.27 (t, J=6.5 Hz, 2H), 2.75 (t, J=6.1 Hz, 2H), 2.01-1.92 (m, 2H), 1.78-1.66 (m, 2H); $^{13}$C NMR (126 MHz, DMSO) δ 163.27, 161.33, 155.43, 143.69, 143.64, 142.56, 130.42, 130.36, 129.58, 129.19, 125.72, 122.10, 116.43, 116.26, 116.19, 115.11, 114.94, 29.63, 28.75, 22.52, 22.43; HRMS (ESI) m/z calcd for $C_{20}H_{19}FN_3$ [M+H]$^+$ 320.1563, found 320.1569.

7-(3-Fluorophenyl)-8,9,10,11-tetrahydro-3H-pyrrolo[3,2-a]phenanthridine

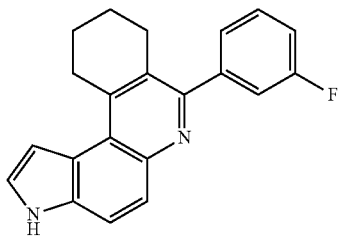

HSD-02-1191

Method A: Off-white solid (160 mg, 50%). $^1$H NMR (500 MHz, Methanol-$d_4$) δ 7.78 (ddd, J=8.9, 2.1, 0.8 Hz, 1H), 7.69 (dd, J=8.9, 3.8 Hz, 1H), 7.55-7.42 (m, 2H), 7.41 (dd, J=3.1, 1.2 Hz, 1H), 7.29 (dt, J=7.6, 1.2 Hz, 1H), 7.26-7.16 (m, 1H), 7.17 (dd, J=3.2, 1.0 Hz, 1H), 3.50-3.41 (m, 2H), 2.71 (t, J=6.3 Hz, 2H), 2.07-1.96 (m, 2H), 1.82-1.72 (m, 2H); $^{13}$C NMR (126 MHz, MeOD) 163.57 (J=245.70 Hz), 154.58, 143.91, 143.32, 142.54, 133.29, 130.38, 129.74, 129.68, 127.97, 127.14, 124.73, 122.96, 122.84, 121.97, 120.21, 116.09, 115.71, 115.54, 114.41, 114.24, 105.80, 29.89, 28.41, 22.39, 22.03; HRMS (ESI) m/z calcd for $C_{21}H_{20}FN_2$ [M+H]$^+$ 319.1611, found 319.1618.

4-(8,9,10,11-Tetrahydro-3H-8,11-methanopyrazolo[4,3-a]phenanthridin-7-yl)phenol 1193

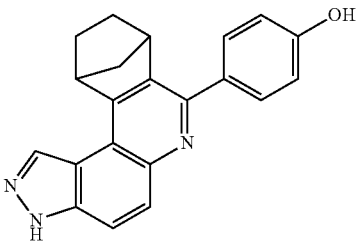

HSD1193

Method C: Off white solid (82 mg, 25%). $^1$H NMR (500 MHz, Methanol-$d_4$) δ 8.64 (s, 1H), 7.97-7.90 (m, 1H), 7.80 (d, J=9.2 Hz, 1H), 7.62 (d, J=8.4 Hz, 2H), 6.97 (d, J=8.4 Hz, 2H), 4.34 (s, 1H), 3.76 (s, 1H), 2.33-2.18 (m, 2H), 1.93 (d, J=9.4 Hz, 1H), 1.77 (d, J=9.0 Hz, 1H), 1.44-1.31 (m, 2H). $^{13}$C NMR (126 MHz, MeOD) δ 157.96, 153.18, 150.46, 144.56, 139.98, 138.03, 134.29, 130.56, 130.03, 128.51, 116.16, 114.92, 113.81, 49.47, 43.72, 42.28, 26.38, 24.64. HRMS (ESI) m/z calcd for $C_{21}H_{18}N_3O$ [M+H]$^+$ 328.1450, found 328.1450.

4-(2-Methyl-8,9,10,11-tetrahydro-3H-pyrrolo[3,2-a]phenanthridin-7-yl)phenol

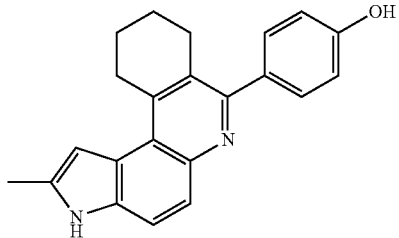

HSD-02-1195

Method A: Off-white solid (135 mg, 41%). $^1$H NMR (500 MHz, Methanol-$d_4$) δ 7.66 (d, J=8.9 Hz, 1H), 7.61 (d, J=8.9 Hz, 1H), 7.34-7.29 (m, 2H), 6.93-6.88 (m, 2H), 6.85 (s, 1H), 3.42 (t, J=6.6 Hz, 2H), 2.73 (t, J=6.3 Hz, 2H), 2.53 (s, 3H), 2.06-1.97 (m, 2H), 1.83-1.73 (m, 2H); $^{13}$C NMR (126 MHz, MeOD) δ 157.11, 155.96, 143.48, 142.28, 133.63, 133.06, 132.20, 129.97, 127.27, 122.10, 121.13, 120.58, 115.11, 114.50, 103.96, 29.91, 28.69, 22.53, 22.23, 12.07; HRMS (ESI) m/z calcd for $C_{22}H_{23}N_2O$ [M+H]$^+$ 331.1810, found 331.1813.

6-(8,9,10,11-Tetrahydro-3H-pyrazolo[4,3-a]phenanthridin-7-yl)pyridin-3-ol

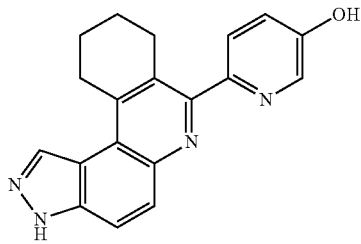

HSD-02-1196

Method A: Off-white solid (124 mg, 39%). $^1$H NMR (500 MHz, Methanol-$d_4$) δ 8.57 (s, 1H), 8.22 (d, J=2.8 Hz, 1H), 7.90 (d, J=9.8 Hz, 1H), 7.83 (d, J=9.0 Hz, 1H), 7.55 (d, J=8.4 Hz, 1H), 7.41 (dd, J=8.5, 2.8 Hz, 1H), 3.38 (s, 2H), 2.82 (t, J=6.2 Hz, 2H), 2.12-2.04 (m, 2H), 1.89-1.80 (m, 2H); $^{13}$C NMR (126 MHz, MeOD) δ 154.85, 154.08, 149.15, 143.75, 142.80, 138.71, 136.11, 135.86, 130.19, 128.51, 125.23, 123.37, 122.48, 116.10, 113.81, 29.62, 27.62, 22.09, 21.91; HRMS (ESI) m/z calcd for $C_{19}H_{17}N_4O$ [M+H]$^+$ 317.1402, found 317.1397.

7-(6-Fluoropyridin-3-yl)-8,9,10,11-tetrahydro-3H-pyrrolo[3,2-a]phenanthridine

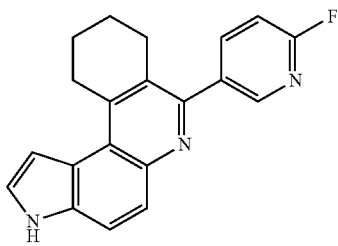

HSD-02-1197

Method A: Off-white solid (201 mg, 61%). $^1$H NMR (500 MHz, Methanol-$d_4$) δ 8.31 (d, J=2.4 Hz, 1H), 8.04 (td, J=8.0, 2.5 Hz, 1H), 7.78 (d, J=8.9 Hz, 1H), 7.68 (d, J=8.9 Hz, 1H), 7.40 (d, J=3.1 Hz, 1H), 7.17 (dd, J=8.4, 2.3 Hz, 1H), 7.12 (d, J=3.1 Hz, 1H), 3.36 (t, J=6.5 Hz, 2H), 2.66 (t, J=6.2 Hz, 2H), 1.95 (ddt, J=12.5, 9.1, 4.6 Hz, 2H), 1.79-1.71 (m, 2H). $^{13}$C NMR (126 MHz, MeOD) δ 164.07, 162.16, 151.30, 147.35, 147.24, 144.14, 142.80, 142.65, 142.58, 134.95, 134.91, 133.32, 127.42, 123.11, 122.96, 122.05, 120.13, 116.37, 116.32, 108.83, 108.54, 105.95, 105.90, 29.82, 28.39, 22.24, 21.95; HRMS (ESI) m/z calcd for $C_{20}H_{19}FN_3$ [M+H]$^+$ 320.1563, found 320.1566.

7-(Pyridin-3-yl)-8,9,10,11-tetrahydro-3H-pyrazolo[4,3-a]phenanthridine

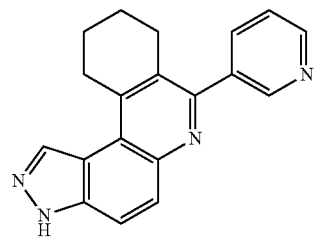

HSD1199

Method A: Off-white solid (135 mg, 45%). $^1$H NMR (500 MHz, Methanol-$d_4$) δ 9.06 (s, 2H), 8.73 (s, 1H), 8.42 (d, J=7.3 Hz, 1H), 8.11 (d, J=8.4 Hz, 1H), 7.96 (d, J=8.8 Hz, 2H), 3.55-3.46 (m, 2H), 2.95-2.81 (m, 2H), 2.20-2.08 (m, 2H), 1.99-1.84 (m, 2H); $^{13}$C NMR (126 MHz, MeOD) δ 150.86, 148.85, 148.27, 147.36, 140.15, 138.36, 131.44, 123.81, 122.94, 119.15, 115.51, 30.47, 27.89, 21.51, 21.42; HRMS (ESI) m/z calcd for $C_{19}H_{17}N_4$ [M+H]$^+$ 301.1453, found 301.1453.

7-(2-Bromophenyl)-8,9,10,11-tetrahydro-3H-pyrrolo[3,2-a]phenanthridine

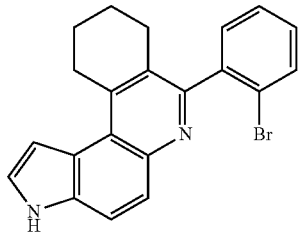

HSD-02-1200

Method A: Off-white solid (223 mg, 59%). $^1$H NMR (500 MHz, Methanol-$d_4$) δ 7.81 (dd, J=8.9, 0.8 Hz, 1H), 7.73 (dd, J=8.5, 1.2 Hz, 1H), 7.69 (d, J=8.9 Hz, 1H), 7.51 (td, J=7.5, 1.2 Hz, 1H), 7.44 (d, J=3.1 Hz, 1H), 7.40-7.36 (m, 2H), 7.21 (dd, J=3.2, 0.9 Hz, 1H), 3.50 (td, J=6.4, 1.4 Hz, 2H), 2.57 (ddt, J=68.3, 17.0, 6.3 Hz, 2H), 2.08-1.98 (m, 2H), 1.92-1.78 (m, 2H). $^{13}$C NMR (126 MHz, MeOD) δ 155.07, 143.75, 142.37, 141.72, 133.32, 132.31, 130.23, 130.19, 129.54, 129.50, 127.66, 127.44, 123.14, 122.89, 122.52, 121.82, 120.27, 116.01, 105.69, 29.80, 27.36, 22.39, 21.88; HRMS (ESI) m/z calcd for $C_{21}H_{20}BrN_2$ [M+H]$^+$ 379.0810, found 379.0817.

3-Fluoro-4-(8,9,10,11-tetrahydro-3H-pyrrolo[3,2-a]phenanthridin-7-yl)phenol

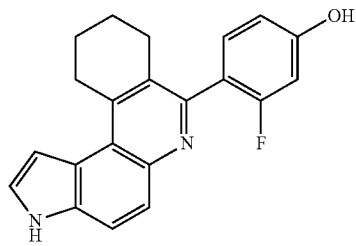

HSD-02-1202

Method A: Off-white solid (184 mg, 55%). $^1$H NMR (500 MHz, Methanol-d$_4$) δ 11.65 (s, 1H), 9.02 (d, J=8.9 Hz, 1H), 8.80 (d, J=9.0 Hz, 1H), 8.60 (s, 1H), 8.34 (t, J=8.5 Hz, 1H), 8.13 (s, 1H), 7.72 (d, J=8.1 Hz, 2H), 4.37 (s, 2H), 3.52 (d, J=6.3 Hz, 2H), 2.93-2.78 (m, 2H), 2.61 (s, 2H). $^{13}$C NMR (126 MHz, MeOD) δ 163.03, 162.14, 160.18, 134.61, 133.62, 131.43, 127.83, 124.37, 122.33, 120.67, 113.54, 107.72, 104.37, 104.18, 31.98, 28.02, 22.84, 22.19; HRMS (ESI) m/z calcd for C$_{21}$H$_{20}$FN$_2$O [M+H]$^+$ 335.1560, found 335.1566.

2-Fluoro-4-(2-methyl-8,9,10,11-tetrahydro-3H-pyrrolo[3,2-a]phenanthridin-7-yl)phenol

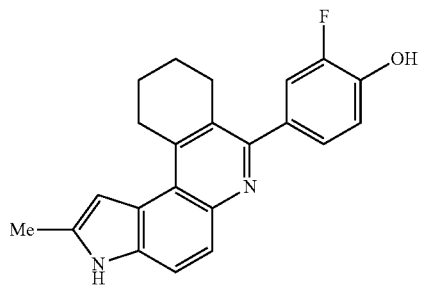

HSD 02-1203

Method A: Off-white solid (164 mg, 47%). $^1$H NMR (500 MHz, Methanol-d$_4$) δ 7.66 (d, J=8.9 Hz, 1H), 7.61 (d, J=8.9 Hz, 1H), 7.20 (dd, J=11.8, 2.0 Hz, 1H), 7.13-7.08 (m, 1H), 7.05-7.00 (m, 1H), 6.84 (s, 1H), 3.39 (t, J=6.5 Hz, 2H), 2.72 (t, J=6.2 Hz, 2H), 2.52 (s, 3H), 2.04-1.94 (m, 2H), 1.82-1.70 (m, 2H); $^{13}$C NMR (126 MHz, MeOD) δ 154.57, 152.03, 150.11, 144.90, 143.84, 142.21, 133.78, 133.12, 132.62, 127.08, 125.12, 122.26, 121.10, 120.50, 117.06, 116.55, 116.40, 115.35, 104.03, 29.91, 28.58, 22.44, 22.15, 12.08; HRMS (ESI) m/z calcd for C$_{22}$H$_{22}$FN$_2$O [M+H]$^+$ 349.1716, found 349.1720.

4-(8,9,10,11-Tetrahydro-3H-pyrazolo[4,3-a]phenanthridin-7-yl)benzimidamide hydrochloride

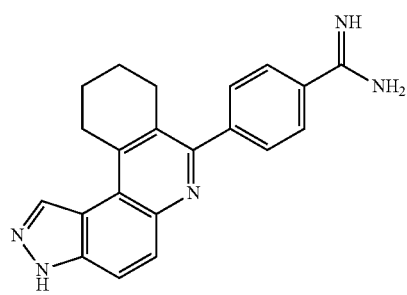

HSD-02-1204

Method A: Off-white solid (172 mg, 50%). $^1$H NMR (500 MHz, DMSO-d$_6$) δ 9.69 (s, 2H), 9.47 (s, 2H), 8.71 (s, 1H), 8.16-8.06 (m, 4H), 7.94 (d, J=8.0 Hz, 2H), 3.42-3.33 (m, 2H), 2.76 (t, J=6.2 Hz, 2H), 2.07-1.97 (m, 2H), 1.81-1.65 (m, 2H); $^{13}$C NMR (126 MHz, DMSO) δ 165.63, 151.52, 140.26, 134.84, 130.64, 130.34, 129.16, 128.63, 123.10, 115.22, 30.40, 28.25, 21.97, 21.83; HRMS (ESI) m/z calcd for C$_{21}$H$_{22}$N$_5$ [+H]$^+$ 344.1875, found 344.1879.

N-hydroxy-4-(8,9,10,11-tetrahydro-3H-pyrazolo[4,3-a]phenanthridin-7-yl)benzimidamide

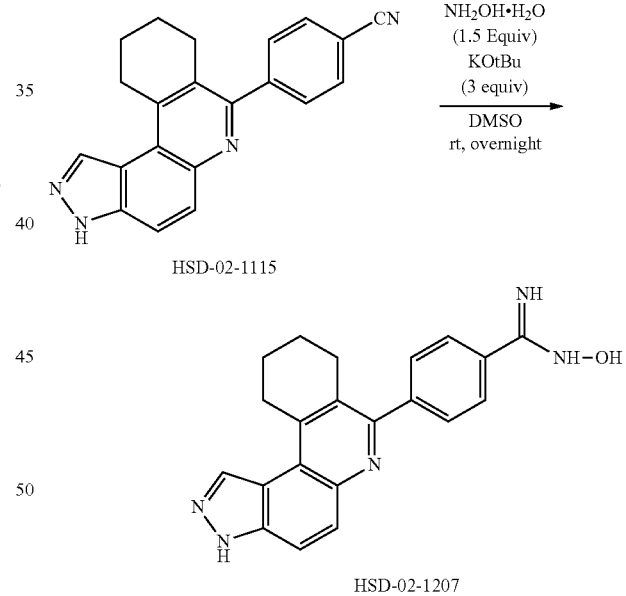

In a solution of NH$_2$OH·H$_2$O (1.5 equiv) in DMSO (3 mL), KOtBut (3 equiv) was added slowly at 0° C. and the suspension was stirred for 30 min. After this 4-(8,9,10,11-Tetrahydro-3H-pyrazolo[4,3-a]phenanthridin-7-yl)benzonitrile (0.5 mmol) was added to the mixture and reaction was continued for 4 h at room temperature. After completion of reaction cold water was added to the reaction mixture and the resulting precipitate was filtered and washed with water and dried. Solid was recrystallized with ethanol to get the desired product.

Off-white solid (162 mg, 90%). $^1$H NMR (500 MHz, DMSO-d$_6$) δ 9.71 (s, 1H), 8.56 (s, 1H), 7.88-7.82 (m, 2H), 7.79-7.76 (m, 2H), 7.59-7.54 (m, 2H), 5.89 (s, 2H), 2.79 (t, J=6.1 Hz, 2H), 2.00 (ddt, J=9.3, 6.5, 3.1 Hz, 2H), 1.74 (tt, J=8.6, 5.4 Hz, 2H); $^{13}$C NMR (126 MHz, DMSO) δ 156.48, 151.11, 145.66, 143.64, 142.45, 141.74, 138.70, 136.39, 133.15, 129.67, 129.32, 125.43, 121.88, 116.46, 114.44, 29.69, 28.96, 22.60, 22.52; HRMS (ESI) m/z calcd for $C_{21}H_{22}N_5O$ [M+H]$^+$ 360.1824, found 360.1827.

N-(4-(8,9,10,11-Tetrahydro-3H-pyrazolo[4,3-a]phenanthridin-7-yl)phenyl)acetamide

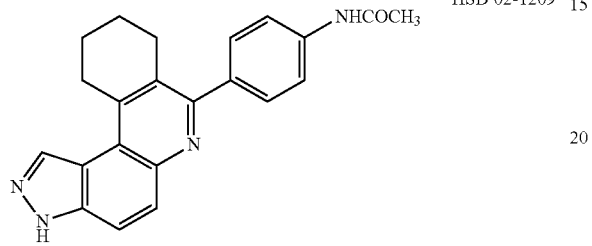

HSD 02-1209

Method A: Off-white solid (201 mg, 51%). $^1$H NMR (500 MHz, DMSO-d$_6$) δ 10.08 (s, 1H), 8.50 (s, 1H), 7.81 (s, 2H), 7.70 (d, J=8.4 Hz, 2H), 7.49 (d, J=8.5 Hz, 2H), 3.24 (t, J=6.0 Hz, 2H), 2.75 (t, J=6.1 Hz, 2H), 2.08 (s, 3H), 1.96-1.89 (m, 2H), 1.67 (tt, J=8.3, 5.4 Hz, 2H); $^{13}$C NMR (126 MHz, DMSO) δ 168.87, 156.52, 143.62, 142.22, 139.37, 138.62, 136.27, 135.92, 129.99, 129.62, 129.35, 121.66, 118.79, 116.48, 114.22, 29.63, 29.05, 24.54, 22.59, 22.54; HRMS (ESI) m/z calcd for $C_{22}H_{23}N_4O$ [M+H]$^+$ 359.1872, found 359.1875.

4-(3,8-Dihydro-2H-furo[3,2-c]pyrrolo[3,2-f]quinolin-4-yl)phenol

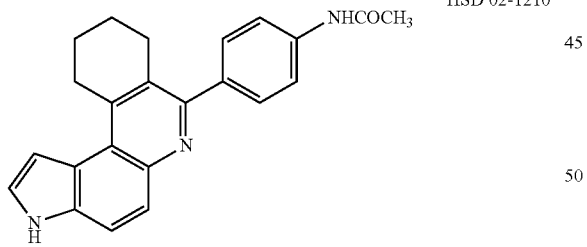

HSD 02-1210

Method A: Off-white solid (171 mg, 48%). $^1$H NMR (500 MHz, DMSO-d$_6$) δ 11.74 (t, J=2.4 Hz, 1H), 10.05 (s, 1H), 7.78 (d, J=8.8 Hz, 1H), 7.68 (d, J=8.3 Hz, 2H), 7.63 (d, J=8.8 Hz, 1H), 7.51-7.46 (m, 3H), 7.10 (d, J=2.8 Hz, 1H), 3.38-3.35 (m, 2H), 2.77 (t, J=6.2 Hz, 2H), 2.08 (s, 3H), 1.99-1.92 (m, 2H), 1.71 (ddt, J=12.3, 9.5, 4.4 Hz, 2H); $^{13}$C NMR (126 MHz, DMSO) δ 168.82, 155.57, 143.41, 142.25, 139.16, 136.45, 133.19, 129.95, 127.55, 124.10, 123.88, 122.36, 120.37, 118.76, 116.42, 106.27, 29.98, 29.18, 24.55, 22.90, 22.61; HRMS (ESI) m/z calcd for $C_{23}H_{24}N_3O$ [M+H]$^+$ 358.1919, found 358.1922.

4-(3,8-Dihydro-2H-furo[3,2-c]pyrrolo[3,2-f]quinolin-4-yl)phenol

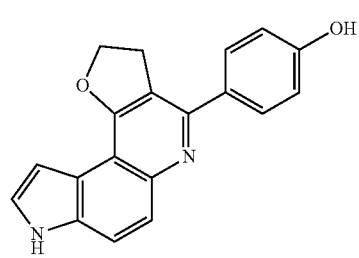

HSD 02-1211

Method B: Off-white solid (76 mg, 25%). $^1$H NMR (500 MHz, Methanol-d$_4$) δ 8.62 (s, 1H), 7.77 (d, J=9.0 Hz, 1H), 7.67 (d, J=9.0 Hz, 1H), 7.42-7.32 (m, 3H), 7.11 (d, J=3.0 Hz, 1H), 6.96-6.89 (m, 2H), 3.71 (t, J=7.1 Hz, 2H), 3.07 (t, J=7.1 Hz, 2H); $^{13}$C NMR (126 MHz, MeOD) δ 157.38, 156.71, 133.00, 132.35, 131.76, 130.10, 129.51, 123.71, 122.39, 121.62, 120.57, 116.48, 114.65, 106.36, 100.91, 61.71, 35.83; HRMS (ESI) m/z calcd for $C_{19}H_{17}N_2O_2$ [M+H]$^+$ 305.1290, found 305.1299.

2-Fluoro-4-(1-methyl-8,9,10,11-tetrahydro-3H-pyrazolo[4,3-a]phenanthridin-7-yl)phenol

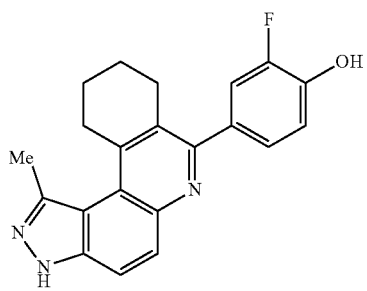

HSD 02-1213

Method A: Off-white solid (157 mg, 45%). $^1$H NMR (500 MHz, Methanol-d$_4$) δ 7.76 (s, 1H), 7.71 (d, J=8.6 Hz, 1H), 7.21 (d, J=11.7 Hz, 1H), 7.12 (d, J=8.4 Hz, 1H), 7.04 (t, J=8.5 Hz, 1H), 3.51-3.40 (m, 2H), 2.89 (s, 3H), 2.84-2.76 (m, 2H), 1.92-1.80 (m, 4H); C NMR (126 MHz, MeOD) δ 157.03, 155.85, 152.11, 150.19, 144.98, 143.53, 132.05, 128.98, 128.70, 125.04, 123.95, 117.20, 116.48, 116.32, 113.04, 31.86, 27.70, 22.03, 21.87; HRMS (ESI) m/z calcd for $C_{21}H_{21}FN_3O$ [M+H]$^+$ 350.1669, found 350.1677.

4-(8,9,10,11-Tetrahydro-3H-pyrrolo[3,2-a]phenanthridin-7-yl)benzonitrile

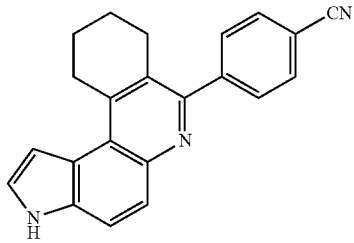

HSD 02-1214

Method A: Off-white solid (195 mg, 60%). $^1$H NMR (500 MHz, DMSO-$d_6$) δ 11.80 (s, 1H), 7.92 (d, J=8.5 Hz, 1H), 7.81 (dd, J=8.9, 0.8 Hz, 1H), 7.75 (d, J=8.9 Hz, 2H), 7.64 (d, J=8.9 Hz, 1H), 7.51 (t, J=2.8 Hz, 1H), 7.15-7.11 (m, 1H), 3.38 (t, J=6.1 Hz, 2H), 2.73 (t, J=6.1 Hz, 2H), 2.00-1.93 (m, 3H), 1.76-1.68 (m, 2H); $^{13}$C NMR (126 MHz, DMSO) δ 154.08, 146.45, 143.42, 142.77, 133.40, 132.39, 130.61, 127.28, 124.14, 124.07, 122.82, 120.26, 119.41, 116.85, 110.74, 106.41, 29.95, 28.81, 22.76, 22.41; HRMS (ESI) m/z calcd for $C_{22}H_{20}N_3$ [M+H]$^+$ 326.1657, found 326.1662.

Methyl 4-(8,9,10,11-tetrahydro-3H-pyrazolo[4,3-a]phenanthridin-7-yl)benzoate

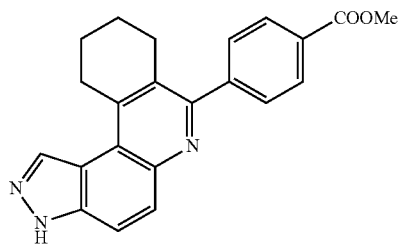

HSD 02-1215

Method A: Off-white solid (198 mg, 55%). $^1$H NMR (500 MHz, DMSO-$d_6$) δ 8.69 (s, 1H), 8.14 (dd, J=10.7, 7.0 Hz, 4H), 7.87 (d, J=7.6 Hz, 2H), 3.90 (s, 3H), 3.35 (d, J=6.2 Hz, 2H), 2.73 (t, J=5.8 Hz, 2H), 2.06-1.96 (m, 2H), 1.75 (d, J=7.1 Hz, 2H); $^{13}$C NMR (126 MHz, DMSO) δ 166.53, 155.59, 145.92, 143.71, 142.57, 138.77, 136.40, 130.03, 129.92, 129.65, 129.55, 129.25, 129.09, 122.12, 116.33, 114.56, 52.63, 29.59, 28.75, 22.48, 22.38; HRMS (ESI) m/z calcd for $C_{22}H_{22}N_3O_2$ [M+H]$^+$ 360.1712, found 360.1718.

4-(8,9,10,11-Tetrahydro-3H-pyrazolo[4,3-a]phenanthridin-7-yl)benzamide

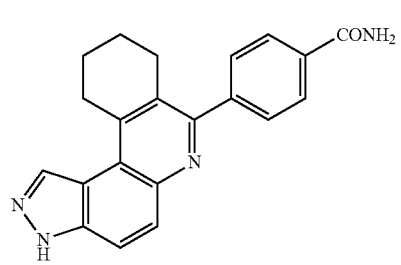

HSD 02-1217

Method A: Off-white solid (172 mg, 50%). $^1$H NMR (500 MHz, DMSO-$d_6$) δ 8.60 (s, 1H), 8.05 (s, 1H), 7.97 (d, J=8.0 Hz, 2H), 7.86 (d, J=9.1 Hz, 1H), 7.81 (d, J=9.1 Hz, 1H), 7.63 (d, J=8.0 Hz, 2H), 7.41 (s, 1H), 3.39-3.34 (m, 2H), 2.77 (t, J=6.1 Hz, 2H), 2.04-1.98 (m, 2H), 1.79-1.69 (m, 2H); $^{13}$C NMR (126 MHz, DMSO) δ 168.13, 156.17, 144.02, 143.77, 142.55, 133.95, 129.63, 129.40, 129.29, 127.64, 122.07, 116.23, 29.68, 28.86, 22.58, 22.49; HRMS (ESI) m/z calcd for $C_{21}H_{21}N_4O$ [M+H]$^+$ 345.1715, found 345.1719.

Methyl 4-(8,9,10,11-tetrahydro-3H-pyrrolo[3,2-a]phenanthridin-7-yl)benzoate

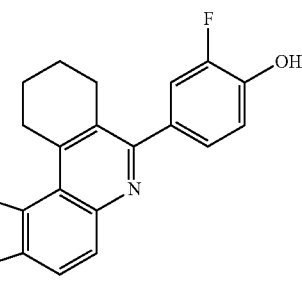

HSD 02-1218

Method A: Off-white solid (105 mg, 30%). $^1$H NMR (500 MHz, Methanol-$d_4$) δ 7.68 (dd, J=8.9, 0.8 Hz, 1H), 7.62 (d, J=8.9 Hz, 1H), 7.22 (dd, J=11.8, 2.0 Hz, 1H), 7.13 (ddd, J=8.2, 2.1, 0.9 Hz, 1H), 7.03 (dt, J=8.9, 8.2 Hz, 1H), 6.87 (s, 1H), 3.48-3.40 (m, 2H), 2.76 (t, J=6.2 Hz, 2H), 2.54 (s, 3H), 2.07-1.99 (m, 2H), 1.86-1.75 (m, 2H); $^{13}$C NMR (126 MHz, MeOD) δ 154.38, 152.03 (J=241.92 Hz), 144.97, 144.23, 141.91, 133.92, 133.16, 132.30, 127.16, 125.13, 122.28, 121.10, 120.18, 117.07, 116.57, 116.41, 115.50, 104.05, 29.98, 28.55, 22.44, 22.14, 12.07; HRMS (ESI) m/z calcd for $C_{22}H_{22}FN_2O$ [M+H]$^+$ 349.1716, found 349.1717.

Methyl 4-(8,9,10,11-tetrahydro-3H-pyrrolo[3,2-a]phenanthridin-7-yl)benzoate

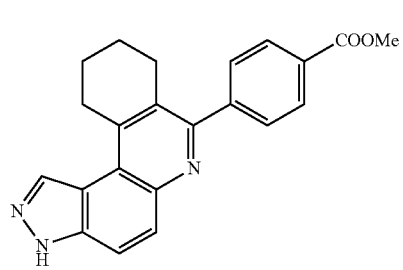

HSD 02-1219

Method A: Off-white solid (179 mg, 50%). $^1$H NMR (500 MHz, DMSO-$d_6$) δ 12.38 (s, 1H), 8.13 (d, J=8.0 Hz, 2H), 8.08 (d, J=8.7 Hz, 1H), 7.92 (d, J=8.9 Hz, 1H), 7.82 (d, J=8.0 Hz, 2H), 7.69 (t, J=2.7 Hz, 1H), 7.25-7.22 (m, 1H), 3.90 (s, 3H), 3.48 (t, J=6.5 Hz, 2H), 2.72 (t, J=6.2 Hz, 2H), 2.06-1.94 (m, 2H), 1.85-1.67 (m, 3H); $^{13}$C NMR (126 MHz, DMSO) δ 166.31, 150.76, 140.46, 137.32, 133.66, 130.77, 130.49, 130.13, 129.56, 129.56, 129.45, 128.64, 126.02, 123.33, 119.96, 117.68, 106.71, 52.90, 30.82, 28.26, 22.22, 21.82; HRMS (ESI) m/z calcd for $C_{23}H_{23}N_2O_2$ [M+H]$^+$ 359.1760, found 359.1767.

N-Hydroxy-4-(8,9,10,11-tetrahydro-3H-pyrrolo[3,2-a]phenanthridin-7-yl)benzimidamide

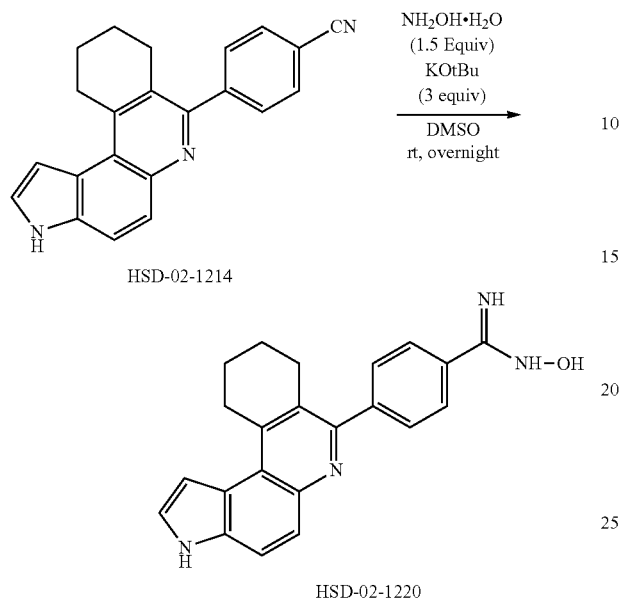

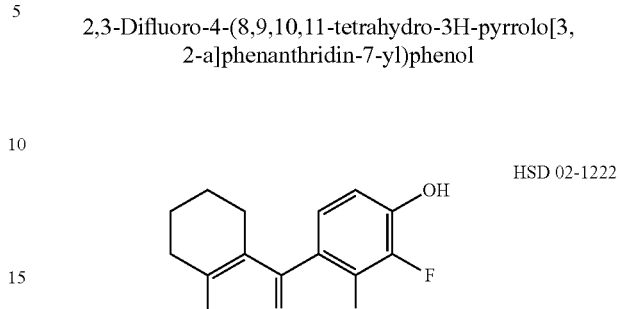

Synthesized by following general procedure for 1207. Off-white solid (163 mg, 91%); NMR (500 MHz, DMSO-$d_6$) δ 11.76 (d, J=2.3 Hz, 1H), 9.69 (s, 1H), 7.78 (t, J=8.9 Hz, 3H), 7.63 (d, J=8.8 Hz, 1H), 7.56-7.52 (m, 2H), 7.49 (t, J=2.8 Hz, 1H), 7.13 (d, J=2.5 Hz, 1H), 5.86 (s, 2H), 3.39 (1, J=6.5 Hz, 3H), 2.77 (t, J=6.2 Hz, 2H), 2.01-1.92 (m, 2H), 1.79-1.69 (m, 2H). $^{3}$C NMR (126 MHz, DMSO) δ 155.44, 151.17, 143.41, 142.38, 142.28, 133.25, 132.92, 129.31, 127.45, 125.38, 124.12, 123.98, 122.52, 120.34, 116.54, 106.31, 29.97, 29.08, 22.87, 22.54; HRMS (ESI) m/z calcd for $C_{22}H_{23}N_4O$ [M+H]$^+$ 359.1872, found 359.1872.

4-(8,9,10,11-Tetrahydro-3H-pyrrolo[3,2-a]phenanthridin-7-yl)benzamide

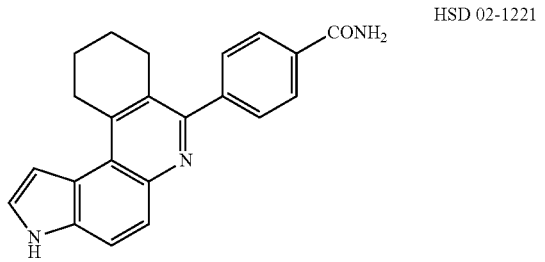 [SMILES: NC(=O)c1ccc(-c2nc3ccc4[nH]ccc4c3c3c2CCCC3)cc1]

Method A: Off-white solid (147 mg, 43%); $^1$H NMR (500 MHz, DMSO-$d_6$) δ 11.77 (t, J=2.3 Hz, 1H), 8.05 (s, 1H), 7.97 (d, J=8.3 Hz, 2H), 7.79 (d, J=8.9 Hz, 1H), 7.64 (d, J=8.9 Hz, 1H), 7.61 (d, J=8.2 Hz, 2H), 7.50 (t, J=2.8 Hz, 1H), 7.41 (s, 1H), 7.13 (t, J=2.5 Hz, 1H), 3.39 (t, J=6.5 Hz, 2H), 2.75 (t, J=6.1 Hz, 2H), 1.98 (q, J=4.3, 3.0 Hz, 3H), 1.73 (ddt, J=9.4, 6.5, 2.8 Hz, 2H). $^{13}$C NMR (126 MHz, DMSO) δ 168.20, 155.18, 144.56, 143.40, 142.47, 133.73, 133.30, 129.39, 127.59, 127.40, 124.11, 124.02, 122.62, 120.33, 116.62, 106.34, 29.97, 28.98, 22.84, 22.50; HRMS (ESI) m/z calcd for $C_{22}H_{22}N_3O$ [M+H]$^+$ 344.1763, found 344.1769.

2,3-Difluoro-4-(8,9,10,11-tetrahydro-3H-pyrrolo[3,2-a]phenanthridin-7-yl)phenol

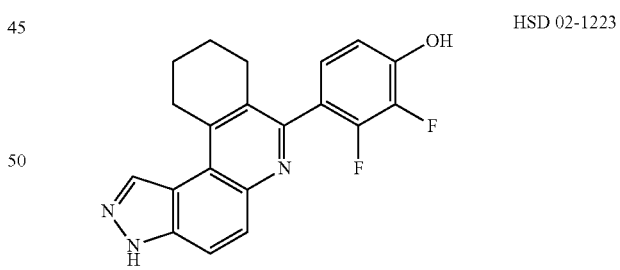

Method A: Yellow solid (166 mg, 47%). $^1$H NMR (500 MHz, DMSO-$d_6$) δ 11.40 (s, 1H), 8.23 (d, J=8.9 Hz, 1H), 8.05 (d, J=8.9 Hz, 1H), 7.80 (t, J=2.9 Hz, 1H), 7.41-7.34 (m, 1H), 7.31 (t, J=2.4 Hz, 1H), 7.15 (t, J=8.2 Hz, 1H), 3.55 (t, J=6.4 Hz, 2H), 2.72 (s, 2H), 2.13-1.96 (m, 2H), 1.81 (dd, J=7.8, 4.1 Hz, 2H). $^{13}$C NMR (126 MHz, DMSO) δ 149.88, 147.97, 147.88, 143.40, 141.12, 141.01, 139.18, 139.07, 134.54, 133.83, 130.60, 127.12, 126.30, 123.79, 121.80, 119.78, 113.94, 111.57, 106.98, 31.22, 27.17, 21.96, 21.33; HRMS (ESI) m/z calcd for $C_{21}H_{19}F_2N_2O$ [M+H]$^+$ 353.1465, found 353.1468.

2,3-Difluoro-4-(8,9,10,11-tetrahydro-3H-pyrazolo[4,3-a]phenanthridin-7-yl)phenol Method A: Off-white solid (177 mg, 50%). $^1$H NMR (500 MHz, DMSO-$d_6$) δ 10.56 (s, 1H), 8.56 (s, 1H), 7.92-7.76 (m, 2H), 7.05 (td, J=8.2, 2.0 Hz, 1H), 6.90 (td, J=8.3, 1.6 Hz, 1H), 3.32 (d, J=7.6 Hz, 2H), 2.62 (t, J=6.1 Hz, 2H), 1.96 (dt, J=11.1, 5.9 Hz, 2H), 1.75 (p, J=5.8 Hz, 2H); $^{13}$C NMR (126 MHz, DMSO) δ 151.48, 149.77, 147.83, 147.75, 147.03, 143.67, 142.40, 141.06, 140.95, 139.02, 138.74, 136.40, 130.47, 129.50, 125.40, 122.18, 120.81, 120.70, 116.39, 114.56, 113.32, 29.50, 27.48, 22.58, 22.19; HRMS (ESI) m/z calcd for $C_{20}F_{16}F_2N_3O$ [M+H]$^+$ 352.1261, found 352.1256.

2-Fluoro-5-(8,9,10,11-tetrahydro-3H-pyrazolo[4,3-a]phenanthridin-7-yl)benzonitrile

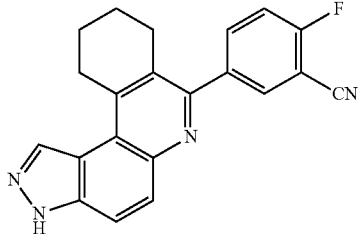

HSD 02-1224

Method A: Off-white solid (169 mg, 49%). $^1$H NMR (500 MHz, DMSO-d$_6$) δ 8.52 (s, 1H), 8.14 (dd, J=6.3, 2.3 Hz, 1H), 8.01-7.95 (m, 1H), 7.85 (d, J=9.0 Hz, 1H), 7.81 (d, J=9.3 Hz, 1H), 7.61 (t, J=9.0 Hz, 1H), 3.26 (d, J=6.7 Hz, 2H), 2.75 (t, J=6.1 Hz, 2H), 2.03-1.92 (m, 2H), 1.79-1.68 (m, 2H); $^{13}$C NMR (126 MHz, DMSO) δ 163.50 (J=257.04 Hz), 153.77, 143.56, 142.81, 138.70, 137.36, 137.29, 136.44, 134.73, 129.49, 122.20, 116.85, 116.69, 116.30, 114.70, 114.42, 100.43, 100.31, 29.62, 28.60, 22.47, 22.40; HRMS (ESI) m/z calcd for C$_{21}$H$_{18}$FN$_4$ [M+H]$^+$ 345.1515, found 345.1519.

2-Fluoro-5-(8,9,10,11-tetrahydro-3H-pyrrolo[3,2-a]phenanthridin-7-yl)benzonitrile

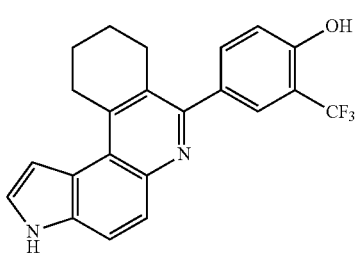

HSD 02-1225

Method A: Off-white solid (131 mg, 38%). $^1$H NMR (500 MHz, Methanol-d$_4$) δ 8.09 (dd, J=6.1, 2.3 Hz, 1H), 8.04 (d, J=9.0 Hz, 1H), 8.00 (ddd, J=8.7, 5.1, 2.3 Hz, 1H), 7.78 (d, J=9.0 Hz, 1H), 7.63-7.58 (m, 2H), 7.35-7.32 (m, 1H), 3.62 (t, 2H), 2.80 (t, J=6.2 Hz, 2H), 2.13-2.09 (m, 2H), 1.93-1.87 (m, 2H); $^{13}$C NMR (126 MHz, MeOD) δ 164.50, 162.42, 149.33, 138.09, 136.46, 134.57, 133.67, 128.43, 124.75, 123.69, 120.09, 119.05, 117.10, 116.70, 116.53, 112.81, 106.28, 101.63, 30.66, 27.94, 21.86, 21.54; HRMS (ESI) m/z calcd for C$_{22}$H$_{19}$FN$_3$ [M+H]$^+$ 344.1563, found 344.1565.

3-Methoxy-4-(8,9,10,11-tetrahydro-3H-pyrazolo[4,3-a]phenanthridin-7-yl)phenol

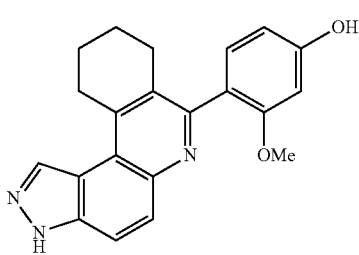

HSD 02-1228

Method A: Off-white solid (87 mg, 25%). $^1$H NMR (500 MHz, DMSO-d$_6$) δ 9.59 (s, 1H), 8.53 (s, 1H), 7.84-7.74 (m, 2H), 6.97 (d, J=8.1 Hz, 1H), 6.50 (d, J=2.2 Hz, 1H), 6.45 (dd, J=8.1, 2.2 Hz, 1H), 3.63 (s, 3H), 3.34-3.31 (m, 1H), 3.29-3.20 (m, 1H), 2.72-2.62 (m, 1H), 2.47-2.38 (m, 1H), 2.02-1.87 (m, 2H), 1.83-1.62 (m, 2H); $^{13}$C NMR (126 MHz, DMSO) δ 159.02, 157.89, 155.92, 143.53, 141.09, 138.58, 136.19, 131.12, 129.60, 121.67, 121.44, 116.57, 113.84, 107.41, 99.24, 55.49, 29.45, 27.19, 22.74, 22.27; HRMS (ESI) m/z calcd for C$_{21}$H$_{22}$N$_3$O$_2$ [M+H]$^+$ 348.1712, found 348.1717.

4-(8,9,10,11-Tetrahydro-3H-pyrrolo[3,2-a]phenanthridin-7-yl)-2-(trifluoromethyl)phenol

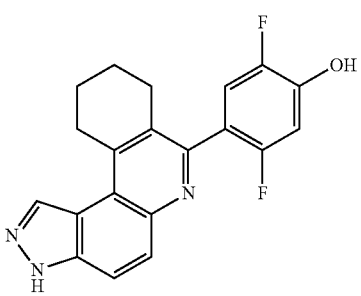

HSD 02-1232

Method A: Yellow solid (219 mg, 57%). $^1$H NMR (500 MHz, DMSO-d$_6$) δ 11.75 (s, 1H), 10.73 (s, 1H), 7.78 (d, J=8.9 Hz, 1H), 7.67 (dq, J=3.7, 2.2 Hz, 2H), 7.63 (d, J=8.8 Hz, 1H), 7.49 (t, J=2.8 Hz, 1H), 7.14-7.08 (m, 2H), 3.37 (t, J=6.6 Hz, 3H), 2.77 (t, J=6.1 Hz, 2H), 2.03-1.93 (m, 2H), 1.78-1.68 (m, 2H); $^{13}$C NMR (126 MHz, DMSO) δ 155.74, 154.41, 143.42, 142.51, 134.89, 133.22, 132.30, 127.65, 127.50, 125.67 (q, J=273.42 Hz), 124.05, 123.95, 122.46, 120.32, 116.82, 116.55, 115.52, 115.28, 106.29, 29.99, 29.12, 22.83, 22.58; HRMS (ESI) adz calcd for C$_{22}$H$_{20}$F$_3$N$_2$O [M H]$^+$ 385.1528, found 385.1530.

2,5-Difluoro-4-(8,9,10,11-tetrahydro-3H-pyrazolo[4,3-a]phenanthridin-7-yl)phenol

HSD 02-1233

Method A: Off-white solid (159 mg, 45%). $^1$H NMR (500 MHz, Methanol-d$_4$) δ 8.57 (s, 1H), 7.86 (q, J=9.1 Hz, 2H), 7.15 (dd, J=10.8, 6.7 Hz, 1H), 6.81 (dd, J=10.5, 7.1 Hz, 1H), 3.38 (s, 2H), 2.73 (s, 2H), 2.08 (p, J=6.1 Hz, 2H), 1.86 (d, J=9.8 Hz, 2H); $^{13}$C NMR (126 MHz, MeOD) δ 156.74 (J=239.16 Hz), 151.59, 148.92 (J=238.14 Hz), 146.61, 143.45, 143.06, 138.67, 135.89, 130.94, 128.32, 122.39, 118.20, 116.93, 116.06, 113.85, 104.69, 29.48, 27.05, 22.11, 21.80; HRMS (ESI) m/z calcd for C$_{20}$H$_{218}$F$_2$N$_3$O [M+H]$^+$ 354.1418, found 354.1421.

7-(3-(Trifluoromethyl)-1H-pyrazol-4-yl)-8,9,10,11-tetrahydro-3H-pyrrolo[3,2-a]phenanthridine

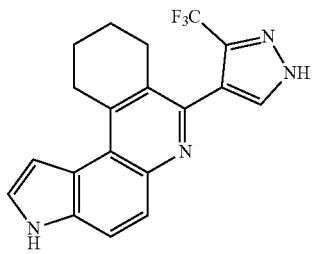

HSD 02-1234

Method A: Off-white solid (135 mg, 38%). $^1$H NMR (500 MHz, Methanol-$d_4$) δ 7.92 (s, 1H), 7.79 (d, J=9.0 Hz, 1H), 7.71-7.65 (m, 1H), 7.45-7.40 (m, 1H), 7.18 (d, J=3.2 Hz, 1H), 3.46 (t, J=6.4 Hz, 2H), 2.65 (t, J=6.3 Hz, 2H), 2.01 (dp, J=9.8, 3.3 Hz, 2H), 1.85 (qd, J=6.5, 3.2 Hz, 2H); $^{13}$C NMR (126 MHz, MeOD) δ 146.73, 143.44, 142.52, 133.34, 130.08, 129.00, 123.12, 122.85, 121.93, 120.17, 119.38, 116.04, 105.77, 29.74, 27.88, 22.38, 21.90; HRMS (ESI) m/z calcd for $C_{19}H_{16}F_3N_4$ [M+H]$^+$ 357.1327, found 357.1327.

7-(3-methyl-1H-pyrazol-4-yl)-8,9,10,11-tetrahydro-3H-pyrrolo[3,2-a]phenanthridine

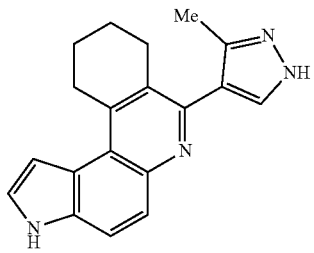

HSD 02-1235

Method A: Off-white solid (181 mg, 60%). $^1$H NMR (500 MHz, DMSO-$d_6$) δ 8.15 (d, J=8.9 Hz, 1H), 8.09-8.02 (m, 1H), 7.74 (t, J=2.9 Hz, 1H), 7.23 (t, J=2.4 Hz, 1H), 3.46 (t, J=6.4 Hz, 2H), 2.80 (t, J=6.3 Hz, 2H), 2.30 (s, 3H), 2.03-1.94 (m, 2H), 1.84-1.74 (m, 2H); $^{13}$C NMR (126 MHz, DMSO) δ 144.36, 134.42, 133.65, 130.53, 126.80, 122.88, 120.88, 119.84, 113.93, 110.98, 106.60, 31.17, 27.69, 22.00, 21.57, 19.02; HRMS (ESI) m/z calcd for $C_{19}H_{19}N_4$ [M+H]$^+$ 303.1610, found 303.1611.

1-Methyl-7-(3-(trifluoromethyl)-1H-pyrazol-4-yl)-8,9,10,11-tetrahydro-3H-pyrazolo[4,3-a]phenanthridine

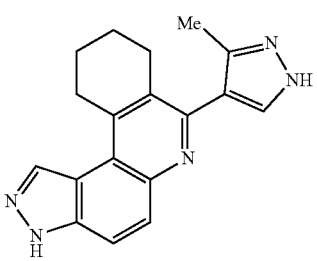

HSD 02-1236

Method A: Off-white solid (179 mg, 59%). $^1$H NMR (500 MHz, DMSO-$d_6$) δ 8.53 (s, 1H), 7.84-7.74 (m, 3H), 3.33 (s, 3H), 2.85 (t, J=6.1 Hz, 2H), 2.33 (s, 2H), 2.00-1.97 (m, 2H), 1.81-1.77 (m, 2H); $^{13}$C NMR (126 MHz, DMSO) δ 151.10, 143.71, 141.83, 138.63, 136.21, 130.12, 129.59, 121.02, 118.17, 116.48, 114.04, 29.70, 28.62, 22.63; HRMS (ESI) m/z calcd for $C_{18}H_{18}N_5$ [M+H]$^+$ 304.1562, found 304.1565.

1-Methyl-7-(3-(trifluoromethyl)-1H-pyrazol-4-yl)-8,9,10,11-tetrahydro-3H-pyrazolo[4,3-a]phenanthridine

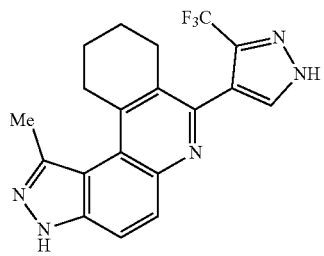

HSD 02-1237

Method A: Off-white solid (150 mg, 42%). $^1$H NMR (500 MHz, Methanol-$d_4$) δ 8.38 (d, J=0.9 Hz, 1H), 8.19 (d, J=9.2 Hz, 1H), 7.88 (d, J=9.2 Hz, 1H), 3.84-3.71 (m, 2H), 3.04 (s, 3H), 2.83-2.80 (m, 2H), 2.00-1.98 (m, 4H); $^{13}$C NMR (126 MHz, MeOD) δ 155.05, 144.54, 141.22, 140.08 (q=38 Hz), 135.79, 133.55, 132.43, 126.71, 124.45 (q, J=270 Hz), 123.66, 120.18, 118.65, 112.60, 109.60, 33.05, 26.90, 21.14, 20.63, 17.53; HRMS (ESI) m/z calcd for $C_{18}H_{15}F_3N_5$ [M+H]$^+$ 358.1280, found 358.1288.

4-(8,9,10,11-Tetrahydro-3H-pyrrolo[3,2-a]phenanthridin-7-yl)-3-(trifluoromethyl)phenol

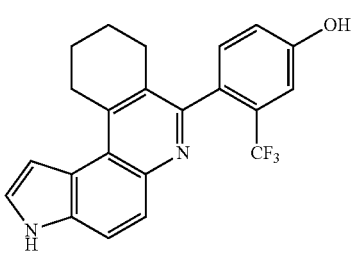

HSD 02-1238

Method A: Yellow solid (154 mg, 40%). $^1$H NMR (500 MHz, Methanol-$d_4$) δ 7.78 (d, J=9.0 Hz, 1H), 7.66 (d, J=8.9 Hz, 1H), 7.40 (d, J=3.0 Hz, 1H), 7.23-7.18 (m, 2H), 7.16 (d, J=2.8 Hz, 1H), 7.11 (dd, J=8.3, 2.3 Hz, 1H), 3.43 (t, J=6.6 Hz, 2H), 2.57-2.41 (m, 2H), 2.07-1.87 (m, 2H), 1.83-1.68 (m, 2H); $^{13}$C NMR (126 MHz, MeOD) δ 157.58, 153.68, 143.62, 141.79, 133.27, 132.02, 129.99, 129.72, 129.38 (J=30.24 Hz), 128.34, 122.95 (J=262.08 Hz), 122.88, 121.56, 118.37, 116.02, 114.80, 112.68, 105.70, 29.74, 27.85, 22.40, 21.83; HRMS (ESI) m/z calcd for $C_{22}H_{20}F_3N_2O$ [M+H]$^+$ 385.1528, found 385.1530.

4-(8,9,10,11-Tetrahydro-3H-pyrazolo[4,3-a]phenanthridin-7-yl)-3-(trifluoromethyl)phenol

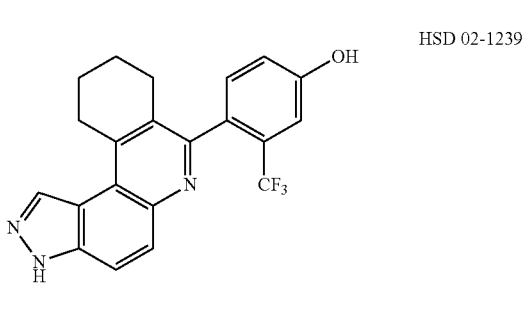 [SMILES: Oc1ccc(-c2nc3ccc4[nH]ncc4c3c3c2CCCC3)c(C(F)(F)F)c1]

HSD 02-1239

Method A: Off-white solid (142 mg, 36%). $^1$H NMR (500 MHz, DMSO-$d_6$) δ 10.24 (s, 1H), 8.55 (s, 1H), 7.84 (d, J=9.0 Hz, 1H), 7.77 (d, J=8.8 Hz, 1H), 7.24 (d, J=8.3 Hz, 1H), 7.19 (d, J=2.5 Hz, 1H), 7.11 (dd, J=8.3, 2.5 Hz, 1H), 3.44-3.24 (m, 2H), 2.57-2.50 (m, 1H), 2.34 (dt, J=17.0, 5.6 Hz, 1H), 2.00-1.83 (m, 2H), 1.82-1.62 (m, 2H); $^{13}$C NMR (126 MHz, DMSO) δ 157.55, 155.48, 143.04, 141.85, 138.71, 136.25, 132.68, 130.30, 129.99, 129.54, 128.57 (q, J=30.24 Hz), 125.45 (q, J=274.68 Hz), 122.04, 119.30, 116.44, 114.27, 113.02, 112.98, 29.41, 28.15, 22.58, 22.19; HRMS (ESI) m/z calcd for $C_{21}H_{19}F_3N_3O$ [M+H]$^+$ 386.1480, found 386.1488.

7-(5-(Trifluoromethyl)-1H-pyrazol-3-yl)-8,9,10,11-tetrahydro-3H-pyrazolo[4,3-a]phenanthridine

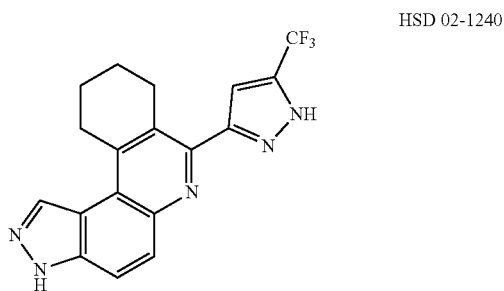 [SMILES: FC(F)(F)c1cc(-c2nc3ccc4[nH]ncc4c3c3c2CCCC3)n[nH]1]

HSD 02-1240

Method A: Off-white solid (150 mg, 42%). $^1$H NMR (500 MHz, DMSO-$d_6$) δ 8.56 (s, 1H), 7.91 (d, J=8.7 Hz, 2H), 7.17 (s, 1H), 3.33-3.28 (m, 3H), 3.00 (t, J=6.2 Hz, 2H), 2.02-1.95 (m, 2H), 1.88-1.80 (m, 2H); $^{13}$C NMR (126 MHz, DMSO) δ 144.59, 143.32, 142.97, 142.16, (J=36.83 Hz), 138.87, 136.55, 129.44, 125.49 (J=270.51 Hz), 122.50, 116.27, 115.12, 104.88, 29.83, 27.83, 22.26, 22.22; HRMS (ESI) m/z calcd for $C_{18}H_{15}F_3N_5$ [M+H]$^+$ 358.1280, found 358.1289.

4-(9-(Trifluoromethyl)-8,9,10,11-tetrahydro-3H-pyrrolo[3,2-a]phenanthridin-7-yl)phenol

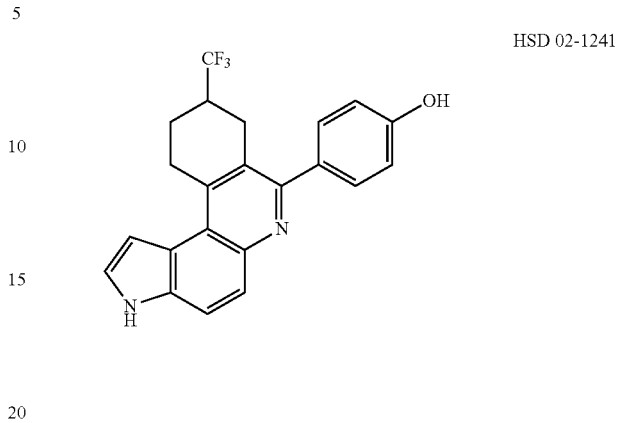

HSD 02-1241

Method A: Off-white solid (157 mg, 41%). $^1$H NMR (500 MHz, DMSO-$d_6$) δ 11.93 (s, 1H), 9.74 (s, 1H), 7.84 (d, J=8.8 Hz, 1H), 7.67 (s, 1H), 7.60-7.50 (m, 1H), 7.39 (d, J=8.0 Hz, 2H), 7.21-7.07 (m, 1H), 6.99-6.83 (m, 2H), 3.65 (dd, J=18.1, 5.8 Hz, 1H), 3.01-2.93 (m, 1H), 2.89-2.81 (m, 1H), 2.78-2.65 (m, 1H), 2.43-2.31 (m, 1H), 1.92-1.77 (m, 1H); $^{13}$C NMR (126 MHz, DMSO) δ 157.87, 155.35, 133.27, 131.96, 130.83, 129.75, 127.53, 124.57, 124.44, 121.71, 120.23, 117.24, 115.32, 106.11, 37.63 (q=26.6 Hz), 29.04, 27.78, 21.66; HRMS (ESI) m/z calcd for $C_{22}H_{20}F_3N_2O$ [M+H]$^+$ 385.1528, found 385.1532.

4-(9-(Trifluoromethyl)-8,9,10,11-tetrahydro-3H-pyrazolo[4,3-a]phenanthridin-7-yl)phenol

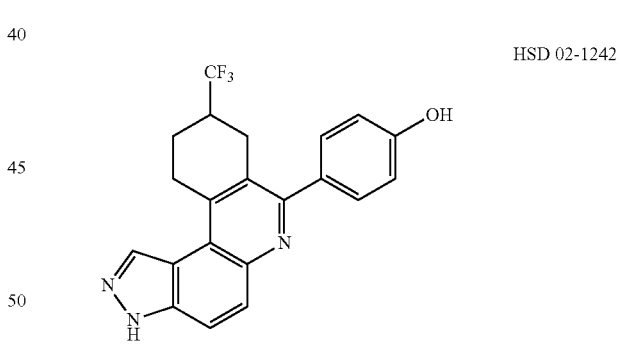

HSD 02-1242

Method A: Ulf-white solid (165 mg, 43%). $^1$H NMR (500 MHz, DMSO-$d_6$) δ 10.27 (s, 1H), 8.60 (s, 1H), 8.11-7.90 (m, 2H), 7.57 (d, J=8.2 Hz, 2H), 7.03 (d, J=8.3 Hz, 2H), 3.54-3.43 (m, 1H), 3.40-3.28 (m, 1H), 3.10-2.97 (m, 1H), 2.90-2.82 (m, 1H), 2.79-2.68 (m, 1H), 2.39-2.30 (m, 1H), 1.94-1.79 (m, 1H); $^{13}$C NMR (126 MHz, DMSO) δ 159.74, 152.87, 148.17, 137.78, 131.71, 129.43 (q, J=278.46 Hz), 127.87, 122.81, 121.71, 115.86, 115.01, 37.62 (q, J=26.46 Hz), 29.44, 27.22, 20.90; HRMS (ESI) m/z calcd for $C_{21}H_{19}F_3N_3O$ [M+H]$^+$ 386.1480, found 386.1484.

4-(9,9-Difluoro-8,9,10,11-tetrahydro-3H-pyrrolo[3,2-a]phenanthridin-7-yl)phenol

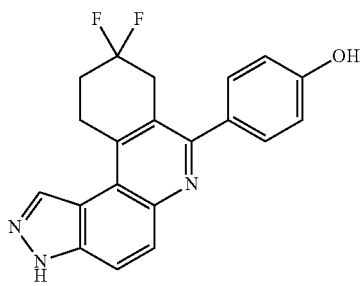

HSD-02-1243

Method A: Off-white solid (152 mg, 43%). $^1$H NMR (500 MHz, DMSO-$d_6$) δ 9.71 (s, 1H), 8.59 (s, 1H), 7.90 (d, J=9.1 Hz, 1H), 7.87-7.81 (m, 1H), 7.41 (d, J=8.5 Hz, 2H), 6.89 (d, J=8.5 Hz, 2H), 3.63-3.55 (m, 2H), 3.41-3.36 (m, 2H), 2.55-2.50 (m, 2H); $^{13}$C NMR (126 MHz, DMSO) δ 157.94, 156.62, 144.16, 139.61, 138.71, 136.27, 131.03, 130.86, 129.49, 125.65, 124.54, 123.75, 121.86, 120.55, 116.30, 115.37, 115.11, 37.18 (J=26.46 Hz), 29.37 (J=23.94 Hz), 28.01; HRMS (ESI) m/z calcd for $C_{20}H_{18}F_2N_3O$ [M+H]$^+$ 354.1418, found 354.1421.

4-(9,9-Difluoro-8,9,10,11-tetrahydro-3H-pyrrolo[3,2-a]phenanthridin-7-yl)phenol

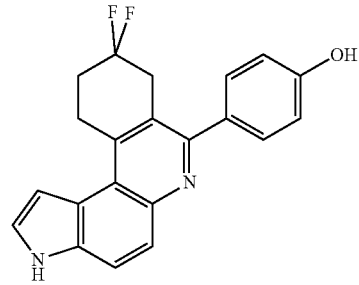

HSD 02-1244

Method A: Off-white solid (180 mg, 49%). $^1$H NMR (500 MHz, DMSO-$d_6$) δ 11.84 (s, 1H), 7.84 (d, J=8.8 Hz, 1H), 7.67 (d, J=8.8 Hz, 1H), 7.53 (d, J=3.0 Hz, 1H), 7.39 (d, J=8.1 Hz, 2H), 7.13 (d, J=3.1 Hz, 1H), 6.88 (d, J=8.1 Hz, 2H), 3.63 (t, J=7.1 Hz, 2H), 3.33 (t, J=14.5 Hz, 2H), 2.48-2.38 (m, 2H); $^{13}$C NMR (126 MHz, DMSO) δ 157.78, 155.53, 143.87, 139.53, 133.29, 131.52, 130.80, 125.76, 124.38, 123.95, 123.87, 122.78, 121.98, 121.20, 120.23, 117.15, 115.32, 106.13, 37.50 (J=26.46 Hz), 29.55 (J=23.94 Hz), 28.22; HRMS (ESI) m/z calcd for $C_{21}H_{19}F_2N_2O$ [M+H]$^+$ 353.1465, found 353.1470.

Ethyl 8,9,10,11-tetrahydro-3H-pyrazolo[4,3-a]phenanthridine-7-carboxylate

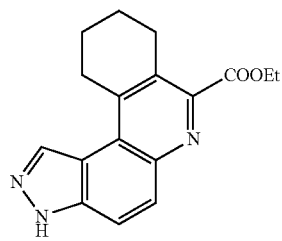

HSD 02-1246

Method A: Off-white solid (151 mg, 51%). $^1$H NMR (500 MHz, DMSO-$d_6$) δ 8.58 (s, 1H), 7.90 (d, J=9.1 Hz, 1H), 7.85 (d, J=9.1 Hz, 1H), 4.38 (q, J=7.1 Hz, 2H), 2.94 (t, J=6.3 Hz, 2H), 1.98 (tt, J=7.7, 6.0, 4.6 Hz, 2H), 1.84 (dd, J=7.6, 3.9 Hz, 2H), 1.34 (t, J=7.1 Hz, 3H). $^{13}$C NMR (126 MHz, DMSO) δ 167.34, 148.23, 143.50, 142.89, 139.08, 136.66, 129.37, 128.75, 123.47, 116.23, 115.28, 61.64, 29.54, 26.54, 22.29, 21.87, 14.60; HRMS (ESI) m/z calcd for $C_{17}H_{20}N_3O_2$ [M+H]$^+$ 298.1556, found 298.1562.

7-(4-Hydroxyphenyl)-8,9,10,11-tetrahydro-3H-pyrrolo[3,2-a]phenanthridine-1-carbonitrile

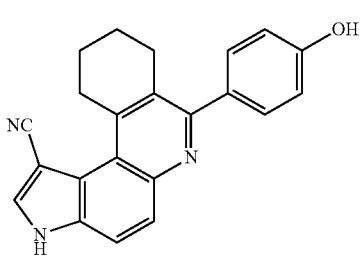

HSD 02-1247

Method A: Off-white solid (140 mg, 41%). Method A: Off-white solid (182 mg, 56%). $^1$H NMR (500 MHz, DMSO-$d_6$) δ 10.36 (s, 1H), 8.70 (d, J=3.1 Hz, 1H), 8.27 (d, J=8.9 Hz, 1H), 8.19 (d, J=9.1 Hz, 1H), 7.59 (d, J=8.0 Hz, 2H), 7.04 (d, J=8.1 Hz, 2H), 3.77 (t, J=6.3 Hz, 2H), 2.84 (t, J=6.3 Hz, 2H), 1.99-1.91 (m, 2H), 1.87-1.77 (m, 2H); $^{13}$C NMR (126 MHz, DMSO) δ 160.39, 153.97, 152.19, 138.86, 135.26, 135.01, 131.92, 130.79, 123.33, 122.29, 121.56, 119.23, 117.69, 117.36, 115.99, 89.30, 33.48, 27.99, 21.34, 21.30; HRMS (ESI) m/z calcd for $C_{22}H_{20}N_3O$ [M+H]$^+$ 342.1606, found 342.1611.

4-(7,8,9,10-Tetrahydrophenanthridin-6-yl)phenol

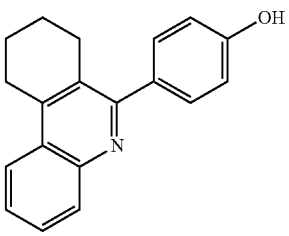

HSD 02-1248

Method A: Off-white solid (75 mg, 20%). ¹H NMR (500 MHz, Methanol-d₄) δ 8.42 (d, J=8.5 Hz, 1H), 8.16 (d, J=8.5 Hz, 1H), 8.04 (t, J=7.7 Hz, 1H), 7.92 (t, J=7.8 Hz, 1H), 7.60 (d, J=8.2 Hz, 2H), 7.07 (d, J=8.3 Hz, 2H), 3.52 (t, J=6.5 Hz, 2H), 2.90 (t, J=6.2 Hz, 2H), 2.12-2.06 (m, 2H), 1.95-1.84 (m, 2H); ¹³C NMR (126 MHz, MeOD) δ 160.77, 156.16, 155.60, 135.74, 132.96, 131.15, 130.92, 129.04, 127.05, 124.04, 122.18, 120.19, 115.59, 27.66, 26.87, 21.56, 20.93; HRMS (ESI) m/z calcd for C₁₉H₂₀NO [M+H]⁺ 378.1545, found 378.1546.

4-(6,7,8,9-Tetrahydro-3H-pyrrolo[3,2-c]phenanthridin-5-yl)phenol

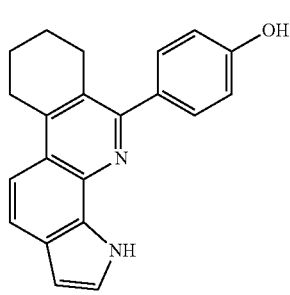

HSD-02-1252

Method A: Yale yellow solid (119 mg, 38%). ¹H NMR (500 MHz, Methanol-d₄) δ 7.73 (d, J=8.8 Hz, 1H), 7.58 (d, J=8.8 Hz, 1H), 7.39-7.32 (m, 3H), 6.96-6.89 (m, 2H), 6.62 (d, J=3.0 Hz, 1H), 3.24 (tt, J=6.6, 1.2 Hz, 2H), 2.72 (t, J=6.3 Hz, 2H), 1.95 (td, J=6.5, 3.0 Hz, 2H), 1.82-1.73 (m, 2H); ¹³C NMR (126 MHz, MeOD) δ 157.94, 157.43, 143.79, 134.49, 131.77, 130.32, 129.91, 126.79, 126.36, 123.54, 122.78, 120.97, 114.65, 113.55, 102.78, 28.24, 26.19, 22.54, 22.16; HRMS (ESI) m/z calcd for C₂₁H₁₉N₂O [M+H]⁺ 315.1497, found 315.1498.

4-(3-(2-Hydroxyethyl)-8,9,10,11-tetrahydro-3H-pyrazolo[4,3-a]phenanthridin-7-yl)phenol

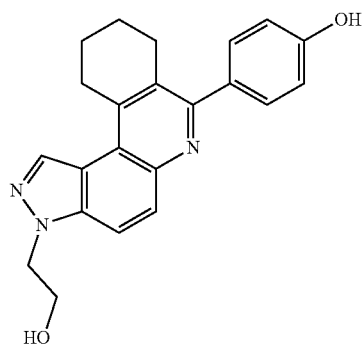

HSD 02-1253

Method A: Off-white solid (177 mg, 49%). ¹H NMR (500 MHz, DMSO-d₆) δ 9.59 (s, 1H), 8.51 (s, 1H), 7.96 (d, J=9.1 Hz, 1H), 7.81 (d, J=9.1 Hz, 1H), 7.39 (d, J=8.5 Hz, 2H), 6.86-6.82 (m, 2H), 4.55 (t, J=5.6 Hz, 2H), 3.88-3.82 (m, 2H), 3.32-3.27 (m, 2H), 2.79 (t, J=6.2 Hz, 2H), 2.01-1.96 (m, 2H), 1.77-1.70 (m, 2H); ¹³C NMR (126 MHz, DMSO) δ 157.58, 157.01, 143.57, 142.09, 138.61, 135.29, 131.97, 130.89, 129.53, 129.38, 121.31, 117.15, 115.09, 114.17, 60.84, 51.76, 29.69, 29.23, 22.64; HRMS (ESI) m/z calcd for C₁₂H₂₄N₃O₂ [M+H]⁺ 362.1869, found 362.1871.

7-(3-(δ 8.26 (s, 1H), 7.95 (d, J=9.1 Hz, 1H), 7.86 (d, J=9.1 Hz, 1H), 3.55 (t, J=6.3 Hz, 2H), 2.72 (t, J=6.3 Hz, 2H), 1.95-1.86 (m, 2H), 1.84-1.77 (m, 2H); ¹³C NMR (126 MHz, DMSO) δ 150.24, 144.55, 143.03, 140.24, 139.34, 131.66, 131.35, 130.73, 125.49 (J=2704.68 Hz), 121.28, 121.28, 119.78, 119.14, 117.84, 116.46, 114.90, 31.80, 28.11, 21.99; HRMS (ESI) m/z calcd for C₁₉H₁₄F₃N₆ [M+H]⁺ 383.1232, found 383.1238.

6-(8,9,10,11-Tetrahydro-3H-pyrrolo[3,2-a]phenanthridin-7-yl)benzo[d]thiazol-2-amine

HSD-02-1256

Method A: Pale yellow solid (115 mg, 31%). ¹H NMR (500 MHz, DMSO-d₆) δ 7.83 (t, J=1.2 Hz, 1H), 7.77 (dd, J=8.8, 0.8 Hz, 1H), 7.62 (d, J=8.7 Hz, 1H), 7.52 (s, 2H), 7.49 (t, J=2.8 Hz, 1H), 7.42-7.36 (m, 2H), 7.15-7.09 (m, 1H), 3.38 (t, J=6.5 Hz, 2H), 2.80 (1, J=6.1 Hz, 2H), 2.01-1.93 (m, 2H), 1.78-1.68 (m, 2H); ¹³C NMR (126 MHz, DMSO) δ 167.48, 155.93, 152.75, 143.42, 142.23, 134.61, 133.18, 131.13, 127.69, 127.23, 124.12, 123.91, 122.33, 122.08, 120.39, 117.29, 116.41, 106.26, 30.02, 29.30, 22.94, 22.64; HRMS (ESI) m/z calcd for C₂₂H₁₉N₄S [M+H]⁺ 371.1330, found 371.1339.

6-(3,8,9,10-Tetrahydrocyclopenta[c]pyrazolo[4,3-f]quinolin-7-yl)benzo[d]thiazol-2-amine

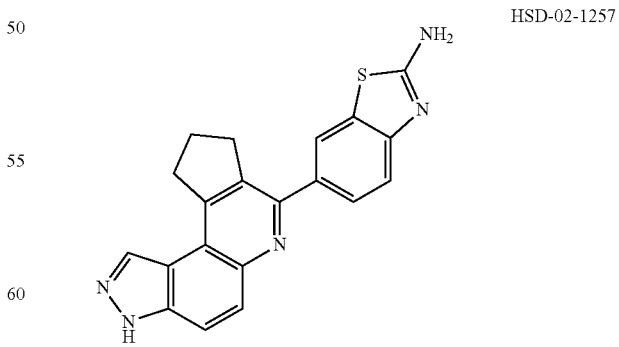

HSD-02-1257

Method A: Yellow solid (118 mg, 33%). ¹H NMR (500 MHz, DMSO-d₆) δ 8.44 (s, 1H), 8.20 (d, J=1.8 Hz, 1H), 7.90 (d, J=9.2 Hz, 1H), 7.84 (d, J=9.0 Hz, 1H), 7.77 (dd, J=8.3, 1.9 Hz, 1H), 7.60 (s, 2H), 7.43 (d, J=8.3 Hz, 1H), 3.48 (t, J=7.5 Hz, 2H), 3.29 (t, J=7.6 Hz, 2H), 2.25 (p, J=7.5 Hz, 2H); ¹³C NMR (126 MHz, DMSO) δ 167.94, 153.47, 152.28, 149.49, 144.86, 138.15, 135.97, 135.08, 133.41, 131.62, 129.24, 126.75, 121.54, 118.85, 117.60, 116.83, 114.58, 33.57, 33.43, 25.01; HRMS (ESI) m/z calcd for $C_{20}H_{16}N_5S$ [M+H]⁺ 358.1126, found 358.1128.

N-(4-(2-methyl-8,9,10,11-tetrahydro-3H-pyrrolo[3,2-a]phenanthridin-7-yl)phenyl)methanesulfonamide

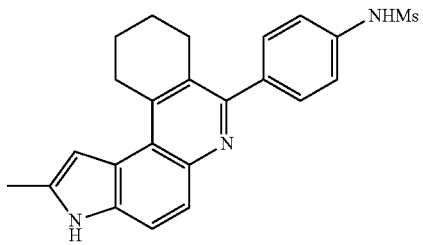

HSD-02-1258

Method A: Pale yellow solid (205 mg, 50%). ¹H NMR (500 MHz, DMSO-d₆) δ 7.24 (d, J=8.9 Hz, 1H), 6.92 (d, J=8.9 Hz, 1H), 6.86 (d, J=8.3 Hz, 2H), 6.70 (d, J=8.3 Hz, 2H), 6.28 (s, 1H), 2.86-2.78 (m, 2H), 2.29 (s, 3H), 2.11-2.02 (m, 2H), 1.81 (s, 2H), 1.39-1.28 (m, 2H), 1.14-1.04 (m, 2H); ¹³C NMR (126 MHz, DMSO) δ 154.13, 148.50, 140.10, 136.74, 132.90, 129.61, 128.08, 126.79, 122.08, 120.26, 119.11, 118.09, 110.65, 104.05, 37.63, 30.40, 26.94, 20.76, 20.43, 11.29; HRMS (ESI) m/z calcd for $C_{23}H_{28}N_3O_2S$ [M+H]⁺ 410.1902, found 410.1907.

N-(4-(3,8,9,10-Tetrahydrocyclopenta[c]pyrrolo[3,2-f]quinolin-7-yl)phenyl)methanesulfonamide

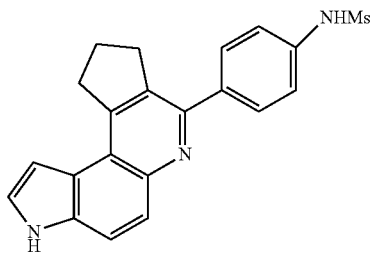

HSD-02-1259

Method A: Ulf-white solid (179 mg, 47%). ¹H NMR (500 MHz, DMSO-d₆) δ 11.69 (t, J=2.3 Hz, 1H), 9.91 (s, 1H), 7.89-7.84 (m, 2H), 7.77 (dd, J=8.9, 0.8 Hz, 1H), 7.70 (d, J=8.9 Hz, 1H), 7.48 (t, J=2.7 Hz, 1H), 7.37-7.29 (m, 2H), 7.01-6.96 (m, 1H), 3.50 (t, J=7.5 Hz, 2H), 3.24 (t, J=7.5 Hz, 2H), 3.05 (s, 3H), 2.24 (p, J=7.6 Hz, 2H); ¹³C NMR (126 MHz, DMSO) δ 150.60, 149.35, 144.61, 138.77, 136.41, 134.23, 132.57, 129.96, 124.46, 123.67, 120.85, 120.10, 119.48, 116.78, 104.29, 33.87, 33.12, 25.08; HRMS (ESI) m/z calcd for $C_{21}H_{22}N_3O_2S$ [M+H]⁺ 380.1433, found 380.1440.

7-(2-Aminobenzo[d]thiazol-6-yl)-8,9,10,11-tetrahydro-3H-pyrrolo[3,2-a]phenanthridine-1-carbonitrile

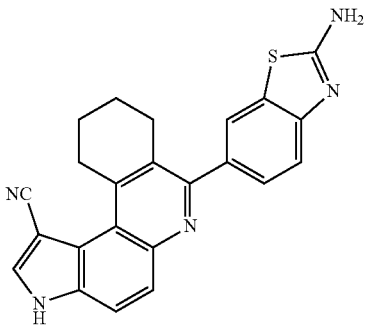

HSD-02-1260

Method A: rale yellow solid (119 mg, 30%). ¹H NMR (500 MHz, DMSO-d₆) δ 9.19 (s, 2H), 8.69 (d, J=3.1 Hz, 1H), 8.29-8.20 (m, 3H), 7.71 (dd, J=8.3, 1.8 Hz, 1H), 7.66 (d, J=8.3 Hz, 1H), 3.75 (t, J=6.3 Hz, 2H), 2.83 (t, J=6.4 Hz, 2H), 2.02-1.91 (m, 2H), 1.86-1.72 (m, 2H); ¹³C NMR (126 MHz, DMSO) δ 169.71, 154.01, 151.40, 138.84, 135.50, 135.06, 130.71, 128.82, 128.33, 126.00, 124.16, 123.58, 121.67, 119.22, 117.85, 117.28, 116.11, 114.43, 89.32, 33.49, 27.97, 21.30; HRMS (ESI) m/z calcd for $C_{23}H_{18}N_5S$ [M+H]⁺ 396.1283, found 396.1288.

6-(1-Methyl-8,9,10,11-tetrahydro-3H-pyrazolo[4,3-a]phenanthridin-7-yl)benzo[d]thiazol-2-amine

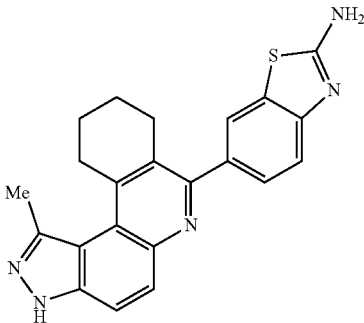

HSD-02-1261

Method A: Off-white solid (116 mg, 30%). ¹H NMR (500 MHz, Methanol-d₄) δ 7.77 (d, J=9.1 Hz, 1H), 7.75-7.68 (m, 2H), 7.53-7.47 (m, 1H), 7.38 (dd, J=8.2, 1.8 Hz, 1H), 3.52-3.42 (m, 2H), 2.90 (s, 3H), 2.81 (q, J=4.3, 3.1 Hz, 2H), 1.89-1.82 (m, 4H); ¹³C NMR (126 MHz, MeOD) δ 169.08, 156.70, 151.68, 143.60, 143.42, 143.25, 141.25, 133.99, 130.75, 128.98, 128.59, 126.61, 123.95, 121.19, 116.95, 115.76, 113.89, 31.88, 27.83, 22.07, 21.90, 17.96; HRMS (EST) m/z calcd for $C_{22}H_{20}N_5S$ [M+H]⁺ 386.1439, found 386.1447.

7-(3,5-Dimethyl-1H-pyrazol-4-yl)-8,9,10,11-tetra-hydro-3H-pyrazolo[4,3-a]phenanthridine

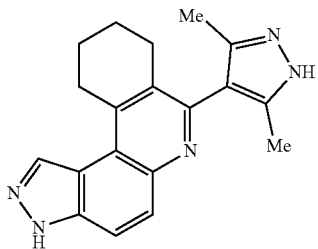

ND-02-1262

Method A: Off-white solid (193 mg, 60%). $^1$H NMR (500 MHz, DMSO-d$_6$) δ 8.58-8.53 (m, 1H), 7.82 (dd, J=9.1, 0.9 Hz, 1H), 7.76 (d, J=9.0 Hz, 1H), 3.30 (t, J=6.5 Hz, 2H), 2.56 (t, J=6.2 Hz, 2H), 2.00 (s, 9H), 1.76 (qd, J=8.6, 7.2, 4.1 Hz, 2H); $^{13}$C NMR (126 MHz, DMSO) δ 151.69, 144.07, 141.77, 139.31, 135.31, 131.30, 129.63, 121.60, 117.69, 116.32, 114.93, 29.51, 27.72, 22.74, 22.45; HRMS (EST) m/z calcd for C$_{19}$H$_{24}$N$_5$ [M+H]$^+$ 322.2032, found 322.2036.

7-(1H-Indazol-5-yl)-1-methyl-8,9,10,11-tetrahydro-3H-pyrazolo[4,3-a]phenanthridine

HSD-02-1263

Method A: Off-white solid (161 mg, 45%). $^1$H NMR (500 MHz, DMSO-d$_6$) δ 8.20 (s, 1H), 8.05 (s, 1H), 7.97 (d, J=8.9 Hz, 1H), 7.91 (d, J=9.2 Hz, 1H), 7.71 (d, J=8.6 Hz, 1H), 7.59 (dd, J=8.6, 1.6 Hz, 1H), 3.51 (q, J=7.4, 6.5 Hz, 2H), 2.93-2.87 (m, 2H), 2.79 (t, J=6.2 Hz, 2H), 1.88-1.73 (m, 4H); $^{13}$C NMR (126 MHz, DMSO)$^{13}$C NMR (126 MHz, DMSO) δ 153.72, 148.28, 140.25, 139.38, 136.90, 134.68, 130.29, 127.67, 124.60, 123.00, 122.54, 114.31, 110.60, 32.28, 27.98, 22.08, 21.72; HRMS (ESI) m/z calcd for C$_{22}$H$_{24}$N$_5$ [M+H]$^+$ 358.2032, found 358.2033.

7-(1H-Indazol-5-yl)-1,2-dimethyl-8,9,10,11-tetra-hydro-2H-pyrazolo[4,3-a]phenanthridine

HSD-02-1264

Method A: Off-white solid (159 mg, 43%). $^1$H NMR (500 MHz, DMSO-d$_6$) δ 8.12 (s, 1H), 7.93 (dd, J=1.6, 0.8 Hz, 1H), 7.75 (d, J=9.0 Hz, 1H), 7.60 (dt, J=8.6, 1.0 Hz, 1H), 7.55 (dd, J=8.6, 1.6 Hz, 1H), 7.38 (d, J=9.0 Hz, 1H), 4.10 (s, 3H), 3.61 (t, J=6.6 Hz, 3H), 2.79 (t, J=6.2 Hz, 2H), 2.63 (s, 3H), 1.94-1.89 (m, 2H), 1.75-1.65 (m, 3H); $^{13}$C NMR (126 MHz, DMSO) δ 158.06, 147.33, 144.38, 143.84, 139.78, 134.44, 133.66, 132.84, 128.49, 128.17, 123.76, 123.05, 121.87, 121.40, 118.85, 118.33, 109.89, 37.78, 30.37, 29.10, 22.71, 22.60, 9.69; HRMS (ESI) m/z calcd for C$_{23}$H$_{24}$N$_5$ [M H]$^+$ 370.2032, found 370.2039.

7-(1H-indazol-5-yl)-2-methyl-8,9,10,11-tetrahydro-3H-pyrrolo[3,2-a]phenanthridine

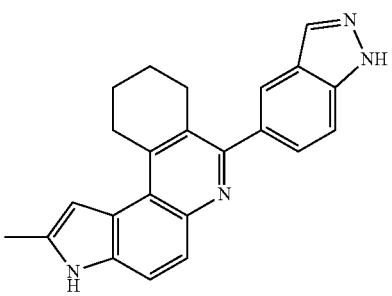

HSD-02-1266

Method A: Off-white solid (146 mg, 41%). $^1$H NMR (500 MHz, Methanol-d$_4$) δ 8.13 (s, 1H), 7.89 (t, J=1.1 Hz, 1H), 7.69 (d, J=8.9 Hz, 1H), 7.67-7.62 (m, 2H), 7.52 (dd, J=8.5, 1.5 Hz, 1H), 6.89 (s, 1H), 3.46 (t, J=6.5 Hz, 2H), 2.74 (t, J=6.2 Hz, 2H), 2.54 (s, 3H), 2.07-1.98 (m, 3H), 1.85-1.75 (m, 2H); $^{13}$C NMR (126 MHz, MeOD) δ 156.00, 143.82, 142.24, 139.73, 133.98, 133.79, 133.15, 127.95, 127.34, 122.81, 122.28, 121.16, 120.90, 120.51, 115.34, 109.38, 104.02, 29.95, 28.71, 22.50, 22.19, 12.08; HRMS (ESI) m/z calcd for C$_{23}$H$_{25}$N$_4$ [M H]$^+$ 357.2079, found 357.2079.

7-(1H-Indazol-5-yl)-1-methyl-8,9,10,11-tetrahydro-3H-pyrazolo[4,3-a]phenanthridine

HSD-02-1268

Method A: Off-white solid (163 mg, 46%). $^1$H NMR (500 MHz, MeOD-d$_4$) δ 9.51 (s, 1H), 8.8 (s, 1H), 8.33-8.31 (m, 2H), 8.24 (d, J=8.5 Hz, 1H), 8.13 (d, J=9.5 Hz, 1H), 8.00 (d, J=7.7 Hz, 1H), 4.25 (s, 3H), 3.69 (t, J=6.2 Hz, 2H), 2.91 (t, J=5.9 Hz, 2H), 2.24-2.19 (m, 2H), 1.97-1.92 (m, 2H); $^{13}$C NMR (126 MHz, MeOD) δ 156.46, 155.04, 149.36, 143.88, 134.90, 134.50, 133.73, 132.46, 132.17, 129.92, 127.08, 124.13, 121.16, 119.24, 116.83, 114.80, 113.44, 32.47, 30.98, 27.74, 21.22, 21.10; HRMS (ESI) m/z calcd for $C_{22}H_{20}N_5$ [M+H]$^+$ 354.1719, found 354.1722.

7-(1H-Pyrrolo[3,2-c]pyridin-3-yl)-8,9,10,11-tetra-hydro-3H-pyrazolo[4,3-a]phenanthridine

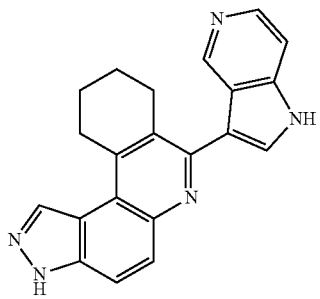

HSD-02-1270

Method A: Off-white solid (129 mg, 38%). $^1$H NMR (500 MHz, DMSO-d$_6$) δ 11.82 (s, 1H), 9.49 (d, J=1.8 Hz, 1H), 8.57 (s, 1H), 8.23 (dd, J=5.7, 2.2 Hz, 1H), 7.93 (d, J=2.1 Hz, 1H), 7.89-7.82 (m, 2H), 7.44 (dd, J=5.9, 1.8 Hz, 1H), 3.33 (s, 17H), 3.07 (t, J=6.2 Hz, 2H), 2.04 (dtt, J=12.3, 6.4, 2.2 Hz, 2H), 1.89-1.78 (m, 2H); $^{13}$C NMR (126 MHz, DMSO) δ 151.34, 145.38, 143.85, 142.15, 140.91, 139.91, 129.62, 129.54, 128.05, 124.66, 120.76, 116.46, 115.21, 107.29, 29.95, 28.95, 22.80, 22.62; HRMS (ESI) m/z calcd for $C_{21}H_{18}N_5$ [M+H]$^+$ 340.1562, found 340.1566.

7-(4-Chloro-1H-pyrrolo[2,3-b]pyridin-3-yl)-8,9,10,11-tetrahydro-3H-pyrazolo[4,3-a]phenanthridine

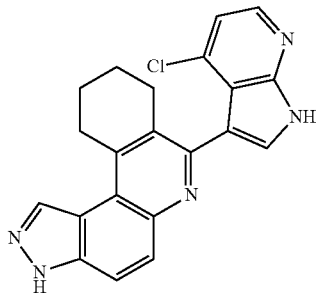

HSD-02-1271

Method A: Off-white solid (180 mg, 48%). $^1$H NMR (500 MHz, Methanol-d$_4$) δ 8.61 (s, 1H), 8.19 (d, J=5.5 Hz, 1H), 7.87 (q, J=9.3 Hz, 2H), 7.61 (s, 1H), 7.14 (d, J=5.1 Hz, 1H), 3.40 (s, 3H), 2.75-2.66 (m, 2H), 2.06 (p, J=6.3, 5.7 Hz, 2H), 1.89-1.80 (m, 2H); $^{13}$C NMR (126 MHz, MeOD) δ 151.51, 148.69, 143.14, 142.97, 142.52, 136.07, 135.88, 132.62, 128.15, 126.03, 122.42, 117.52, 116.46, 116.07, 113.67, 29.52, 28.07, 22.18, 21.86; HRMS (ESI) m/z calcd for $C_{21}H_{17}ClN_5$ [M+H]$^+$ 374.1172, found 374.1176.

7-(1H-Pyrrolo[2,3-b]pyridin-3-yl)-8,9,10,11-tetra-hydro-3H-pyrrolo[3,2-a]phenanthridine

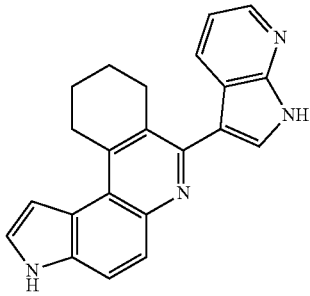

HSD-02-1273

Method A: Off-white solid (142 mg, 42%). $^1$H NMR (500 MHz, DMSO-d$_6$) δ 11.92 (s, 1H), 11.72 (s, 1H), 8.57 (dd, J=7.9, 1.7 Hz, 1H), 8.27 (dd, J=4.7, 1.7 Hz, 1H), 7.90 (s, 1H), 7.77 (d, J=8.8 Hz, 1H), 7.68 (d, J=8.9 Hz, 1H), 7.47 (t, J=2.4 Hz, 1H), 7.18-7.12 (m, 1H), 7.11 (d, J=3.0 Hz, 1H), 3.40 (t, J=6.5 Hz, 2H), 3.05 (t, J=6.1 Hz, 2H), 2.05-1.97 (m, 2H), 1.81 (ddt, J=9.3, 6.3, 2.8 Hz, 2H); $^{13}$C NMR (126 MHz, DMSO) δ 150.58, 148.89, 143.52, 143.39, 142.01, 133.07, 130.54, 127.92, 127.10, 124.02, 123.76, 121.43, 120.44, 120.16, 116.48, 116.27, 114.39, 106.19, 30.22, 28.95, 22.89, 22.82; HRMS (ESI) m/z calcd for $C_{22}H_9N_4$ [M+H]$^+$ 339.1610, found 339.1615.

7-(5H-Pyrrolo[3,2-d]pyrimidin-7-yl)-8,9,10,11-tetra-hydro-3H-pyrazolo[4,3-a]phenanthridine

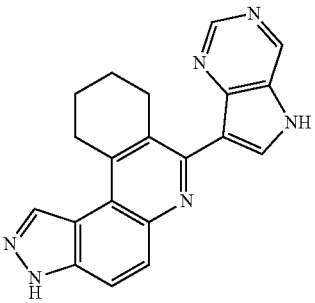

HSD-02-1274

Method A: Off-white solid (171 mg, 50%). $^1$H NMR (500 MHz, DMSO-d$_6$) δ 9.72 (s, 1H), 8.83 (s, 1H), 8.55 (s, 1H), 8.07 (s, 1H), 7.93 (d, J=9.2 Hz, 1H), 7.89-7.83 (m, 1H), 3.39-3.33 (m, 2H), 3.11 (t, J=6.1 Hz, 2H), 2.08-2.01 (m, 2H), 1.91-1.81 (m, 2H); $^{13}$C NMR (126 MHz, DMSO) δ 151.93, 151.87, 150.53, 143.67, 142.83, 142.42, 138.64, 136.29, 129.63, 129.46, 128.35, 120.83, 118.56, 116.50, 114.42, 29.99, 28.80, 22.74, 22.53; HRMS (ESI) m/z calcd for $C_{20}H_{17}N_6$ [M+H]$^+$ 341.1515, found 341.1517.

7-(6-Chloro-1H-pyrrolo[2,3-b]pyridin-3-yl)-8,9,10,11-tetrahydro-3H-pyrazolo[4,3-a]phenanthridine

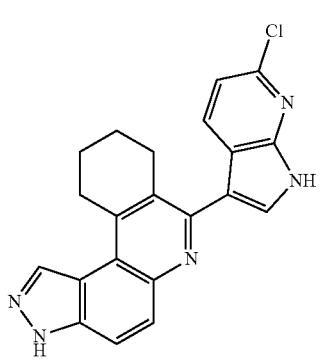

HSD-02-1275

Method A: un-white solid (183 mg, 49%). $^1$H NMR (500 MHz, DMSO-d$_6$) δ 11.82 (s, 1H), 9.50 (d, J=1.1 Hz, 1H), 8.55 (s, 1H), 8.23 (d, J=5.6 Hz, 1H), 7.96-7.78 (m, 3H), 7.44 (dd, J=5.6, 1.1 Hz, 1H), 3.35 (s, 2H), 3.07 (t, J=6.1 Hz, 2H), 2.04 (tdd, J=9.2, 5.5, 2.2 Hz, 2H), 1.84 (qd, J=8.8, 7.3, 4.1 Hz, 2H); $^{13}$C NMR (126 MHz, DMSO) δ 151.36, 145.39, 143.74, 142.15, 140.92, 139.90, 138.58, 136.23, 129.62, 128.04, 127.85, 124.65, 120.72, 116.59, 115.20, 114.23, 107.27, 29.96, 28.95, 22.80, 22.62; HRMS (ESI) m/z calcd for C$_{21}$H$_{17}$ClN$_5$ [M+H]$^+$ 374.1172, found 374.1178.

7-(1H-Pyrrolo[3,2-b]pyridin-3-yl)-8,9,10,11-tetrahydro-3H-pyrazolo[4,3-a]phenanthridine

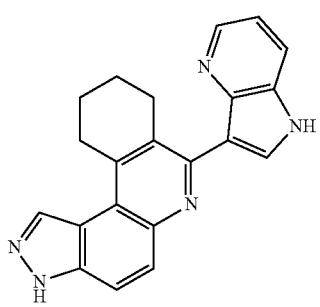

HSD-02-1276

Method A: Off-white solid (153 mg, 45%). $^1$H NMR (500 MHz, DMSO-d$_6$) δ 11.60 (d, J=3.1 Hz, 1H), 8.56 (s, 1H), 8.32 (dq, J=4.3, 1.8 Hz, 1H), 7.88-7.77 (m, 4H), 7.17-7.10 (m, 1H), 3.38-3.33 (m, 2H), 2.94 (t, J=6.1 Hz, 2H), 2.03-1.93 (m, 2H), 1.77-1.65 (m, 2H); $^{13}$C NMR (126 MHz, DMSO) δ 152.37, 144.53, 143.65, 142.86, 141.35, 138.56, 136.22, 131.63, 129.70, 129.50, 128.91, 121.53, 119.42, 117.39, 116.76, 116.64, 113.84, 29.65, 27.96, 22.77, 22.43; HRMS (ESI) adz calcd for C$_{21}$H$_{18}$N$_5$ [M+H]$^+$ 340.1562, found 340.1567.

4-(8,9,10,11-Tetrahydro-3H-pyrazolo[4,3-a]phenanthridin-7-yl)benzenesulfonamide

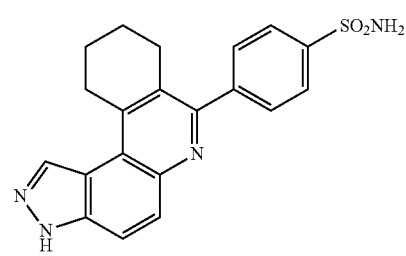

HSD-02-1279

Method A: Off-white solid (197 mg, 52%). $^1$H NMR (500 MHz, DMSO-d$_6$) δ 8.59 (s, 1H), 7.93 (d, J=8.4 Hz, 2H), 7.87 (dd, J=9.1, 0.9 Hz, 1H), 7.80 (d, J=9.1 Hz, 1H), 7.75 (d, J=8.5 Hz, 2H), 3.32 (t, J=6.5 Hz, 2H), 2.76 (t, J=6.1 Hz, 2H), 2.03-1.95 (m, 2H), 1.78-1.69 (m, 2H); $^{13}$C NMR (126 MHz, DMSO) δ 155.52, 144.57, 143.84, 143.78, 142.71, 139.77, 135.26, 130.10, 129.57, 129.20, 125.83, 122.19, 116.19, 115.57, 31.16, 29.66, 28.81, 22.54, 22.43; HRMS (ESI) m/z calcd for C$_{20}$H$_{19}$N$_4$O$_2$S [M+H]$^+$ 379.1229, found 379.1234.

4-(8,9,10,11-Tetrahydro-3H-pyrrolo[3,2-a]phenanthridin-7-yl)benzenesulfonamide

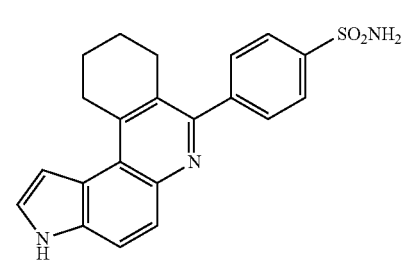

HSD-02-1280

Method A: Off-white solid (162 mg, 43%). $^1$H NMR (500 MHz, DMSO-d$_6$) δ 11.80 (s, 1H), 7.91 (d, J=8.4 Hz, 2H), 7.80 (d, J=8.9 Hz, 1H), 7.73 (d, J=8.4 Hz, 2H), 7.63 (d, J=8.8 Hz, 1H), 7.51 (d, J=3.1 Hz, 1H), 7.39 (s, 2H), 7.14 (d, J=3.1 Hz, 1H), 3.40 (t, J=6.5 Hz, 2H), 2.75 (t, J=6.2 Hz, 2H), 2.03-1.97 (m, 2H), 1.74 (qd, J=8.8, 7.3, 4.2 Hz, 2H); $^{13}$C NMR (126 MHz, DMSO) δ 154.57, 145.05, 143.70, 143.40, 142.65, 133.35, 130.06, 127.32, 125.76, 124.09, 122.72, 120.30, 116.75, 106.36, 29.96, 28.94, 22.81, 22.46; HRMS (ESI) m/z calcd for C$_{21}$H$_{20}$N$_3$O$_2$S [M+H]$^+$ 378.1276, found 378.1279.

7-(1H-Pyrrolo[2,3-b]pyridin-5-yl)-8,9,10,11-tetrahydro-3H-pyrazolo[4,3-a]phenanthridine

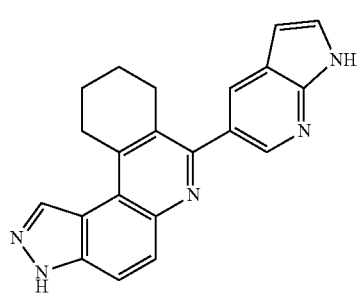

HSD-02-1282

Method A: Off-white solid (143 mg, 42%). $^1$H NMR (500 MHz, DMSO-$d_6$) δ 11.76 (d, J=2.2 Hz, 1H), 8.56 (s, 1H), 8.41 (d, J=2.1 Hz, 1H), 8.15 (d, J=2.0 Hz, 1H), 7.85 (s, 2H), 7.53 (dd, J=3.4, 2.5 Hz, 1H), 6.51 (dd, J=3.4, 1.8 Hz, 1H), 3.33-3.29 (m, 2H), 2.83 (t, J=6.1 Hz, 2H), 2.04-1.95 (m, 2H), 1.79-1.68 (m, 2H); $^{13}$C NMR (126 MHz, DMSO) δ 155.77, 148.32, 143.79, 142.36, 138.66, 136.36, 129.95, 129.71, 129.03, 128.96, 127.21, 121.73, 119.22, 116.50, 114.34, 100.67, 29.73, 29.23, 22.62; HRMS (ESI) m/z calcd for $C_{21}H_{18}N_5$ [M+H]$^+$ 340.1562, found 340.1565.

7-(1-Methyl-1H-indazol-5-yl)-8,9,10,11-tetrahydro-3H-pyrazolo[4,3-a]phenanthridine

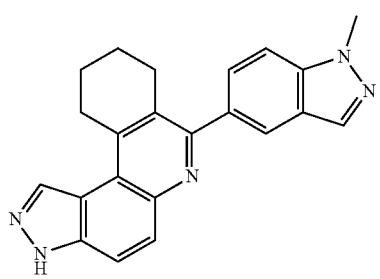

HSD1286

Method A: Off-white solid (164 mg, 46%). $^1$H NMR (500 MHz, Methanol-$d_4$) δ 9.13 (s, 1H), 8.84 (s, 1H), 8.26 (d, J=9.2 Hz, 1H), 8.21 (s, 1H), 8.13-8.06 (m, 2H), 7.89 (dd, J=8.5, 1.4 Hz, 1H), 3.63 (t, J=6.4 Hz, 2H), 2.91 (t, J=6.1 Hz, 2H), 2.32-2.11 (m, 2H), 2.05-1.81 (m, 2H); $^{13}$C NMR (126 MHz, MeOD) δ 153.92, 150.61, 144.58, 135.63, 135.49, 134.39, 132.24, 129.30, 126.03, 123.77, 119.99, 117.90, 114.89, 112.48, 31.75, 30.86, 27.89, 21.33, 21.22; HRMS (ESI) m/z calcd for $C_{22}H_{20}N_5$ [M+H]$^+$ 354.1719, found 354.1721.

9-Methyl-7-(3-(trifluoromethyl)-1H-pyrazol-4-yl)-8,9,10,11-tetrahydro-3H-pyrazolo[4,3-a]phenanthridine

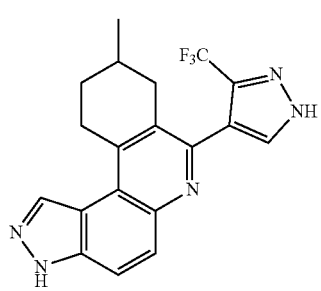

HSD1287

Method A: Off-white solid (178 mg, 48%). $^1$H NMR (500 MHz, Methanol-$d_4$) δ 8.60 (s, 1H), 7.97 (d, J=1.1 Hz, 1H), 7.86 (s, 2H), 3.56-3.48 (m, 1H), 3.39-3.32 (m, 2H), 2.77-2.70 (m, 1H), 2.38-2.28 (m, 1H), 2.27-2.18 (m, 1H), 1.97-1.85 (m, 1H), 1.66-1.53 (m, 1H), 1.09 (d, J=6.5 Hz, 3H); $^{13}$C NMR (126 MHz, MeOD) δ 148.72, 143.06, 142.82, 139.74 (J=28.98 Hz) 134.66, 131.35, 131.12, 131.01, 128.37, 123.01, 122.23, 120.84 (J=269.64 Hz), 115.93, 114.67, 36.13, 30.14, 29.44, 28.15, 20.47; HRMS (ESI) m/z calcd for $C_{18}H_{18}N_5$ [M+H]$^+$ 304.1562, found 304.1565.

7-(3-(Trifluoromethyl)-1H-pyrazol-4-yl)-3,8,9,10-tetrahydrocyclopenta[c]pyrazolo[4,3-f]quinoline

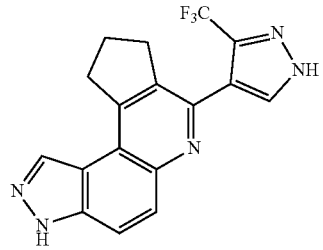

HSD1288

Method A: Off-white solid (185 mg, 54%). $^1$H NMR (500 MHz, MeOD) δ 8.76 (s, 1H), 8.44 (s, 1H), 8.33 (d, J=9.3 Hz, 1H), 8.05 (d, J=9.3 Hz, 1H), 3.86 (t, J=7.7 Hz, 2H), 3.21 (t, J=7.7 Hz, 2H), 2.57-2.53 (m, 2H); $^{13}$C NMR (126 MHz, MeOD) δ 160.67, 141.10, 140.00, 138.86, 136.50, 133.37, 132.59, 122.324 J=269.64 Hz), 121.78, 121.15, 118.59, 115.19, 110.20, 35.03, 30.90, 23.82; HRMS (ESI) m/z calcd for $C_{17}H_{13}F_3N_5$ [M+H]$^+$ 334.1123, found 334.1121.

7-(3-(Trifluoromethyl)-1H-pyrazol-4-yl)-3,8,9,10,11,12-hexahydrocyclohepta[c]pyrazolo[4,3-f]quinoline

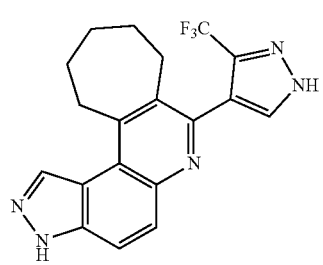

HSD1289

Method A: Off-white solid (185 mg, 50%). $^1$H NMR (500 MHz, Methanol-$d_4$) δ 8.98-8.87 (m, 1H), 8.37-8.27 (m, 2H), 7.99 (d, J=9.2 Hz, 1H), 3.86 (d, J=5.3 Hz, 2H), 3.17-3.04 (m, 2H), 2.05 (p, J=2.7 Hz, 4H), 1.78-1.65 (m, 2H); $^{13}$C NMR (126 MHz, MeOD) δ 160.75, 140.27, 136.43, 133.66, 132.53, 123.83, 122.46, 122.13, 121.07, 120.17 (q, J=269.64 Hz), 118.79, 114.94, 114.65, 110.56, 110.56, 32.30, 30.64, 29.52, 25.85, 23.75; HRMS (EST) m/z calcd for $C_{19}H_{17}F_3N_5$ [M+H]$^+$ 372.1436, found 372.1438.

7-(3-(Trifluoromethyl)-1H-pyrazol-4-yl)-8,9-dihydro-3H-cyclobuta[c]pyrazolo[4,3-f]quinolone

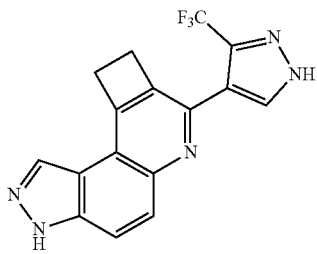

HSD1290

Method A: Off-white solid (49 mg, 15%). $^1$H NMR (500 MHz, MeOD) δ 8.69 (d, J=0.9 Hz, 1H), 8.53 (d, J=0.9 Hz, 1H), 8.32 (dd, J=9.4, 1.0 Hz, 1H), 8.11 (d, J=9.4 Hz, 1H), 4.01-3.93 (m, 2H), 3.72 (t, J=4.0 Hz, 2H). $^{13}$C NMR (126 MHz, MeOD) δ 161.67, 140.75, 139.64, 137.73, 136.67, 133.55, 133.12, 122.29 (q, J=268.38 Hz), 121.46, 119.65, 119.42, 113.74, 108.80, 30.70, 29.72; HRMS (ESI) m/z calcd for $C_{16}H_{11}F_3N_5$ [M+H]$^+$ 330.0967, found 330.0970.

9-Methyl-7-(3-(trifluoromethyl)-1H-pyrazol-4-yl)-3H-pyrazolo[4,3-f]quinoline

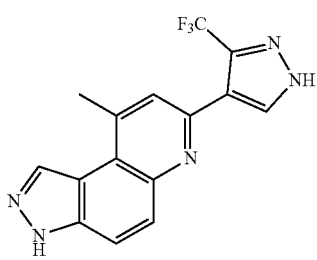

HSD1291

Method A: Off-white solid (136 mg, 43%). $^1$H NMR (500 MHz, MeOD) δ 8.51 (s, 1H), 8.29-8.21 (m, 1H), 7.91-7.81 (m, 2H), 7.62 (s, 1H), 2.89 (s, 3H); $^{13}$C NMR (126 MHz, MeOD) δ 147.45, 145.74, 144.37, 139.03, 138.40, 135.27, 130.97, 128.87, 125.13 (J=269.64 Hz), 122.50, 121.51, 120.86, 116.35, 114.74, 21.45; HRMS (ESI) m/z calcd for $C_{15}H_{11}F_3N_5$ [M+H]$^+$ 318.0967, found 318.0971.

7-(1H-1,2,3-Triazol-4-yl)-8,9,10,11-tetrahydro-3H-pyrazolo[4,3-a]phenanthridine

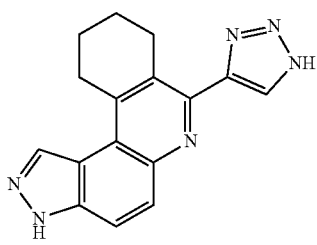

HSD1292

Method A: Off-white solid (159 mg, 55%). $^1$H NMR (500 MHz, DMSO-d$_6$) 8.57 (s, 1H), 8.31 (d, J=1.9 Hz, 1H), 7.87 (d, J=9.2 Hz, 1H), 7.82 (dd, J=9.1, 1.9 Hz, 1H), 3.30 (d, J=6.6 Hz, 2H), 3.12 (d, J=6.4 Hz, 2H), 2.05-1.94 (m, 2H), 1.84 (dtd, J=10.1, 6.9, 6.3, 3.3 Hz, 2H); $^{13}$C NMR (126 MHz, DMSO) δ 146.46, 143.65, 142.93, 131.52, 129.80, 129.48, 122.18, 116.16, 115.49, 29.87, 28.27, 22.37; HRMS (ESI) m/z calcd for $C_{16}H_{15}N_6$ [M+H]$^+$ 291.1358, found 291.1360.

Methyl 3-(8,9,10,11-tetrahydro-3H-pyrazolo[4,3-a]phenanthridin-7-yl)-1H-pyrrole-2-carboxylate

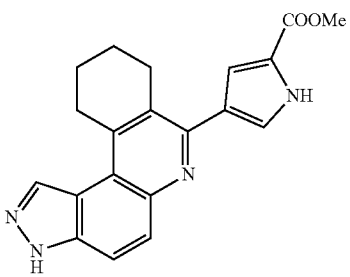

HSD1293

Method A: Off-white solid (142 mg, 41%). $^1$H NMR (500 MHz, DMSO-d$_6$) δ 12.20 (s, 1H), 8.50 (s, 1H), 7.52 (s, 1H), 7.34 (s, 1H), 3.80 (s, 3H), 3.32-3.24 (m, 2H), 3.01 (t, J=6.1 Hz, 2H), 2.03-1.91 (m, 2H), 1.88-1.74 (m, 2H); $^{13}$C NMR (126 MHz, DMSO) δ 161.40, 150.78, 143.78, 142.06, 138.38, 136.17, 136.16, 129.69, 129.00, 125.75, 125.46, 122.08, 121.04, 116.53, 114.14, 51.67, 29.86, 28.94, 22.68, 22.50; HRMS (ESI) m/z calcd for $C_{20}H_{19}N_4O_2$ [M+H]$^+$ 347.1508, found 347.1513.

2-(4-(8,9,10,11-Tetrahydro-3H-pyrazolo[4,3-a]phenanthridin-7-yl)-1H-pyrazol-1-yl)ethan-1-ol

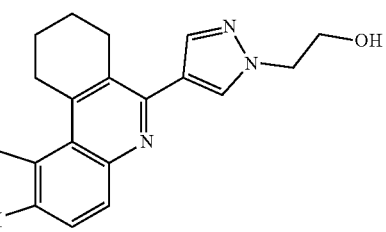

HSD1294

Method A: Off-white solid (126 mg, 38%). $^1$H NMR (500 MHz, Methanol-d$_4$) δ 8.51 (s, 1H), 8.12 (s, 1H), 7.99 (s, 1H), 7.87 (d, J=9.2 Hz, 1H), 7.79 (d, J=9.0 Hz, 1H), 4.34 (t, J=5.4 Hz, 2H), 3.97 (t, J=5.4 Hz, 2H), 3.35-3.32 (m, 2H), 3.00 (t, J=6.2 Hz, 2H), 2.10-2.03 (m, 2H), 1.95-1.86 (m, 2H). $^{13}$C NMR (126 MHz, MeOD) δ 149.36, 143.28, 143.07, 139.58, 138.49, 135.72, 131.37, 129.45, 128.70, 121.71, 121.43, 116.16, 113.49, 60.48, 54.17, 29.73, 28.38, 22.12, 22.03; HRMS (ESI) m/z calcd for $C_{19}H_{20}N_5O$ [M+H]$^+$ 334.1668, found 334.1675.

7-(1,3-Dimethyl-1H-pyrazol-4-yl)-8,9,10,11-tetrahydro-3H-pyrazolo[4,3-a]phenanthridine

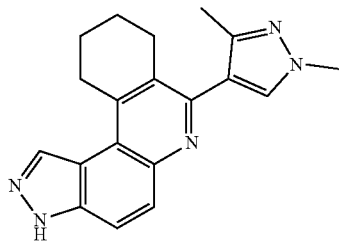

HSD1295

Method A: Off-white solid (180 mg, 57%). $^1$H NMR (500 MHz, DMSO-d$_6$) δ 8.53 (s, 1H), 7.92 (s, 1H), 7.81 (d, J=9.0 Hz, 1H), 7.76 (d, J=9.1 Hz, 1H), 3.82 (s, 3H), 3.27 (t, J=6.5 Hz, 3H), 2.81 (t, J=6.2 Hz, 2H), 2.26 (s, 3H), 2.01-1.88 (m, 2H), 1.82-1.67 (m, 2H); $^{13}$C NMR (126 MHz, DMSO) δ 150.70, 147.24, 143.71, 141.82, 139.32, 135.07, 131.72, 129.87, 129.57, 121.05, 118.85, 116.35, 114.88, 38.70, 29.70, 28.60, 22.60, 13.53; HRMS (ESI) m/z calcd for C$_{19}$H$_{20}$N$_5$ [M+H]$^+$ 318.1719, found 318.1725.

7-(1H-Imidazol-4-yl)-8,9,10,11-tetrahydro-3H-pyrazolo[4,3-a]phenanthridine

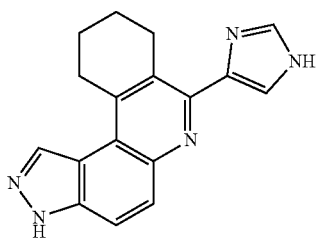

HSD1296

Method A: Off-white solid (168 mg, 58%). $^1$H NMR (500 MHz, DMSO-d$_6$) δ 8.62-8.53 (m, 2H), 7.93-7.82 (m, 3H), 3.36-3.23 (m, 2H), 3.09-2.97 (m, 2H), 2.02-1.94 (m, 2H), 1.90-1.78 (m, 2H); $^{13}$C NMR (126 MHz, DMSO) δ 144.79, 143.75, 142.88, 138.70, 136.05, 132.80, 131.40, 129.06, 128.65, 122.65, 121.92, 116.12, 115.25, 29.94, 27.98, 22.22; HRMS (ESI) m/z calcd for C$_{17}$H$_6$N$_5$ [M+H]$^+$ 290.1406, found 290.1415.

1-Iodo-7-(3-(trifluoromethyl)-1H-pyrazol-4-yl)-8,9,10,11-tetrahydro-3H-pyrazolo[4,3-a]phenanthridine

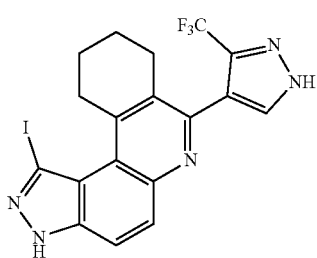

HSD1297

Method A: Off-white solid (145 mg, 30%). $^1$H NMR (500 MHz, Methanol-d$_4$) δ 8.90 (s, 1H), 8.35 (s, 1H), 8.33 (d, J=9.1 Hz, 1H), 8.00 (d, J=9.2 Hz, 1H), 3.67 (t, J=6.4 Hz, 2H), 2.81 (t, J=6.2 Hz, 2H), 2.18 (qd, J=7.8, 6.3, 4.5 Hz, 2H), 2.04-1.90 (m, 2H); $^{13}$C NMR (126 MHz, MeOD) δ 154.90, 142.03, 140.54, 139.83, 134.96, 134.44, 134.02, 132.40, 124.40, 122.30 (J=269.64 Hz), 121.60, 118.81, 114.76, 109.91, 30.80, 27.22, 21.20, 20.87; HRMS (ESI) m/z calcd for C$_{17}$H$_{16}$N$_5$ [M+H]$^+$ 484.0246, found 484.0252.

7-(3-Phenyl-1H-pyrazol-4-yl)-8,9,10,11-tetrahydro-3H-pyrazolo[4,3-a]phenanthridine

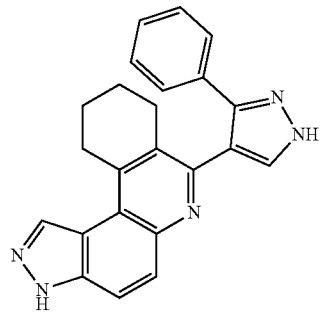

HSD1303

Method A: Off-white solid (168 mg, 45%). $^1$H NMR (500 MHz, DMSO-d$_6$) δ 8.81 (s, 1H), 8.27 (d, J=9.1 Hz, 2H), 8.17 (d, J=9.2 Hz, 1H), 7.35-7.22 (m, 5H), 3.51-3.43 (m, 2H), 2.55-2.49 (m, OH), 1.95-1.82 (m, 2H), 1.72-1.61 (m, 2H); $^{13}$C NMR (126 MHz, DMSO) δ 145.52, 135.52, 132.94, 129.41, 128.96, 128.85, 128.19, 126.99, 123.39, 120.03, 114.91, 109.66, 30.80, 27.32, 21.75, 21.27; HRMS (ESI) adz calcd for C23H20N5 [M+H]$^+$ 366.1719, found 366.1726.

7-(3-(Trifluoromethyl)-1H-pyrazol-4-yl)-8,9,10,11-tetrahydro-3H-pyrazolo[4,3-a]phenanthridin-9-amine

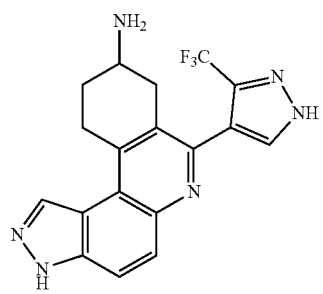

HSD1304

Method A: Off-white solid (137 mg, 37%). $^1$H NMR (500 MHz, Methanol-d$_4$) δ 8.57 (d, J=7.7 Hz, 1H), 8.03-8.00 (m, 1H), 7.87-7.83 (m, 2H), 3.92-3.82 (m, 1H), 3.65-3.53 (m, 1H), 3.49-3.38 (m, 1H), 2.81-2.65 (m, 2H), 2.25-2.17 (m, 1H), 2.08-1.96 (m, 1H); $^{13}$C NMR (126 MHz, MeOD) δ 148.28, 143.27, 142.44, 142.22, 139.73, 134.64, 130.59, 129.31, 128.37, 122.83 (q, J=269.64 Hz), 122.00, 118.74, 115.86, 115.82, 114.97, 46.06, 36.25, 30.30, 28.58; HRMS (ESI) m/z calcd for C$_{18}$H$_{16}$F$_3$N$_6$ [M+H]$^+$ 373.1389, found 373.1393.

251

3-Methyl-3-(4-(8,9,10,11-tetrahydro-3H-pyrazolo[4,3-a]phenanthridin-7-yl)-1H-pyrazol-1-yl)tetrahydrothiophene 1,1-dioxide

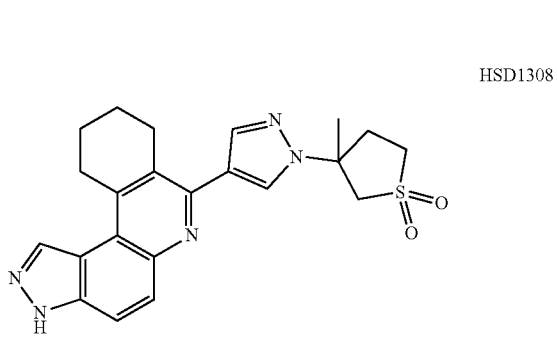 [SMILES: CC1(n2cc(-c3nc4ccc5[nH]ncc5c4c4c3CCCC4)cn2)CCS(=O)(=O)C1]

HSD1308

Method A: Off-white solid (126 mg, 30%). $^1$H NMR (500 MHz, DMSO-$d_6$) δ 8.54-8.48 (m, 1H), 8.47 (s, 1H), 8.08 (s, 1H), 7.81 (s, 2H), 4.22 (dd, J=14.1, 1.7 Hz, 1H), 3.59 (d, J=14.1 Hz, 1H), 3.42 (ddd, J=12.7, 7.7, 4.6 Hz, 1H), 3.29 (d, J=6.5 Hz, 2H), 3.19 (ddd, J=13.1, 9.6, 7.5 Hz, 1H), 3.15-3.07 (m, 1H), 2.55 (ddd, J=13.9, 9.6, 7.7 Hz, 1H), 1.98 (ddt, J=12.1, 6.1, 3.3 Hz, 2H), 1.84 (qd, J=9.1, 7.4, 4.0 Hz, 2H), 1.75 (s, 3H); $^{13}$C NMR (126 MHz, DMSO) δ 149.12, 143.66, 142.26, 140.19, 138.52, 136.20, 129.53, 129.02, 128.80, 123.04, 121.18, 116.52, 114.29, 65.32, 61.46, 51.53, 35.09, 29.87, 28.53, 27.91, 22.63, 22.50.

7-(3-(Pyridin-3-yl)-1H-pyrazol-4-yl)-8,9,10,11-tetrahydro-3H-pyrazolo[4,3-a]phenanthridine

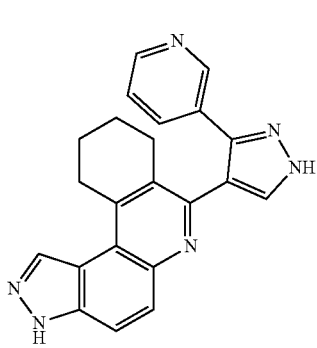

HSD1310

Method A: Off-white solid (172 mg, 47%). $^1$H NMR (500 MHz, DMSO-$d_6$) δ 8.56 (d, J=1.0 Hz, 1H), 8.49 (dd, J=2.2, 0.9 Hz, 1H), 8.36 (dd, J=4.7, 1.7 Hz, 1H), 7.98 (s, 1H), 7.83 (dd, J=9.0, 0.9 Hz, 1H), 7.72 (d, J=8.0, 2.3, 1.7 Hz, 1H), 7.68 (d, J=9.0 Hz, 1H), 7.25 (ddd, J=8.0, 4.8, 0.9 Hz, 1H), 3.29 (t, J=6.5 Hz, 2H), 2.58 (t, J=6.2 Hz, 2H), 1.89 (ddt, J=9.2, 6.4, 4.2 Hz, 2H), 1.73-1.64 (m, 2H); $^{13}$C NMR (126 MHz, DMSO) δ 150.81, 148.62, 147.71, 143.91, 143.51, 142.22, 140.11, 135.03, 134.04, 133.41, 130.51, 129.58, 129.11, 123.91, 121.95, 119.13, 116.29, 115.55, 29.57, 28.27, 22.59, 22.35; HRMS (ESI) m/z calcd for $C_{22}H_{19}N_6$ [M+H]$^+$ 367.1671, found 367.1675.

252

7-(1-Phenyl-1H-pyrazol-4-yl)-8,9,10,11-tetrahydro-3H-pyrazolo[4,3-a]phenanthridine

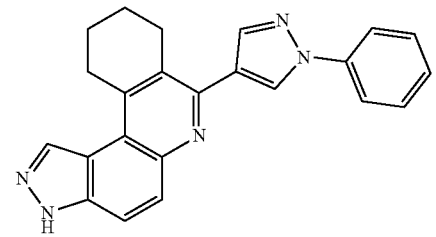

HSD1311

Method A: Off-white solid (186 mg, 51%). $^1$H NMR (500 MHz, DMSO-$d_6$) δ 8.55 (s, 1H), 7.95 (s, 1H), 7.88-7.73 (m, 2H), 7.37-7.23 (m, 1H), 6.79 (s, 1H), 6.63 (s, 1H), 3.31 (t, J=6.4 Hz, 2H), 2.58 (t, J=6.1 Hz, 2H), 1.94-1.85 (m, 2H), 1.74-1.65 (m, 2H); $^{13}$C NMR (126 MHz, DMSO) δ 150.93, 143.68, 142.18, 138.73, 136.97, 136.67, 136.31, 131.22, 130.28, 129.55, 127.67, 125.20, 123.94, 122.00, 118.02, 116.54, 114.31, 29.56, 28.10, 22.55, 22.32; HRMS (ESI) m/z calcd for $C_{23}H_{20}N_5$ [M+H]$^+$ 366.1719, found 366.1720.

7-(3-(Thiophen-3-yl)-1H-pyrazol-4-yl)-8,9,10,11-tetrahydro-3H-pyrazolo[4,3-a]phenanthridine

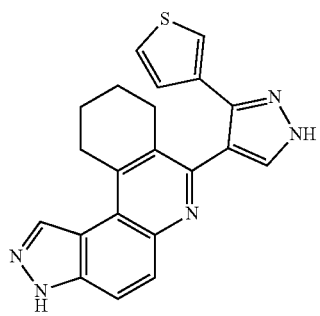

HSD1312

Method A: Off-white solid (177 mg, 46%). $^1$H NMR (500 MHz, DMSO-$d_6$) δ 8.89 (d, J=1.8 Hz, 1H), 8.55 (s, 1H), 8.29 (d, J=1.7 Hz, 1H), 7.95 (d, J=8.2 Hz, 2H), 7.83 (s, 2H), 7.57-7.46 (m, 2H), 7.39-7.28 (m, 1H), 3.29 (d, J=6.5 Hz, 2H), 3.07 (t, J=6.2 Hz, 2H), 2.03-1.94 (m, 2H), 1.86 (tt, J=9.6, 5.4 Hz, 2H); $^{13}$C NMR (126 MHz, DMSO) δ 148.63, 143.82, 142.45, 142.18, 141.18, 140.01, 139.07, 130.03, 129.57, 129.19, 127.95, 126.90, 124.53, 121.44, 119.01, 118.46, 116.29, 29.86, 28.53, 22.57, 22.45; HRMS (ESI) m/z calcd for $C_{21}H_{18}N_5S$ [M+H]$^+$ 372.1283, found 372.1286.

7-(3-(tert-Butyl)-1H-pyrazol-4-yl)-8,9,10,11-tetra-hydro-3H-pyrazolo[4,3-a]phenanthridine

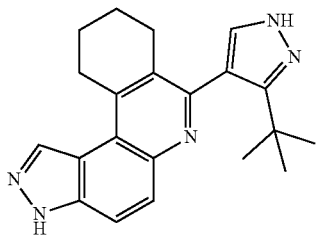

HSD1313

Method A: Off-white solid (176 mg, 51%). $^1$H NMR (500 MHz, MeOD) 8.55 (s, 1H), 7.88-7.79 (m, 2H), 7.53 (s, 1H), 3.37-3.31 (m, 2H), 2.67 (t, J=6.2 Hz, 2H), 2.08-1.97 (m, 2H), 1.90-1.81 (m, 2H); $^{13}$C NMR (126 MHz, MeOD) δ 152.31, 143.08, 142.67, 138.68, 135.79, 131.90, 128.29, 122.19, 116.70, 116.13, 113.68, 32.29, 32.24, 29.44, 29.30, 28.47, 22.15, 21.89; HRMS (ESI) m/z calcd for $C_{21}H_{24}N_5$ [M H]$^+$ 346.2032, found 346.2021.

4-(8,9,10,11-Tetrahydro-3H-pyrazolo[4,3-a]phenanthridin-7-yl)-1H-pyrazole-3-carboxylic Acid

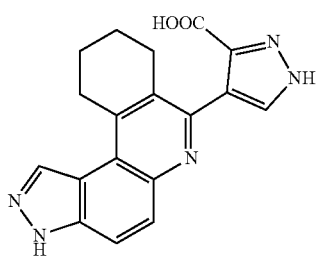

HSD1314

Method A: Off-white solid (167 mg, 50%). $^1$H NMR (500 MHz, DMSO-$d_6$) δ 8.62 (s, 1H), 8.25 (s, 1H), 7.99 (d, J=9.1 Hz, 1H), 7.76 (d, J=9.4 Hz, 1H), 3.30 (t, J=6.5 Hz, 2H), 2.93-2.78 (m, 2H), 2.03-1.91 (m, 2H), 1.83-1.74 (m, 2H); $^{13}$C NMR (126 MHz, DMSO) δ 162.03, 148.76, 145.57, 139.73, 137.07, 136.25, 131.58, 128.69, 123.61, 122.18, 121.89, 116.71, 115.13, 30.40, 28.34, 21.77. HRMS (ESI) m/z calcd for $C_{18}H_{16}N_5O_2$ [M+H]$^+$ 334.1304, found 334.1308.

7-(1-(2-Chloroethyl)-1H-pyrazol-4-yl)-8,9,10,11-tetrahydro-3H-pyrazolo[4,3-a]phenanthridine

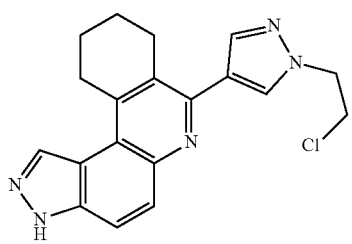

HSH124

Method A: Off-white solid Yield: (26 mg, 28%) $^1$H NMR (500 MHz, Methanol-$d_4$) δ 8.83 (s, 1H), 8.55 (d, J=0.8 Hz, 1H), 8.29-8.20 (m, 2H), 8.12 (d, J=9.2 Hz, 1H), 4.68 (t, J=5.6 Hz, 2H), 4.11-4.04 (m, 2H), 3.62 (t, J=6.4 Hz, 2H), 3.13 (t, J=6.2 Hz, 2H), 2.25-2.15 (m, 2H), 2.07-1.97 (m, 2H); $^{13}$C NMR (126 MHz, Methanol-$d_4$) δ 154.27, 143.82, 140.54, 134.63, 133.72, 131.88, 122.97, 118.99, 114.92, 112.57, 53.74, 42.44, 31.04, 27.80, 21.23.

2,3-Dimethyl-7-(3-(trifluoromethyl)-1H-pyrazol-4-yl)-3,6,8,9,10,11-hexahydro-2H-pyrazolo[3,4-a]phenanthridine

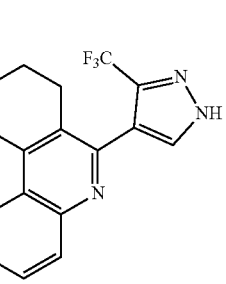

HSH127

Method A Off-white solid, Yield: (40 mg, 20%) $^1$H NMR (500 MHz, Methanol-$d_4$) δ 8.33 (s, 1H), 8.27 (d, J=9.0 Hz, 1H), 7.53 (d, J=9.0 Hz, 1H), 4.27 (s, 3H), 3.95 (t, J=6.4 Hz, 2H), 2.79-2.76 (m, 5H), 2.13-2.05 (m, 2H), 1.98-1.86 (m, 2H); $^{13}$C NMR (126 MHz, Methanol-4) δ 156.81, 142.12, 141.73, 138.79, 135.59, 132.97, 132.27, 129.07, 122.32 (q, J=268), 121.35, 119.06, 111.69, 110.05, 36.88, 31.69, 27.09, 21.21, 20.94, 8.19.

5-Fluoro-7-(3-(trifluoromethyl)-1H-pyrazol-4-yl)-8,9,10,11-tetrahydro-3H-pyrazolo[4,3-a]phenanthridine

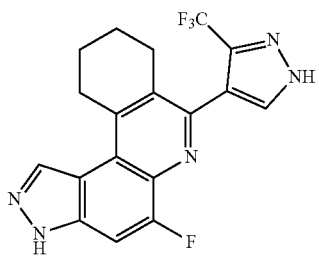

HSH156

Method A White solid, Yield: (94 mg, 25%) $^1$H NMR (500 MHz, DMSO-$d_6$) δ 8.60 (s, 1H), 8.25 (s, 1H), 7.69 (d, J=9.9 Hz, 1H), 3.29 (t, J=6.4 Hz, 2H), 2.71 (t, J=6.2 Hz, 2H), 1.95 (dt, J=12.3, 4.6 Hz, 2H), 1.87-1.71 (m, 2H); $^{13}$C NMR (126 MHz, DMSO-$d_6$) δ 158.10, 156.09, 148.56, 142.63, 134.68, 134.59, 131.84, 131.42, 123.43 (q, J=268), 122.90, 119.33, 112.71, 29.54, 28.19, 22.40, 22.13. HRMS (ESI) m/z calcd for $C_{18}H_{14}F_4N_5$[M+H]$^+$ 376.1185, found 376.1185.

7-(3-(Trifluoromethyl)-1H-pyrazol-4-yl)-8,9,10,11-tetrahydro-3H-pyrazolo[4,3-a]phenanthridin-5-ol

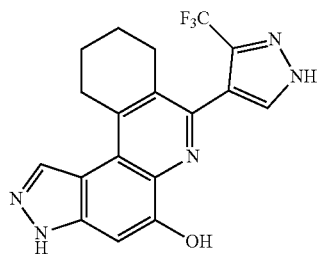

Method A Off-white solid, Yield: (21 mg, 11%) $^1$H NMR (500 MHz, Methanol-d$_4$) δ 9.05 (s, 1H), 8.35 (t, J=1.0 Hz, 1H), 8.19 (s, 1H), 3.63 (t, J=6.4 Hz, 2H), 2.79 (t, J=6.2 Hz, 2H), 2.24-2.14 (m, 2H), 2.06-1.90 (m, 2H); $^{13}$C NMR (126 MHz, Methanol-d$_4$) δ 154.95, 142.50, 139.83, 135.25, 134.31, 133.85, 132.44, 123.87, 122.28 (q, J=269.64), 120.97, 115.06, 109.89, 30.71, 27.27, 21.14, 20.80.

5-Bromo-7-(3-(trifluoromethyl)-1H-pyrazol-4-yl)-8,9,10,11-tetrahydro-3H-pyrazolo[4,3-a]phenanthridine

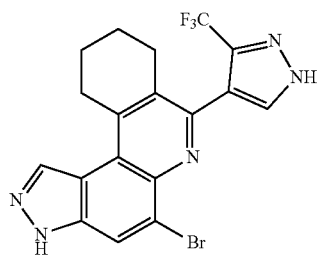

Method A Off-white solid, Yield: (10 mg, 2%) $^1$H NMR (500 MHz, DMSO-d$_6$) δ 8.61 (s, 1H), 8.29 (s, 2H), 3.32-3.28 (m, 2H), 2.75 (t, J=6.2 Hz, 2H), 1.96 (m, 2H), 1.78 (m, 2H); $^{13}$C NMR (126 MHz, DMSO-d$_6$) δ 148.91, 143.00, 139.74, 139.73, 139.70, 131.56, 131.54, 131.51, 124.67, 123.42, 122.68, 121.27 (q, J=270.9 Hz), 119.30, 55.37, 29.71, 28.24, 22.49, 22.17.

5-Chloro-7-(3-(trifluoromethyl)-1H-pyrazol-4-yl)-8,9,10,11-tetrahydro-3H-pyrazolo[4,3-a]phenanthridine

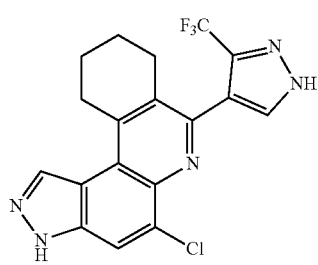

Method A Off-white solid, Yield: (12 mg, 5%) $^1$H NMR (500 MHz, DMSO-d$_6$) δ 8.62 (s, 1H), 8.29 (s, 1H), 8.09 (s, 1H), 3.31-3.26 (m, 2H), 2.75 (t, J=6.2 Hz, 2H), 2.06-1.87 (m, 2H), 1.82-1.67 (m, 2H); $^{13}$C NMR (126 MHz, DMSO-d$_6$) δ 148.69, 143.00, 139.26, 132.77, 131.55, 131.55, 129.57, 123.42 (q, J=269), 122.85, 119.37, 119.36, 115.32, 29.72, 28.23, 22.48, 22.16.

4-Methyl-7-(3-(trifluoromethyl)-1H-pyrazol-4-yl)-8,9,10,11-tetrahydro-3H-pyrazolo[4,3-a]phenanthridine

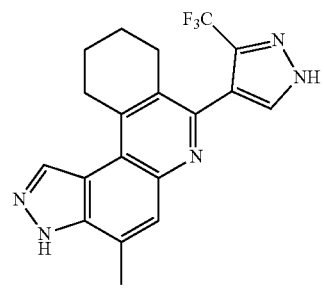

Method A Off-white solid, Yield: (20 mg, 5%). $^1$H NMR (500 MHz, DMSO-d$_6$) δ 8.55 (s, 1H), 8.20 (s, 1H), 7.56 (s, 1H), 3.32-3.30 (m, 2H), 2.68 (t, J=6.2 Hz, 2H), 2.63 (s, 3H), 1.96 (m, 2H), 1.77 (m, 2H); $^{13}$C NMR (126 MHz, DMSO-d$_6$) δ 148.32, 144.01, 141.68, 139.48, 136.72, 131.12, 129.51, 128.11, 124.44, 123.55 (q, J=269), 121.41, 119.83, 116.19, 29.44, 28.13, 22.61, 22.41, 17.46.

7-(3-(Trifluoromethyl)-1H-pyrazol-4-yl)-8,9,10,11-tetrahydro-3H-[1,2,3]triazolo[4,5-a]phenanthridine

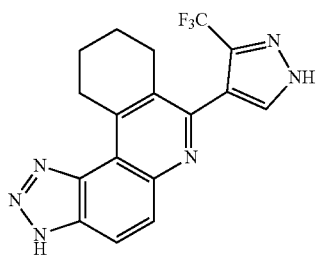

Method A Off-white solid, Yield: (72 mg, 20%). $^1$H NMR (500 MHz, Methanol-d$_4$) δ 8.40 (d, J=9.2 Hz, 1H), 8.33 (s, 1H), 8.05 (d, J=9.2 Hz, 1H), 4.01 (t, J=6.4 Hz, 2H), 2.82 (t, J=6.3 Hz, 2H), 2.13 (dp, J=9.3, 3.1 Hz, 2H), 2.02-1.93 (m, 2H); $^{13}$C NMR (126 MHz, MeOD) δ 154.39, 145.35, 140.07, 139.75, 138.56, 137.77, 134.33, 132.14, 122.37 (q, J=269.6 Hz), 121.20, 120.95, 116.39, 111.31, 30.87, 27.26, 21.12, 21.07; HRMS (ESI) m/z calcd for C$_{17}$H$_{14}$F$_3$N$_6$ [M+H]$^+$ 359.1232, found 359.1239.

7-(3-(Trifluoromethyl)-1H-pyrazol-4-yl)-8,9,10,11-tetrahydroisoxazolo[4,5-a]phenanthridine

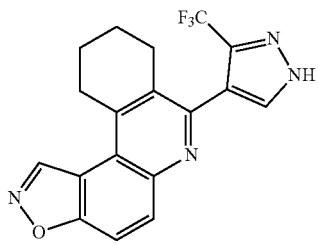

HSD1316

Method A: Off-white solid (126 mg, 35%). ¹H NMR (500 MHz, Methanol-d₄) δ 9.70-9.59 (m, 1H), 8.34-8.22 (m, 3H), 3.62 (t, J=6.4 Hz, 2H), 2.79 (t, J=6.3 Hz, 2H), 2.19-2.08 (m, 2H), 2.00-1.86 (m, 2H). HRMS (ESI) m/z calcd for C₁₈H₁₄F₃N₄O [M+H]⁺ 359.1120, found 359.1122.

7-(3-(Trifluoromethyl)-1H-pyrazol-4-yl)-8,9,10,11-tetrahydroisothiazolo[4,5-a]phenanthridine

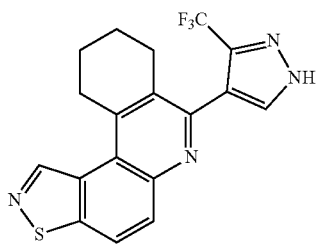

HSD1317

Method A: Off-white solid (120 mg, 32%). ¹H NMR (500 MHz, Methanol-d₄) δ 9.94 (s, 1H), 8.78 (d, J=8.9 Hz, 1H), 8.41 (s, 1H), 8.21 (d, J=8.9 Hz, 1H), 3.85 (t, J=6.1 Hz, 2H), 2.87 (t, J=6.1 Hz, 2H), 2.24-2.13 (m, 2H), 2.00 (td, J=11.2, 9.5, 5.6 Hz, 2H); ¹³C NMR (126 MHz, MeOD) δ156.17, 155.87, 155.79, 145.11, 140.04, 139.75, 136.42, 135.01, 132.65, 129.80, 125.95, 125.43, 121.58, 120.19, 118.46, 109.79, 32.51, 27.76, 21.37, 20.63; HRMS (ESI) m/z calcd for C₁₈H₁₄F₃N₄S [M+H]⁺ 375.0891, found 375.0899.

3-Methyl-7-(3-(trifluoromethyl)-1H-pyrazol-4-yl)-8,9,10,11-tetrahydro-3H-pyrazolo[4,3-a]phenanthridine

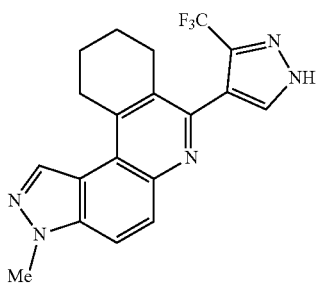

HSD1318

Method A: Off-white solid (148 mg, 40%). ¹H NMR (500 MHz, Methanol-d₄) δ 8.77 (d, J=0.9 Hz, 1H), 8.42 (dd, J=9.3, 0.9 Hz, 1H), 8.38 (d, J=0.9 Hz, 1H), 8.07 (d, J=9.3 Hz, 1H), 4.32 (s, 3H), 3.68 (t, J=6.3 Hz, 2H), 2.82 (t, J=6.2 Hz, 2H), 2.22-2.12 (m, 2H), 2.05-1.92 (m, 2H); ¹³C NMR (126 MHz, MeOD) δ 155.03, 142.35, 140.13 (q, J=37.8 Hz), 138.47, 135.21, 134.39, 134.19, 132.52, 124.04, 122.33 (q, J=269.6 Hz), 119.30, 118.65, 115.97, 109.85, 35.32, 30.84, 27.26, 21.19, 20.86; HRMS (ESI) m/z calcd for C₁₉H₁₇F₃N₅ [M+H]⁺ 372.1436, found 372.1438.

6-(5-Fluoro-8,9,10,11-tetrahydro-3H-pyrazolo[4,3-a]phenanthridin-7-yl)benzo[d]thiazol-2-amine

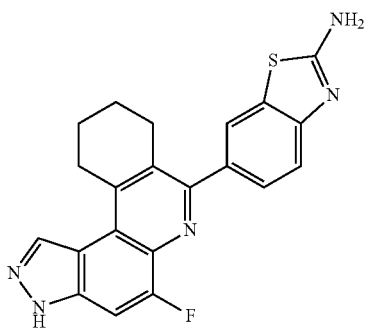

HSD1319

Method A: Off-white solid (148 mg, 38%). ¹H NMR (500 MHz, DMSO-d₆) δ 8.56 (s, 1H), 7.91-7.84 (m, 1H), 7.70 (d, J=9.8 Hz, 1H), 7.57 (d, J=2.4 Hz, 2H), 7.45-7.38 (m, 2H), 3.36-3.32 (m, 2H), 2.84 (t, J=6.1 Hz, 2H), 2.04-1.97 (m, 2H), 1.79-1.71 (m, 2H); ¹³C NMR (126 MHz, DMSO) δ 167.68, 158.36 (d, J=253.26 Hz), 157.08, 153.14, 142.83, 136.76, 136.49, 134.35, 133.64, 131.24, 131.14, 127.29, 122.53, 122.22, 117.37, 113.06, 98.20, 29.80, 29.24, 22.52, 22.44; HRMS (ESI) m/z calcd for C₂₁H₁₇FN₅S [M+H]⁺ 390.1189, found 390.1195.

6-(8,9,10,11-Tetrahydro-3H-[1,2,3]triazolo[4,5-a]phenanthridin-7-yl)benzo[d]thiazol-2-amine

HSD1320

Method A: Off-white solid (112 mg, 30%). ¹H NMR (500 MHz, DMSO-d₆) δ 8.03 (d, J=9.1 Hz, 1H), 7.92-7.88 (m, 2H), 7.57 (s, 2H), 7.44 (dd, J=8.2, 1.7 Hz, 1H), 7.40 (d, J=8.2 Hz, 1H), 3.69 (t, J=6.5 Hz, 2H), 2.85 (t, J=6.2 Hz, 2H), 2.02-1.98 (m, 2H), 1.79-1.73 (m, 2H); ¹³C NMR (126 MHz, DMSO) δ 167.75, 158.87, 153.15, 145.33, 143.19, 139.18, 133.64, 131.24, 130.36, 130.18, 127.24, 122.15, 118.50, 117.37, 116.27, 29.93, 29.07, 22.66, 22.39. HRMS (ESI) m/z calcd for $C_{20}H_{17}N_6S$ [M+H]$^+$ 373.1235, found 373.1237.

7-(3-Isopropyl-1H-pyrazol-4-yl)-8,9,10,11-tetrahydro-3H-pyrazolo[4,3-a]phenanthridine

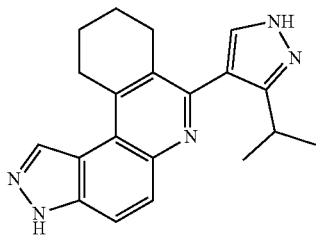

HSD1321

Method A: Off-white solid (136 mg, 41%). $^1$H NMR (500 MHz, DMSO-d$_6$) δ 8.82 (s, 1H), 8.23 (d, J=14.6 Hz, 2H), 7.97 (s, 1H), 3.49 (t, J=6.2 Hz, 2H), 3.02 (dd, J=14.1, 7.3 Hz, 1H), 2.84-2.66 (m, 2H), 2.20-1.96 (m, 2H), 1.91-1.76 (m, 2H), 1.26-1.08 (m, 6H). HRMS (ESI) m/z calcd for $C_{24}H_{22}N_5$ [M+H]$^+$ 332.1875, found 332.1875.

4-(7-(3-(Trifluoromethyl)-1H-pyrazol-4-yl)-8,9,10,11-tetrahydro-3H-pyrazolo[4,3-a]phenanthridin-9-yl)morpholine

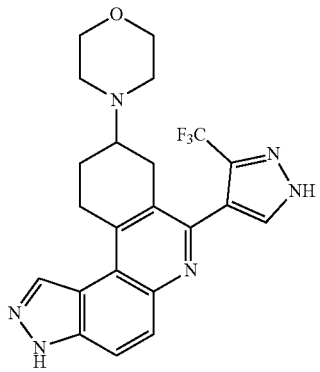

HSD1322

Method A: Off-white solid (110 mg, 25%). $^1$H NMR (500 MHz, Methanol-d$_4$) δ 8.64 (s, 1H), 8.13 (s, 1H), 7.95 (d, J=9.2 Hz, 1H), 7.90 (d, J=9.2 Hz, 1H), 4.17-3.37 (m, 11H), 3.29-3.19 (m, 1H), 3.19-3.08 (m, 1H), 2.85-2.70 (m, 1H), 2.14 (qd, J=12.1, 5.8 Hz, 1H). HRMS (ESI) m/z calcd for $C_{22}H_{22}F_3N_6O$ [M+H]$^+$ 443.1807, found 443.1809.

6-(3-Methyl-8,9,10,11-tetrahydro-3H-pyrazolo[4,3-a]phenanthridin-7-yl)benzo[d]thiazol-2-amine

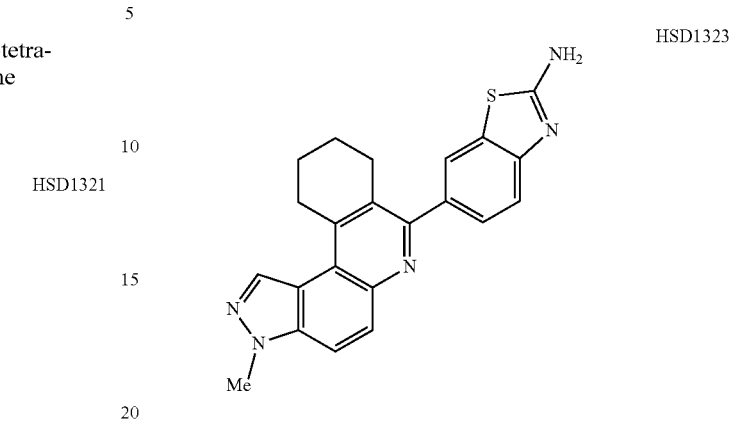

HSD1323

Method A: Off-white solid (138 mg, 36%). $^1$H NMR (500 MHz, DMSO-d$_6$) δ 8.50 (d, J=0.9 Hz, 1H), 8.02-7.95 (m, 1H), 7.91-7.85 (m, 2H), 7.63 (s, 2H), 7.46-7.36 (m, 2H), 4.17 (s, 3H), 3.31 (t, J=6.5 Hz, 2H), 2.82 (t, J=6.1 Hz, 2H), 2.01-1.95 (m, 2H), 1.83-1.66 (m, 2H); $^{13}$C NMR (126 MHz, DMSO) δ 167.75, 156.84, 152.94, 143.09, 142.79, 138.18, 135.06, 133.62, 131.17, 129.90, 129.18, 127.28, 122.20, 121.53, 117.29, 117.17, 114.03, 36.31, 29.76, 29.17, 22.58, 22.54. HRMS (ESI) m/z calcd for $C_{22}H_{20}N_5S$ [M+H]$^+$ 386.1439, found 386.1442.

Methyl 7-(2-aminobenzo[d]thiazol-6-yl)-8,9,10,11-tetrahydro-3H-pyrazolo[4,3-a]phenanthridine-1-carboxylate

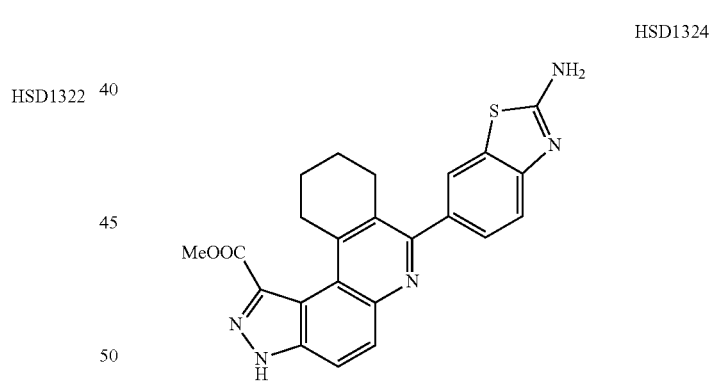

HSD1324

Method A: Off-white solid (120 mg, 28%); $^1$H NMR (500 MHz, DMSO-d$_6$) δ 8.55 (s, 1H), 8.15 (s, 1H), 8.08 (d, J=1.9 Hz, 1H), 7.59 (dt, J=8.3, 1.9 Hz, 1H), 7.56 (dd, J=8.2, 1.8 Hz, 1H), 3.99 (s, 3H), 3.21-3.11 (m, 2H), 2.91-2.77 (m, 2H), 1.87-1.68 (m, 4H); $^{13}$C NMR (126 MHz, DMSO) δ 169.32, 166.59, 153.43, 150.43, 140.96, 140.33, 138.84, 131.42, 129.03, 128.38, 125.04, 123.58, 122.59, 118.02, 116.40, 111.98, 53.45, 30.28, 27.43, 21.69, 21.65. HRMS (ESI) m/z calcd for $C_{23}H_{20}N_5O_2S$ [M+H]$^+$ 430.1338, found 430.1348.

N-(6-(8,9,10,11-Tetrahydro-3H-pyrazolo[4,3-a]phenanthridin-7-yl)benzo[d]thiazol-2-yl)acetamide Compound HSD992 (93 mg, 0.25 mmol) was dissolved in a mixture of DMF (2 mL) and triethylamine (2 equiv), followed by addition of acetyl chloride (30 mg, 1.5 mmol). After that reaction was continued for overnight at room temperature. After completion of reaction, reaction mixture was extracted with ethyl acetate (2×20 mL) and washed with brine solution and the crude was purified with dichloromethane:methanol (90:10) by flash column chromatography to get the desired product as yellow solid (73 mg, 70%).

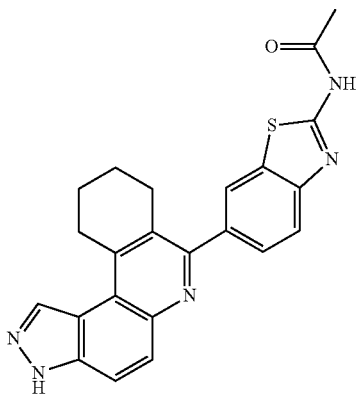

$^1$H NMR (500 MHz, Methanol-$d_4$) δ 8.76 (s, 1H), 8.38 (d, J=9.3 Hz, 1H), 8.31-8.24 (m, 1H), 8.20 (d, J=9.3 Hz, 1H), 7.88-7.84 (m, 1H), 7.76 (d, J=8.4 Hz, 1H), 4.32 (s, 3H), 3.67 (t, J=6.3 Hz, 2H), 2.95 (t, J=6.1 Hz, 2H), 2.26-2.18 (m, 2H), 1.99-1.87 (m, 2H); $^{13}$C NMR (126 MHz, MeOD) δ 170.98, 155.22, 149.49, 141.56, 138.36, 135.15, 134.18, 132.65, 129.29, 127.49, 125.42, 124.19, 123.58, 118.90, 118.87, 115.92, 114.54, 35.36, 31.10, 27.83, 21.22, 21.15; HRMS (ESI) m/z calcd for $C_{23}H_{20}N_5O_2S$ [M+H]$^+$ 414.1389, found 414.1388.

7-(3-(Trifluoromethyl)-1H-pyrazol-4-yl)-8,9,10,11-tetrahydro-3H-imidazo[4,5-a]phenanthridine

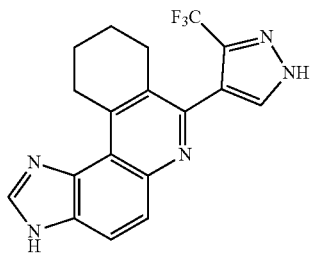

Method A: Off-white solid (75 mg, 21%). $^1$H NMR (500 MHz, Methanol-$d_4$) δ 8.30 (s, 1H), 7.99 (d, J=1.2 Hz, 1H), 7.93 (d, J=9.0 Hz, 1H), 7.83 (d, J=8.9 Hz, 1H), 3.68 (d, J=6.7 Hz, 2H), 2.68 (t, J=6.3 Hz, 2H), 2.08-1.98 (m, 2H), 1.91-1.83 (m, 2H); $^{13}$C NMR (126 MHz, MeOD) δ 149.00, 145.68, 143.27, 142.66, 140.11, 130.25, 130.05, 124.01, 122.80 (q, J=270.51 Hz), 118.99, 118.30, 115.91, 112.78, 94.71, 29.26, 27.75, 22.04, 21.86. HRMS (ESI) m/z calcd for $C_{18}F_{15}F_3N_5$ [M+H]$^+$ 358.1280, found 358.1286.

2-(trifluoromethyl)-7-(3-(trifluoromethyl)-1H-pyrazol-4-yl)-8,9,10,11-tetrahydro-3H-imidazo[4,5-a]phenanthridine

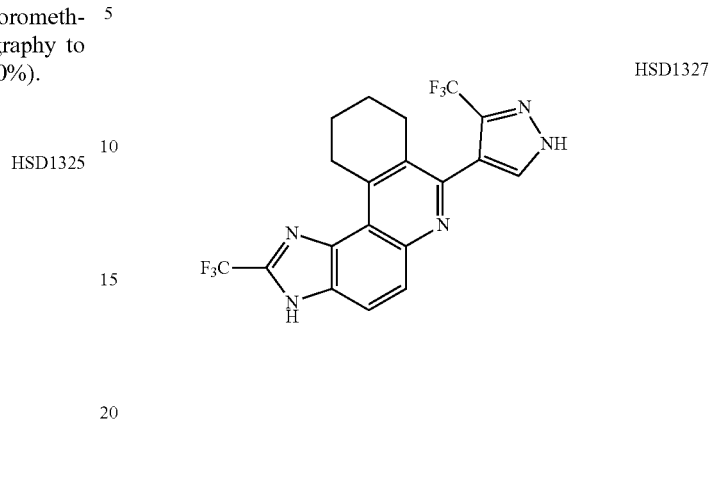

Method A: Off-white solid (106 mg, 25%). $^1$H NMR (500 MHz, Methanol-$d_4$) δ 7.99 (s, 1H), 7.90 (d, J=9.1 Hz, 1H), 7.85 (d, J=9.1 Hz, 1H), 3.91-3.75 (m, 2H), 2.68 (t, J=6.3 Hz, 2H), 2.07-1.92 (m, 2H), 1.94-1.77 (m, 2H). $^{13}$C NMR (126 MHz, MeOD) δ 149.46, 144.26, 143.57, 140.04, 139.76, 137.30, 131.82, 130.86, 130.17, 126.46, 124.94 (q, J=269.64 Hz), 120.67, 120.32 (q, J=268.64 Hz), 118.93, 114.85, 29.42, 27.82, 21.99, 21.94. HRMS (ESI) m/z calcd for $C_{19}H_{14}F_6N_5$ [M+H]$^+$ 426.1153, found 426.1155.

Methyl 7-(3-(trifluoromethyl)-1H-pyrazol-4-yl)-8,9,10,11-tetrahydro-3H-pyrazolo[4,3-a]phenanthridine-1-carboxylate

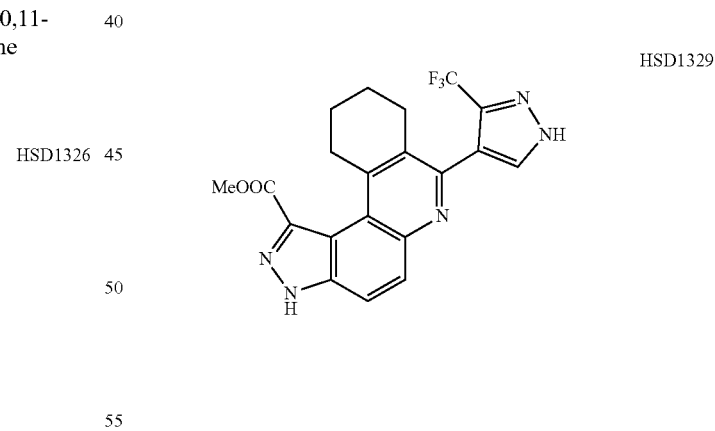

Method A: Off-white solid (83 mg, 20%). $^1$H NMR (500 MHz, Methanol-$d_4$) δ 8.36-8.34 (m, 1H), 8.33 (d, J=9.2 Hz, 1H), 8.07 (d, J=9.2 Hz, 1H), 4.09 (s, 3H), 3.41 (t, J=6.0 Hz, 2H), 2.83 (t, J=6.5 Hz, 2H), 2.04-1.96 (m, 2H), 1.94-1.87 (m, 2H); $^{13}$C NMR (126 MHz, MeOD) δ 165.69, 155.80, 143.04, 140.76, 140.09, 139.80, 136.05, 134.16, 132.40, 124.22, 122.30 (268.38), 120.37, 111.65, 115.75, 109.90, 52.41, 31.10, 26.62, 21.03, 20.75; HRMS (ESI) m/z calcd for $C_{20}H_{17}F_3N_5O_2$ [M+H]$^+$ 416.1334, found 416.1343.

7-(3-(Trifluoromethyl)-1H-pyrazol-4-yl)-8,9,10,11-tetrahydro-3H-pyrazolo[4,3-a]phenanthridine-9-carbonitrile

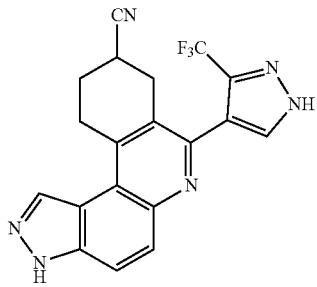

HSD1331

Method A: Off-white solid (100 mg, 26%). $^1$H NMR (500 MHz, DMSO-$d_6$) δ 8.78 (s, 1H), 8.39 (s, 1H), 8.13 (d, J=9.5, 4.5 Hz, 1H), 7.97 (d, J=9.2, 4.4 Hz, 1H), 3.61-3.50 (m, 2H), 3.48-3.36 (m, 1H), 3.12-2.95 (m, 2H), 2.37-2.22 (m, 2H). HRMS (ESI) calcd for $C_{19}H_{14}F_3N_6$ [M+H]$^+$ 383.1232, found 383.1237.

1-Methyl-7-(3-(trifluoromethyl)-1H-pyrazol-4-yl)-8,9,10,11-tetrahydro-3H-pyrazolo[4,3-a]phenanthridine-9-carbonitrile

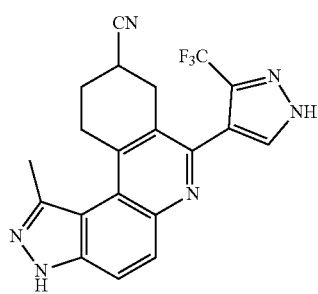

HSH205

Method A: Off-white solid (59 mg, 15%). $^1$H NMR (500 MHz, Methanol-$d_4$) δ 8.37 (d, J=1.0 Hz, 1H), 8.21 (d, J=9.2 Hz, 1H), 7.89 (d, J=9.2 Hz, 1H), 3.94 (t, J=6.6 Hz, 2H), 3.49-3.42 (m, 1H), 3.20 (dd, J=17.3, 5.9 Hz, 1H), 3.09 (d, J=7.5 Hz, 1H), 3.06 (s, 3H), 2.39 (m, J=12.6, 6.0, 3.4 Hz, 1H), 2.21 (m, J=13.3, 8.5, 6.5 Hz, 1H); $^{13}$C NMR (126 MHz, Methanol-$d_4$) δ 151.72, 141.79, 137.08, 132.47, 129.46, 126.34, 123.81, 123.71, 123.64, 122.20 (q, J=270), 112.62, 109.78, 109.78, 30.62, 30.56, 29.87, 24.22, 23.60, 23.54, 17.53.

8,9,10,11-Tetrahydro-3H-pyrazolo[4,3-a]phenanthridine-7-carboxylic Acid (HSD1251)

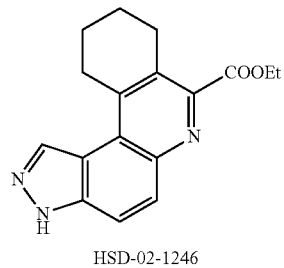

HSD-02-1246 aq NaOH solution
MeOH, rt
overnight
40%

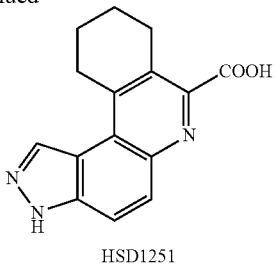

HSD1251

Off-white solid (40%). $^1$H NMR (500 MHz, DMSO-$d_6$) δ 8.60 (s, 1H), 7.90 (d, J=9.0 Hz, 1H), 7.83 (d, J=9.5 Hz, 1H), 3.32-3.26 (m, 11H), 3.06-2.96 (m, 2H), 2.03-1.92 (m, 2H), 1.87-1.75 (m, 2H).

N-Cyclopropyl-8,9,10,11-tetrahydro-3H-pyrazolo[4,3-a]phenanthridine-7-carboxamide

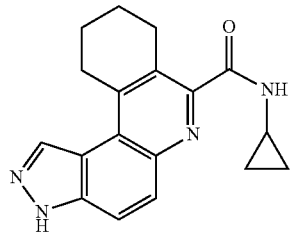

HSD1333

To a solution of HSD1251 (50 mg, 0.18 mmol) in DMF (2.5 mL) was added cyclopropylamine (0.19 mmol), HOBt (0.18 mmol), EDCl·HCl (0.18 mmol) and DIPEA (0.39 mmol). Reaction was continued for 12 h at room temperature and monitored by TLC. After completion, reaction mixture was extracted with ethyl acetate and washed with brine solution and dried over Na$_2$SO$_4$. Crude was purified with flash chromatography to get the desired product as white solid (70% yield, 39 mg). $^1$H NMR (500 MHz, DMSO-$d_6$) δ 8.59-8.53 (m, 2H), 7.91-7.82 (m, 2H), 3.05-2.97 (m, 2H), 2.92-2.82 (m, 1H), 2.02-1.92 (m, 2H), 1.85-1.74 (m, 2H), 0.77-0.66 (m, 2H), 0.62-0.54 (m, 2H); $^{13}$C NMR (126 MHz, DMSO) δ 169.02, 150.75, 143.04, 142.46, 138.96, 136.49, 129.42, 129.13, 123.13, 116.31, 114.78, 29.62, 26.70, 23.08, 22.44, 22.07, 6.21. HRMS (ESI) m/z calcd for $C_{18}H_{19}N_4O$ [M+H]$^+$ 307.1559, found 307.1565.

9-Methyl-7-(3-(trifluoromethyl)-1H-pyrazol-4-yl)-8,9,10,11-tetrahydro-3H-indazolo[5,4-c][2,7]naphthyridine

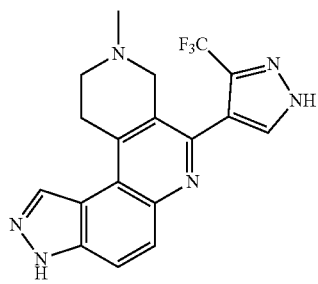

HSD1334

Method A: Off-white solid (96 mg, 26%). ¹H NMR (500 MHz, Methanol-d₄) δ 8.19 (s, 1H), 8.05-7.98 (m, 1H), 7.26 (d, J=8.9 Hz, 1H), 6.81 (d, J=8.9 Hz, 1H), 6.49-6.40 (m, 1H), 4.26 (d, J=11.1 Hz, 1H), 3.66-3.51 (m, 1H), 3.06-2.89 (m, 2H), 2.65-2.53 (m, 1H), 2.32 (s, 3H), 1.96 (t, J=10.9 Hz, 1H); ¹³C NMR (126 MHz, MeOD) δ 139.53, 136.09, 131.98, 131.66, 129.91, 123.14 (q, J=269.6 Hz), 119.98, 118.88, 117.25, 110.66, 107.76, 55.06, 54.96, 51.22, 44.41, 40.51.

6-(9-Methyl-8,9,10,11-tetrahydro-3H-indazolo[5,4-c][2,7]naphthyridin-7-yl)benzo[d]thiazol-2-amine

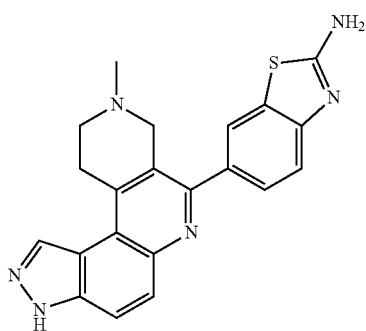

HSD1335

Method A: Off-white solid (81 mg, 21%). ¹H NMR (500 MHz, DMSO-d₆) δ 7.74 (d, J=1.7 Hz, 1H), 7.45 (s, 2H), 7.32 (d, J=8.1 Hz, 1H), 7.26 (dd, J=8.2, 1.8 Hz, 1H), 7.19 (d, J=8.8 Hz, 1H), 6.79 (d, J=8.9 Hz, 1H), 6.33 (d, J=4.8 Hz, 1H), 5.95 (s, 1H), 3.94 (d, J=11.0 Hz, 1H), 3.46-3.40 (m, 2H), 2.80-2.71 (m, 2H), 2.25-2.17 (m, 1H), 2.12 (s, 3H), 1.77 (t, J=10.6 Hz, 1H); ¹³C NMR (126 MHz, DMSO) δ 167.11, 153.11, 140.29, 135.76, 134.70, 132.26, 132.06, 131.56, 125.86, 120.50, 119.90, 118.66, 118.03, 117.84, 111.01, 107.40, 61.27, 55.89, 46.15.

N-(7-(3-(Trifluoromethyl)-1H-pyrazol-4-yl)-8,9,10,11-tetrahydro-3H-pyrazolo[4,3-a]phenanthridin-9-yl)acetamide

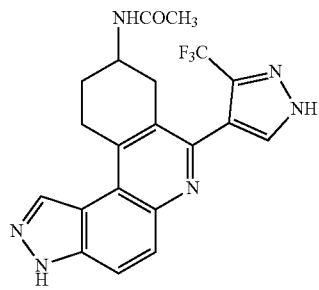

HSD1337

Method A: Off-white solid (137 mg, 33%). ¹H NMR (500 MHz, Methanol-d₄) δ 8.56 (s, 1H), 8.02 (s, 1H), 7.86 (s, 2H), 4.25-4.09 (m, 2H), 3.63-3.55 (m, 1H), 3.50-3.42 (m, 2H), 3.02-2.92 (m, 1H), 2.71-2.59 (m, 1H), 2.40-2.30 (m, 1H), 1.98-1.90 (m, 4H); ¹³C NMR (126 MHz, DMSO) δ 169.42, 153.60, 148.04, 140.41, 138.26, 134.78, 129.37, 127.68, 122.95, 122.23, 115.48, 110.76, 44.12, 34.25, 29.21, 27.37, 23.11. HRMS (ESI) m/z calcd for C₂₀H₁₈F₃N₆O [M+H]⁺ 415.1494, found 415.1498.

7-(3-(Difluoromethyl)-1-methyl-1H-pyrazol-4-yl)-5-fluoro-8,9,10,11-tetrahydro-3H-pyrazolo[4,3-a]phenanthridine

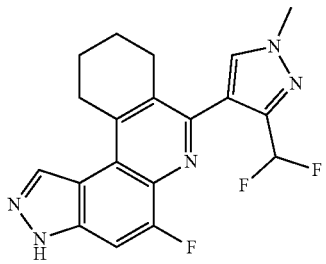

HSD1340

Method A: Off-white solid (37 mg, 10%). ¹H NMR (500 MHz, DMSO-d₆) δ 8.50 (s, 1H), 8.27 (s, 1H), 7.69-7.62 (m, 1H), 7.49 (t, J=54.7 Hz, 1H), 3.97 (s, 3H), 3.32-3.24 (m, 2H), 2.94-2.83 (m, 2H), 2.02-1.92 (m, 2H), 1.85-1.73 (m, 2H); ¹³C NMR (126 MHz, DMSO) δ 158.06, 156.05, 148.40, 144.52, 144.34, 144.16, 143.02, 136.82, 136.43, 134.20, 132.97, 131.01, 122.11, 119.91, 113.31, 112.93, 111.45, 109.58, 98.48, 98.29, 31.15, 29.80, 28.54, 22.27.

7-(3-(Trifluoromethyl)-1H-pyrazol-4-yl)-8,9,10,11-tetrahydro-3H-indazolo[5,4-c][2,7]naphthyridine In this case tert-butyl 4-oxopiperidine-1-carboxylate was used as cyclic ketone using method A, Boc-group was deprotected in-situ due to presence of HCl in the reaction and desired compound was precipitated out in the reaction mixture which was filtered and washed with ethanol.

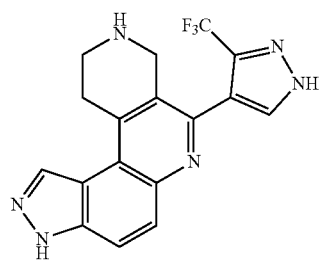

HSD1341

Method A: Off-white solid (100 mg, 28%). ¹H NMR (500 MHz, DMSO-d₆) δ 9.70 (s, 2H), 8.60 (s, 1H), 8.34 (s, 1H), 7.97 (dd, J=9.2, 3.7 Hz, 1H), 7.84 (d, J=9.1 Hz, 1H), 4.37-4.31 (m, 2H), 3.70-3.62 (m, 2H), 3.61-3.53 (m, 2H); ¹³C NMR (126 MHz, DMSO) δ 146.11, 144.36, 139.64 (q, J 36.54 Hz), 138.90, 138.14, 135.96, 131.61, 129.36, 123.35 (q, J=270.9 Hz), 122.70, 120.58, 117.94, 115.98, 43.23, 25.91; C₁₇F₁₄F₃N₆ [M+H]⁺ 359.1232, found 359.1233.

5-fluoro-7-(3-(trifluoromethyl)-1H-pyrazol-4-yl)-8,9,10,11-tetrahydro-3H-indazolo[5,4-c][2,7]naphthyridine

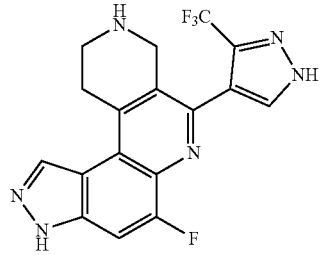

HSD1342

Method A: Same cyclic ketone as in HSD1341: Off-white solid (60 mg, 16%). $^1$H NMR (500 MHz, DMSO-$d_6$) δ 8.60 (s, 1H), 8.28 (s, 1H), 7.71 (d, J=10.0 Hz, 1H), 3.85 (s, 2H), 3.24 (q, J=5.1, 4.2 Hz, 2H), 3.16 (t, J=4.4 Hz, 2H); $^{13}$C NMR (126 MHz, DMSO) δ 158.12 (d, J=253.26 Hz), 146.55, 141.41, 139.52, 139.23, 138.48, 134.96, 131.48, 123.42 (q, J=269.64 Hz), 122.86, 118.58, 112.68, 99.76, 97.55, 55.01, 47.19, 42.89; HRMS (ESI) m/z calcd for $C_{17}H_{13}F_4N_6$ [M+H]$^+$ 377.1138, found 377.1138.

N-(4-((4-methylpiperazin-1-yl)methyl)-3-(trifluoromethyl)phenyl)-8,9,10,11-tetrahydro-3H-pyrazolo[4,3-a]phenanthridine-7-carboxamide

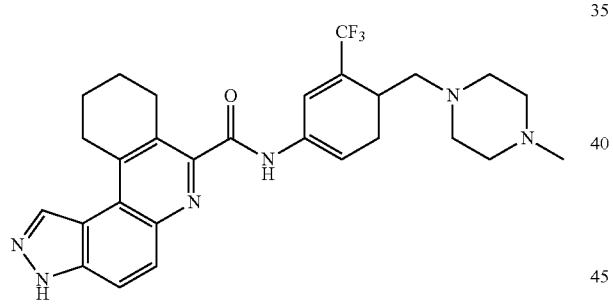

HSD1343

To a solution of HSD1251 (50 mg, 0.18 mmol) in DMF (2.5 mL) was added 4-((4-methylpiperazin-1-yl)methyl)-3-(trifluoromethyl)aniline (0.19 mmol), HATU (0.18 mmol), and DIPEA (0.39 mmol). Reaction was continued for 12 h at room temperature and monitored by TLC. After completion, reaction mixture was extracted with ethyl acetate and washed with brine solution and dried over $Na_2SO_4$. Crude was purified with flash chromatography to get the desired product as Off-white solid (50% yield, 47 mg). $^1$H NMR (500 MHz, DMSO-$d_6$) δ 10.93 (s, 1H), 8.63 (s, 1H), 8.29 (d, J=2.2 Hz, 1H), 8.05 (dd, J=8.5, 2.3 Hz, 1H), 7.98-7.89 (m, 2H), 7.71 (d, J=8.5 Hz, 1H), 3.56 (s, 2H), 3.34-3.30 (m, 2H), 3.13 (t, J=6.2 Hz, 2H), 2.37 (s, 8H), 2.14 (s, 3H), 1.99 (ddt, J=8.9, 6.3, 2.9 Hz, 2H), 1.87-1.79 (m, 2H); $^{13}$C NMR (126 MHz, DMSO) δ 166.54, 149.19, 143.71, 142.60, 138.52, 132.53, 131.81, 129.74, 129.42, 128.11 (q, J=28.9 Hz), 125.91 (q, J=274.6 Hz), 123.78, 123.53, 117.19, 117.14, 116.03, 57.94, 55.22, 53.19, 46.22, 29.73, 26.89, 22.37, 22.07; HRMS (ESI) m/z calcd for $C_{28}H_{30}F_3N_6O$ [M+H]$^+$ 523.2433, found 523.2433.

7-(2-aminobenzo[d]thiazol-6-yl)-3H-pyrazolo[4,3-f]quinoline-9-carboxylic Acid

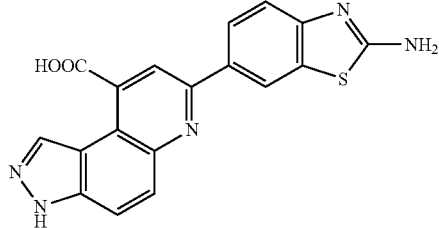

HSD1345

Method A: Brown solid (126 mg, 35%). $^1$H NMR (500 MHz, DMSO-$d_6$) δ 8.70 (d, J=1.8 Hz, 1H), 8.48-8.35 (m, 3H), 8.32 (s, 1H), 8.25 (dd, J=8.5, 1.9 Hz, 1H), 8.00 (d, J=9.2 Hz, 1H), 7.96 (d, J=9.1 Hz, 1H), 7.51 (d, J=8.5 Hz, 1H); $^{13}$C NMR (126 MHz, DMSO) δ 170.36, 169.08, 153.15, 146.62, 138.70, 132.42, 129.93, 129.24, 125.78, 120.77, 117.16, 117.04, 115.21.

7-(Isoquinolin-6-yl)-8,9,10,11-tetrahydro-3H-pyrazolo[4,3-a]phenanthridine

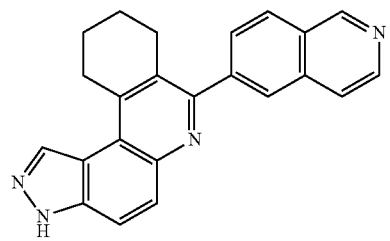

HSD1347

Method A: Off-white solid (178 mg, 51%). $^1$H NMR (500 MHz, DMSO-$d_6$) δ 9.34 (s, 1H), 8.65-8.45 (m, 2H), 8.23-8.08 (m, 2H), 7.94-7.75 (m, 4H), 3.36-3.01 (m, 2H), 2.84-2.64 (m, 2H), 2.03-1.80 (m, 2H), 1.74-1.50 (m, 2H); $^{13}$C NMR (126 MHz, DMSO) δ 155.87, 152.56, 143.58, 143.17, 142.64, 138.79, 136.42, 135.77, 135.39, 129.57, 129.30, 127.89, 127.63, 127.02, 124.06, 122.13, 121.09, 116.40, 114.60, 29.61, 28.83, 22.51, 22.40.

7-(Isoquinolin-8-yl)-8,9,10,11-tetrahydro-3H-pyrazolo[4,3-a]phenanthridine

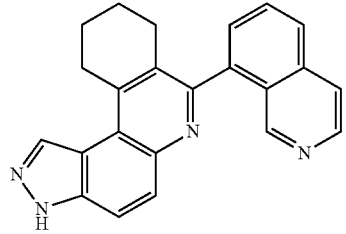

HSD1349

Method A: Brown solid (140 mg, 40%). ¹H NMR (500 MHz, Methanol-d₄) δ 8.67 (d, J=1.0 Hz, 1H), 8.61 (s, 1H), 8.46 (d, J=5.8 Hz, 1H), 8.07 (dt, J=8.4, 1.1 Hz, 1H), 7.95-7.90 (m, 2H), 7.86 (s, 2H), 7.70 (dd, J=7.0, 1.1 Hz, 1H), 3.45-3.36 (m, 2H), 2.71-2.57 (m, 1H), 2.42-2.30 (m, 1H), 2.08-2.02 (m, 2H), 1.84-1.71 (m, 2H); ¹³C NMR (126 MHz, MeOD) δ 154.18, 149.50, 144.02, 143.31, 141.71, 138.68, 136.43, 130.58, 130.53, 128.48, 128.34, 126.97, 126.93, 122.66, 121.40, 115.96, 29.52, 27.69, 22.02, 21.75.

7-(Isoquinolin-7-yl)-8,9,10,11-tetrahydro-3H-pyrazolo[4,3-a]phenanthridine

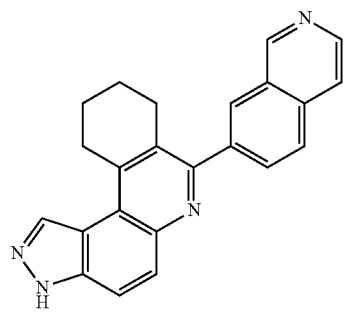

HSD1350

Method A: Off-white solid (105 mg, 30%). ¹H NMR (500 MHz, Methanol-d₄) δ 9.33 (d, J=1.4 Hz, 1H), 8.61 (s, 1H), 8.50 (dd, J=5.9, 1.4 Hz, 1H), 8.29 (s, 1H), 8.09 (d, J=8.4 Hz, 1H), 7.98 (dt, J=8.4, 1.6 Hz, 1H), 7.93-7.85 (m, 2H), 3.47-3.37 (m, 2H), 2.84 (t, J=6.2 Hz, 2H), 2.17-2.08 (m, 2H), 1.89-1.82 (m, 2H); ¹³C NMR (126 MHz, MeOD) δ 156.08, 152.22, 143.84, 143.20, 141.99, 140.04, 138.79, 136.00, 135.65, 132.00, 129.69, 128.57, 128.47, 127.97, 126.35, 122.41, 120.88, 113.80, 29.64, 28.49, 22.13, 22.04.

7-(Quinolin-2-yl)-8,9,10,11-tetrahydro-3H-pyrazolo[4,3-a]phenanthridine

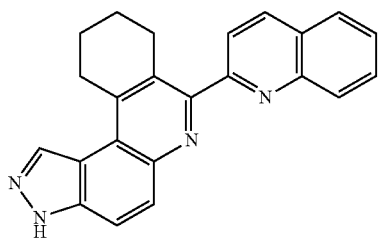

HSD1351

Method A: Off-white solid (150 mg, 43%). ¹H NMR (500 MHz, DMSO-d₆) δ 8.61 (s, 1H), 8.50 (d, J=8.5 Hz, 1H), 8.09-8.03 (m, 2H), 8.00 (d, J=8.4 Hz, 1H), 7.89 (s, 2H), 7.80 (ddd, J=8.3, 6.8, 1.5 Hz, 1H), 7.69-7.62 (m, 1H), 3.38 (d, J=6.6 Hz, 2H), 3.09 (t, J=6.2 Hz, 2H), 2.02 (dp, J=9.3, 3.2 Hz, 2H), 1.82-1.71 (m, 2H); ¹³C NMR (126 MHz, DMSO) δ 159.31, 154.53, 146.93, 143.32, 143.03, 138.94, 136.97, 136.58, 130.38, 130.26, 129.68, 129.51, 128.37, 127.38, 122.95, 122.49, 116.48, 114.65, 29.86, 28.31, 22.54, 22.43; HRMS (EST) m/z calcd for C₂₃H₁₉N₄ [M+H]⁺ 351.1610, found 351.1608.

7-(isoquinolin-4-yl)-8,9,10,11-tetrahydro-3H-pyrazolo[4,3-a]phenanthridine

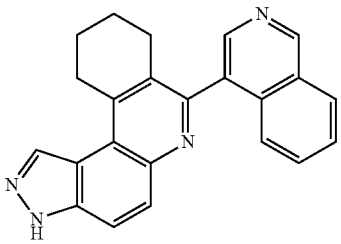

HSD1352

Method A: Off-white solid (262 mg, 75%). ¹H NMR (500 MHz, DMSO-d₆) δ 9.41 (d, J=0.9 Hz, 1H), 8.61 (s, 1H), 8.50 (s, 1H), 8.28-8.14 (m, 1H), 7.94-7.80 (m, 2H), 7.73-7.62 (m, 2H), 7.38-7.31 (m, 1H), 3.44-3.35 (m, 2H), 2.64-2.54 (m, 1H), 2.40-2.27 (m, 1H), 2.00-1.95 (m, 3H), 1.77-1.65 (m, 2H); ¹³C NMR (126 MHz, DMSO) δ 153.43, 152.80, 143.82, 142.90, 142.62, 138.81, 136.47, 134.12, 132.07, 131.60, 130.70, 129.60, 128.54, 128.33, 128.02, 124.62, 122.35, 116.52, 114.67, 29.59, 27.87, 22.50, 22.16. HRMS (ESI) m/z calcd for C₂₃H₁₉N₄ [M+H]⁺ 351.1610, found 351.1611.

9-(Pyridin-2-yl)-7-(3-(trifluoromethyl)-1H-pyrazol-4-yl)-3H-pyrazolo[4,3-f]quinoline

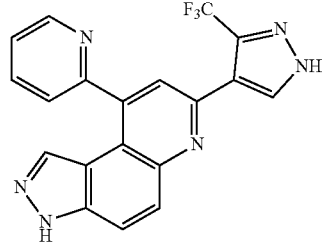

HSD1356

Method C: Off-white solid (160 mg, 42%). ¹H NMR (500 MHz, Methanol-d₄) δ 8.80 (ddt, J=5.0, 1.7, 0.7 Hz, 1H), 8.37 (s, 1H), 8.14 (td, J=7.7, 1.7 Hz, 1H), 8.01 (d, J=9.2 Hz, 1H), 7.92 (dd, J=9.3, 0.9 Hz, 1H), 7.82-7.65 (m, 3H), 6.69 (s, 1H); ¹³C NMR (126 MHz, MeOD) δ 157.76, 157.73, 149.27, 147.72, 146.52, 145.30, 139.22 (q, J=36.54 Hz), 138.53, 131.12, 129.05, 129.02, 124.48, 124.45, 124.33, 123.02 (q, J=268.38 Hz), 121.14, 120.71, 119.57, 115.74.

7-(Quinolin-6-yl)-8,9,10,11-tetrahydro-3H-pyrazolo[4,3-a]phenanthridine

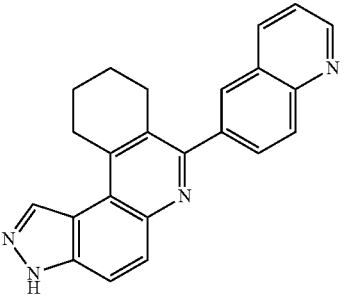

HSD1357

Method A: Off-solid (192 mg, 55%). ¹H NMR (500 MHz, DMSO-d₆) δ 9.01 (dd, J=4.6, 1.7 Hz, 1H), 8.62 (s, 1H), 8.13 (d, J=8.5 Hz, 1H), 7.90 (d, J=9.1 Hz, 1H), 7.82 (d, J=8.8 Hz, 1H), 7.77 (t, J=7.6 Hz, 1H), 7.59-7.52 (m, 1H), 7.49 (t, J=7.6 Hz, 1H), 7.34 (d, J=8.3 Hz, 1H), 3.49-3.36 (m, 2H), 2.61-2.54 (m, 2H), 2.39-2.23 (m, 1H), 2.02-1.87 (m, 2H), 1.77-1.60 (m, 2H); ¹³C NMR (126 MHz, DMSO) δ 153.87, 150.73, 148.39, 146.91, 143.65, 142.78, 138.83, 136.48, 130.02, 129.95, 129.78, 129.52, 127.55, 126.67, 125.91, 122.43, 121.73, 116.49, 114.82, 29.57, 27.63, 22.47, 22.06 HRMS (ESI) m/z calcd for $C_{23}H_{19}N_4$ [M+H]⁺ 351.1610, found 351.1611.

7-(Quinolin-3-yl)-8,9,10,11-tetrahydro-3H-pyrazolo[4,3-a]phenanthridine

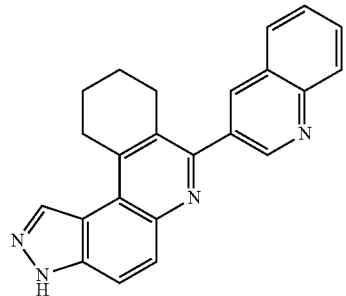

HSD1358

Method A: Off-white solid (162 mg, 46%). ¹H NMR (500 MHz, DMSO-d₆) δ 9.14 (s, 1H), 8.61-8.60 (m, 2H), 8.10 (t, J=7.25 Hz, 2H), 7.89 (s, 2H), 7.83 (t, J=6.95 Hz, 1H), 7.68 (d, J=7.8 Hz, 1H), 3.39 (t, J=5.65 Hz, 2H), 2.92 (1, J=5.75 Hz, 2H), 2.06-2.02 (m, 2H), 2.07-1.98 (m, 2H), 1.78-1.77 (m, 2H); ¹³C NMR (126 MHz, MeOD) δ 153.88, 151.60, 147.28, 143.90, 142.87, 138.80, 136.53, 136.17, 134.00, 130.35, 129.97, 129.70, 129.19, 128.96, 127.45, 122.16, 116.44, 114.74, 29.75, 28.86, 22.58; HRMS (ESI) m/z calcd for $C_{23}H_{19}N_4$ [M+H]⁺ 351.1610, found 351.1613.

3-Chloro-4-(8,9,10,11-tetrahydro-3H-pyrazolo[4,3-a]phenanthridin-7-yl)phenol

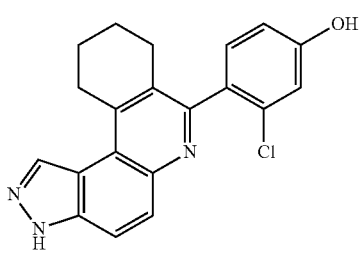

HSD1359

Method A: Off-white solid (178 mg, 51%). ¹H NMR (500 MHz, Methanol-d₄) δ 8.55 (s, 1H), 7.88-7.76 (m, 2H), 7.18 (d, J=8.3 Hz, 1H), 6.97 (d, J=2.4 Hz, 1H), 6.88 (dd, J=8.3, 2.4 Hz, 1H), 3.39-3.31 (m, 2H), 2.67 (dt, J=17.3, 6.3 Hz, 1H), 2.54 (dt, J=17.2, 6.2 Hz, 1H), 2.07-1.98 (m, 2H), 1.91-1.74 (m, 2H); ¹³C NMR (126 MHz, MeOD) δ 158.50, 155.40, 143.33, 142.83, 138.70, 135.81, 132.99, 130.85, 130.10, 128.23, 122.36, 116.12, 115.69, 114.11, 113.67, 29.44, 27.16, 22.10, 21.82. HRMS (ESI) m/z calcd for $C_{20}H_{17}ClN_3O$ [M+H]⁺ 350.1060, found 350.1063.

3-Fluoro-5-(8,9,10,11-tetrahydro-3H-pyrazolo[4,3-a]phenanthridin-7-yl)phenol

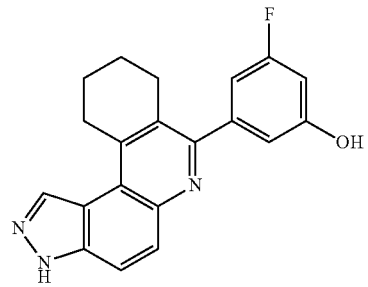

HSD1360

Method A: Off-white solid (117 mg, 35%). ¹H NMR (500 MHz, Methanol-d₄) δ 8.59 (s, 1H), 7.91-7.82 (m, 2H), 7.20 (d, J=8.3 Hz, 1H), 6.98 (d, J=2.4 Hz, 1H), 6.89 (dd, J=8.3, 2.4 Hz, 1H), 3.48-3.35 (m, 2H), 2.70 (dt, J=17.3, 6.3 Hz, 1H), 2.57 (dt, J=17.2, 6.2 Hz, 1H), 2.10-2.03 (m, 2H), 1.92-1.82 (m, 2H); ¹³C NMR (126 MHz, MeOD) δ 158.52, 155.48, 143.37, 142.83, 135.85, 132.99, 130.91, 130.84, 130.11, 128.26, 122.39, 116.16, 115.69, 114.11, 113.71, 29.48, 27.18, 22.13, 21.84.

7-(Isoquinolin-1-yl)-8,9,10,11-tetrahydro-3H-pyrazolo[4,3-a]phenanthridine

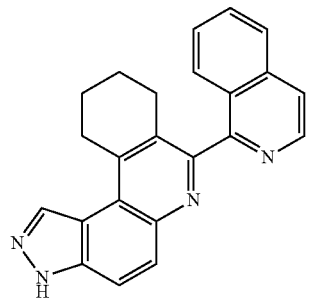

HSD1361

Method A: Off-white solid (172 mg, 49%). ¹H NMR (500 MHz, Methanol-d₄) 8.67 (s, 1H), 8.59 (dd, J=5.9, 1.3 Hz, 1H), 8.07 (d, J=8.3 Hz, 1H), 7.98 (d, J=5.8 Hz, 1H), 7.90 (s, 2H), 7.81 (ddd, J=8.3, 6.7, 1.4 Hz, 1H), 7.62-7.55 (m, 1H), 7.52 (d, J=8.4 Hz, 1H), 3.49 (d, J=8.1 Hz, 2H), 2.54 (s, 2H), 2.13-2.05 (m, 2H), 1.87-1.76 (m, 2H); ¹³C NMR (126 MHz, MeOD) δ 158.92, 153.77, 144.17, 140.73, 136.98, 131.02, 130.39, 128.41, 128.05, 127.21, 126.99, 126.27, 123.01, 121.47, 29.53, 26.71, 22.03, 21.60. HRMS (ESI) m/z calcd for $C_{23}H_{19}N_4$ [M+H]⁺ 351.1610, found 351.1606.

1-Methoxy-7-(3-(trifluoromethyl)-1H-pyrazol-4-yl)-8,9,10,11-tetrahydro-3H-pyrazolo[4,3-a]phenanthridine

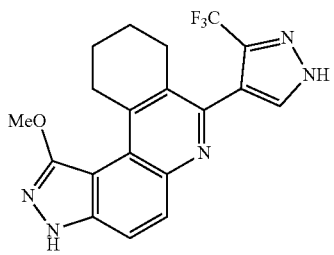

HSD1362

Method A: Off-white solid (163 mg, 42%). ¹H NMR (500 MHz, Methanol-d₄) δ 8.22 (s, 1H), 7.92 (d, J=9.2 Hz, 1H), 7.86 (d, J=9.2 Hz, 1H), 4.15 (d, J=1.1 Hz, 3H), 3.79 (t, J=6.1 Hz, 2H), 2.73 (t, J=6.2 Hz, 2H), 2.01-1.83 (m, 4H); ¹³C NMR (126 MHz, MeOD) δ 158.09, 154.86, 141.34, 135.93, 132.97, 131.61, 125.26, 123.06, 118.25, 118.16, 101.38, 56.07, 31.36, 27.62, 21.62, 21.18. HRMS (ESI) m/z calcd for $C_{19}H_{17}F_3N_5O$ [M+H]⁺ 388.1385, found 388.1390.

1-Methyl-7-(1-methyl-3-(trifluoromethyl)-1H-pyrazol-4-yl)-8,9,10,11-tetrahydro-3H-pyrazolo[4,3-a]phenanthridine-9-carbonitrile

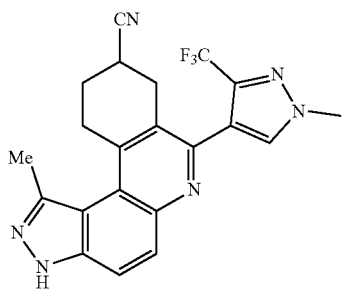

HSD1363

Method A: Off-white solid (54 mg, 13%). ¹H NMR (500 MHz, Methanol-d₄) δ 7.96 (s, 1H), 7.85-7.75 (m, 2H), 4.07 (s, 3H), 3.74-3.64 (m, 2H), 3.14-3.07 (m, 1H), 3.03-2.96 (m, 1H), 2.33-2.25 (m, 1H), 2.13-2.04 (m, 1H); ¹³C NMR (126 MHz, MeOD) δ 147.28, 143.95, 143.52, 141.31, 141.20, 139.12, 132.56, 128.83, 126.48, 123.95, 122.46 (q, J=269.64 Hz), 121.58, 118.93, 114.92, 114.10, 38.46, 30.48, 29.49, 25.02, 24.24. HRMS (ESI) m/z calcd for $C_{21}H_{15}F_3N_6$ [M+H]⁺ 411.1545 found 411.1548.

7-(1-Methyl-3-(trifluoromethyl)-1H-pyrazol-4-yl)-8,9,10,11-tetrahydro-3H-pyrazolo[4,3-a]phenanthridine

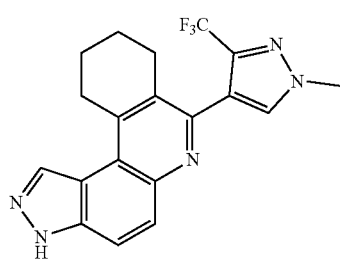

HSD1365

Method A: Off-white solid (112 mg, 30%). ¹H NMR (500 MHz, DMSO-d₆) δ 8.58-8.53 (m, 1H), 8.20-8.13 (m, 1H), 7.88-7.80 (m, 1H), 7.80-7.73 (m, 1H), 4.03-3.96 (m, 3H), 3.28-3.14 (m, 2H), 2.69 (t, J=6.6 Hz, 2H), 2.01-1.93 (m, 2H), 1.81-1.75 (m, 2H); ¹³C NMR (126 MHz, DMSO) δ 148.11, 143.48, 142.15, 138.76, 138.47, 136.40, 133.48, 130.33, 129.58, 123.20 (q, J=270.9 Hz), 121.98, 120.45, 116.40, 114.51, 29.54, 28.23, 22.57, 22.30. HRMS (ESI) m/z calcd for $C_{19}H_{17}F_3N_5$ [M+H]⁺ 372.1436, found 372.1444.

7-(3-(Trifluoromethyl)-1H-pyrazol-4-yl)-3,8,10,11-tetrahydropyrazolo[4,3-f]thiopyrano[3,4-c]quinolone

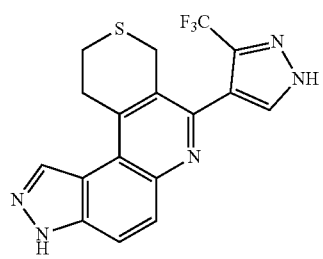

HSD1366

Method A: Gray solid (124 mg, 33%). ¹H NMR (500 MHz, DMSO-d₆) δ 8.78 (s, 1H), 8.44 (s, 1H), 8.15 (d, J=9.1 Hz, 1H), 8.02 (d, J=9.2 Hz, 1H), 3.80 (s, 2H), 3.69 (t, J=6.1 Hz, 2H), 3.17 (t, J=6.0 Hz, 2H). HRMS (ESI) m/z calcd for $C_{17}H_{13}F_3N_5S$ [M+H]⁺ 376.0844, found 376.0840.

1-(7-(3-(Trifluoromethyl)-1H-pyrazol-4-yl)-3,8,10,11-tetrahydro-9H-indazolo[5,4-c][2,7]naphthyridin-9-yl)ethan-1-one

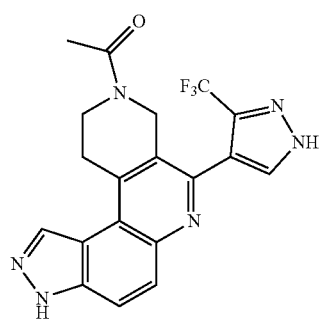

HSD1370

Method C: Off-white solid (60 mg, 15%). ¹H NMR (500 MHz, DMSO-d₆) δ 8.76 (d, J=27.3 Hz, 1H), 8.45 (d, J=10.1 Hz, 1H), 8.13 (d, J=9.1 Hz, 1H), 7.90 (d, J=9.1 Hz, 1H), 4.61 (s, 2H), 3.93 (t, J=5.8 Hz, 2H), 3.64 (d, J=6.0 Hz, 2H), 3.49 (d, J=6.1 Hz, 1H), 2.16 (s, 2H), 1.99 (s, 1H); ¹³C NMR (126 MHz, DMSO) δ 169.21, 140.24, 139.55, 139.27, 134.78, 132.70, 131.88, 128.81, 123.06, 122.63, 120.92, 115.44, 67.49, 42.57, 42.23, 30.01, 25.60. HRMS (ESI) m/z calcd for $C_{19}H_{16}F_3N_6O$ [M+H]⁺ 401.1338, found 401.1328.

9-Cyclopropyl-7-(3-(trifluoromethyl)-1H-pyrazol-4-yl)-3H-pyrazolo[4,3-f]quinolone

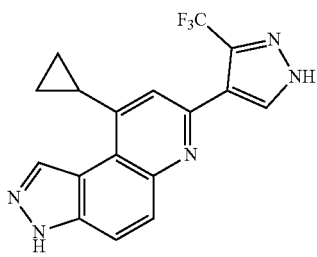

HSD1371

Method A: Off-white solid (124 mg, 36%). $^1$H NMR (500 MHz, DMSO-d$_6$) 8.80 (s, 1H), 8.66 (s, 1H), 7.91 (dd, J=9.1, 2.8 Hz, 1H), 7.80 (d, J=9.1 Hz, 1H), 7.62 (d, J=2.8 Hz, 1H), 2.69-2.53 (m, 1H), 1.28 (dq, J=9.3, 4.0, 3.2 Hz, 2H), 0.94 (dt, J=5.2, 2.4 Hz, 2H); $^{13}$C NMR (126 MHz, DMSO) δ 148.26, 147.74, 145.97, 145.51, 138.44, 131.97, 129.51, 123.71, 122.38, 121.62, 121.41, 118.34, 116.44, 115.57, 16.42, 7.59.

4-(3,8,9,10,11,12-Hexahydrocyclohepta[c]pyrazolo[4,3-f]quinolin-7-yl)-2,6-diiodophenol

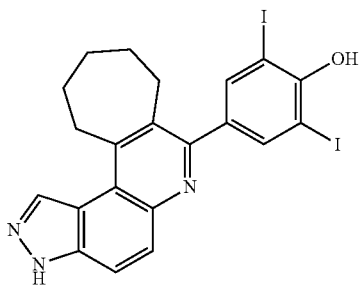

HSD1376

Method A: Yellow solid (203 mg, 35%). $^1$H NMR (500 MHz, DMSO-d$_6$) δ 9.92 (s, 1H), 8.72 (d, J=17.9 Hz, 1H), 8.00 (d, J=9.1 Hz, 1H), 7.93-7.84 (m, 3H), 3.61-3.52 (m, 2H), 3.04-2.96 (m, 2H), 1.97-1.81 (m, 4H), 1.70-1.59 (m, 2H); $^{13}$C NMR (126 MHz, DMSO) δ 156.48, 150.93, 145.52, 141.82, 140.39, 137.85, 136.37, 133.12, 128.72, 121.97, 115.53, 87.03, 31.53, 31.18, 30.00, 26.90, 24.65. HRMS (ESI) m/z calcd for C$_{21}$H$_{18}$I$_2$N$_3$O [M+H]$^+$ 581.9539, found 581.9544.

7-(4-Hydroxy-3,5-diiodophenyl)-8,9,10,11-tetrahydro-3H-pyrazolo[4,3-a]phenanthridin-9-ol

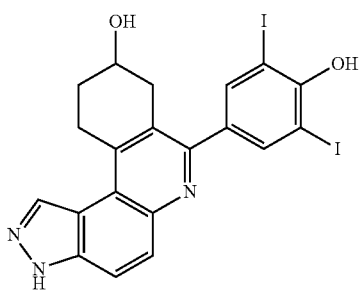

HSD1377

Method A: Yellow solid (175 mg, 30%). $^1$H NMR (500 MHz, DMSO-d$_6$) δ 10.20 (s, 1H), 8.80 (s, 1H), 8.22 (d, J=9.3 Hz, 1H), 8.16 (d, J=9.1 Hz, 1H), 8.12 (s, 2H), 4.07 (dq, J=10.8, 6.9, 4.9 Hz, 1H), 3.56 (dt, J=19.1, 6.2 Hz, 1H), 3.50-3.46 (m, 1H), 2.99 (dd, J=16.5, 4.1 Hz, 1H), 2.75 (dd, J=16.5, 6.7 Hz, 1H), 2.20-2.09 (m, 1H), 2.07-1.96 (m, 1H); $^{13}$C NMR (126 MHz, DMSO) δ 157.81, 154.46, 148.61, 140.62, 136.28, 135.37, 130.03, 122.73, 114.93, 87.09, 63.37, 36.50, 29.26, 28.51. HRMS (ESI) m/z calcd for C$_{20}$H$_{16}$I$_2$N$_3$O$_2$ [M+H]$^+$ 583.9332, found 583.9336.

2,6-Dibromo-4-(8,9,10,11-tetrahydro-3H-pyrazolo[4,3-a]phenanthridin-7-yl)phenol

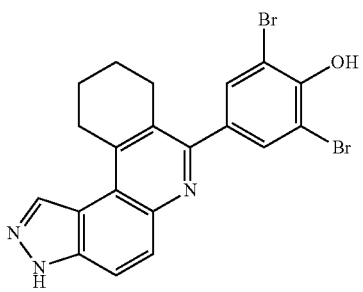

HSD1379

Method A: Off-white solid (113 mg, 24%). $^1$H NMR (500 MHz, DMSO-d$_6$) δ 10.25 (s, 1H), 8.58 (s, 1H), 7.92 (d, J=9.1 Hz, 1H), 7.85 (d, J=9.1 Hz, 1H), 7.79 (s, 2H), 3.29 (d, J=6.6 Hz, 2H), 2.80 (t, J=6.1 Hz, 2H), 2.03-1.93 (m, 2H), 1.79-1.67 (m, 2H); $^{13}$C NMR (126 MHz, DMSO) δ 152.73, 151.40, 144.73, 142.09, 136.53, 133.76, 133.49, 129.93, 127.88, 122.31, 115.95, 111.95, 29.92, 28.66, 22.34. HRMS (ESI) m/z calcd for C$_{20}$H$_{16}$Br$_2$N$_3$O [M+H]$^+$ 471.9660, found 471.9645.

7-(4-Hydroxy-3,5-diiodophenyl)-8,9,10,11-tetrahydro-3H-pyrazolo[4,3-a]phenanthridine-1-carbonitrile

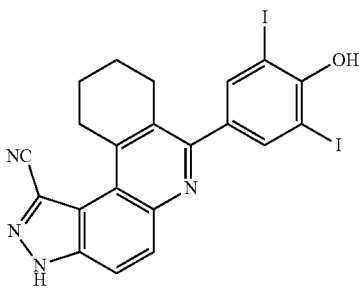

HSD1380

Method A: Yellow solid (224 mg, 38%). $^1$H NMR (500 MHz, DMSO-d$_6$) δ 9.77 (s, 1H), 7.93 (s, 2H), 7.86-7.77 (m, 2H), 3.40 (t, J=6.5 Hz, 2H), 2.77 (t, J=6.2 Hz, 2H), 1.90 (ddt, J=9.2, 6.5, 3.0 Hz, 2H), 1.75 (ddt, J=9.2, 6.4, 3.0 Hz, 2H); $^{13}$C NMR (126 MHz, DMSO) δ 155.88, 155.23, 144.40, 143.50, 140.00, 139.78, 136.45, 131.67, 129.81, 121.16, 120.30, 117.66, 116.23, 114.52, 86.91, 31.76, 28.66, 22.03, 21.81. HRMS (ESI) m/z calcd for C$_{22}$H$_{15}$I$_2$N$_3$O [M+H]$^+$ 590.9304, found 590.9325.

2,6-Diiodo-4-(1-methyl-8,9,10,11-tetrahydro-3H-pyrazolo[4,3-a]phenanthridin-7-yl)phenol

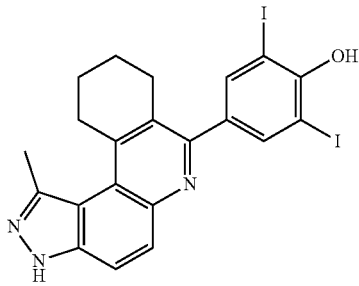

HSD1381

Method A: Yellow solid (244 mg, 42%). $^1$H NMR (500 MHz, DMSO-d$_6$) δ 10.08 (s, 1H), 8.04 (d, J=9.6 Hz, 3H), 7.95 (d, J=8.9 Hz, 1H), 3.61-3.50 (m, 2H), 2.92 (s, 3H), 2.82-2.71 (m, 2H), 1.87-1.74 (m, 4H). $^{13}$C NMR (126 MHz, DMSO) δ 157.30, 140.34, 130.74, 125.25, 87.10, 32.52, 27.67, 21.87, 21.55. HRMS (ESI) m/z calcd for C$_{21}$H$_{18}$I$_2$N$_3$O [M+H]$^+$ 581.9539 found 581.9534.

(5-(8,9,10,11-Tetrahydro-3H-pyrazolo[4,3-a]phenanthridin-7-yl)thiophen-3-yl)boronic Acid

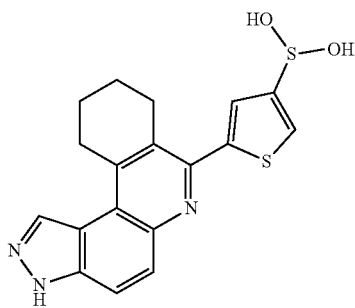

HSH-2-52

Method A: Off-white solid (157, 45%). $^1$H NMR (500 MHz, DMSO-d$_6$) δ 8.54 (s, 1H), 8.08 (s, 2H), 8.05 (s, 1H), 7.91 (d, J=6.8 Hz, 1H), 7.84 (d, J=9.1 Hz, 1H), 7.78 (d, J=9.0 Hz, 1H), 3.11 (t, J=6.1 Hz, 2H), 2.46 (s, 2H), 2.06-1.98 (m, 2H), 1.88 (qd, J=8.6, 7.1, 3.9 Hz, 2H); $^{13}$C NMR (126 MHz, DMSO-d$_6$) δ 149.49, 145.18, 143.33, 143.01, 138.66, 137.70, 136.36, 133.33, 129.32, 128.70, 121.48, 116.41, 114.79, 30.05, 29.29, 22.62, 22.38.

N-(2-(4-Methylpiperazin-1-yl)ethyl)-7-(3-(trifluoromethyl)-1H-pyrazol-4-yl)-8,9,10,11-tetrahydro-3H-pyrazolo[4,3-a]phenanthridine-1-carboxamide

HSD1385

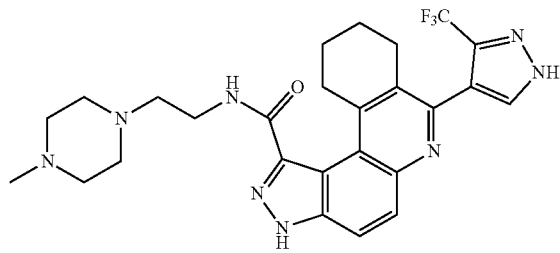

Pale yellow solid. $^1$H NMR (500 MHz, Methanol-d$_4$) δ 8.29 (s, 1H), 8.25 (d, J=9.2 Hz, 1H), 8.03 (d, J=9.2 Hz, 1H), 3.75 (t, J=6.4 Hz, 2H), 3.58 (t, J=6.0 Hz, 2H), 3.41 (s, 4H), 3.19-3.05 (m, 4H), 3.01-2.96 (m, 2H), 2.91 (s, 3H), 2.81 (t, J=6.5 Hz, 2H), 2.01-1.92 (m, 2H), 1.92-1.87 (m, 2H); $^{13}$C NMR (126 MHz, MeOD) δ 167.01, 154.73, 144.30, 143.47, 140.67, 136.64, 133.59, 132.09, 124.38, 122.36 (q, J=268.38 Hz), 121.24, 119.27, 111.50, 110.90, 55.67, 52.74, 49.61, 42.13, 36.36, 30.49, 26.83, 21.20, 20.97. HRMS (ESI) m/z calcd for C$_{26}$H$_{30}$F$_3$N$_8$O [M+H]$^+$ 527.2495, found 527.2495.

1-Methyl-7-(3-(trifluoromethyl)-1H-pyrazol-4-yl)-8,9,10,11-tetrahydro-3H-pyrazolo[4,3-a]phenanthridin-9-amine

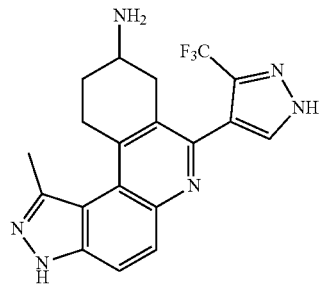

HSD1386

Method A: Off-white solid (89 mg, 23%). $^1$H NMR (500 MHz, DMSO-d$_6$) δ 8.55 (s, 2H), 8.44 (s, 1H), 8.10 (d, J=9.1 Hz, 1H), 8.02 (d, J=9.3 Hz, 1H), 3.82-3.71 (m, 2H), 3.68-3.59 (m, 1H), 3.14-3.04 (m, 1H), 2.94 (s, 3H), 2.90-2.79 (m, 1H), 2.42-2.28 (m, 1H), 1.91-1.78 (m, 1H); $^{13}$C NMR (126 MHz, DMSO) δ 144.18, 140.74, 139.47, 139.18, 138.89, 132.95, 129.06, 125.24, 122.97 (q, J=269.64 Hz), 113.03, 45.50, 31.39, 30.49, 26.00, 18.97. HRMS (ESI) m/z calcd for C$_{19}$H$_{18}$F$_3$N$_6$ [M+H]$^+$ 387.1545, found 387.1540.

(2-Methoxy-5-(8,9,10,11-tetrahydro-3H-pyrazolo[4,3-a]phenanthridin-7-yl)phenyl)boronic Acid

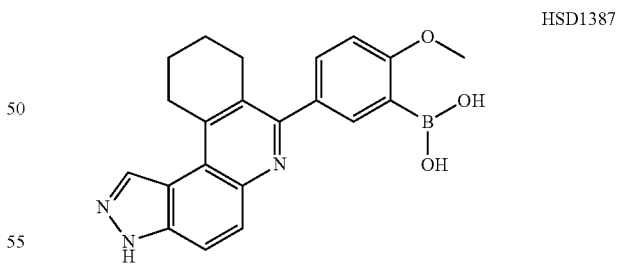

HSD1387

Method A: White solid (166 mg, 48%). $^1$H NMR (500 MHz, DMSO-d$_6$) δ 8.57-8.51 (m, 1H), 7.83 (s, 2H), 7.76 (d, J=6.0 Hz, 3H), 7.60 (dd, J=8.5, 2.4 Hz, 1H), 7.06 (d, J=8.5 Hz, 1H), 3.87 (s, 3H), 3.36-3.32 (m, 2H), 2.78 (t, J=6.1 Hz, 2H), 2.05-1.95 (m, 2H), 1.78-1.69 (m, 2H); $^{13}$C NMR (126 MHz, DMSO) δ 163.59, 156.90, 143.67, 142.28, 138.64, 136.72, 136.33, 133.31, 132.83, 129.70, 129.44, 121.61, 116.55, 114.27, 110.23, 55.95, 29.73, 29.20, 22.67, 22.62. HRMS (ESI) m/z calcd for C$_{21}$H$_{21}$BN$_3$O$_3$ [M+H]$^+$ 374.1676, found 374.1671.

(5-(8,9,10,11-Tetrahydro-3H-pyrazolo[4,3-a]
phenanthridin-7-yl)furan-2-yl)boronic Acid

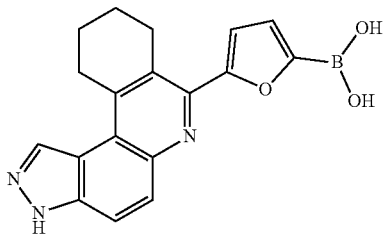

Method A: Yellow solid (133 mg, 40%). $^1$H NMR (500 MHz, DMSO-$d_6$) δ 8.64-8.60 (m, 1H), 8.02-7.94 (m, 2H), 7.31-7.21 (m, 1H), 6.79 (m, 1H), 3.35-3.34 (m, 2H), 3.07-3.03 (m, 2H), 2.00 (s, 2H), 1.86 (s, 2H); $^{13}$C NMR (126 MHz, DMSO) δ 154.27, 145.25, 129.18, 122.17, 116.19, 112.66, 30.33, 28.05, 22.07. HRMS (ESI) m/z calcd for $C_{18}H_{17}BN_3O_3$ [M+H]$^+$ 334.1363, found 334.1363.

5-Fluoro-7-(1H-pyrazol-4-yl)-8,9,10,11-tetrahydro-3H-pyrazolo[4,3-a]phenanthridine

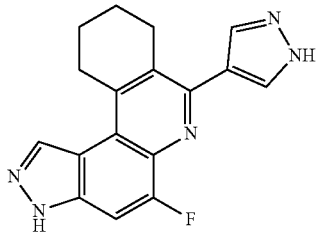

Method A: Off-white solid (64 mg, 21%). $^1$H NMR (500 MHz, Methanol-$d_4$) δ 8.81 (s, 1H), 8.29 (s, 2H), 8.00 (d, J=10.3 Hz, 1H), 3.57 (t, J=6.4 Hz, 2H), 3.09 (t, J=6.2 Hz, 2H), 2.20-2.10 (m, 2H), 2.03-1.82 (m, 2H); $^{13}$C NMR (126 MHz, MeOD) δ 153.31, 146.28, 135.79, 133.97, 133.51, 126.93, 123.44, 112.98, 111.93, 103.01, 30.97, 27.96, 21.18. HRMS (ESI) m/z calcd for $C_{17}H_{15}FN_5$ [M+H]$^+$ 308.1311, found 308.1312.

(7-(3-(Trifluoromethyl)-1H-pyrazol-4-yl)-8,9,10,11-tetrahydro-3H-pyrazolo[4,3-a]phenanthridin-1-yl)
methanol Compound HSD1329 (100 mg) was dissolved in anhydrous THF and cooled on using dry ice acetone under argon. After that LAH (1 molar solution in THF, 1 equiv.) was added dropwise and reaction was continued to stir for overnight at room temperature. Reaction was quenched by slow addition of water and THF mixture slowly under cooling contion. Reaction mixture filtered and purified by flash column chromatography.

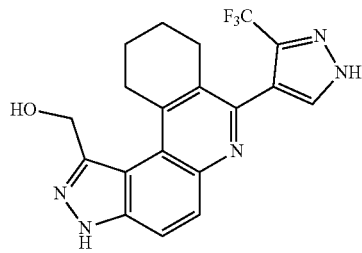

white solid (75 mg, 80%). $^1$H NMR (500 MHz, Methanol-$d_4$) δ 7.98 (s, 1H), 7.79 (d, J=8.4 Hz, 2H), 5.24 (s, 2H), 3.70 (s, 2H), 2.71 (t, J=5.8 Hz, 2H), 2.00-1.84 (m, 4H); $^{13}$C NMR (126 MHz, MeOD) δ 148.12, 144.28, 143.66, 139.73, 133.60, 130.48, 130.17, 128.88, 124.42, 118.85, 114.15, 60.41, 29.11, 27.68, 22.06, 21.83. HRMS (ESI) m/z calcd for $C_{19}H_{17}F_3N_5O$ [M+H]$^+$ 388.1385, found 388.1380.

1-Methyl-7-(3-(trifluoromethyl)-1H-pyrazol-4-yl)-8,9,10,11-tetrahydro-3H-pyrazolo[4,3-a]phenanthridine-8,8,9,9,10,10-$d_6$ Deuterated (D8) cyclohexanone was used as a ketone using same method A

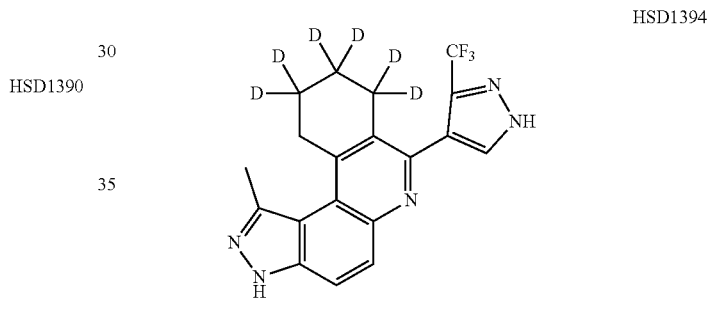

Method A: Off-white solid (68 mg, 18%). $^1$H NMR (500 MHz, Methanol-$d_4$) δ 8.20 (s, 1H), 7.72 (d, J=8.9 Hz, 1H), 7.68 (d, J=8.7 Hz, 1H), 3.40-3.37 (m, 2H), 2.89 (s, 3H); HRMS (ESI) m/z calcd for $C_{19}H_{11}D_6F_3N_5$ [M+H]$^+$ 378.1813, found 378.1804.

5-Fluoro-7-(3-(trifluoromethyl)-1H-pyrazol-4-yl)-8,9,10,11-tetrahydro-3H-pyrazolo[4,3-a]phenanthridine-8,8,9,9,10,10,-$d_6$ Deuterated (D$_8$) cyclohexanone was used as a ketone using same method A

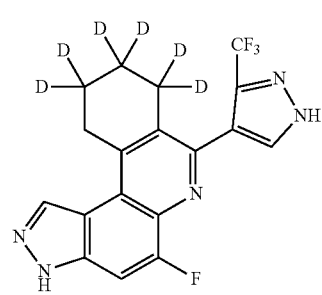

Method A: Off-white solid (76 mg, 20%). $^1$H NMR (500 MHz, Methanol-$d_4$) δ 8.80 (s, 1H), 8.24 (s, 1H), 7.96 (d, J=9.9 Hz, 1H), 3.53 (s, 2H); $^{13}$C NMR (126 MHz, MeOD) δ 154.06 (q, J=255.78 Hz), 144.99, 140.18, 139.89, 139.23, 134.60, 134.02, 131.99, 128.78, 124.39, 122.45 (q, J=269.64 Hz), 118.14, 112.31, 111.91, 102.86, 30.30, 26.74, 20.13, 16.82. HRMS (ESI) m/z calcd for $C_{18}H_8D_6F_4N_5$ [M+H]$^+$ 382.1562 found 382.1556.

7-(3-(Trifluoromethyl)-1H-pyrazol-4-yl)-3H-pyrazolo[4,3-f]quinoline-9-carboxylic Acid Pyruvic acid as ketone substrate.

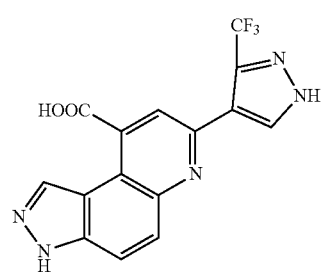

HSD1396

Method A: Pale yellow solid (100 mg, 29%). $^1$H NMR (500 MHz, Methanol-$d_4$) δ 8.69 (s, 1H), 8.32 (s, 1H), 7.96-7.87 (m, 2H), 7.82 (s, 1H); $^{13}$C NMR (126 MHz, MeOD) δ 173.72, 147.71, 146.35, 143.54, 139.55, 138.93, 134.30, 131.27, 128.76, 122.98 (q, J=269.64 Hz), 120.75, 118.19, 117.21, 116.10, 115.45.

3,3-Dimethyl-5-(8,9,10,11-tetrahydro-3H-pyrazolo[4,3-a]phenanthridin-7-yl)benzo[c][1,2]oxaborol-1(3H)-ol

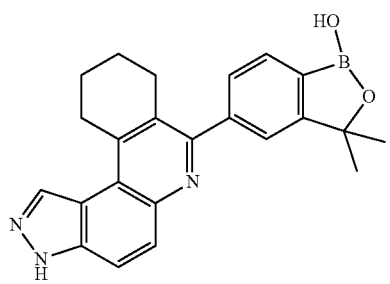

HSD1398

Method A: Off-white solid (54 mg, 14%). $^1$H NMR (500 MHz, Methanol-$d_4$) δ 7.83 (d, J=9.1 Hz, 1H), 7.77 (d, J=9.1 Hz, 1H), 7.73-7.68 (m, 1H), 7.47 (t, J=1.1 Hz, 1H), 7.41 (dd, J=7.4, 1.4 Hz, 1H), 3.24 (t, J=6.5 Hz, 2H), 2.69 (t, J=6.2 Hz, 2H), 2.05-1.94 (m, 2H), 1.79-1.71 (m, 2H), 1.56 (s, 6H); $^{13}$C NMR (126 MHz, MeOD) δ 162.29, 157.20, 143.50, 143.12, 129.88, 129.44, 128.35, 127.81, 122.15, 120.98, 119.24, 119.15, 115.90, 110.35, 98.72, 84.23, 29.51, 29.30, 28.40, 28.29, 22.07, 21.97; HRMS (ESI) calcd for $C_{23}H_{23}BN_3O_2$ [M+H]$^+$ 384.1883 found 384.1882.

3,3-Dimethyl-6-(8,9,10,11-tetrahydro-3H-pyrazolo[4,3-a]phenanthridin-7-yl)benzo[c][1,2]oxaborol-1(3H)-ol

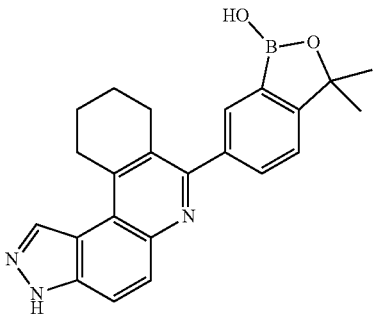

HSD1399

Method A: Off-white solid (62 mg, 16%). $^1$H NMR (500 MHz, Methanol-$d_4$) δ 8.62 (s, 1H), 7.88 (dd, J=17.5, 9.0 Hz, 2H), 7.79-7.68 (m, 1H), 7.65-7.59 (m, 1H), 7.55-7.46 (m, 1H), 3.53-3.40 (m, 2H), 2.93-2.72 (m, 2H), 2.11 (dt, J=11.5, 6.6 Hz, 2H), 1.94-1.76 (m, 2H), 1.60 (s, 6H); $^{13}$C NMR (126 MHz, MeOD) δ 162.13, 157.52, 154.20, 143.64, 139.57, 138.67, 131.57, 130.39, 129.75, 128.47, 122.21, 120.28, 113.77, 84.16, 29.64, 28.56, 28.27, 22.16, 22.05. HRMS (ESI) m/z calcd for $C_{23}H_{23}BN_3O_2$ [M+H]$^+$ 384.1883 found 384.1880.

(2-Methoxy-3-(8,9,10,11-tetrahydro-3H-pyrazolo[4,3-a]phenanthridin-7-yl)phenyl)boronic Acid

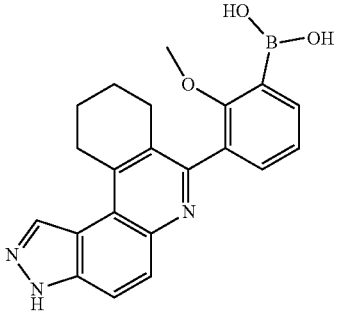

HSD1400

Method A: Off-white solid (41 mg, 11%). $^1$H NMR (500 MHz, Methanol-$d_4$) δ 8.58 (s, 1H), 7.89 (d, J=9.2 Hz, 1H), 7.83 (d, J=9.1 Hz, 1H), 7.42 (d, J=7.3 Hz, 1H), 7.32 (d, J=7.4 Hz, 1H), 7.24 (t, J=7.4 Hz, 1H), 3.48 (s, 3H), 3.44-3.35 (m, 2H), 2.82 (dd, J=15.9, 7.2 Hz, 1H), 2.51 (dt, J=17.3, 5.9 Hz, 1H), 2.09-2.00 (m, 2H), 1.89-1.82 (m, 1H), 1.81-1.76 (m, 1H); $^{13}$C NMR (126 MHz, MeOD) δ 159.79, 155.68, 142.96, 133.21, 132.37, 131.13, 130.91, 128.28, 124.23, 123.00, 122.24, 60.00, 29.48, 27.03, 22.16, 21.79. HRMS (ESI) m/z calcd for $C_{21}H_{21}BN_3O_3$ [M H]$^+$ 374.1676, found 374.1670.

(7-(3-(Trifluoromethyl)-1H-pyrazol-4-yl)-8,9,10,11-tetrahydro-3H-pyrazolo[4,3-a]phenanthridin-5-yl)ethane-1,2-diamine $N^1,N^1,N^2$, Trimethylethane-1,2-diamine (0.5 mL) was added to mixture of compound HSH-1-156 (50 mg, 0.13 mmol) and powdered K$_2$CO$_3$ (2 equiv), dissolved in DMSO (1 mL). The reaction mixture was heated at 200° C. in a pressure tube for 24 h. After completion of reaction, reaction was purified by silica-gel flash chromatography using dichloromethane:methanol (80:20) as solvent system.

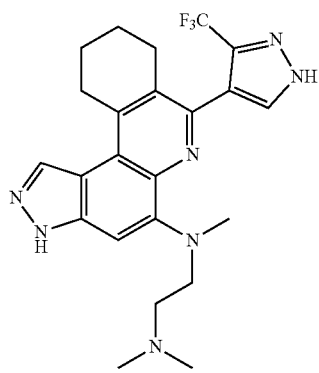

Yellow solid (8 mg, 13%). $^1$H NMR (500 MHz, Methanol-d$_4$) δ 8.51 (s, 1H), 8.07 (s, 1H), 7.45 (s, 1H), 3.52 (t, J=6.4 Hz, 2H), 3.37 (t, J=6.4 Hz, 2H), 3.21-3.16 (m, 2H), 2.98 (s, 3H), 2.66 (t, J=6.6 Hz, 2H), 2.43 (s, 6H), 2.10-2.04 (m, 2H), 1.92-1.84 (m, 2H); $^{13}$C NMR (126 MHz, MeOD) δ 148.52, 146.67, 143.98, 139.58, 138.84, 131.49, 131.11, 123.95, 122.86, 120.72, 119.24, 112.05, 56.25, 52.86, 44.02, 43.71, 39.62, 29.85, 27.71, 22.14, 21.75; HRMS (ESI) m/z calcd for C$_{23}$H$_{24}$F$_3$N$_7$ [M+H]$^+$ 458.2280, found 458.2276.

5-(Piperidin-1-yl)-7-(3-(trifluoromethyl)-1H-pyrazol-4-yl)-8,9,10,11-tetrahydro-3H-pyrazolo[4,3-a]phenanthridine

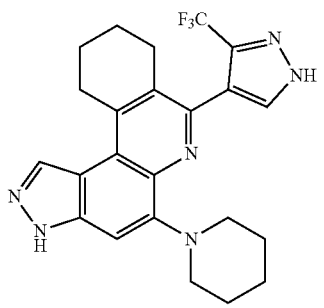

Method A: Off-white solid (66 mg, 15%). $^1$H NMR (500 MHz, DMSO-d$_6$) δ 8.39 (s, 1H), 8.15 (s, 1H), 7.12 (s, 1H), 3.24 (d, J=6.4 Hz, 2H), 3.17 (t, J=5.2 Hz, 4H), 2.62 (t, J=6.2 Hz, 2H), 1.93 (tt, J=7.6, 5.2, 4.3 Hz, 2H), 1.80-1.72 (m, 2H), 1.64 (t, J=5.8 Hz, 4H), 1.53 (q, J=6.1 Hz, 2H); $^{13}$C NMR (126 MHz, DMSO) δ 150.46, 146.47, 142.38, 139.11, 136.28, 131.34, 130.26, 123.57 (q, J=263.34 Hz), 123.19, 120.16, 120.08, 111.84, 53.57, 31.18, 29.81, 28.19, 26.16, 24.64, 22.68, 22.29; HRMS (ESI) m/z calcd for C$_{23}$H$_{24}$F$_3$N$_6$ [M+H]$^+$ 441.2015, found 441.2012.

7-(4-Fluoro-3-nitrophenyl)-8,9,10,11-tetrahydro-3H-pyrazolo[4,3-a]phenanthridine

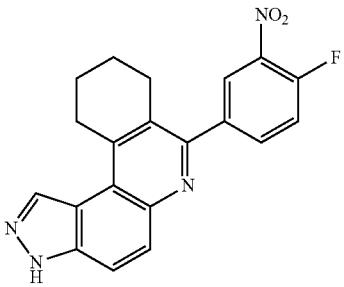

Method A: Yellow solid (145 mg, 40%). $^1$H NMR (500 MHz, Methanol-d$_4$) δ 8.63 (s, 1H), 8.31 (dd, J=7.2, 2.2 Hz, 1H), 7.96 (ddd, J=8.6, 4.3, 2.3 Hz, 1H), 7.93-7.87 (m, 2H), 7.58 (dd, J=11.0, 8.6 Hz, 1H), 3.44 (d, J=7.2 Hz, 3H), 2.84 (t, J=6.2 Hz, 2H), 2.18-2.08 (m, 2H), 1.94-1.83 (m, 2H); $^{13}$C NMR (126 MHz, MeOD) δ 153.80, 144.17, 137.50, 137.15, 136.31, 129.49, 128.62, 128.52, 126.50, 125.92, 122.66, 118.07, 117.90, 29.65, 28.38, 22.02.

2-Fluoro-5-(8,9,10,11-tetrahydro-3H-naphtho[1,2-e]indazol-7-yl)aniline

Compound HSD1404 (100 mg) was dissolved in 5 mL THF and purged with argon for 15 minute. After that palladium (10% on carbon, 20 mol %) was added and hydrogen ballon was used for hydrogenation for 6 h. After completion, reaction mixture was filtered through sintered funnel, concentrated and purified by flash column chromatography.

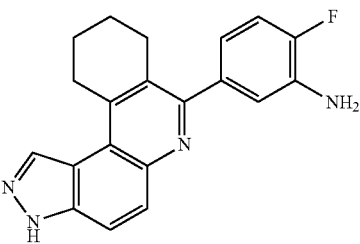

Pale yellow solid (83 mg, 90%). $^1$H NMR (500 MHz, Methanol-d$_4$) δ 8.55 (s, 1H), 7.90-7.78 (m, 2H), 7.07 (dd, J=11.3, 8.2 Hz, 1H), 6.96 (dd, J=8.6, 2.1 Hz, 1H), 6.74 (ddd, J=8.2, 4.3, 2.1 Hz, 1H), 3.34 (d, J=7.9 Hz, 3H), 2.77 (t, J=6.2 Hz, 2H), 2.06 (td, J=8.6, 7.2, 4.6 Hz, 2H), 1.88-1.78 (m, 2H); $^{13}$C NMR (126 MHz, MeOD) δ 157.17, 153.73, 152.53 (d, J=239.4 Hz) 143.38, 136.87, 135.81, 135.63, 135.52, 129.70, 128.38, 122.05, 117.94, 117.38, 116.11, 114.39, 114.24, 113.58, 29.59, 28.41, 22.17, 22.06. HRMS (ESI) m/z calcd for C$_{21}$H$_{19}$FN$_3$ [M+H]$^+$ 332.1563, found 332.1560.

7-(3-Fluoro-4-nitrophenyl)-8,9,10,11-tetrahydro-3H-pyrazolo[4,3-a]phenanthridine

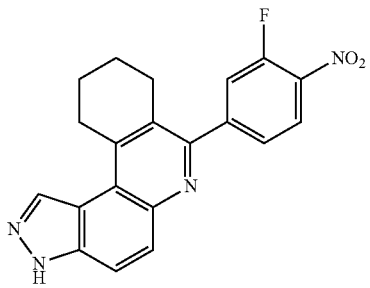

HSD1409

Method A: Yellow solid (145 mg, 40%) $^1$H NMR (500 MHz, DMSO-d$_6$) δ 8.57 (s, 1H), 8.26 (t, J=8.2 Hz), 7.89-7.81 (m, 3H), 7.66 (dd, J=8.4, 1.4 Hz, 1H), 3.32 (s, 2H), 2.81 (t, J=5.8 Hz, 2H), 2.01-2.79 (m, 2H), 1.76-1.74 (m, 2H); $^{13}$C NMR (126 MHz, DMSO) δ 155.83, 153.75, 153.45, 149.27, 149.20, 143.60, 143.07, 139.01, 136.56, 129.52, 126.51, 122.60, 119.60, 119.43, 116.28, 114.94, 29.66, 228.50, 22.45, 22.33.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES

1) Ten things you should know about protein kinases: IUPHAR Review 14. Fabbro et al. *Br J Pharmacol* 2015, 172, 2675.
2) 25 years of small molecular weight kinase inhibitors: potentials and limitations. Fabbro *Mol Pharmacol* 2015, 87, 766.
3) Bcr-Abl kinase domain mutations, drug resistance, and the road to a cure for chronic myeloid leukemia O'Hare et al. *Blood* 2007 110, 2242-2249.
4) Aberrant activation of the PI3K/mTOR pathway promotes resistance to sorafenib in AML. Lindblad et al. *Oncogene* 2016, 35 (39), 5119-31
5) Rho kinase regulates the survival and transformation of cells bearing oncogenic forms of KIT, FLT3, and BCR-ABL. Mali et al. *Cancer Cell* 2011, 20 (3), 357-69.
6) Jakinibs: a new class of kinase inhibitors in cancer and autoimmune disease. Kontzias et al. *Curr. Opin. Pharmacol.* 2012, 12 (4), 464-70.
7) Rho Kinase (ROCK) inhibitors. James et al. *J Cardiovasc Pharmacol.* 2007, 50 (1), 17-24
8) An emerging treatment option for glaucoma: Rho kinase inhibitors. Wang and Chang *Clin Ophthalmol.* 2014, 8, 883-90.
9) LRRK2 in Parkinson's disease: protein domains and functional insights. Mata et al. *Trends Neurosci.* 2006, 29 (5), 286-93
10) Recent synthetic developments in a powerful imino Diels-Alder reaction (Povarov reaction): application to the synthesis of N-polyheterocycles and related alkaloids. Kouznetsov Tetrahedron, 2009, 65, 2721; b) Povarov and Mikhailov *Izv Akad Nauk SSR, Ser Khim* 1963, 953.

The invention claimed is:
1. A compound having a formula

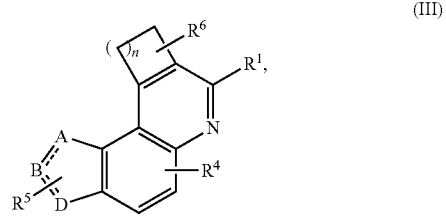

(III)

or a pharmaceutically acceptable salt thereof, wherein n is 3-5; the bonding between A and B and bonding between B and D can be a single bond or a double bond, but both bonds between A and B and between B and D cannot be a double bond at the same time; A, B, and D each represent, independently, C, O, N, or S, wherein at least one of A, B, and D is a heteroatom;

R$^1$ is amino, hydroxyl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

R$^4$ represents two substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or the two substituents are taken together with the attached carbons to form an optionally substituted cyclic or heterocyclic moiety;

depending on A, B, and D, R$^5$ represents two or three substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and depending on the value of n, R$^6$ represents four to six substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

2. The compound according to claim 1, wherein $R^1$ is

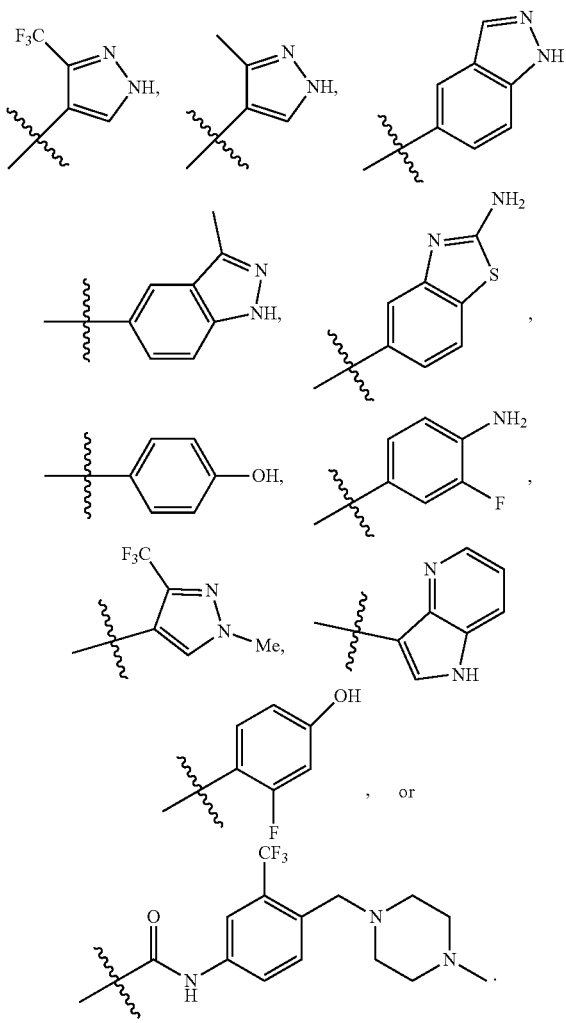

3. A compound having a formula

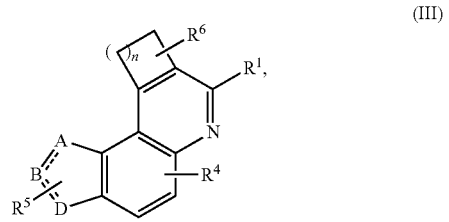

or a pharmaceutically acceptable salt thereof, wherein n is 3; the bonding between A and B and bonding between B and D can be a single bond or a double bond, but both bonds between A and B and between B and D cannot be a double bond at the same time; A, B, and D each represent, independently, C, O, N, or S, wherein at least one of A, B, and D is a heteroatom;

$R^1$ is heterocyclyl or heteroaryl either of which is optionally substituted;

$R^4$ represents two substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted;

or the two substituents are taken together with the attached carbons to form an optionally substituted cyclic or heterocyclic moiety;

depending on A, B, and D, $R^5$ represents two or three substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and $R^6$ represents four substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted.

4. The compound according to claim 1, wherein the bond between A and B is a double bond, wherein each A and B represents, independently, $CR^8$, N, or $NR^9$, wherein $R^8$ and $R^9$ represent independently hydrogen, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted;

depending on A and B, $R^5$ represents one or two substituents, each independently selected from the group consisting of hydrogen, deuterium, halo, azido, cyano, nitro, hydroxy, amino, thio, carboxy, ester, amide, acyl, sulfoxyl, sulfonyl, phosphate, phosphoryl, alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, aryl, heteroaryl, arylalkyl, arylalkenyl, and arylalkynyl, each of which is optionally substituted; and D is N—$R^7$, wherein $R^7$ is a hydrogen alkyl, alkenyl, alkynyl, heteroalkyl, heteroalkenyl, heteroalkynyl, heterocyclyl, cycloalkyl, cycloalkenyl, cycloheteroalkyl, cycloheteroalkenyl, acyl, aryl, heteroaryl, arylalkyl, arylalkenyl, or arylalkynyl, each of which is optionally substituted.

5. The compound according to claim 4, wherein R[1] is
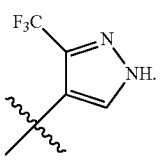 [SMILES: *c1c[nH]nc1C(F)(F)F]
6. The compound according to claim 4, wherein R[1] is
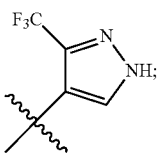
A is carbon (C); B is nitrogen (N); and R[5], R[6], and R[7] all represent hydrogen.
7. The compound according to claim 3, wherein the compound is
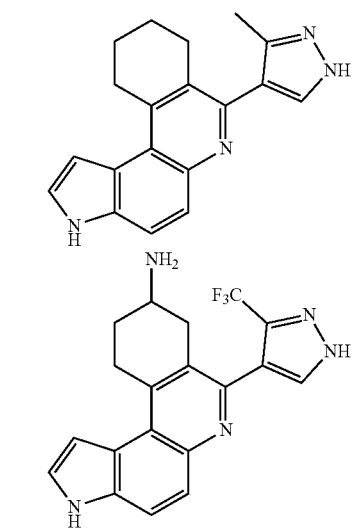
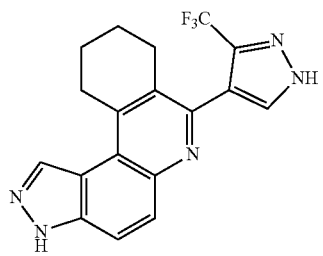
HSD1169
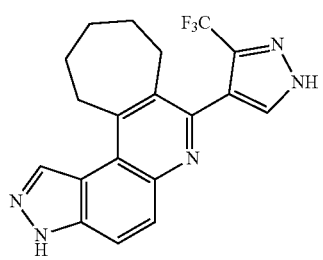
HSD1289
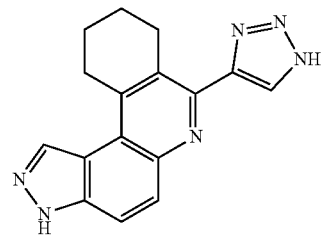
HSD1292
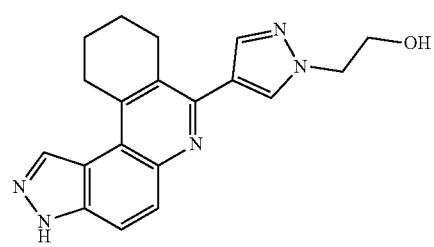
HSD1294
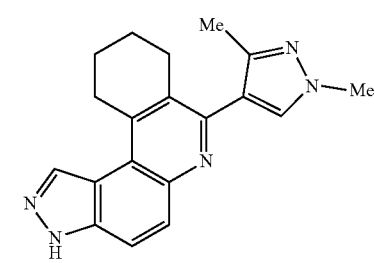
HSD1295
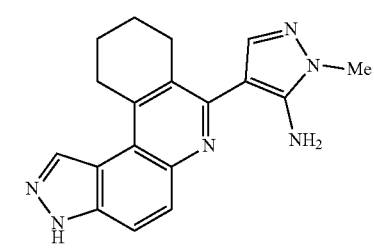
HSD1302
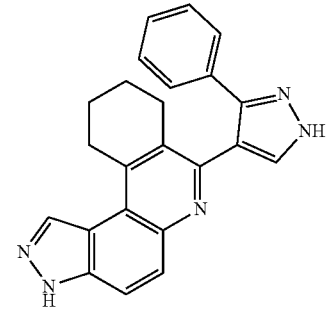
HSD303
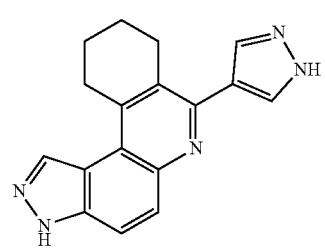
HSD1077

291
-continued
HSD-02-1234
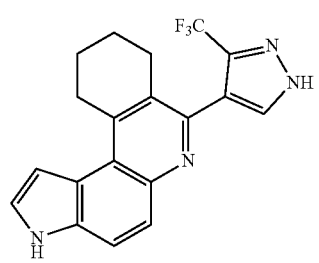
HSD-02-1236
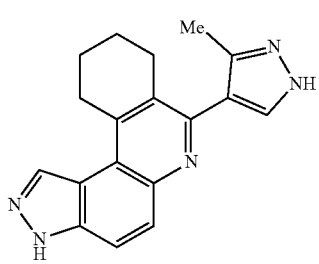 [SMILES: FC(F)(F)c1n[nH]cc1-c1nc2ccc3[nH]ncc3c2c2c1CCCC2]
HSD-02-1240
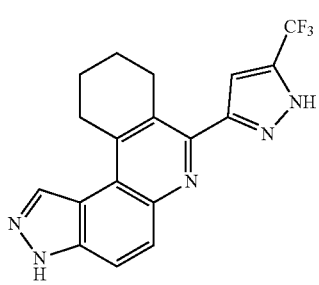
HSD-02-1262
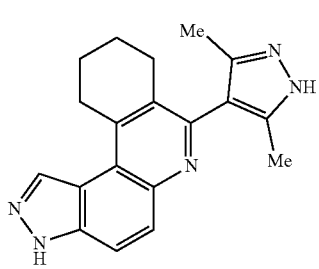
HSD1304
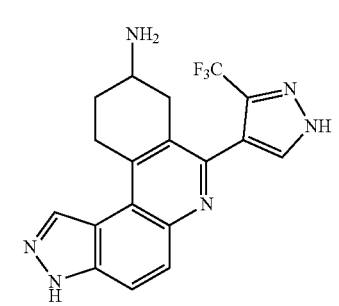
HSD1308
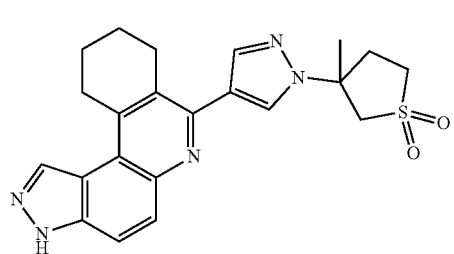
292
-continued
HSD1310
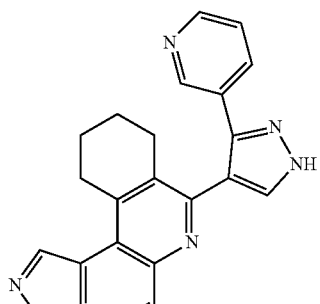
HSD311
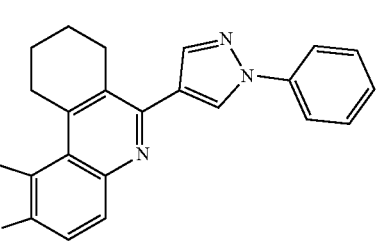
HSD312
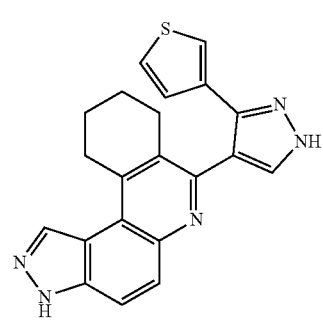
HSD1313
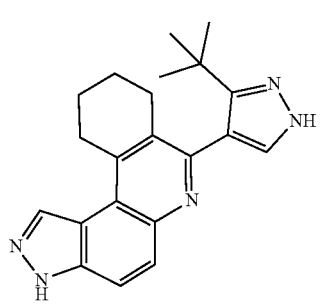
HSD1314
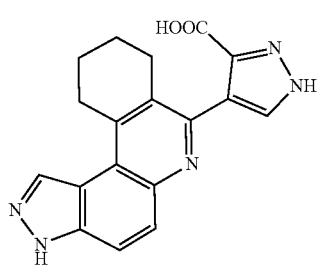

-continued

HSH124
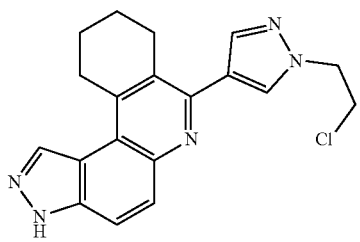

HSD1321
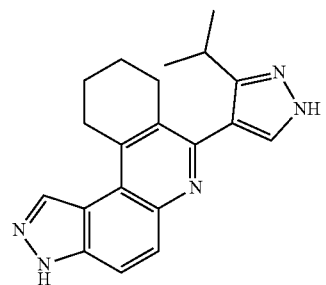

HSD1332
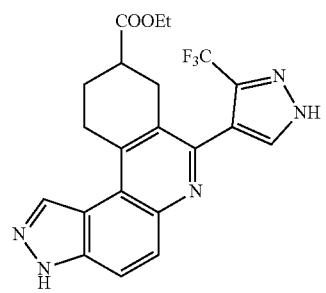

HSD1337
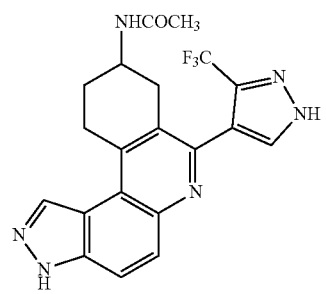

-continued

HSD1365
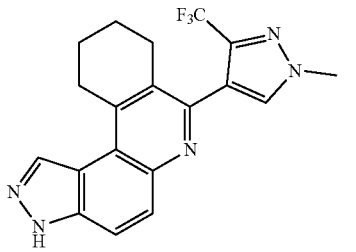

or

HSD1287
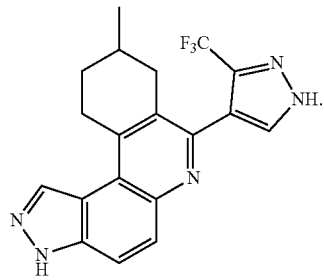

8. A pharmaceutical composition comprising:
a compound of claim 7, or a pharmaceutically acceptable salt thereof, and a pharmaceutically acceptable diluent, excipient, or carrier.

9. The compound according to claim 3, wherein the compound is:

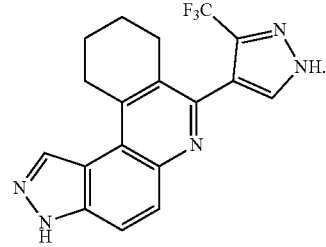

10. A pharmaceutical composition comprising a compound of claim 9 or a pharmaceutically acceptable salt thereof, and a pharmaceutically acceptable carrier, excipient, or diluent.

* * * * *